US012679893B2

(12) United States Patent (10) Patent No.: US 12,679,893 B2
Glaser et al. (45) Date of Patent: \*Jul. 14, 2026

(54) PD-L1 BINDING AGENTS AND USES THEREOF

(71) Applicant: EXELIXIS, INC., Alameda, CA (US)

(72) Inventors: Bryan Glaser, Madison, WI (US);
Bonnie Hammer, Madison, WI (US);
Seema Kantak, Pacifica, CA (US)

(73) Assignee: EXELIXIS, INC., Alameda, CA (US)

( * ) Notice: Subject to any disclaimer, the term of this
patent is extended or adjusted under 35
U.S.C. 154(b) by 742 days.

This patent is subject to a terminal dis-
claimer.

(21) Appl. No.: 18/018,863

(22) PCT Filed: Aug. 3, 2021

(86) PCT No.: PCT/US2021/044330
§ 371 (c)(1),
(2) Date: Jan. 30, 2023

(87) PCT Pub. No.: WO2022/031695
PCT Pub. Date: Feb. 10, 2022

(65) Prior Publication Data
US 2023/0303699 A1 Sep. 28, 2023

Related U.S. Application Data

(60) Provisional application No. 63/061,109, filed on Aug.
4, 2020.

(51) Int. Cl.
C07K 16/00 (2006.01)
C07K 16/28 (2006.01)

(52) U.S. Cl.
CPC ...... C07K 16/2827 (2013.01); C07K 2317/24
(2013.01); C07K 2317/35 (2013.01); C07K
2317/565 (2013.01); C07K 2317/567
(2013.01); C07K 2317/92 (2013.01)

(58) Field of Classification Search
None
See application file for complete search history.

(56) References Cited

U.S. PATENT DOCUMENTS

| | | | |
|---|---|---|---|
| 11,739,151 B2 | 8/2023 | Liu et al. |
| 12,110,332 B2 | 10/2024 | Guo |
| 2009/0094717 A1 | 4/2009 | Troukhan et al. |
| 2010/0028354 A1 | 2/2010 | McKinnon et al. |
| 2010/0203056 A1 | 8/2010 | Irving et al. |
| 2016/0046711 A1 | 2/2016 | Bialucha et al. |
| 2016/0304591 A1 | 10/2016 | Kelley et al. |
| 2017/0368169 A1 | 12/2017 | Loew et al. |
| 2019/0062306 A1 | 2/2019 | Coburn et al. |
| 2019/0106494 A1 | 4/2019 | Wang et al. |
| 2019/0127472 A1 | 5/2019 | Koide et al. |
| 2020/0270345 A1 | 8/2020 | Solovyev et al. |
| 2021/0332131 A1 | 10/2021 | De Boer et al. |
| 2025/0197502 A1 | 6/2025 | Glaser et al. |

FOREIGN PATENT DOCUMENTS

| | | | |
|---|---|---|---|
| JP | 2019528083 A | 10/2019 |
| JP | 2019532013 A | 11/2019 |
| JP | 2020511133 A | 4/2020 |
| JP | 2020517239 A | 6/2020 |
| WO | WO 2017161976 A1 | 9/2017 |
| WO | WO 2017220990 A1 | 12/2017 |
| WO | WO 2017220990 A9 | 12/2017 |
| WO | WO 2018005682 A2 | 1/2018 |
| WO | WO 2018005682 A3 | 1/2018 |
| WO | WO 2018162749 A1 | 9/2018 |
| WO | WO 2018195226 A1 | 10/2018 |
| WO | WO 2019040791 A1 | 2/2019 |
| WO | WO 2019095358 A1 | 5/2019 |
| WO | WO 2019109876 A1 | 6/2019 |
| WO | WO 2019129211 A1 | 7/2019 |
| WO | WO 2019179434 A1 | 9/2019 |
| WO | WO 2019185035 A1 | 10/2019 |
| WO | WO 2021142448 A2 | 7/2021 |
| WO | WO 2021142448 A3 | 7/2021 |
| WO | WO 2022031710 A2 | 2/2022 |
| WO | WO 2022031710 A3 | 2/2022 |
| WO | WO 2023154730 A2 | 8/2023 |

OTHER PUBLICATIONS

Almagro & Franssen, Frontiers in Bioscience, 13:1619-33 (2008).*
Edwards et al., J Mol Biol 334:103-118 (2003).*
Marchalonis et al., Dev & Comp Immunol. 30:223-247 (2006).*
Lippow et al., Nature Biotechnology, 25(10):1171-1176 (2007).*
Sulea et al., Scientific Reports, 8(260):1-11 (2018).*
Hasegawa et al., MABS, vol. 9, No. 5, pp. 854-873 (2017).*
Altshuler et al., Biochemistry (Moscow), 75(13):1584-1605 (2010).*
Vajda et al., Current Opinion in Structural Biology, 67 pp. 226-231
(2021).*
Marks et al., J. Biol. Chem. 295(29) 9823-9837 (2020).*
Akbar et al., Cell Reports 34, 108856, (Mar. 16, 2021).*
Lo et al., BMC Genomics vol. 22, Article No. 116 (2021).*
Cembrola et al., 2019, "Rapid Affinity Maturation of Novel Anti-
PD-L1 Antibodies by a Fast Drop of the Antigen Concentration and
FACS Selection of Yeast Libraries," Biomed. Res. Int., 2019:6051870
(22 pages).
International Searching Authority, International Search Report and
Written Opinion for International Patent Application No. PCT/
US2021/044330 (Pub No. WO 2022031695) mailed Jan. 5, 2022
(13 pages).
International Searching Authority, International Search Report and
Written Opinion for International Patent Application No. PCT/
US2021/044356 (Pub No. WO 2022031710) mailed Jan. 31, 2022
(13 pages).

(Continued)

*Primary Examiner* — Meera Natarajan

(74) *Attorney, Agent, or Firm* — JONES DAY

(57) ABSTRACT

The present disclosure provides PD-L1 binding agents (e.g.,
antibodies, including multispecific antibodies, such as bis-
pecific antibodies) and uses thereof.

16 Claims, 20 Drawing Sheets

Specification includes a Sequence Listing.

(56)             References Cited

OTHER PUBLICATIONS

International Searching Authority, International Search Report and Written Opinion for International Patent Application No. PCT/US2023/062185 (Pub No. WO 2023154730) mailed Jul. 28, 2023 (14 pages).

Lakhani et al., 2020, "A phase lb study of the anti-CD47 antibody magrolimab with the PD-L1 inhibitor avelumab (A) in solid tumor (ST) and ovarian cancer (OC) patients," Meeting Abstract, 2020 ASCO-SITC Clinical Immuno-Oncology Symposium, J. Clin. Oncol., 38(5_Suppl): Abstract 18 (2 pages).

Lian et al., 2019, "Dual blockage of both PD-L1 and CD47 enhances immunotherapy against circulating tumor cells," Sci. Rep., 9(1):4532.

Liu et al., 2018, "Elimination of tumor by CD47/PD-L1 dual-targeting fusion protein that engages innate and adaptive immune responses," MAbs, 10(2):315-324 and supplemental material (Epub 2017) (15 pages).

Shi et al., 2020, "The identification of a CD47-blocking "hotspot" and design of a CD47/PD-L1 dual-specific antibody with limited hemagglutination," Signal Transduct Target Ther., 5(1):16 (3 pages).

\* cited by examiner

P31.2

| # | Time | Area | Height | Width | Area% | Symmetry |
|---|------|------|--------|-------|-------|----------|
| 1 | 13.82 | 676.8 | 32.8 | 0.3047 | 97.926 | 0.64 |
| 2 | 15.103 | 14.3 | 7.8E-1 | 0.2451 | 2.074 | 0.987 |

| # | Time | Area | Height | Width | Area% | Symmetry |
|---|------|------|--------|-------|-------|----------|
| 1 | 11.492 | 1206.1 | 30.7 | 0.5536 | 65.678 | 0.537 |
| 2 | 12.784 | 630.3 | 6.6 | 1.2702 | 34.322 | 0.236 |

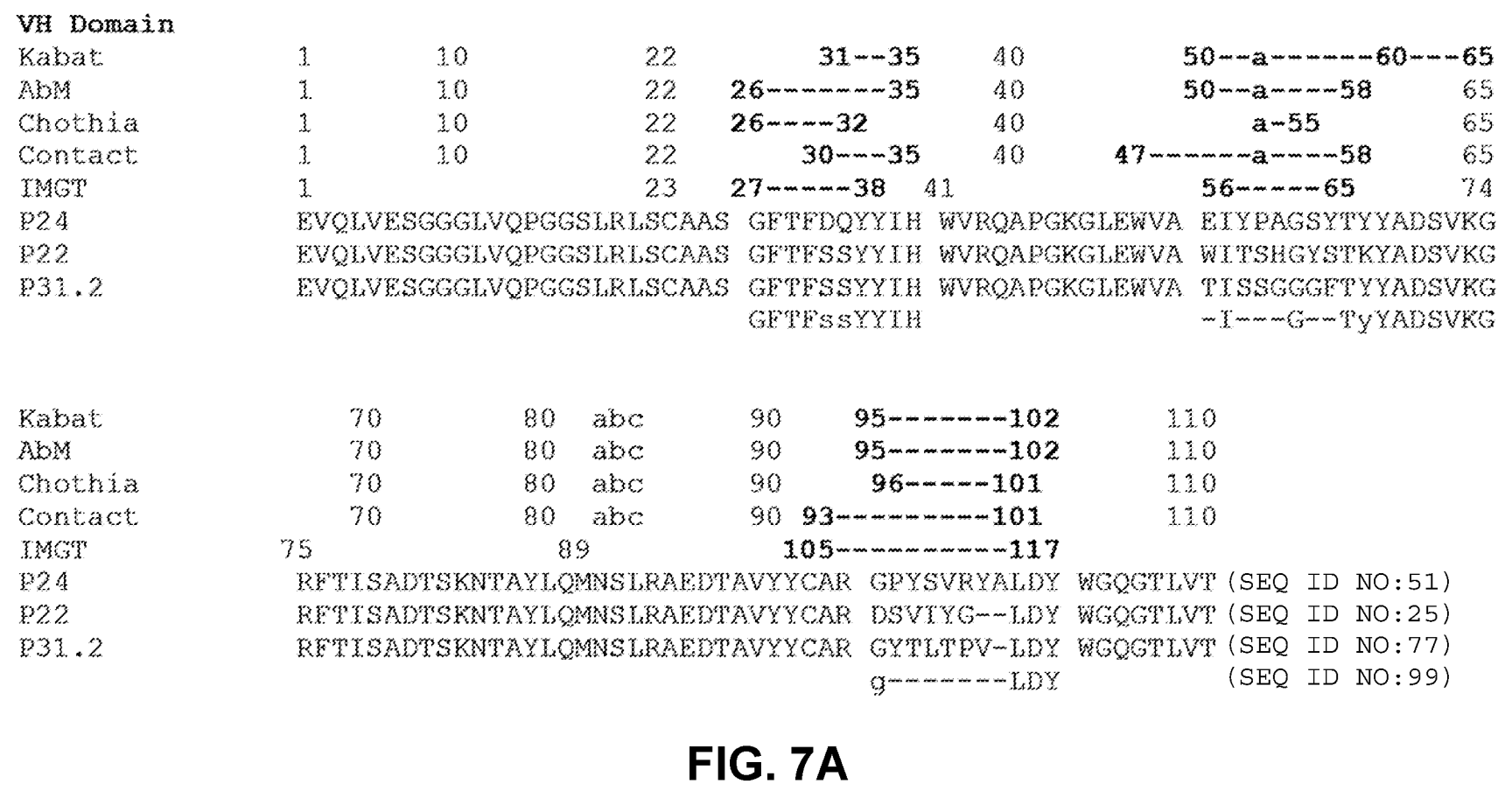

VH Domain

```
Kabat    1    10    22       31--35    40           50--a----60--65
AbM      1    10    22  26--------35    40           50--a----58  65
Chothia  1    10    22  26----32        40              a-55       65
Contact  1    10    22    26----35      40        47--------a--58  65
IMGT     1    10    23    27----38 41                  56----65     74

P24   EVQLVESGGGLVQPGGSLRLSCAAS GFTFDQYIH  WVRQAPGKGLEWVA EIYPAGSYTYYADSVKG
P22   EVQLVESGGGLVQPGGSLRLSCAAS GFTFSSYYIH WVRQAPGKGLEWVA WITSHGYSTKYADSVKG
P31.2 EVQLVESGGGLVQPGGSLRLSCAAS GFTFSSYYIH WVRQAPGKGLEWVA TISSGGFTYYADSVKG
                              GFTFssYYIH                  -I----G--TyYADSVKG
```

```
Kabat    70    80  abc    90    95--------102    110
AbM      70    80  abc    90    95--------102    110
Chothia  70    80  abc    90    96------101      110
Contact  70    80  abc    90    93--------101    110
IMGT     75             89    105----------117

P24   RFTISADTSKNTAYLQMNSLRAEDTAVYYCAR GPYSVRYALDY   WGQGTLVT (SEQ ID NO:51)
P22   RFTISADTSKNTAYLQMNSLRAEDTAVYYCAR DSVTYG--LDY   WGQGTLVT (SEQ ID NO:25)
P31.2 RFTISADTSKNTAYLQMNSLRAEDTAVYYCAR GYTLTPV-LDY   WGQGTLVT (SEQ ID NO:77)
                                      g------LDY             (SEQ ID NO:99)
```

FIG. 7A

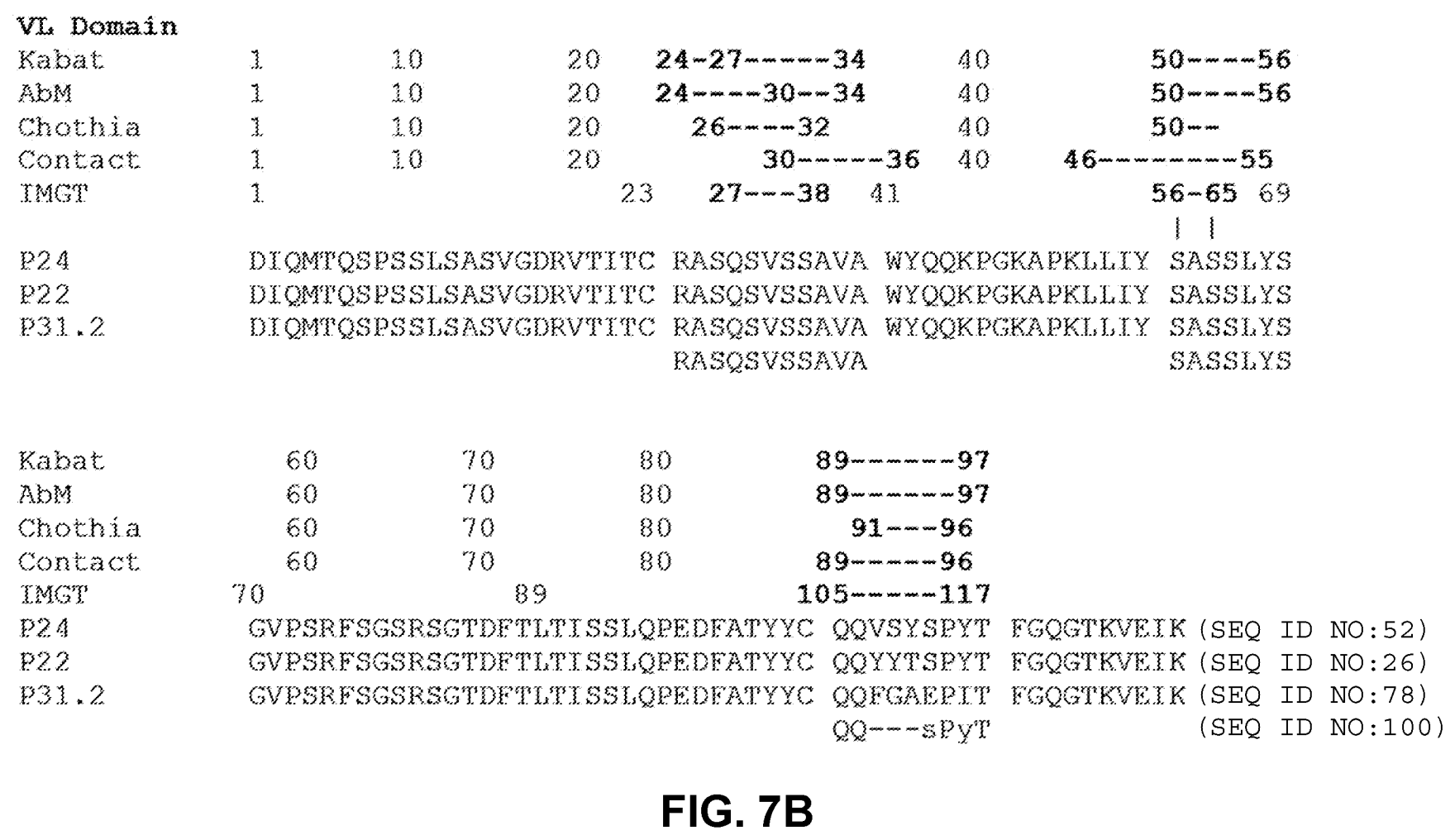

VL Domain

```
           1        10        20        24-27----34   40   50----56
Kabat
AbM        1        10        20        24----30--34  40   50----56
Chothia    1        10        20        26----32      40   50--
Contact    1        10        20              30----36  40
IMGT       1        10        20     23 27---38 41          46----55  56-65 69
                                                                        --

P24    DIQMTQSPSSLSASVGDRVTITC RASQSVSSAVA WYQQKPGKAPKLLIY SASSLYS
P22    DIQMTQSPSSLSASVGDRVTITC RASQSVSSAVA WYQQKPGKAPKLLIY SASSLYS
P31.2  DIQMTQSPSSLSASVGDRVTITC RASQSVSSAVA WYQQKPGKAPKLLIY SASSLYS
                               RASQSVSSAVA                 SASSLYS 60    70    80    89----97
Kabat      60    70    80    89----97
AbM        60    70    80    89-----97
Chothia    60    70    80       91----96
Contact    60    70    80    89----96
IMGT    70       89          105----117

P24    GVPSRFSGSRSGTDFTLTISSLQPEDFATYYC QQVSYSPYT FGQGTKVEIK (SEQ ID NO:52)
P22    GVPSRFSGSRSGTDFTLTISSLQPEDFATYYC QQYYTSPYT FGQGTKVEIK (SEQ ID NO:26)
P31.2  GVPSRFSGSRSGTDFTLTISSLQPEDFATYYC QQFGAEPIT FGQGTKVEIK (SEQ ID NO:78)
                                        QQ---SPYT            (SEQ ID NO:100)
```

FIG. 7B

SEQUENCE LISTING

```
<160> NUMBER OF SEQ ID NOS: 101

<210> SEQ ID NO 1
<211> LENGTH: 10
<212> TYPE: PRT
<213> ORGANISM: Artificial Sequence
<220> FEATURE:
<223> OTHER INFORMATION: Antibody P22 VH CDR1 (Exemplary, AbM)

<400> SEQUENCE: 1

Gly Phe Thr Phe Ser Ser Tyr Tyr Ile His
1               5                   10

<210> SEQ ID NO 2
<211> LENGTH: 17
<212> TYPE: PRT
<213> ORGANISM: Artificial Sequence
<220> FEATURE:
<223> OTHER INFORMATION: Antibody P22 VH CDR2 (Exemplary, Kabat)

<400> SEQUENCE: 2

Trp Ile Thr Ser His Gly Tyr Ser Thr Lys Tyr Ala Asp Ser Val Lys
1               5                   10                  15

Gly

<210> SEQ ID NO 3
<211> LENGTH: 9
<212> TYPE: PRT
<213> ORGANISM: Artificial Sequence
<220> FEATURE:
<223> OTHER INFORMATION: Antibody P22 VH CDR3 (Exemplary, Kabat, AbM)

<400> SEQUENCE: 3

Asp Ser Val Ile Tyr Gly Leu Asp Tyr
1               5

<210> SEQ ID NO 4
<211> LENGTH: 11
<212> TYPE: PRT
<213> ORGANISM: Artificial Sequence
<220> FEATURE:
<223> OTHER INFORMATION: Antibody P22 VL CDR1 (Exemplary, Kabat, AbM)

<400> SEQUENCE: 4

Arg Ala Ser Gln Ser Val Ser Ser Ala Val Ala
1               5                   10

<210> SEQ ID NO 5
<211> LENGTH: 7
```

```
<212> TYPE: PRT
<213> ORGANISM: Artificial Sequence
<220> FEATURE:
<223> OTHER INFORMATION: Antibody P22 VL CDR2 (Exemplary, Kabat, AbM)

<400> SEQUENCE: 5

Ser Ala Ser Ser Leu Tyr Ser
1               5

<210> SEQ ID NO 6
<211> LENGTH: 9
<212> TYPE: PRT
<213> ORGANISM: Artificial Sequence
<220> FEATURE:
<223> OTHER INFORMATION: Antibody P22 VL CDR3 (Exemplary, IMGT, Kabat,
      AbM)

<400> SEQUENCE: 6

Gln Gln Tyr Tyr Thr Ser Pro Tyr Thr
1               5

<210> SEQ ID NO 7
<211> LENGTH: 8
<212> TYPE: PRT
<213> ORGANISM: Artificial Sequence
<220> FEATURE:
<223> OTHER INFORMATION: Antibody P22 VH CDR1 (IMGT)

<400> SEQUENCE: 7

Gly Phe Thr Phe Ser Ser Tyr Tyr
1               5

<210> SEQ ID NO 8
<211> LENGTH: 8
<212> TYPE: PRT
<213> ORGANISM: Artificial Sequence
<220> FEATURE:
<223> OTHER INFORMATION: Antibody P22 VH CDR2 (IMGT)

<400> SEQUENCE: 8

Ile Thr Ser His Gly Tyr Ser Thr
1               5

<210> SEQ ID NO 9
<211> LENGTH: 11
<212> TYPE: PRT
<213> ORGANISM: Artificial Sequence
<220> FEATURE:
<223> OTHER INFORMATION: Antibody P22 VH CDR3 (IMGT)

<400> SEQUENCE: 9

Ala Arg Asp Ser Val Ile Tyr Gly Leu Asp Tyr
1               5                   10

<210> SEQ ID NO 10
<211> LENGTH: 6
<212> TYPE: PRT
<213> ORGANISM: Artificial Sequence
<220> FEATURE:
<223> OTHER INFORMATION: Antibody P22 VL CDR1 (IMGT)

<400> SEQUENCE: 10

Gln Ser Val Ser Ser Ala
1               5

<210> SEQ ID NO 11
<211> LENGTH: 3
```

```
<212> TYPE: PRT
<213> ORGANISM: Artificial Sequence
<220> FEATURE:
<223> OTHER INFORMATION: Antibody P22 VL CDR2 (IMGT, Chothia)

<400> SEQUENCE: 11

Ser Ala Ser
1

<210> SEQ ID NO 12
<211> LENGTH: 5
<212> TYPE: PRT
<213> ORGANISM: Artificial Sequence
<220> FEATURE:
<223> OTHER INFORMATION: Antibody P22 VH CDR1 (Kabat)

<400> SEQUENCE: 12

Ser Tyr Tyr Ile His
1               5

<210> SEQ ID NO 13
<211> LENGTH: 7
<212> TYPE: PRT
<213> ORGANISM: Artificial Sequence
<220> FEATURE:
<223> OTHER INFORMATION: Antibody P22 VH CDR1 (Chothia)

<400> SEQUENCE: 13

Gly Phe Thr Phe Ser Ser Tyr
1               5

<210> SEQ ID NO 14
<211> LENGTH: 4
<212> TYPE: PRT
<213> ORGANISM: Artificial Sequence
<220> FEATURE:
<223> OTHER INFORMATION: Antibody P22 VH CDR2 (Chothia)

<400> SEQUENCE: 14

Ser His Gly Tyr
1

<210> SEQ ID NO 15
<211> LENGTH: 7
<212> TYPE: PRT
<213> ORGANISM: Artificial Sequence
<220> FEATURE:
<223> OTHER INFORMATION: Antibody P22 VH CDR3 (Chothia)

<400> SEQUENCE: 15

Ser Val Ile Tyr Gly Leu Asp
1               5

<210> SEQ ID NO 16
<211> LENGTH: 7
<212> TYPE: PRT
<213> ORGANISM: Artificial Sequence
<220> FEATURE:
<223> OTHER INFORMATION: Antibody P22 VL CDR1 (Chothia)

<400> SEQUENCE: 16

Ser Gln Ser Val Ser Ser Ala
1               5

<210> SEQ ID NO 17
<211> LENGTH: 6
<212> TYPE: PRT
```

-continued

```
<213> ORGANISM: Artificial Sequence
<220> FEATURE:
<223> OTHER INFORMATION: Antibody P22 VL CDR3 (Chothia)

<400> SEQUENCE: 17

Tyr Tyr Thr Ser Pro Tyr
1               5

<210> SEQ ID NO 18
<211> LENGTH: 6
<212> TYPE: PRT
<213> ORGANISM: Artificial Sequence
<220> FEATURE:
<223> OTHER INFORMATION: Antibody P22 VH CDR1 (Contact)

<400> SEQUENCE: 18

Ser Ser Tyr Tyr Ile His
1               5

<210> SEQ ID NO 19
<211> LENGTH: 13
<212> TYPE: PRT
<213> ORGANISM: Artificial Sequence
<220> FEATURE:
<223> OTHER INFORMATION: Antibody P22 VH CDR2 (Contact)

<400> SEQUENCE: 19

Trp Val Ala Trp Ile Thr Ser His Gly Tyr Ser Thr Lys
1               5                   10

<210> SEQ ID NO 20
<211> LENGTH: 10
<212> TYPE: PRT
<213> ORGANISM: Artificial Sequence
<220> FEATURE:
<223> OTHER INFORMATION: Antibody P22 VH CDR3 (Contact)

<400> SEQUENCE: 20

Ala Arg Asp Ser Val Ile Tyr Gly Leu Asp
1               5                   10

<210> SEQ ID NO 21
<211> LENGTH: 7
<212> TYPE: PRT
<213> ORGANISM: Artificial Sequence
<220> FEATURE:
<223> OTHER INFORMATION: Antibody P22 VL CDR1 (Contact)

<400> SEQUENCE: 21

Ser Ser Ala Val Ala Trp Tyr
1               5

<210> SEQ ID NO 22
<211> LENGTH: 10
<212> TYPE: PRT
<213> ORGANISM: Artificial Sequence
<220> FEATURE:
<223> OTHER INFORMATION: Antibody P22 VL CDR2 (Contact)

<400> SEQUENCE: 22

Leu Leu Ile Tyr Ser Ala Ser Ser Leu Tyr
1               5                   10

<210> SEQ ID NO 23
<211> LENGTH: 8
<212> TYPE: PRT
<213> ORGANISM: Artificial Sequence
```

```
<220> FEATURE:
<223> OTHER INFORMATION: Antibody P22 VL CDR3 (Contact)

<400> SEQUENCE: 23

Gln Gln Tyr Tyr Thr Ser Pro Tyr
1               5

<210> SEQ ID NO 24
<211> LENGTH: 10
<212> TYPE: PRT
<213> ORGANISM: Artificial Sequence
<220> FEATURE:
<223> OTHER INFORMATION: Antibody P22 VH CDR2 (AbM)

<400> SEQUENCE: 24

Trp Ile Thr Ser His Gly Tyr Ser Thr Lys
1               5                   10

<210> SEQ ID NO 25
<211> LENGTH: 115
<212> TYPE: PRT
<213> ORGANISM: Artificial Sequence
<220> FEATURE:
<223> OTHER INFORMATION: Antibody P22 VH Sequence

<400> SEQUENCE: 25

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Tyr Ile His Trp Val Arg Gln Ala Pro Gly Lys Gly Leu Glu Trp Val
            35                  40                  45

Ala Trp Ile Thr Ser His Gly Tyr Ser Thr Lys Tyr Ala Asp Ser Val
        50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Asp Ser Val Ile Tyr Gly Leu Asp Tyr Trp Gly Gln Gly Thr
            100                 105                 110

Leu Val Thr
        115

<210> SEQ ID NO 26
<211> LENGTH: 107
<212> TYPE: PRT
<213> ORGANISM: Artificial Sequence
<220> FEATURE:
<223> OTHER INFORMATION: Antibody P22 VL Sequence

<400> SEQUENCE: 26

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
                20                  25                  30

Val Ala Trp Tyr Gln Gln Lys Pro Gly Lys Ala Pro Lys Leu Leu Ile
            35                  40                  45

Tyr Ser Ala Ser Ser Leu Tyr Ser Gly Val Pro Ser Arg Phe Ser Gly
        50                  55                  60

Ser Arg Ser Gly Thr Asp Phe Thr Leu Thr Ile Ser Ser Leu Gln Pro
65                  70                  75                  80
```

-continued

Glu Asp Phe Ala Thr Tyr Tyr Cys Gln Gln Tyr Tyr Thr Ser Pro Tyr
                85                  90                  95

Thr Phe Gly Gln Gly Thr Lys Val Glu Ile Lys
            100                 105

<210> SEQ ID NO 27
<211> LENGTH: 10
<212> TYPE: PRT
<213> ORGANISM: Artificial Sequence
<220> FEATURE:
<223> OTHER INFORMATION: Antibody P24 VH CDR1 (Exemplary, AbM)

<400> SEQUENCE: 27

Gly Phe Thr Phe Asp Gln Tyr Tyr Ile His
1               5                   10

<210> SEQ ID NO 28
<211> LENGTH: 17
<212> TYPE: PRT
<213> ORGANISM: Artificial Sequence
<220> FEATURE:
<223> OTHER INFORMATION: Antibody P24 VH CDR2 (Exemplary, Kabat)

<400> SEQUENCE: 28

Glu Ile Tyr Pro Ala Gly Ser Tyr Thr Tyr Tyr Ala Asp Ser Val Lys
1               5                   10                  15

Gly

<210> SEQ ID NO 29
<211> LENGTH: 11
<212> TYPE: PRT
<213> ORGANISM: Artificial Sequence
<220> FEATURE:
<223> OTHER INFORMATION: Antibody P24 VH CDR3 (Exemplary, Kabat, AbM)

<400> SEQUENCE: 29

Gly Pro Tyr Ser Val Arg Tyr Ala Leu Asp Tyr
1               5                   10

<210> SEQ ID NO 30
<211> LENGTH: 11
<212> TYPE: PRT
<213> ORGANISM: Artificial Sequence
<220> FEATURE:
<223> OTHER INFORMATION: Antibody P24 VL CDR1 (Exemplary, Kabat, AbM)

<400> SEQUENCE: 30

Arg Ala Ser Gln Ser Val Ser Ser Ala Val Ala
1               5                   10

<210> SEQ ID NO 31
<211> LENGTH: 7
<212> TYPE: PRT
<213> ORGANISM: Artificial Sequence
<220> FEATURE:
<223> OTHER INFORMATION: Antibody P24 VL CDR2 (Exemplary, Kabat, AbM)

<400> SEQUENCE: 31

Ser Ala Ser Ser Leu Tyr Ser
1               5

<210> SEQ ID NO 32
<211> LENGTH: 9
<212> TYPE: PRT
<213> ORGANISM: Artificial Sequence

```
<220> FEATURE:
<223> OTHER INFORMATION: Antibody P24 VL CDR3 (Exemplary, IMGT, Kabat,
      AbM)

<400> SEQUENCE: 32

Gln Gln Val Ser Tyr Ser Pro Tyr Thr
1               5

<210> SEQ ID NO 33
<211> LENGTH: 8
<212> TYPE: PRT
<213> ORGANISM: Artificial Sequence
<220> FEATURE:
<223> OTHER INFORMATION: Antibody P24 VH CDR1 (IMGT)

<400> SEQUENCE: 33

Gly Phe Thr Phe Asp Gln Tyr Tyr
1               5

<210> SEQ ID NO 34
<211> LENGTH: 8
<212> TYPE: PRT
<213> ORGANISM: Artificial Sequence
<220> FEATURE:
<223> OTHER INFORMATION: Antibody P24 VH CDR2 (IMGT)

<400> SEQUENCE: 34

Ile Tyr Pro Ala Gly Ser Tyr Thr
1               5

<210> SEQ ID NO 35
<211> LENGTH: 13
<212> TYPE: PRT
<213> ORGANISM: Artificial Sequence
<220> FEATURE:
<223> OTHER INFORMATION: Antibody P24 VH CDR3 (IMGT)

<400> SEQUENCE: 35

Ala Arg Gly Pro Tyr Ser Val Arg Tyr Ala Leu Asp Tyr
1               5                   10

<210> SEQ ID NO 36
<211> LENGTH: 6
<212> TYPE: PRT
<213> ORGANISM: Artificial Sequence
<220> FEATURE:
<223> OTHER INFORMATION: Antibody P24 VL CDR1 (IMGT)

<400> SEQUENCE: 36

Gln Ser Val Ser Ser Ala
1               5

<210> SEQ ID NO 37
<211> LENGTH: 3
<212> TYPE: PRT
<213> ORGANISM: Artificial Sequence
<220> FEATURE:
<223> OTHER INFORMATION: Antibody P24 VL CDR2 (IMGT, Chothia)

<400> SEQUENCE: 37

Ser Ala Ser
1

<210> SEQ ID NO 38
<211> LENGTH: 5
<212> TYPE: PRT
<213> ORGANISM: Artificial Sequence
```

-continued

```
<220> FEATURE:
<223> OTHER INFORMATION: Antibody P24 VH CDR1 (Kabat)

<400> SEQUENCE: 38

Gln Tyr Tyr Ile His
1               5

<210> SEQ ID NO 39
<211> LENGTH: 7
<212> TYPE: PRT
<213> ORGANISM: Artificial Sequence
<220> FEATURE:
<223> OTHER INFORMATION: Antibody P24 VH CDR1 (Chothia)

<400> SEQUENCE: 39

Gly Phe Thr Phe Asp Gln Tyr
1               5

<210> SEQ ID NO 40
<211> LENGTH: 4
<212> TYPE: PRT
<213> ORGANISM: Artificial Sequence
<220> FEATURE:
<223> OTHER INFORMATION: Antibody P24 VH CDR2 (Chothia)

<400> SEQUENCE: 40

Pro Ala Gly Ser
1

<210> SEQ ID NO 41
<211> LENGTH: 9
<212> TYPE: PRT
<213> ORGANISM: Artificial Sequence
<220> FEATURE:
<223> OTHER INFORMATION: Antibody P24 VH CDR3 (Chothia)

<400> SEQUENCE: 41

Pro Tyr Ser Val Arg Tyr Ala Leu Asp
1               5

<210> SEQ ID NO 42
<211> LENGTH: 7
<212> TYPE: PRT
<213> ORGANISM: Artificial Sequence
<220> FEATURE:
<223> OTHER INFORMATION: Antibody P24 VL CDR1 (Chothia)

<400> SEQUENCE: 42

Ser Gln Ser Val Ser Ser Ala
1               5

<210> SEQ ID NO 43
<211> LENGTH: 6
<212> TYPE: PRT
<213> ORGANISM: Artificial Sequence
<220> FEATURE:
<223> OTHER INFORMATION: Antibody P24 VL CDR3 (Chothia)

<400> SEQUENCE: 43

Val Ser Tyr Ser Pro Tyr
1               5

<210> SEQ ID NO 44
<211> LENGTH: 6
<212> TYPE: PRT
<213> ORGANISM: Artificial Sequence
<220> FEATURE:
```

<223> OTHER INFORMATION: Antibody P24 VH CDR1 (Contact)

<400> SEQUENCE: 44

Asp Gln Tyr Tyr Ile His
1               5

<210> SEQ ID NO 45
<211> LENGTH: 13
<212> TYPE: PRT
<213> ORGANISM: Artificial Sequence
<220> FEATURE:
<223> OTHER INFORMATION: Antibody P24 VH CDR2 (Contact)

<400> SEQUENCE: 45

Trp Val Ala Glu Ile Tyr Pro Ala Gly Ser Tyr Thr Tyr
1               5                   10

<210> SEQ ID NO 46
<211> LENGTH: 12
<212> TYPE: PRT
<213> ORGANISM: Artificial Sequence
<220> FEATURE:
<223> OTHER INFORMATION: Antibody P24 VH CDR3 (Contact)

<400> SEQUENCE: 46

Ala Arg Gly Pro Tyr Ser Val Arg Tyr Ala Leu Asp
1               5                   10

<210> SEQ ID NO 47
<211> LENGTH: 7
<212> TYPE: PRT
<213> ORGANISM: Artificial Sequence
<220> FEATURE:
<223> OTHER INFORMATION: Antibody P24 VL CDR1 (Contact)

<400> SEQUENCE: 47

Ser Ser Ala Val Ala Trp Tyr
1               5

<210> SEQ ID NO 48
<211> LENGTH: 10
<212> TYPE: PRT
<213> ORGANISM: Artificial Sequence
<220> FEATURE:
<223> OTHER INFORMATION: Antibody P24 VL CDR2 (Contact)

<400> SEQUENCE: 48

Leu Leu Ile Tyr Ser Ala Ser Ser Leu Tyr
1               5                   10

<210> SEQ ID NO 49
<211> LENGTH: 8
<212> TYPE: PRT
<213> ORGANISM: Artificial Sequence
<220> FEATURE:
<223> OTHER INFORMATION: Antibody P24 VL CDR3 (Contact)

<400> SEQUENCE: 49

Gln Gln Val Ser Tyr Ser Pro Tyr
1               5

<210> SEQ ID NO 50
<211> LENGTH: 10
<212> TYPE: PRT
<213> ORGANISM: Artificial Sequence
<220> FEATURE:
<223> OTHER INFORMATION: Antibody P24 VH CDR2 (AbM)

<400> SEQUENCE: 50

Glu Ile Tyr Pro Ala Gly Ser Tyr Thr Tyr
1               5                   10

<210> SEQ ID NO 51
<211> LENGTH: 117
<212> TYPE: PRT
<213> ORGANISM: Artificial Sequence
<220> FEATURE:
<223> OTHER INFORMATION: Antibody P24 VH Sequence

<400> SEQUENCE: 51

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asp Gln Tyr
            20                  25                  30

Tyr Ile His Trp Val Arg Gln Ala Pro Gly Lys Gly Leu Glu Trp Val
            35                  40                  45

Ala Glu Ile Tyr Pro Ala Gly Ser Tyr Thr Tyr Tyr Ala Asp Ser Val
        50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Gly Pro Tyr Ser Val Arg Tyr Ala Leu Asp Tyr Trp Gly Gln
                100                 105                 110

Gly Thr Leu Val Thr
            115

<210> SEQ ID NO 52
<211> LENGTH: 107
<212> TYPE: PRT
<213> ORGANISM: Artificial Sequence
<220> FEATURE:
<223> OTHER INFORMATION: Antibody P24 VL Sequence

<400> SEQUENCE: 52

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
            35                  40                  45

Tyr Ser Ala Ser Ser Leu Tyr Ser Gly Val Pro Ser Arg Phe Ser Gly
        50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Val Ser Tyr Ser Pro Tyr
                85                  90                  95

Thr Phe Gly Gln Gly Thr Lys Val Glu Ile Lys
                100                 105

<210> SEQ ID NO 53
<211> LENGTH: 10
<212> TYPE: PRT
<213> ORGANISM: Artificial Sequence
<220> FEATURE:
<223> OTHER INFORMATION: Antibody P31.2 VH CDR1 (Exemplary, AbM)

-continued

```
<400> SEQUENCE: 53

Gly Phe Thr Phe Ser Ser Tyr Tyr Ile His
1               5                   10

<210> SEQ ID NO 54
<211> LENGTH: 17
<212> TYPE: PRT
<213> ORGANISM: Artificial Sequence
<220> FEATURE:
<223> OTHER INFORMATION: Antibody P31.2 VH CDR2 (Exemplary, Kabat)

<400> SEQUENCE: 54

Thr Ile Ser Ser Gly Gly Gly Phe Thr Tyr Tyr Ala Asp Ser Val Lys
1               5                   10                  15

Gly

<210> SEQ ID NO 55
<211> LENGTH: 10
<212> TYPE: PRT
<213> ORGANISM: Artificial Sequence
<220> FEATURE:
<223> OTHER INFORMATION: Antibody P31.2 VH CDR3 (Exemplary, Kabat, AbM)

<400> SEQUENCE: 55

Gly Tyr Thr Leu Thr Pro Val Leu Asp Tyr
1               5                   10

<210> SEQ ID NO 56
<211> LENGTH: 11
<212> TYPE: PRT
<213> ORGANISM: Artificial Sequence
<220> FEATURE:
<223> OTHER INFORMATION: Antibody P31.2 VL CDR1 (Exemplary, Kabat, AbM)

<400> SEQUENCE: 56

Arg Ala Ser Gln Ser Val Ser Ser Ala Val Ala
1               5                   10

<210> SEQ ID NO 57
<211> LENGTH: 7
<212> TYPE: PRT
<213> ORGANISM: Artificial Sequence
<220> FEATURE:
<223> OTHER INFORMATION: Antibody P31.2 VL CDR2 (Exemplary, Kabat, AbM)

<400> SEQUENCE: 57

Ser Ala Ser Ser Leu Tyr Ser
1               5

<210> SEQ ID NO 58
<211> LENGTH: 9
<212> TYPE: PRT
<213> ORGANISM: Artificial Sequence
<220> FEATURE:
<223> OTHER INFORMATION: Antibody P31.2 VL CDR3 (Exemplary, IMGT, Kabat,
     AbM)

<400> SEQUENCE: 58

Gln Gln Phe Gly Ala Glu Pro Ile Thr
1               5

<210> SEQ ID NO 59
<211> LENGTH: 8
<212> TYPE: PRT
<213> ORGANISM: Artificial Sequence
<220> FEATURE:
```

<223> OTHER INFORMATION: Antibody P31.2 VH CDR1 (IMGT)

<400> SEQUENCE: 59

Gly Phe Thr Phe Ser Ser Tyr Tyr
1               5

<210> SEQ ID NO 60
<211> LENGTH: 8
<212> TYPE: PRT
<213> ORGANISM: Artificial Sequence
<220> FEATURE:
<223> OTHER INFORMATION: Antibody P31.2 VH CDR2 (IMGT)

<400> SEQUENCE: 60

Ile Ser Ser Gly Gly Gly Phe Thr
1               5

<210> SEQ ID NO 61
<211> LENGTH: 12
<212> TYPE: PRT
<213> ORGANISM: Artificial Sequence
<220> FEATURE:
<223> OTHER INFORMATION: Antibody P31.2 VH CDR3 (IMGT)

<400> SEQUENCE: 61

Ala Arg Gly Tyr Thr Leu Thr Pro Val Leu Asp Tyr
1               5                   10

<210> SEQ ID NO 62
<211> LENGTH: 6
<212> TYPE: PRT
<213> ORGANISM: Artificial Sequence
<220> FEATURE:
<223> OTHER INFORMATION: Antibody P31.2 VL CDR1 (IMGT)

<400> SEQUENCE: 62

Gln Ser Val Ser Ser Ala
1               5

<210> SEQ ID NO 63
<211> LENGTH: 3
<212> TYPE: PRT
<213> ORGANISM: Artificial Sequence
<220> FEATURE:
<223> OTHER INFORMATION: Antibody P31.2 VL CDR2 (IMGT, Chothia)

<400> SEQUENCE: 63

Ser Ala Ser
1

<210> SEQ ID NO 64
<211> LENGTH: 5
<212> TYPE: PRT
<213> ORGANISM: Artificial Sequence
<220> FEATURE:
<223> OTHER INFORMATION: Antibody P31.2 VH CDR1 (Kabat)

<400> SEQUENCE: 64

Ser Tyr Tyr Ile His
1               5

<210> SEQ ID NO 65
<211> LENGTH: 7
<212> TYPE: PRT
<213> ORGANISM: Artificial Sequence
<220> FEATURE:
<223> OTHER INFORMATION: Antibody P31.2 VH CDR1 (Chothia)

<400> SEQUENCE: 65

Gly Phe Thr Phe Ser Ser Tyr
1               5

<210> SEQ ID NO 66
<211> LENGTH: 4
<212> TYPE: PRT
<213> ORGANISM: Artificial Sequence
<220> FEATURE:
<223> OTHER INFORMATION: Antibody P31.2 VH CDR2 (Chothia)

<400> SEQUENCE: 66

Ser Gly Gly Gly
1

<210> SEQ ID NO 67
<211> LENGTH: 8
<212> TYPE: PRT
<213> ORGANISM: Artificial Sequence
<220> FEATURE:
<223> OTHER INFORMATION: Antibody P31.2 VH CDR3 (Chothia)

<400> SEQUENCE: 67

Tyr Thr Leu Thr Pro Val Leu Asp
1               5

<210> SEQ ID NO 68
<211> LENGTH: 7
<212> TYPE: PRT
<213> ORGANISM: Artificial Sequence
<220> FEATURE:
<223> OTHER INFORMATION: Antibody P31.2 VL CDR1 (Chothia)

<400> SEQUENCE: 68

Ser Gln Ser Val Ser Ser Ala
1               5

<210> SEQ ID NO 69
<211> LENGTH: 6
<212> TYPE: PRT
<213> ORGANISM: Artificial Sequence
<220> FEATURE:
<223> OTHER INFORMATION: Antibody P31.2 VL CDR3 (Chothia)

<400> SEQUENCE: 69

Phe Gly Ala Glu Pro Ile
1               5

<210> SEQ ID NO 70
<211> LENGTH: 6
<212> TYPE: PRT
<213> ORGANISM: Artificial Sequence
<220> FEATURE:
<223> OTHER INFORMATION: Antibody P31.2 VH CDR1 (Contact)

<400> SEQUENCE: 70

Ser Ser Tyr Tyr Ile His
1               5

<210> SEQ ID NO 71
<211> LENGTH: 13
<212> TYPE: PRT
<213> ORGANISM: Artificial Sequence
<220> FEATURE:
<223> OTHER INFORMATION: Antibody P31.2 VH CDR2 (Contact)

```
<400> SEQUENCE: 71

Trp Val Ala Thr Ile Ser Ser Gly Gly Gly Phe Thr Tyr
1               5                   10

<210> SEQ ID NO 72
<211> LENGTH: 11
<212> TYPE: PRT
<213> ORGANISM: Artificial Sequence
<220> FEATURE:
<223> OTHER INFORMATION: Antibody P31.2 VH CDR3 (Contact)

<400> SEQUENCE: 72

Ala Arg Gly Tyr Thr Leu Thr Pro Val Leu Asp
1               5                   10

<210> SEQ ID NO 73
<211> LENGTH: 7
<212> TYPE: PRT
<213> ORGANISM: Artificial Sequence
<220> FEATURE:
<223> OTHER INFORMATION: Antibody P31.2 VL CDR1 (Contact)

<400> SEQUENCE: 73

Ser Ser Ala Val Ala Trp Tyr
1               5

<210> SEQ ID NO 74
<211> LENGTH: 10
<212> TYPE: PRT
<213> ORGANISM: Artificial Sequence
<220> FEATURE:
<223> OTHER INFORMATION: Antibody P31.2 VL CDR2 (Contact)

<400> SEQUENCE: 74

Leu Leu Ile Tyr Ser Ala Ser Ser Leu Tyr
1               5                   10

<210> SEQ ID NO 75
<211> LENGTH: 8
<212> TYPE: PRT
<213> ORGANISM: Artificial Sequence
<220> FEATURE:
<223> OTHER INFORMATION: Antibody P31.2 VL CDR3 (Contact)

<400> SEQUENCE: 75

Gln Gln Phe Gly Ala Glu Pro Ile
1               5

<210> SEQ ID NO 76
<211> LENGTH: 10
<212> TYPE: PRT
<213> ORGANISM: Artificial Sequence
<220> FEATURE:
<223> OTHER INFORMATION: Antibody P31.2 VH CDR2 (AbM)

<400> SEQUENCE: 76

Thr Ile Ser Ser Gly Gly Gly Phe Thr Tyr
1               5                   10

<210> SEQ ID NO 77
<211> LENGTH: 116
<212> TYPE: PRT
<213> ORGANISM: Artificial Sequence
<220> FEATURE:
<223> OTHER INFORMATION: Antibody P31.2 VH Sequence

<400> SEQUENCE: 77
```

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Tyr Ile His Trp Val Arg Gln Ala Pro Gly Lys Gly Leu Glu Trp Val
        35                  40                  45

Ala Thr Ile Ser Ser Gly Gly Gly Phe Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Gly Tyr Thr Leu Thr Pro Val Leu Asp Tyr Trp Gly Gln Gly
            100                 105                 110

Thr Leu Val Thr
        115
```

```
<210> SEQ ID NO 78
<211> LENGTH: 107
<212> TYPE: PRT
<213> ORGANISM: Artificial Sequence
<220> FEATURE:
<223> OTHER INFORMATION: Antibody P31.2 VL Sequence

<400> SEQUENCE: 78
```

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ser Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Gly Ala Glu Pro Ile
                85                  90                  95

Thr Phe Gly Gln Gly Thr Lys Val Glu Ile Lys
            100                 105
```

```
<210> SEQ ID NO 79
<211> LENGTH: 288
<212> TYPE: PRT
<213> ORGANISM: Homo sapiens
<220> FEATURE:
<223> OTHER INFORMATION: Full-length amino acid sequence of human PD-1

<400> SEQUENCE: 79
```

```
Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Ser Pro Ala Leu Leu Val Val Thr Glu Gly Asp
            35                  40                  45

Asn Ala Thr Phe Thr Cys Ser Phe Ser Asn Thr Ser Glu Ser Phe Val
    50                  55                  60

Leu Asn Trp Tyr Arg Met Ser Pro Ser Asn Gln Thr Asp Lys Leu Ala
```

```
65              70              75              80

Ala Phe Pro Glu Asp Arg Ser Gln Pro Gly Gln Asp Cys Arg Phe Arg
            85              90              95

Val Thr Gln Leu Pro Asn Gly Arg Asp Phe His Met Ser Val Val Arg
            100             105             110

Ala Arg Arg Asn Asp Ser Gly Thr Tyr Leu Cys Gly Ala Ile Ser Leu
            115             120             125

Ala Pro Lys Ala Gln Ile Lys Glu Ser Leu Arg Ala Glu Leu Arg Val
    130             135             140

Thr Glu Arg Arg Ala Glu Val Pro Thr Ala His Pro Ser Pro Ser Pro
145             150             155             160

Arg Pro Ala Gly Gln Phe Gln Thr Leu Val Val Gly Val Val Gly Gly
            165             170             175

Leu Leu Gly Ser Leu Val Leu Leu Val Trp Val Leu Ala Val Ile Cys
            180             185             190

Ser Arg Ala Ala Arg Gly Thr Ile Gly Ala Arg Arg Thr Gly Gln Pro
            195             200             205

Leu Lys Glu Asp Pro Ser Ala Val Pro Val Phe Ser Val Asp Tyr Gly
    210             215             220

Glu Leu Asp Phe Gln Trp Arg Glu Lys Thr Pro Glu Pro Pro Val Pro
225             230             235             240

Cys Val Pro Glu Gln Thr Glu Tyr Ala Thr Ile Val Phe Pro Ser Gly
            245             250             255

Met Gly Thr Ser Ser Pro Ala Arg Arg Gly Ser Ala Asp Gly Pro Arg
            260             265             270

Ser Ala Gln Pro Leu Arg Pro Glu Asp Gly His Cys Ser Trp Pro Leu
            275             280             285
```

```
<210> SEQ ID NO 80
<211> LENGTH: 290
<212> TYPE: PRT
<213> ORGANISM: Homo sapiens
<220> FEATURE:
<223> OTHER INFORMATION: Full-length amino acid sequence of human PD-L1

<400> SEQUENCE: 80
```

```
Met Arg Ile Phe Ala Val Phe Ile Phe Met Thr Tyr Trp His Leu Leu
1               5               10              15

Asn Ala Phe Thr Val Thr Val Pro Lys Asp Leu Tyr Val Val Glu Tyr
            20              25              30

Gly Ser Asn Met Thr Ile Glu Cys Lys Phe Pro Val Glu Lys Gln Leu
            35              40              45

Asp Leu Ala Ala Leu Ile Val Tyr Trp Glu Met Glu Asp Lys Asn Ile
    50              55              60

Ile Gln Phe Val His Gly Glu Glu Asp Leu Lys Val Gln His Ser Ser
65              70              75              80

Tyr Arg Gln Arg Ala Arg Leu Leu Lys Asp Gln Leu Ser Leu Gly Asn
            85              90              95

Ala Ala Leu Gln Ile Thr Asp Val Lys Leu Gln Asp Ala Gly Val Tyr
            100             105             110

Arg Cys Met Ile Ser Tyr Gly Gly Ala Asp Tyr Lys Arg Ile Thr Val
            115             120             125

Lys Val Asn Ala Pro Tyr Asn Lys Ile Asn Gln Arg Ile Leu Val Val
    130             135             140

Asp Pro Val Thr Ser Glu His Glu Leu Thr Cys Gln Ala Glu Gly Tyr
```

```
145               150               155               160

Pro Lys Ala Glu Val Ile Trp Thr Ser Ser Asp His Gln Val Leu Ser
                165               170               175

Gly Lys Thr Thr Thr Thr Asn Ser Lys Arg Glu Glu Lys Leu Phe Asn
                180               185               190

Val Thr Ser Thr Leu Arg Ile Asn Thr Thr Thr Asn Glu Ile Phe Tyr
                195               200               205

Cys Thr Phe Arg Arg Leu Asp Pro Glu Glu Asn His Thr Ala Glu Leu
            210               215               220

Val Ile Pro Glu Leu Pro Leu Ala His Pro Pro Asn Glu Arg Thr His
225               230               235               240

Leu Val Ile Leu Gly Ala Ile Leu Leu Cys Leu Gly Val Ala Leu Thr
                245               250               255

Phe Ile Phe Arg Leu Arg Lys Gly Arg Met Met Asp Val Lys Lys Cys
                260               265               270

Gly Ile Gln Asp Thr Asn Ser Lys Lys Gln Ser Asp Thr His Leu Glu
                275               280               285

Glu Thr
    290

<210> SEQ ID NO 81
<211> LENGTH: 222
<212> TYPE: PRT
<213> ORGANISM: Artificial Sequence
<220> FEATURE:
<223> OTHER INFORMATION: Exemplary Fc region sequence

<400> SEQUENCE: 81

Cys Pro Pro Cys Pro Ala Pro Glu Leu Leu Gly Gly Pro Ser Val Phe
1               5                 10                15

Leu Phe Pro Pro Lys Pro Lys Asp Thr Leu Met Ile Ser Arg Thr Pro
                20                25                30

Glu Val Thr Cys Val Val Val Asp Val Ser His Glu Asp Pro Glu Val
                35                40                45

Lys Phe Asn Trp Tyr Val Asp Gly Val Glu Val His Asn Ala Lys Thr
    50                55                60

Lys Pro Arg Glu Glu Gln Tyr Asn Ser Thr Tyr Arg Val Val Ser Val
65                70                75                80

Leu Thr Val Leu His Gln Asp Trp Leu Asn Gly Lys Glu Tyr Lys Cys
                85                90                95

Lys Val Ser Asn Lys Ala Leu Pro Ala Pro Ile Glu Lys Thr Ile Ser
                100               105               110

Lys Ala Lys Gly Gln Pro Arg Glu Pro Gln Val Tyr Thr Leu Pro Pro
            115               120               125

Ser Arg Asp Glu Leu Thr Lys Asn Gln Val Ser Leu Thr Cys Leu Val
            130               135               140

Lys Gly Phe Tyr Pro Ser Asp Ile Ala Val Glu Trp Glu Ser Asn Gly
145               150               155               160

Gln Pro Glu Asn Asn Tyr Lys Thr Thr Pro Pro Val Leu Asp Ser Asp
                165               170               175

Gly Ser Phe Phe Leu Tyr Ser Lys Leu Thr Val Asp Lys Ser Arg Trp
                180               185               190

Gln Gln Gly Asn Val Phe Ser Cys Ser Val Met His Glu Ala Leu His
            195               200               205

Asn His Tyr Thr Gln Lys Ser Leu Ser Leu Ser Pro Gly Lys
```

-continued 210             215             220

```
<210> SEQ ID NO 82
<211> LENGTH: 222
<212> TYPE: PRT
<213> ORGANISM: Artificial Sequence
<220> FEATURE:
<223> OTHER INFORMATION: Exemplary variant Fc region (silent Fc)
      sequence

<400> SEQUENCE: 82

Cys Pro Pro Cys Pro Ala Pro Glu Ala Ala Gly Gly Pro Ser Val Phe
1               5                   10                  15

Leu Phe Pro Pro Lys Pro Lys Asp Thr Leu Met Ile Ser Arg Thr Pro
            20                  25                  30

Glu Val Thr Cys Val Val Val Asp Val Ser His Glu Asp Pro Glu Val
        35                  40                  45

Lys Phe Asn Trp Tyr Val Asp Gly Val Glu Val His Asn Ala Lys Thr
    50                  55                  60

Lys Pro Arg Glu Glu Gln Tyr Asn Ser Thr Tyr Arg Val Val Ser Val
65                  70                  75                  80

Leu Thr Val Leu His Gln Asp Trp Leu Asn Gly Lys Glu Tyr Lys Cys
                85                  90                  95

Lys Val Ser Asn Lys Ala Leu Lys Ala Pro Ile Glu Lys Thr Ile Ser
            100                 105                 110

Lys Ala Lys Gly Gln Pro Arg Glu Pro Gln Val Tyr Thr Leu Pro Pro
        115                 120                 125

Ser Arg Asp Glu Leu Thr Lys Asn Gln Val Ser Leu Thr Cys Leu Val
        130                 135                 140

Lys Gly Phe Tyr Pro Ser Asp Ile Ala Val Glu Trp Glu Ser Asn Gly
145                 150                 155                 160

Gln Pro Glu Asn Asn Tyr Lys Thr Thr Pro Pro Val Leu Asp Ser Asp
            165                 170                 175

Gly Ser Phe Phe Leu Tyr Ser Lys Leu Thr Val Asp Lys Ser Arg Trp
            180                 185                 190

Gln Gln Gly Asn Val Phe Ser Cys Ser Val Met His Glu Ala Leu His
            195                 200                 205

Asn His Tyr Thr Gln Lys Ser Leu Ser Leu Ser Pro Gly Lys
    210                 215                 220

<210> SEQ ID NO 83
<211> LENGTH: 10
<212> TYPE: PRT
<213> ORGANISM: Artificial Sequence
<220> FEATURE:
<223> OTHER INFORMATION: PD-L1 VH CDR1
<220> FEATURE:
<221> NAME/KEY: misc_feature
<222> LOCATION: (5)..(6)
<223> OTHER INFORMATION: Xaa can be any naturally occurring amino acid

<400> SEQUENCE: 83

Gly Phe Thr Phe Xaa Xaa Tyr Tyr Ile His
1               5                   10

<210> SEQ ID NO 84
<211> LENGTH: 17
<212> TYPE: PRT
<213> ORGANISM: Artificial Sequence
<220> FEATURE:
<223> OTHER INFORMATION: PD-L1 VH CDR2
```

-continued

```
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(5)
<223> OTHER INFORMATION: Xaa can be any naturally occurring amino acid
<220> FEATURE:
<221> NAME/KEY: misc_feature
<222> LOCATION: (7)..(8)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid

<400> SEQUENCE: 84

Xaa Ile Xaa Xaa Xaa Gly Xaa Xaa Thr Xaa Tyr Ala Asp Ser Val Lys
1               5                   10                  15

Gly

<210> SEQ ID NO 85
<211> LENGTH: 11
<212> TYPE: PRT
<213> ORGANISM: Artificial Sequence
<220> FEATURE:
<223> OTHER INFORMATION: PD-L1 VH CDR3
<220> FEATURE:
<221> NAME/KEY: misc_feature
<222> LOCATION: (1)..(8)
<223> OTHER INFORMATION: Xaa can be any naturally occurring amino acid

<400> SEQUENCE: 85

Xaa Xaa Xaa Xaa Xaa Xaa Xaa Xaa Leu Asp Tyr
1               5                   10

<210> SEQ ID NO 86
<211> LENGTH: 11
<212> TYPE: PRT
<213> ORGANISM: Artificial Sequence
<220> FEATURE:
<223> OTHER INFORMATION: PD-L1 VL CDR1

<400> SEQUENCE: 86

Arg Ala Ser Gln Ser Val Ser Ser Ala Val Ala
1               5                   10

<210> SEQ ID NO 87
<211> LENGTH: 7
<212> TYPE: PRT
<213> ORGANISM: Artificial Sequence
<220> FEATURE:
<223> OTHER INFORMATION: PD-L1 VL CDR2

<400> SEQUENCE: 87

Ser Ala Ser Ser Leu Tyr Ser
1               5

<210> SEQ ID NO 88
<211> LENGTH: 9
<212> TYPE: PRT
<213> ORGANISM: Artificial Sequence
<220> FEATURE:
<223> OTHER INFORMATION: PD-L1 VL CDR3
<220> FEATURE:
<221> NAME/KEY: misc_feature
<222> LOCATION: (3)..(6)
<223> OTHER INFORMATION: Xaa can be any naturally occurring amino acid
<220> FEATURE:
```

```
<221> NAME/KEY: misc_feature
<222> LOCATION: (8)..(8)
<223> OTHER INFORMATION: Xaa can be any naturally occurring amino acid

<400> SEQUENCE: 88

Gln Gln Xaa Xaa Xaa Xaa Pro Xaa Thr
1               5

<210> SEQ ID NO 89
<211> LENGTH: 17
<212> TYPE: PRT
<213> ORGANISM: Artificial Sequence
<220> FEATURE:
<223> OTHER INFORMATION: PD-L1 VH CDR2
<220> FEATURE:
<221> NAME/KEY: MISC_FEATURE
<222> LOCATION: (1)..(1)
<223> OTHER INFORMATION: X is a E, W, or T
<220> FEATURE:
<221> NAME/KEY: MISC_FEATURE
<222> LOCATION: (3)..(3)
<223> OTHER INFORMATION: X is a Y, T, or S
<220> FEATURE:
<221> NAME/KEY: MISC_FEATURE
<222> LOCATION: (4)..(4)
<223> OTHER INFORMATION: X is a P or S
<220> FEATURE:
<221> NAME/KEY: MISC_FEATURE
<222> LOCATION: (5)..(5)
<223> OTHER INFORMATION: X is a A, H, or G
<220> FEATURE:
<221> NAME/KEY: MISC_FEATURE
<222> LOCATION: (7)..(7)
<223> OTHER INFORMATION: X is a S, Y, or G
<220> FEATURE:
<221> NAME/KEY: MISC_FEATURE
<222> LOCATION: (8)..(8)
<223> OTHER INFORMATION: X is a Y, S, or F
<220> FEATURE:
<221> NAME/KEY: MISC_FEATURE
<222> LOCATION: (10)..(10)
<223> OTHER INFORMATION: X is a Y or K

<400> SEQUENCE: 89

Xaa Ile Xaa Xaa Xaa Gly Xaa Xaa Thr Xaa Tyr Ala Asp Ser Val Lys
1               5                   10                  15

Gly

<210> SEQ ID NO 90
<211> LENGTH: 11
<212> TYPE: PRT
<213> ORGANISM: Artificial Sequence
<220> FEATURE:
<223> OTHER INFORMATION: PD-L1 VH CDR3
<220> FEATURE:
<221> NAME/KEY: MISC_FEATURE
<222> LOCATION: (1)..(1)
<223> OTHER INFORMATION: X is a G or D
<220> FEATURE:
<221> NAME/KEY: MISC_FEATURE
<222> LOCATION: (2)..(2)
<223> OTHER INFORMATION: X is a P, S, or Y
<220> FEATURE:
<221> NAME/KEY: MISC_FEATURE
<222> LOCATION: (3)..(3)
<223> OTHER INFORMATION: X is a Y, V, or T
<220> FEATURE:
<221> NAME/KEY: MISC_FEATURE
<222> LOCATION: (4)..(4)
<223> OTHER INFORMATION: X is a S, I, or L
<220> FEATURE:
<221> NAME/KEY: MISC_FEATURE
<222> LOCATION: (5)..(5)
<223> OTHER INFORMATION: X is a V, Y, or T
```

```
<220> FEATURE:
<221> NAME/KEY: MISC_FEATURE
<222> LOCATION: (6)..(6)
<223> OTHER INFORMATION: X is a R, G or P
<220> FEATURE:
<221> NAME/KEY: MISC_FEATURE
<222> LOCATION: (7)..(7)
<223> OTHER INFORMATION: X is a Y or V (or not present)
<220> FEATURE:
<221> NAME/KEY: MISC_FEATURE
<222> LOCATION: (8)..(8)
<223> OTHER INFORMATION: X is an A (or not present)

<400> SEQUENCE: 90

Xaa Xaa Xaa Xaa Xaa Xaa Xaa Xaa Leu Asp Tyr
1               5                   10

<210> SEQ ID NO 91
<211> LENGTH: 9
<212> TYPE: PRT
<213> ORGANISM: Artificial Sequence
<220> FEATURE:
<223> OTHER INFORMATION: PD-L1 VL CDR3
<220> FEATURE:
<221> NAME/KEY: MISC_FEATURE
<222> LOCATION: (3)..(3)
<223> OTHER INFORMATION: X is a V, Y, or F
<220> FEATURE:
<221> NAME/KEY: MISC_FEATURE
<222> LOCATION: (4)..(4)
<223> OTHER INFORMATION: X is a S, Y, or G
<220> FEATURE:
<221> NAME/KEY: MISC_FEATURE
<222> LOCATION: (5)..(5)
<223> OTHER INFORMATION: X is a Y, T, or A
<220> FEATURE:
<221> NAME/KEY: MISC_FEATURE
<222> LOCATION: (6)..(6)
<223> OTHER INFORMATION: X is a S or E
<220> FEATURE:
<221> NAME/KEY: MISC_FEATURE
<222> LOCATION: (8)..(8)
<223> OTHER INFORMATION: X is a Y or I

<400> SEQUENCE: 91

Gln Gln Xaa Xaa Xaa Xaa Pro Xaa Thr
1               5

<210> SEQ ID NO 92
<211> LENGTH: 226
<212> TYPE: PRT
<213> ORGANISM: Artificial Sequence
<220> FEATURE:
<223> OTHER INFORMATION: Phage display heavy chain
<220> FEATURE:
<221> NAME/KEY: misc_feature
<222> LOCATION: (31)..(35)
<223> OTHER INFORMATION: Xaa can be any naturally occurring amino acid
<220> FEATURE:
<221> NAME/KEY: misc_feature
<222> LOCATION: (50)..(66)
<223> OTHER INFORMATION: Xaa can be any naturally occurring amino acid
<220> FEATURE:
<221> NAME/KEY: misc_feature
<222> LOCATION: (99)..(112)
<223> OTHER INFORMATION: Xaa can be any naturally occurring amino acid

<400> SEQUENCE: 92

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Xaa Xaa
            20                  25                  30
```

```
Xaa Xaa Xaa Trp Val Arg Gln Ala Pro Gly Lys Gly Leu Glu Trp Val
        35              40              45

Ala Xaa Xaa Xaa Xaa Xaa Xaa Xaa Xaa Xaa Xaa Xaa Xaa Xaa Xaa Xaa
    50              55              60

Xaa Xaa Arg Phe Thr Ile Ser Ala Asp Thr Ser Lys Asn Thr Ala Tyr
65              70              75              80

Leu Gln Met Asn Ser Leu Arg Ala Glu Asp Thr Ala Val Tyr Tyr Cys
            85              90              95

Ala Arg Xaa Xaa Xaa Xaa Xaa Xaa Xaa Xaa Xaa Xaa Xaa Xaa Xaa Xaa
        100             105             110

Trp Gly Gln Gly Thr Leu Val Thr Val Ser Ser Ala Ser Thr Lys Gly
        115             120             125

Pro Ser Val Phe Pro Leu Ala Pro Ser Ser Lys Ser Thr Ser Gly Gly
    130             135             140

Thr Ala Ala Leu Gly Cys Leu Val Lys Asp Tyr Phe Pro Glu Pro Val
145             150             155             160

Thr Val Ser Trp Asn Ser Gly Ala Leu Thr Ser Gly Val His Thr Phe
            165             170             175

Pro Ala Val Leu Gln Ser Ser Gly Leu Tyr Ser Leu Ser Ser Val Val
        180             185             190

Thr Val Pro Ser Ser Ser Leu Gly Thr Gln Thr Tyr Ile Cys Asn Val
        195             200             205

Asn His Lys Pro Ser Asn Thr Lys Val Asp Lys Lys Val Glu Pro Lys
    210             215             220

Ser Cys
225
```

```
<210> SEQ ID NO 93
<211> LENGTH: 214
<212> TYPE: PRT
<213> ORGANISM: Artificial Sequence
<220> FEATURE:
<223> OTHER INFORMATION: Phage display light chain
<220> FEATURE:
<221> NAME/KEY: misc_feature
<222> LOCATION: (89)..(97)
<223> OTHER INFORMATION: Xaa can be any naturally occurring amino acid

<400> SEQUENCE: 93
```

```
Asp Ile Gln Met Thr Gln Ser Pro Ser Ser Leu Ser Ala Ser Val Gly
1               5               10              15

Asp Arg Val Thr Ile Thr Cys Arg Ala Ser Gln Ser Val Ser Ser Ala
        20              25              30

Val Ala Trp Tyr Gln Gln Lys Pro Gly Lys Ala Pro Lys Leu Leu Ile
        35              40              45

Tyr Ser Ala Ser Ser Leu Tyr Ser Gly Val Pro Ser Arg Phe Ser Gly
    50              55              60

Ser Arg Ser Gly Thr Asp Phe Thr Leu Thr Ile Ser Ser Leu Gln Pro
65              70              75              80

Glu Asp Phe Ala Thr Tyr Tyr Cys Xaa Xaa Xaa Xaa Xaa Xaa Xaa Xaa
            85              90              95

Xaa Phe Gly Gln Gly Thr Lys Val Glu Ile Lys Arg Thr Val Ala Ala
        100             105             110

Pro Ser Val Phe Ile Phe Pro Pro Ser Asp Ser Gln Leu Lys Ser Gly
        115             120             125

Thr Ala Ser Val Val Cys Leu Leu Asn Asn Phe Tyr Pro Arg Glu Ala
    130             135             140
```

-continued

```
Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
            195                 200                 205

Phe Asn Arg Gly Glu Cys
        210
```

```
<210> SEQ ID NO 94
<211> LENGTH: 330
<212> TYPE: PRT
<213> ORGANISM: Artificial Sequence
<220> FEATURE:
<223> OTHER INFORMATION: Full length IgGs, the heavy chain constant
      regions

<400> SEQUENCE: 94

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
                35                  40                  45

Gly Val His Thr Phe Pro Ala Val Leu Gln Ser Ser Gly Leu Tyr Ser
            50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
                100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
        130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
```

|     | 275 |     | 280 |     | 285 |

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 95
<211> LENGTH: 107
<212> TYPE: PRT
<213> ORGANISM: Artificial Sequence
<220> FEATURE:
<223> OTHER INFORMATION: Full length IgGs, the light chain constant
      region

<400> SEQUENCE: 95

Arg Thr Val Ala Ala Pro Ser Val Phe Ile Phe Pro Pro Ser Asp Ser
1                   5                   10                  15

Gln Leu Lys Ser Gly Thr Ala Ser Val Val Cys Leu Leu Asn Asn Phe
                20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 96
<211> LENGTH: 330
<212> TYPE: PRT
<213> ORGANISM: Artificial Sequence
<220> FEATURE:
<223> OTHER INFORMATION: Exemplary IgG heavy chain comprises any VH
      domain

<400> SEQUENCE: 96

Ala Ser Thr Lys Gly Pro Ser Val Phe Pro Leu Ala Pro Ser Ser Lys
1                   5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys

-continued

```
        130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

```
<210> SEQ ID NO 97
<211> LENGTH: 107
<212> TYPE: PRT
<213> ORGANISM: Artificial Sequence
<220> FEATURE:
<223> OTHER INFORMATION: Exemplary light chain (e.g., for pairing with
      an IgG heavy chain) comprises any VL domain

<400> SEQUENCE: 97

Arg Thr Val Ala Ala Pro Ser Val Phe Ile Phe Pro Pro Ser Asp Ser
1                   5                   10                  15

Gln Leu Lys Ser Gly Thr Ala Ser Val Val Cys Leu Leu Asn Asn Phe
                20                  25                  30

Tyr Pro Arg Glu Ala Lys Val Gln Trp Lys Val Asp Asn Ala Leu Gln
            35                  40                  45

Ser Gly Asn Ser Gln Glu Ser Val Thr Glu Gln Asp Ser Lys Asp Ser
        50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
                100                 105
```

```
<210> SEQ ID NO 98
<211> LENGTH: 330
<212> TYPE: PRT
<213> ORGANISM: Artificial Sequence
<220> FEATURE:
<223> OTHER INFORMATION: Exemplary IgG heavy chain comprises any VH
      domain
```

```
<400> SEQUENCE: 98

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
            115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Lys Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 99
<211> LENGTH: 38
<212> TYPE: PRT
<213> ORGANISM: Artificial Sequence
<220> FEATURE:
<223> OTHER INFORMATION: VH consensus sequence
<220> FEATURE:
<221> NAME/KEY: MISC_FEATURE
<222> LOCATION: (5)..(5)
<223> OTHER INFORMATION: X is a D or S
<220> FEATURE:
<221> NAME/KEY: MISC_FEATURE
<222> LOCATION: (6)..(6)
```

```
<223> OTHER INFORMATION: X is a Q or S
<220> FEATURE:
<221> NAME/KEY: MISC_FEATURE
<222> LOCATION: (11)..(11)
<223> OTHER INFORMATION: X is a E, W, or T
<220> FEATURE:
<221> NAME/KEY: MISC_FEATURE
<222> LOCATION: (13)..(13)
<223> OTHER INFORMATION: X is a Y, T, or S
<220> FEATURE:
<221> NAME/KEY: MISC_FEATURE
<222> LOCATION: (14)..(14)
<223> OTHER INFORMATION: X is a P or S
<220> FEATURE:
<221> NAME/KEY: MISC_FEATURE
<222> LOCATION: (15)..(15)
<223> OTHER INFORMATION: X is a A, H, or G
<220> FEATURE:
<221> NAME/KEY: MISC_FEATURE
<222> LOCATION: (17)..(17)
<223> OTHER INFORMATION: X is a S, Y, or G
<220> FEATURE:
<221> NAME/KEY: MISC_FEATURE
<222> LOCATION: (18)..(18)
<223> OTHER INFORMATION: X is a Y, S, or F
<220> FEATURE:
<221> NAME/KEY: MISC_FEATURE
<222> LOCATION: (20)..(20)
<223> OTHER INFORMATION: X is a Y or K
<220> FEATURE:
<221> NAME/KEY: MISC_FEATURE
<222> LOCATION: (28)..(28)
<223> OTHER INFORMATION: X is a G or D
<220> FEATURE:
<221> NAME/KEY: MISC_FEATURE
<222> LOCATION: (29)..(29)
<223> OTHER INFORMATION: X is a P, S, or Y
<220> FEATURE:
<221> NAME/KEY: MISC_FEATURE
<222> LOCATION: (30)..(30)
<223> OTHER INFORMATION: X is a Y, V, or T
<220> FEATURE:
<221> NAME/KEY: MISC_FEATURE
<222> LOCATION: (31)..(31)
<223> OTHER INFORMATION: X is a S, I, or L
<220> FEATURE:
<221> NAME/KEY: MISC_FEATURE
<222> LOCATION: (32)..(32)
<223> OTHER INFORMATION: X is a V, Y, or T
<220> FEATURE:
<221> NAME/KEY: MISC_FEATURE
<222> LOCATION: (33)..(33)
<223> OTHER INFORMATION: X is a R, G or P
<220> FEATURE:
<221> NAME/KEY: MISC_FEATURE
<222> LOCATION: (34)..(34)
<223> OTHER INFORMATION: X is a Y or V (or not present)
<220> FEATURE:
<221> NAME/KEY: MISC_FEATURE
<222> LOCATION: (35)..(35)
<223> OTHER INFORMATION: X is an A (or not present)

<400> SEQUENCE: 99

Gly Phe Thr Phe Xaa Xaa Tyr Tyr Ile His Xaa Ile Xaa Xaa Xaa Gly
1               5                   10                  15

Xaa Xaa Thr Xaa Tyr Ala Asp Ser Val Lys Gly Xaa Xaa Xaa Xaa Xaa
            20                  25                  30

Xaa Xaa Xaa Leu Asp Tyr
        35

<210> SEQ ID NO 100
<211> LENGTH: 27
<212> TYPE: PRT
<213> ORGANISM: Artificial Sequence
<220> FEATURE:
```

```
<223> OTHER INFORMATION: VL consensus sequence
<220> FEATURE:
<221> NAME/KEY: MISC_FEATURE
<222> LOCATION: (21)..(21)
<223> OTHER INFORMATION: X is a V, Y, or F
<220> FEATURE:
<221> NAME/KEY: MISC_FEATURE
<222> LOCATION: (22)..(22)
<223> OTHER INFORMATION: X is a S, Y, or G
<220> FEATURE:
<221> NAME/KEY: MISC_FEATURE
<222> LOCATION: (23)..(23)
<223> OTHER INFORMATION: X is a Y, T, or A
<220> FEATURE:
<221> NAME/KEY: MISC_FEATURE
<222> LOCATION: (24)..(24)
<223> OTHER INFORMATION: X is a S or E
<220> FEATURE:
<221> NAME/KEY: MISC_FEATURE
<222> LOCATION: (26)..(26)
<223> OTHER INFORMATION: X is a Y or I

<400> SEQUENCE: 100

Arg Ala Ser Gln Ser Val Ser Ser Ala Val Ala Ser Ala Ser Ser Leu
1               5                   10                  15

Tyr Ser Gln Gln Xaa Xaa Xaa Xaa Pro Xaa Thr
            20                  25

<210> SEQ ID NO 101
<211> LENGTH: 10
<212> TYPE: PRT
<213> ORGANISM: Artificial Sequence
<220> FEATURE:
<223> OTHER INFORMATION: PD-L1 VH CDR1
<220> FEATURE:
<221> NAME/KEY: MISC_FEATURE
<222> LOCATION: (5)..(5)
<223> OTHER INFORMATION: X is a D or S
<220> FEATURE:
<221> NAME/KEY: MISC_FEATURE
<222> LOCATION: (6)..(6)
<223> OTHER INFORMATION: X is a Q or S

<400> SEQUENCE: 101

Gly Phe Thr Phe Xaa Xaa Tyr Tyr Ile His
1               5                   10
```

PD-L1 BINDING AGENTS AND USES THEREOF

CROSS-REFERENCE TO RELATED APPLICATIONS

This application is a U.S. National Stage Application under 35 U.S.C. § 371 of International Patent Application No. PCT/US2021/044330, filed Aug. 3, 2021, which claims the benefit of U.S. Provisional Application No. 63/061,109, filed Aug. 4, 2020, the disclosure of each of which is incorporated by reference herein in its entirety.

SEQUENCE LISTING

This application incorporates by reference a Sequence Listing submitted with this application as a text file, entitled 14529-007-228_SEQ_LISTING.txt, created on Jul. 29, 2021, and is 52,941 bytes in size.

FIELD

The present disclosure relates generally to binding agents, such as antibodies, that bind to PD-L1, including human PD-L1, and methods of their use.

BACKGROUND

Programmed death ligand 1 (PD-L1) is a cell surface glycoprotein ligand that specifically binds to programmed death receptor 1 (PD-1), a key immune checkpoint receptor. PD-1 is upregulated on activated T cells, B cells, and monocytes and mediates immunosuppression. While PD-L2, the other PD-1 ligand, is expressed primarily on activated antigen-presenting cells (APCs), PD-L1 is broadly expressed, including in cells of hematopoietic lineage, such as activated T cells, B cells, monocytes, dendritic cells and macrophages, and peripheral tissues such as heart, skeletal, muscle, placenta, lung, kidney and liver tissues.

The binding of PD-L1 to PD-1 is a negative checkpoint that can activate the downstream signaling of PD-1 receptor in T cells, thus inhibiting the proliferation, cytokine generation and release, and cytotoxicity of T cells. This inhibition of T cell activation and secretion of effector cytokines can prevent autoimmunity and chronic infection.

However, many tumor cells use this mechanism to protect themselves from immune attack, resulting in tumor immune evasion (e.g., tumor immunity). Many cancers overexpress PD-L1, and its overexpression is often associated with poor prognosis. In cancer, the PD-1/PD-L1 interaction stimulates the downstream signals to suppress T cell activation, resulting in tumor cell survival.

The blockade of PD-1 interaction with its ligands has been proposed as an immunotherapeutic method of enhancing T cell immune responses against tumor cells. Current strategies of PD-1/PD-L1 based immunotherapy have shown efficacy in treating some advanced carcinoma, but have limited effects on many solid tumors and on certain PD-L1 functions. Accordingly, there remains an urgent need in the art for agents that can block or prevent PD-1/PD-L1 interaction and/or that can target PD-L1 to treat, prevent, or alleviate T cell dysfunctional diseases, disorders, or conditions, including those involving tumor cells expressing PD-L1. The PD-L1 binding agents, compositions and methods provide herein satisfy this need and provide related advantages.

SUMMARY

The present disclosure provides PD-L1 binding agents, including human PD-L1 binding agents. Such agents include antibodies that bind to PD-L1, for example, monospecific or multispecific (e.g., bispecific) antibodies that bind to PD-L1. Such antibodies, in some embodiments, compete for the binding of human PD-L1 with an antibody having a heavy chain variable region and a light chain variable region described herein (e.g., Table 1-3).

The present disclosure also provides compositions comprising a PD-L1 binding agent. Such compositions, in some embodiments, include antibodies that bind to PD-L1, for example, monospecific or multispecific (e.g., bispecific) antibodies that bind to PD-L1. Such compositions, in some embodiments, include antibodies that have essentially the same affinity as and/or compete for the binding of human PD-L1 with an antibody having a heavy chain variable region and a light chain variable region described herein (e.g., Table 1-3).

The present disclosure also provides methods of treating, preventing, or alleviating a T cell dysfunctional disease, disorder, or condition, including one or more symptoms of the T cell dysfunctional disease, disorder, or condition with a PD-L1 binding agent or a composition comprising the agent, including a PD-L1 binding agent or composition comprising the agent. Such compositions include antibodies that bind to PD-L1, for example, monospecific or multispecific (e.g., bispecific) antibodies that bind to PD-L1.

BRIEF DESCRIPTION OF THE DRAWINGS

FIGS. 7A-7B show a sequence alignment of heavy chain variable regions and light chain variable regions of P22, P24, and P31.2, including consensus sequences for VH CDR1, VH CDR2, VH CDR3, VL CDR1, VL CDR2, and VL CDR3. Boundaries of CDRs are indicated by Kabat, AbM, Chothia, Contact, and IMGT numbering.

DETAILED DESCRIPTION

Figure 1A:
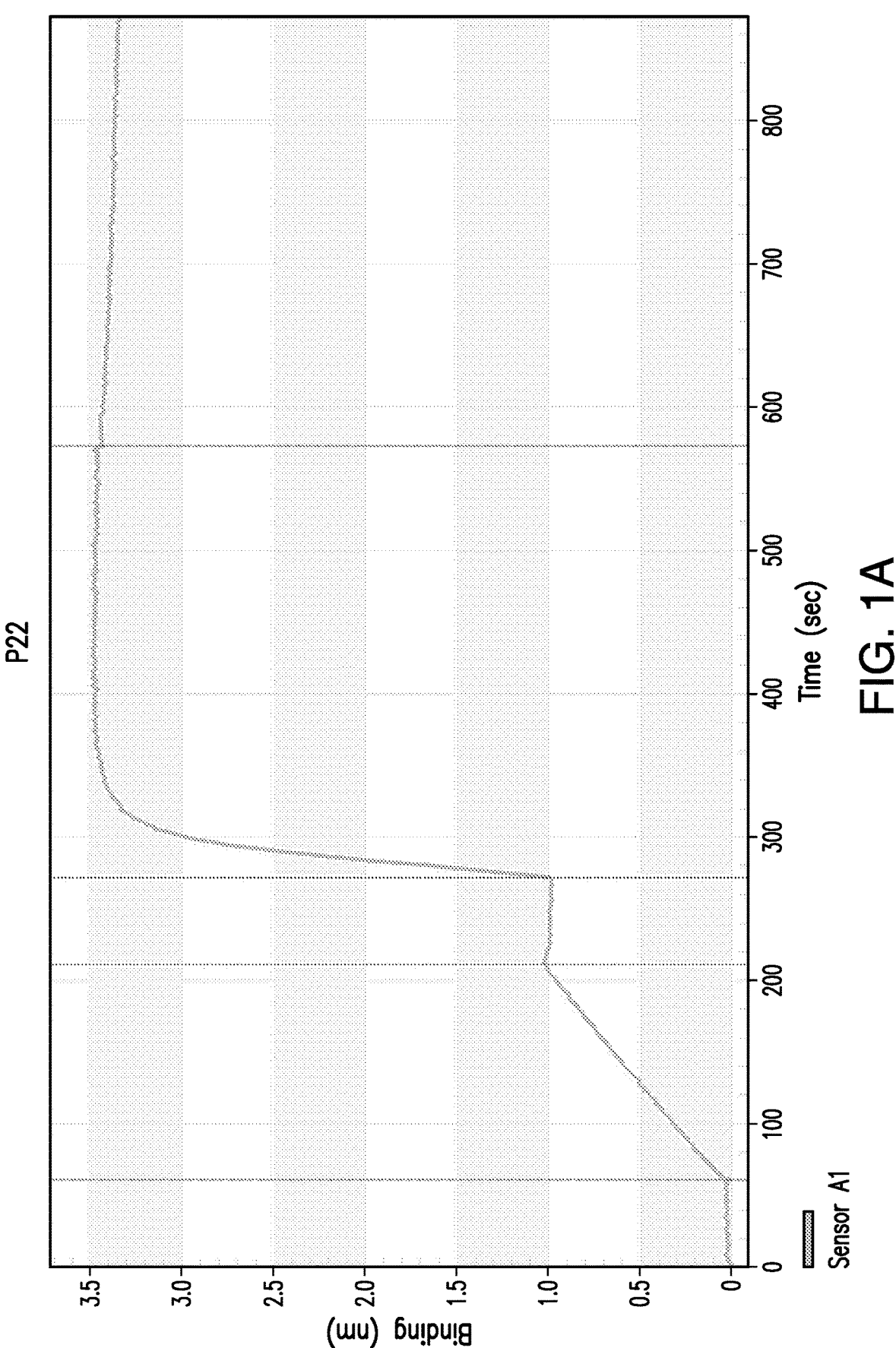
FIGS. 1A-1C illustrate exemplary results from Octet® binding assays, further described in Example 2.

The present disclosure provides PD-L1 binding agents. Such agents include antibodies (e.g., monospecific or multispecific, including bispecific) that bind to PD-L1, including antibodies that bind to human PD-L1. Such binding agents are useful in compositions and in methods of treating, preventing, or alleviating a T cell dysfunctional disease, disorder, or condition, including one or more symptoms of the disease, disorder, or condition. T cell dysfunctional diseases, disorders, and conditions include tumor immunity and associated cancers, including, but not limited to, any cancer wherein the tumor cells express or overexpress PD-L1. Such PD-L1 expressing tumor cells may help tumor cells escape immune surveillance and clearance (e.g., tumor immunity). In addition, PD-L1 binding agents described herein, such as PD-L1 binding antibodies (e.g., monospecific or multispecific antibodies, including bispecific antibodies), are useful to inhibit PD-1 signaling and/or enhance T cell function and thus enhance immune surveillance and removal of tumor cells. PD-L1 binding agents described herein, such as PD-L1 binding antibodies (e.g., monospecific or multispecific antibodies, including bispecific antibodies), are useful in compositions and in methods for enhancing T cell function, including the upregulation of cell-mediated immune responses.

The term "Programmed Cell Death Ligand-1 (PD-L1)," "Programmed Death Ligand-1," "PD-1 ligand 1" or similar terms refers to a polypeptide ("polypeptide" and "protein" are used interchangeably herein) or any native PD-L1 from any vertebrate source, including mammals such as primates (e.g., humans, cynomolgus monkey (cyno)), dogs, and rodents (e.g., mice and rats), unless otherwise indicated. PD-L1, also known as cluster of differentiation 274 (CD274) or B7 homolog 1 (B7-H1) is a protein that in humans is encoded by the CD274 gene. PD-L1 is a one of two naturally-occurring cell surface glycoprotein ligands for PD-1 (the other is PD-L2). Like PD-1, PD-L1 belongs to the immunoglobulin superfamily and consist of two extracellular Ig domains, an N-terminal V domain, and a C-terminal constant domain. PD-L1 is known in the art to downregulate T cell activation and cytokine secretion upon binding to PD-1. The term PD-L1 encompasses "full-length," PD-L1, as well as any form of PD-L1 or any fragment thereof that results from processing in the cell. The term PD-L1 also encompasses naturally occurring variants of PD-L1, such as SNP variants, splice variants and allelic variants. The full-length amino acid sequence of human PD-L1 is provided below (exemplary extracellular domain=underline text):

```
                                      (SEQ ID NO: 80)
MRIFAVFIFMTYWHLLNAFTVTVPKDLYVVEYGSNMTIECKFPVEKQLDL

AALIVYWEMEDKNIIQFVHGEEDLKVQHSSYRQRARLLKDQLSLGNAALQ

ITDVKLQDAGVYRCMISYGGADYKRITVKVNAPYNKINQRILVVDPVTSE

HELTCQAEGYPKAEVIWTSSDHQVLSGKTTTTNSKREEKLFNVTSTLRIN

TTTNEIFYCTFRRLDPEENHTAELVIPELPLAHPPNERTHLVILGAILLC

LGVALTFIFRLRKGRMMDVKKCGIQDTNSKKQSDTHLEET
```

Other related PD-L1 polypeptides that are also encompassed by the term PD-L1 include fragments, derivatives (e.g., substitution, deletion, truncations, and insertion variants), fusion polypeptides, and interspecies homologs that retain PD-L1 activity and/or are sufficient to generate an anti-PD-L1 immune response. As those skilled in the art will appreciate, a PD-L1 binding agent (e.g., an antibody) described herein can bind to a PD-L1 polypeptide, a PD-L1 polypeptide fragment, a PD-L1 antigen, and/or a PD-L1 epitope. An epitope may be part of a larger PD-L1 antigen, which may be part of a larger PD-L1 polypeptide fragment, which, in turn, may be part of a larger PD-L1 polypeptide. PD-L1 may exist in a native or denatured form. PD-L1 polypeptides described herein may be isolated from a variety of sources, such as from human tissue types or from another source, or prepared by recombinant or synthetic methods. A PD-L1 polypeptide may comprise a polypeptide having the same amino acid sequence as a corresponding PD-L1 polypeptide derived from nature. Orthologs to the PD-L1 polypeptide are also well known in the art.

The term "Programmed Cell Death-1 (PD-1)," "Programmed Death-1," "PD-1 receptor" or similar terms refers to a polypeptide ("polypeptide" and "protein" are used interchangeably herein) or any native PD-1 from any vertebrate source, including mammals such as primates (e.g., humans, cynomolgus monkey (cyno)), dogs, and rodents (e.g., mice and rats), unless otherwise indicated. PD-1, also known as CD279 (cluster of differentiation 279), is an immunoinhibitory receptor belonging to the CD28 family. PD-1 is expressed predominantly on previously activated T cells in vivo, and binds to two ligands, PD-L1 and PD-L2. PD-1 belongs to the immunoglobulin superfamily and consist of two extracellular Ig domains, an N-terminal V domain, and a C-terminal constant domain. PD-1 contains two cytoplasmic tyrosine-based signaling motifs, an immunoreceptor tyrosine-based inhibition motif (ITIM) and an immunoreceptor tyrosine-based switch motif (ITSM). The term PD-1 encompasses "full-length," PD-1, as well as any form of PD-1 or any fragment thereof that results from processing in the cell. The term PD-1 also encompasses naturally occurring variants of PD-1, such as SNP variants, splice variants and allelic variants. Following T cell stimulation, PD-1 is known in the art to recruit the tyrosine phosphatase SHP-2 to the ITSM motif within its cytoplasmic tail, leading to, among other things, the dephosphorylation of effector molecules such as CD3 Zeta, PKC theta and ZAP70 that are involved in the CD3 T cell signaling cascade (Carter et al. (2002) Eur J Immunol 32:634-43). The full-length amino acid sequence of human PD-1 is provided below:

```
                                      (SEQ ID NO: 79)
MQIPQAPWPVVWAVLQLGWRPGWFLDSPDRPWNPPTFSPALLVVTEGDNA

TFTCSFSNTSESFVLNWYRMSPSNQTDKLAAFPEDRSQPGQDCRFRVTQL

PNGRDFHMSVVRARRNDSGTYLCGAISLAPKAQIKESLRAELRVTERRAE

VPTAHPSPSPRPAGQFQTLVVGVVGGLLGSLVLLVWVLAVICSRAARGTI

GARRTGQPLKEDPSAVPVFSVDYGELDFQWREKTPEPPVPCVPEQTEYAT

IVFPSGMGTSSPARRGSADGPRSAQPLRPEDGHCSWPL.
```

As used herein, the term "binding agent" or a grammatical equivalent thereof refers to a molecule (e.g., antibody) with one or more antigen binding sites that binds an antigen. In some embodiments, a PD-L1 binding agent as described herein is an antibody, antibody fragment, or other peptide-based molecule that binds to PD-L1, such as human PD-1.

The term "antibody," "immunoglobulin," or "Ig" is used interchangeably herein, and is used in the broadest sense and specifically covers, for example polyclonal antibodies, monoclonal antibodies (including agonist, antagonist, neutralizing antibodies, full length monoclonal antibodies), antibody compositions with polyepitopic or monoepitopic specificity, recombinantly produced antibodies, monospecific antibodies, multispecific antibodies (including bispecific antibodies), synthetic antibodies, chimeric antibodies, humanized antibodies, or human versions of antibodies having full length heavy and/or light chains. The present disclosure also includes antibody fragments (and/or polypeptides that comprise antibody fragments) that retain PD-L1 binding characteristics. Non-limiting examples of antibody fragments include antigen-binding regions and/or effector regions of the antibody, e.g., Fab, Fab', F(ab')$_2$, Fv, scFv, (scFv)$_2$, single chain antibody molecule, dual variable region antibody, single variable region antibody, linear antibody, V region, a multispecific antibody formed from antibody fragments, F(ab)$_2$, Fd, Fc, diabody, di-diabody, disulfide-linked Fvs (dsFv), single-domain antibody (e.g., NANOBODY®) or other fragments (e.g., fragments consisting of the variable regions of the heavy and light chains that are non-covalently coupled). In general terms, a variable (V) region domain may be any suitable arrangement of immunoglobulin heavy (VH) and/or light (VL) chain variable domains. For example, the present disclosure also includes tetrameric antibodies comprising two heavy chain and two light chain molecules, an antibody light chain monomer, and an antibody heavy chain monomer. Thus, for example, the V region domain may be dimeric and contain VH-VH, VH-VL, or VL-VL dimers that bind PD-L1. If desired, the VH and VL chains may be covalently coupled either directly or through a linker to form a single chain Fv (scFv). For ease of reference, scFv proteins are referred to herein as included in the category "antibody fragments." Another form of an antibody fragment is a peptide comprising one or more complementarity determining regions (CDRs) of an antibody. CDRs (also termed "minimal recognition units" or "hypervariable region") can be obtained by constructing polynucleotides that encode the CDR of interest. Such polynucleotides are prepared, for example, by using the polymerase chain reaction to synthesize the variable region using mRNA of antibody-producing cells as a template (see, for example, Larrick et al., Methods: A Companion to Methods in Enzymology, 2:106 (1991); Courtenay-Luck, "Genetic Manipulation of Monoclonal Antibodies," in Monoclonal Antibodies Production, Engineering and Clinical Application, Ritter et al. (eds.), page 166, Cambridge University Press (1995); and Ward et al., "Genetic Manipulation and Expression of Antibodies," in Monoclonal Antibodies: Principles and Applications, Birch et al., (eds.), page 137, Wiley-Liss, Inc. (1995)). Antibody fragments may be incorporated into single domain antibodies, maxibodies, minibodies, intrabodies, diabodies, triabodies, tetrabodies, variable domains of new antigen receptors (v-NAR), and bis-single chain Fv regions (see, e.g., Hollinger and Hudson, Nature Biotechnology, 23(9):1126-1136, 2005). The binding agent, in some embodiments, contains a light chain and/or a heavy chain constant region, such as one or more constant regions, including one or more IgG1, IgG2, IgG3 and/or IgG4 constant regions. In some embodiments, antibodies can include epitope-binding fragments of any of the above. The antibodies described herein can be of any class (e.g., IgG, IgE, IgM, IgD, and IgA) or any subclass (e.g., IgG1, IgG2, IgG3, IgG4, IgA1, and IgA2) of immunoglobulin molecule. Antibodies may be agonistic antibodies or antagonistic antibodies.

The term "monospecific" when used in reference to a binding agent (e.g., an antibody) as used herein denotes a binding agent that has one or more binding sites each of which bind to the same epitope of the same antigen.

The term "bispecific" when used in reference to a binding agent (e.g., an antibody) means that the binding agent is able to specifically bind to at least two distinct antigenic determinants, for example two binding sites each formed by a pair of an antibody heavy chain variable domain (VH) and an antibody light chain variable domain (VL) binding to different antigens or to different epitopes on the same antigen. Such a bispecific binding agent (e.g., an antibody) may have a 1+1 format. Other bispecific binding agent (e.g., an antibody) formats may be 2+1 or 1+2 formats (comprising two binding sites for a first antigen or epitope and one binding site for a second antigen or epitope) or 2+2 formats (comprising two binding sites for a first antigen or epitope and two binding sites for a second antigen or epitope). When a bispecific binding agent (e.g., an antibody) comprises two antigen binding sites, each may bind to a different antigenic determinant. Such a bispecific binding agent (e.g., an antibody) may bind to two different epitopes on the same antigen (e.g., epitopes on PD-L1).

The terms "identical" or percent "identity" in the context of two or more nucleic acids or polypeptides, refer to two or more sequences or subsequences that are the same or have a specified percentage of nucleotides or amino acid residues that are the same, when compared and aligned (introducing gaps, if necessary) for maximum correspondence, not considering any conservative amino acid substitutions as part of the sequence identity. The percent identity can be measured using sequence comparison software or algorithms or by visual inspection. Various algorithms and software that can be used to obtain alignments of amino acid or nucleotide sequences are well-known in the art. These include, but are not limited to, BLAST, ALIGN, MegAlign®, BestFit, GCG Wisconsin Package, and variants thereof. In some embodiments, two nucleic acids or polypeptides are substantially identical, meaning they have at least 70%, at least 75%, at least 80%, at least 85%, at least 90%, and in some embodiments at least 95%, 96%, 97%, 98%, 99% nucleotide or amino acid residue identity, when compared and aligned for maximum correspondence, as measured using a sequence comparison algorithm or by visual inspection. In some embodiments, identity exists over a region of the amino acid sequences that is at least about 10 residues, at least about 20 residues, at least about 40-60 residues, at least about 60-80 residues in length or any integral value there between. In some embodiments, identity exists over a longer region than 60-80 residues, such as at least about 80-100 residues, and in some embodiments the sequences are substantially identical over the full length of the sequences being compared, such as the coding region of a target protein or an antibody. In some embodiments, identity exists over a region of the nucleotide sequences that is at least about 10 bases, at least about 20 bases, at least about 40-60 bases, at least about 60-80 bases in length or any integral value there between. In some embodiments, identity exists over a longer region than 60-80 bases, such as at least about 80-1000 bases or more, and in some embodiments the sequences are substantially identical over the full length of the sequences being compared, such as a nucleotide sequence encoding a protein of interest.

A "conservative amino acid substitution" is one in which one amino acid residue is replaced with another amino acid residue having a side chain with similar chemical characteristics. Families of amino acid residues having similar side chains have been generally defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). For example, substitution of a phenylalanine for a tyrosine is a conservative substitution. Generally, conservative substitutions in the sequences of the polypeptides, soluble proteins, and/or antibodies of the disclosure do not abrogate the binding of the polypeptide, soluble protein, or antibody containing the amino acid sequence, to the target binding site. Methods of identifying amino acid conservative substitutions which do not eliminate binding are well-known in the art.

The terms "polypeptide" refers to polymers of amino acids of any length. The polymer can be linear or branched, it can comprise modified amino acids, and it can include (e.g., be interrupted by) non-amino acids. The terms also encompass an amino acid polymer that has been modified naturally or by intervention; for example, disulfide bond formation, glycosylation, lipidation, acetylation, phosphorylation, or any other manipulation or modification, such as linkage to or conjugation with (directly or indirectly) a moiety such as a labeling component. Also included within the definition are, for example, polypeptides containing one or more analogs of an amino acid (including, for example, unnatural amino acids), as well as other modifications known in the art. It is understood that, because the polypeptides of this disclosure can be based upon antibodies or other members of the immunoglobulin superfamily, in some embodiments, the polypeptides can occur as single chains.

As used herein, an "antigen" is a moiety or molecule that contains an epitope to which a binding agent (e.g., an antibody) can bind. As such, an antigen can be bound by an antibody. In some embodiments, the antigen, to which a binding agent (e.g., an antibody) described herein binds, is PD-L1 (e.g., human PD-L1), or a fragment thereof.

As used herein, an "epitope" is a term in the art and refers to a localized region of an antigen to which an antibody can bind. An epitope can be a linear epitope or a conformational, non-linear, or discontinuous, epitope. In the case of a polypeptide antigen, for example, an epitope can be contiguous amino acids of the polypeptide (a "linear" epitope) or an epitope can comprise amino acids from two or more non-contiguous regions of the polypeptide (a "conformational," "non-linear" or "discontinuous" epitope), e.g., human PD-L1. It will be appreciated by one of skill in the art that, in general, a linear epitope may or may not be dependent on secondary, tertiary, or quaternary structure. For example, in some embodiments, an antibody binds to a group of amino acids regardless of whether they are folded in a natural three dimensional protein structure. In other embodiments, an antibody requires amino acid residues making up the epitope to exhibit a particular conformation (e.g., bend, twist, turn or fold) in order to recognize and bind the epitope.

An antibody binds "an epitope" or "essentially the same epitope" or "the same epitope" as a reference antibody, when the two antibodies recognize identical, overlapping or adjacent epitopes in a three-dimensional space. The most widely used and rapid methods for determining whether two antibodies bind to identical, overlapping or adjacent epitopes in a three-dimensional space are competition assays, which can be configured in a number of different formats, for example, using either labeled antigen or labeled antibody. In some assays, the antigen is immobilized on a 96-well plate, or expressed on a cell surface, and the ability of unlabeled antibodies to block the binding of labeled antibodies is measured using radioactive, fluorescent or enzyme labels.

"Epitope binning" is the process of grouping antibodies based on the epitopes they recognize. More particularly, epitope binning comprises methods and systems for discriminating the epitope recognition properties of different antibodies, using competition assays combined with computational processes for clustering antibodies based on their epitope recognition properties and identifying antibodies having distinct binding specificities.

As used herein, the terms "specifically binds," "specifically recognizes," "immunospecifically binds," "selectively binds," "immunospecifically recognizes" and "immunospecific" are analogous terms in the context of antibodies and refer to molecules that bind to an antigen (e.g., epitope) as such binding is understood by one skilled in the art. In some embodiments, "specifically binds" means, for instance that a polypeptide or molecule interacts more frequently, more rapidly, with greater duration, with greater affinity, or with some combination of the above to the epitope, protein, or target molecule than with alternative substances, including related and unrelated proteins. For example, a molecule that specifically binds to an antigen may bind to other peptides or polypeptides, generally with lower affinity as determined by, e.g., immunoassays, Biacore™, KinExA® 3000 instrument (Sapidyne Instruments, Boise, ID), or other assays known in the art. In some embodiments, an antibody or antigen binding domain binds to or specifically binds to an antigen when it binds to an antigen with higher affinity than to any cross-reactive antigen as determined using experimental techniques, such as radioimmunoassays (RIA) and enzyme linked immunosorbent assays (ELISAs). Typically a specific or selective reaction will be at least twice background signal or noise and may be more than 10 times background. See, e.g., Fundamental Immunology 332-36 (Paul ed., 2d ed. 1989) for a discussion regarding binding specificity. In some embodiments, the extent of binding of an antibody or antigen binding domain to a "non-target" protein is less than about 10% of the binding of the antibody or antigen binding domain to its particular target antigen, for example, as determined by fluorescence activated cell sorting (FACS) analysis or RIA. In some embodiments, molecules that specifically bind to an antigen bind to the antigen with a Ka that is at least 2 logs, 2.5 logs, 3 logs, 4 logs or greater than the Ka when the molecules bind to another antigen. In some embodiments, molecules that specifically bind to an antigen do not cross react with other proteins. In another specific embodiment, molecules that specifically bind to an antigen do not cross react with other non-PD-L1 proteins. In some embodiments "specifically binds" means, for instance, that a polypeptide or molecule binds a protein or target with a KD of about 0.1 mM or less, but more usually less than about 1 µM. In some embodiments, "specifically binds" means that a polypeptide or molecule binds a target with a KD of at least about 0.1 µM or less, at least about 0.01 µM or less, or at least about 1 nM or less. Because of the sequence identity between homologous proteins in different species, specific binding can include a polypeptide or molecule that recognizes a protein or target in more than one species. Likewise, because of homology within certain regions of polypeptide sequences of different proteins, specific binding can include a polypeptide or molecule that recognizes more than one protein or target. It is understood that, in some embodiments, a polypeptide or molecule that specifically binds a first target may or may not specifically bind a second target. As such, "specific binding" does not necessarily require (although it can include) exclusive binding, e.g., binding to a single target. Thus, a polypeptide or molecule can, in some embodiments, specifically bind more than one target. In some embodiments, multiple targets can be bound by the same antigen-binding site on the polypeptide or molecule. For example, an antibody can, in certain instances, comprise two identical antigen-binding sites, each of which specifically binds the same epitope on two or more proteins. In certain alternative embodiments, an antibody can be bispecific and comprise at least two antigen-binding sites with differing specificities. Generally, but not necessarily, reference to "binding" means "specific binding".

"Binding affinity" generally refers to the strength of the sum total of noncovalent interactions between a single binding site of a molecule (e.g., a binding protein such as an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a binding molecule X for its binding partner Y can generally be represented by the dissociation constant ($K_D$). Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the present disclosure. In one embodiment, the "$K_D$" or "$K_D$ value" may be measured by biolayer interferometry (BLI) using, for example, the Octet®QK384 sytem (ForteBio, Menlo Park, CA). Alternatively, the $K_D$ may be also be measured in a radiolabeled antigen binding assay (RIA), for example, performed with the Fab version of an antibody of interest and its antigen (Chen, et al., (1999) J. Mol Biol 293:865-881) or using surface plasmon resonance (SPR) assays by Biacore™, using, for example, a BIAcore™TM-2000 or a BIAcore™TM-3000 BIAcore, Inc., Piscataway, NJ). An "on-rate" or "rate of association" or "association rate" or "$k_{on}$," as well as an "off-rate" or "rate of dissociation" or "dissociation rate" or "$k_{off}$" may can also be determined with the same SPR or BLI techniques described above using, for example, the Octet®QK384 sytem (ForteBio, Menlo Park, CA) or a BIAcore™TM-2000 or a BIAcore™TM-3000 (BIAcore, Inc., Piscataway, NJ), respectively.

The term "compete" when used in the context of PD-L1 binding agents (e.g., antibodies) means binding agents that compete for the same epitope or binding site on a target, which includes competition between such binding agents as determined by an assay in which the binding agent under study prevents or inhibits the specific binding of a reference molecule (e.g., a reference ligand, or reference antigen binding protein, such as a reference antibody) to a common antigen (e.g., PD-L1). Numerous types of competitive binding assays can be used to determine if a test binding agent competes with a reference molecule for binding to PD-L1 (e.g., human PD-L1). Examples of assays that can be employed include solid phase direct or indirect radioimmunoassay (RIA), solid phase direct or indirect enzyme immunoassay (EIA), sandwich competition assay (see, e.g., Stahli et al., (1983) Methods in Enzymology 9:242-253); solid phase direct biotin-avidin EIA (see, e.g., Kirkland et al., (1986) J. Immunol. 137:3614-3619) solid phase direct labeled assay, solid phase direct labeled sandwich assay (see, e.g., Harlow and Lane, (1988) Antibodies, A Laboratory Manual, Cold Spring Harbor Press); solid phase direct label RIA using 1-125 label (see, e.g., Morel et al., (1988) Molec. Immunol. 25:7-15); solid phase direct biotin-avidin EIA (see, e.g., Cheung, et al., (1990) Virology 176:546-552); and direct labeled RIA (Moldenhauer et al., (1990) Scand. J. Immunol. 32:77-82). Typically, such an assay involves the use of a purified antigen (e.g., PD-L1, such as human PD-L1) bound to a solid surface or cells bearing either of an unlabelled test antigen binding protein (e.g., test PD-L1 antibody) or a labeled reference antigen binding protein (e.g., reference PD-L1 antibody). Competitive inhibition may be measured by determining the amount of label bound to the solid surface or cells in the presence of the test antigen binding protein. Usually the test antigen binding protein is present in excess. Antibodies identified by competition assay (competing antibodies) include antibodies binding to the same epitope as the reference antibody and/or antibodies binding to an adjacent epitope sufficiently proximal to the epitope bound by the reference for antibodies steric hindrance to occur (e.g., similar epitope or overlapping epitope). Additional details regarding methods for determining competitive binding are described herein, as shown in Example 6. Usually, when a competing antibody is present in excess, it will inhibit specific binding of a reference antibody to a common antigen by at least 20%, for example, at least 20%, 25%, 30%, 35%, 40%, 45%, 50%, 55%, 60%, 65%, 70% or 75%. In some instance, binding is inhibited by at least 80%, 85%, 90%, 95%, 96% or 97%, 98%, 99% or more.

As used herein, the term "constant region" or "constant domain" is a well-known antibody term of art and refers to an antibody portion, e.g., for example, a carboxyl terminal portion of a light and/or heavy chain which is not directly involved in binding of an antibody to antigen but which can exhibit various effector functions, such as interaction with the Fc receptor. The term include the portion of an immunoglobulin molecule having a generally more conserved amino acid sequence relative to an immunoglobulin variable domain.

Antibody "effector functions" refer to those biological activities attributable to the Fc region (e.g., a native sequence Fc region or amino acid sequence variant Fc region) of an antibody, and vary with the antibody isotype. Examples of antibody effector functions include: C1q binding and complement dependent cytotoxicity; Fc receptor binding; antibody-dependent cell-mediated cytotoxicity (ADCC); phagocytosis; down regulation of cell surface receptors (e.g., B cell receptor); and B cell activation.

The term "Fc region" herein is used to define a C-terminal region of an immunoglobulin heavy chain, including, for example, native sequence Fc regions, recombinant Fc regions, and variant Fc regions. Although the boundaries of the Fc region of an immunoglobulin heavy chain might vary, the human IgG heavy chain Fc region is often defined to stretch from an amino acid residue at position Cys226 (according to the EU numbering system), or from Pro230 (according to the EU numbering system), to the carboxyl-terminus thereof. The C-terminal lysine (residue 447 according to the EU numbering system) of the Fc region may be removed, for example, during production or purification of the antibody, or by recombinantly engineering the nucleic acid encoding a heavy chain of the antibody. An exemplary Fc region sequence is provided below (CH2 domain=bold text; CH3 domain=underline text):

```
                                    (SEQ ID NO: 81)
CPPCPAPELLGGPSVFLFPPKPKDTLMISRTPEVTCVVVDVSHEDPEVKF

NWYVDGVEVHNAKTKPREEQYNSTYRVVSVLTVLHQDWLNGKEYKCKVSN

KALPAPIEKTISKAKGQPREPQVYTLPPSRDELTKNQVSLTCLVKGFYPS

DIAVEWESNGQPENNYKTTPPVLDSDGSFFLYSKLTVDKSRWQQGNVFSC

SVMHEALHNHYTQKSLSLSPGK.
```

A "functional Fc region" possesses an "effector function" of a native sequence Fc region. Exemplary "effector functions" include C1q binding; complement dependent cytotoxicity (CDC); Fc receptor binding; antibody-dependent cell-mediated cytotoxicity (ADCC); phagocytosis; down regulation of cell surface receptors (e.g., B cell receptor; BCR), etc. Such effector functions generally require the Fc region to be combined with a binding region or binding domain (e.g., an antibody variable region or domain) and can be assessed using various assays as disclosed.

A "native sequence Fc region" comprises an amino acid sequence identical to the amino acid sequence of an Fc region found in nature, and not manipulated, modified, and/or changed (e.g., isolated, purified, selected, including or combining with other sequences such as variable region sequences) by a human. Native sequence human Fc regions include a native sequence human IgG1 Fc region (non-A and A allotypes); native sequence human IgG2 Fc region; native sequence human IgG3 Fc region; and native sequence human IgG4 Fc region as well as naturally occurring variants thereof.

A "variant Fc region" comprises an amino acid sequence which differs from that of a native sequence Fc region by virtue of at least one amino acid modification, (e.g., substituting, addition, or deletion) preferably one or more amino acid substitution(s). In some embodiments, the variant Fc region has at least one amino acid substitution compared to a native sequence Fc region or to the Fc region of a parent polypeptide, for example, from about one to about ten amino acid substitutions, and preferably from about one to about five amino acid substitutions in a native sequence Fc region or in the Fc region of the parent polypeptide. The variant Fc region described herein can possess at least about 80% homology with a native sequence Fc region and/or with an Fc region of a parent polypeptide, or at least about 90% homology therewith, for example, at least about 95% homology therewith. The variant Fc region herein described herein may have a loss of effector function (e.g., silent Fc). An exemplary variant Fc region ("silent Fc") sequence is provided below (CH2 domain=bold text with amino acid changes underlined; CH3 domain=underline text):

(SEQ ID NO: 82)
CPPCPAPE_AA_GGPSVFLFPPKPKDTLMISRTPEVTCVVVDVSHEDPEVKF

NWYVDGVEVHNAKTKPREEQYNSTYRVVSVLTVLHQDWLNGKEYKCKVSN

KALKAP_IEKT_ISKAKGQPREPQVYTLPPSRDELTKNQVSLTCLVKGFYPS

DIAVEWESNGQPENNYKTTPPVLDSDGSFFLYSKLTVDKSRWQQGNVFSC

SVMHEALHNHYTQKSLSLSPGK.

As used herein, the term "heavy chain" when used in reference to an antibody refers to a polypeptide chain of about 50-70 kDa, wherein the amino-terminal portion includes a variable region of about 120 to 130 or more amino acids, and a carboxy-terminal portion includes one or more constant regions. The "heavy chain" can refer to any distinct types, e.g., for example, alpha ($\alpha$), delta ($\delta$), epsilon ($\varepsilon$), gamma ($\gamma$) and mu ($\mu$), based on the amino acid sequence of the constant domain, which give rise to IgA, IgD, IgE, IgG and IgM classes of antibodies, respectively, including subclasses of IgG, e.g., IgG1, IgG2, IgG3 and IgG4.

As used herein, the term "light chain" when used in reference to an antibody can refer to a polypeptide chain of about 25 kDa, wherein the amino-terminal portion includes a variable region of about 100 to about 110 or more amino acids, and a carboxy-terminal portion includes a constant region. The approximate length of a light chain is 211 to 217 amino acids. There are two distinct types, e.g., kappa ($\kappa$) of lambda ($\lambda$) based on the amino acid sequence of the constant domains. Light chain amino acid sequences are well known in the art.

The terms "antigen binding fragment," "antigen binding domain," "antigen binding region," and similar terms refer to that portion of an antibody, which comprises the amino acid residues that interact with an antigen and confer on the binding fragment, domain, or region its specificity and affinity for the antigen (e.g., the CDRs). "Antigen binding fragment" as used herein include "antibody fragment," which comprise a portion of an antibody including one or more CDRs, such as the antigen binding or variable region of the antibody.

Antibodies described herein include, but are not limited to, synthetic antibodies, monoclonal antibodies, recombinantly produced antibodies, multispecific antibodies (e.g., including bispecific antibodies), human antibodies, humanized antibodies, chimeric antibodies, intrabodies, single-chain Fvs (scFv) (e.g., including monospecific, bispecific, etc.), camelized antibodies, Fab fragments, F(ab') fragments, disulfide-linked Fvs (sdFv), anti-idiotypic (anti-Id) antibodies, and epitope-binding fragments of any of the above.

In some embodiments, antibodies described herein include immunoglobulin molecules and immunologically active portions of immunoglobulin molecules, including molecules that contain one or more antigen binding sites that bind to a PD-L1 antigen. Antibodies can be of any type (e.g., IgG, IgE, IgM, IgD, IgA or IgY), any class, (e.g., IgG1, IgG2, IgG3, IgG4, IgA1 or IgA2), or any subclass (e.g., IgG2a or IgG2b) of immunoglobulin molecule. In some embodiments, antibodies described herein are IgG antibodies (e.g., human IgG), or a class (e.g., human IgG1, IgG2, IgG3 or IgG4) or subclass thereof.

In some embodiments, an antibody is a 4-chain antibody unit comprising two heavy (H) chain/light (L) chain pairs, wherein the amino acid sequences of the H chains are identical and the amino acid sequences of the L chains are identical. In some embodiments, the H and L chains comprise constant regions, for example, human constant regions. In some embodiments, the L chain constant region of such antibodies is a kappa or lambda light chain constant region, for example, a human kappa or lambda light chain constant region. In some embodiments, the H chain constant region of such antibodies comprise a gamma heavy chain constant region, for example, a human gamma heavy chain constant region. In some embodiments, such antibodies comprise IgG constant regions, for example, human IgG constant regions (e.g., IgG1, IgG2, IgG3, and/or IgG4 constant regions).

An antibody or fragment thereof may preferentially bind to PD-L1, such as human PD-L1, meaning that the antibody or fragment thereof binds PD-L1 with greater affinity than it binds to an unrelated control protein and/or binds human PD-L1 with greater affinity than it binds to an unrelated control protein. For example, the antibody or fragment thereof may specifically recognize and bind PD-L1 or a portion thereof. "Specific binding" means that the antibody or fragment thereof binds to PD-L1 with an affinity that is at least 5, 10, 15, 20, 25, 50, 100, 250, 500, 1000, or 10,000 times greater than the affinity for an unrelated control protein (e.g., hen egg white lysozyme). In some embodiments, the antibody or fragment thereof may bind PD-L1 substantially exclusively (e.g., is able to distinguish PD-L1 from other known polypeptides, for example, by virtue of measurable differences in binding affinity). In some embodiments, a PD-L1 binding agent (e.g., an antibody) may react with PD-L1 sequences other than human PD-L1 sequences (e.g., cynomolgous PD-L1 sequences).

The term "variable region" or "variable domain" refers to a portion of the light or heavy chains of an antibody that is generally located at the amino-terminal of the light or heavy chain and has a length of about 120 to 130 amino acids in the heavy chain and about 100 to 110 amino acids in the light chain, and are used in the binding and specificity of each particular antibody for its particular antigen. The variable region of the heavy chain may be referred to as "VH." The variable region of the light chain may be referred to as "VL." The term "variable" refers to the fact that certain segments of the variable regions differ extensively in sequence among antibodies. The V region mediates antigen binding and defines specificity of a particular antibody for its particular antigen. However, the variability is not evenly distributed across the 110-amino acid span of the variable regions. Instead, the V regions consist of less variable (e.g., relatively invariant) stretches called framework regions (FRs) of about 15-30 amino acids separated by shorter regions of greater variability (e.g., extreme variability) called "hypervariable regions" or alternatively called "complementarity determining regions." The variable regions of heavy and light chains each comprise four FRs (FR1, FR2, FR3 and FR4), largely adopting a β sheet configuration, connected by three hypervariable regions, which form loops connecting, and in some cases forming part of, the β sheet structure. The hypervariable regions in each chain are held together in close proximity by the FRs and, with the hypervariable regions from the other chain, contribute to the formation of the antigen-binding site of antibodies (see, e.g., Kabat et al., Sequences of Proteins of Immunological Interest, 5th Ed. Public Health Service, National Institutes of Health, Bethesda, MD, 1991)). The constant regions are not involved directly in binding an antibody to an antigen, but exhibit various effector functions, such as participation of the antibody in antibody dependent cellular cytotoxicity (ADCC) and complement dependent cytotoxicity (CDC). The variable regions differ extensively in sequence between different antibodies. The variability in sequence is concentrated in the CDRs while the less variable portions in the variable region are referred to as framework regions (FR). The CDRs of the light and heavy chains are primarily responsible for the interaction of the antibody with antigen. In specific embodiments, the variable region is a human variable region.

The term "hypervariable region," "HVR," "HV," "complementarity determining region," or "CDR" when used herein refers to the regions of an antibody variable region that are hypervariable in sequence and/or form structurally defined loops. Generally, antibodies comprise six hypervariable regions; three in the VH (H1, H2, H3), and three in the VL (L1, L2, L3). A number of hypervariable region delineations are in use and are encompassed herein. The Kabat CDRs are based on sequence variability and are the most commonly used (see, e.g., Kabat et al., Sequences of Proteins of Immunological Interest, 5th Ed. Public Health Service, National Institutes of Health, Bethesda, MD. (1991)). Chothia refers instead to the location of the structural loops (see, e.g., Chothia and Lesk, J. Mol. Biol. 196:901-917 (1987)). The end of the Chothia CDR-H1 loop when numbered using the Kabat numbering convention varies between H32 and H34 depending on the length of the loop (this is because the Kabat numbering scheme places the insertions at H35A and H35B; if neither 35A nor 35B is present, the loop ends at 32; if only 35A is present, the loop ends at 33; if both 35A and 35B are present, the loop ends at 34). The AbM hypervariable regions represent a compromise between the Kabat CDRs and Chothia structural loops, and are used by Oxford Molecular's AbM antibody modeling software (see, e.g., Martin, in Antibody Engineering, Vol. 2, Chapter 3, Springer Verlag). The "contact" hypervariable regions are based on an analysis of the available complex crystal structures. The residues from each of these hypervariable regions or CDRs are noted below.

A universal numbering system has been developed and widely adopted, ImMunoGeneTics (IMGT) Information System® (Lefranc et al., Dev. Comp. Immunol. 27(1):55-77 (2003)). IMGT is an integrated information system specializing in immunoglobulins (IG), T cell receptors (TR) and major histocompatibility complex (MHC) of human and other vertebrates. Herein, the CDRs are referred to in terms of both the amino acid sequence and the location within the light or heavy chain. As the "location" of the CDRs within the structure of the immunoglobulin variable domain is conserved between species and present in structures called loops, by using numbering systems that align variable domain sequences according to structural features, CDR and framework residues and are readily identified. This information can be used in grafting and replacement of CDR residues from immunoglobulins of one species into an acceptor framework from, typically, a human antibody. An additional numbering system (AHon) has been developed by Honegger and Pluckthun, J. Mol. Biol. 309: 657-670 (2001). Correspondence between the numbering system, including, for example, the Kabat numbering and the IMGT unique numbering system, is well known to one skilled in the art (see, e.g., Kabat, supra; Chothia and Lesk, supra; Martin, supra; Lefranc et al., supra) and is also illustrated below. An Exemplary system, shown herein, combines Kabat and Chothia.

| | Exemplary | IMGT | Kabat | AbM | Chothia | Contact |
|---|---|---|---|---|---|---|
| VH CDR1 | 26-35 | 27-38 | 31-35 | 26-35 | 26-32 | 30-35 |
| VH CDR2 | 50-65 | 56-65 | 50-65 | 50-58 | 52a/53-55 | 47-58 |
| VH CDR3 | 95-102 | 105-117 | 95-102 | 95-102 | 96-101 | 93-101 |
| VL CDR1 | 24-34 | 27-38 | 24-34 | 24-34 | 26-32 | 30-36 |
| VL CDR2 | 50-56 | 56-65 | 50-56 | 50-56 | 50-52 | 46-55 |
| VL CDR3 | 89-97 | 105-117 | 89-97 | 89-97 | 91-96 | 89-96 |

Hypervariable regions may comprise "extended hypervariable regions" as follows: 24-36 or 24-34 (L1), 46-56 or 50-56 (L2) and 89-97 or 89-96 (L3) in the VL and 26-35 or 26-35A (H1), 50-65 or 49-65 (H2) and 93-102, 94-102, or 95-102 (H3) in the VH. As used herein, the terms "hypervariable region," "HVR," "HV," "complementarity determining region," or "CDR" are used interchangeably.

The term "vector" refers to a substance that is used to carry or include a nucleic acid sequences, including for example, in order to introduce a nucleic acid sequence into a host cell. Vectors applicable for use include, for example, expression vectors, plasmids, phage vectors, viral vectors, episomes and artificial chromosomes, which can include selection sequences or markers operable for stable integration into a host cell's chromosome. Additionally, the vectors can include one or more selectable marker genes and appropriate expression control sequences. Selectable marker genes that can be included, for example, provide resistance to antibiotics or toxins, complement auxotrophic deficiencies, or supply critical nutrients not in the culture media. Expression control sequences can include constitutive and inducible promoters, transcription enhancers, transcription terminators, and the like which are well known in the art. When two or more nucleic acid molecules are to be co-expressed (e.g. both an antibody heavy and light chain or an antibody VH and VL) both nucleic acid molecules can be inserted, for example, into a single expression vector or in separate expression vectors. For single vector expression, the encoding nucleic acids can be operationally linked to one common expression control sequence or linked to different expression control sequences, such as one inducible promoter and one constitutive promoter. The introduction of nucleic acid molecules into a host cell can be confirmed using methods well known in the art. Such methods include, for example, nucleic acid analysis such as Northern blots or polymerase chain reaction (PCR) amplification of mRNA, or immunoblotting for expression of gene products, or other suitable analytical methods to test the expression of an introduced nucleic acid sequence or its corresponding gene product. It is understood by those skilled in the art that the nucleic acid molecules are expressed in a sufficient amount to produce a desired product (e.g., a PD-L1 binding agent as described herein), and it is further understood that expression levels can be optimized to obtain sufficient expression using methods well known in the art.

"Dysfunction" in the context of immune dysfunction, refers to a state of immune reduced responsiveness to antigenic stimulation. The term includes the common elements of both exhaustion and/or anergy in which antigen recognition may occur, but the ensuing immune response is ineffective to control infection or tumor growth.

A "T cell dysfunctional disease" and "T cell dysfunctional disorder" and "T cell dysfunctional condition" are used interchangeably and refer to any disease, disorder or condition of T cells characterized by decreased responsivemess to antigenic stimulation. A T cell dysfunctional disease includes a disease, disorder or condition that is completely or partially caused by or is the result of PD-L1 or the interaction of PD-L1 with PD-1 and/or alternatively any disease, disorder, or condition in which it is desirable to inhibit the in vivo effects of the interaction of PD-L1 with PD-1. In some embodiments, a T cell dysfunctional disease is a disease, disorder or contition that is specifically associated with inappropriate increased signaling through PD-1. In some embodiments, a T cell dysfunctional disease is one in which T cells are anergic or have decreased ability to secrete cytokines, proliferate, or execute cytolytic activity. In some embodiments, the decreased responsiveness results in ineffective control of a pathogen or tumor, including but not limited to tumors expressing PD-L1. Examples of a T cell dysfunctional disease characterized by T cell dysfunction include unresolved acute infection, chronic infection and tumor immunity (e.g., from any cancers, including but not limited to cancers that express or overexpress PD-L1).

"Tumor immunity" refers to the process in which tumors evade immune recognition and clearance. Thus, as a therapeutic concept, tumor immunity is "treated" when such evasion is attenuated and the tumors are recognized and attacked by the immune system. Such treatment thus includes treatment of any cancer. Examples of tumor recognition include tumor binding, tumor strinkage and tumor clearance.

"Enhancing T cell function" means to induce, cause or stimulate a T cell to have a sustained or increased biological function, or renew or reactivate exhausted or inactive T cells. Examples of enhancing T cell function include: increased secretion of cytokines (e.g., TNFα, IFNγ) from CD8$^+$ T cells, increased proliferation, increased antigen responsiveness (e.g., tumor cell removal) relative to such levels before the intervention. In some embodiments, the level of enhancement is as least 50%, alternatively 60%, 70%, 80%, 90%, 100%, 120%, 150%, 200%. The manner of measuring this enhancement is known to one of ordinary skill in the art.

An "effective amount" is generally an amount sufficient to reduce the severity and/or frequency of symptoms, eliminate the symptoms and/or underlying cause, prevent the occurrence of symptoms and/or their underlying cause, and/or improve or remediate the damage that results from or is associated with a disease, disorder, or condition. In some embodiments, the effective amount is a therapeutically effective amount or a prophylactically effective amount.

The term "therapeutically effective amount" as used herein refers to the amount of an agent (e.g., an antibody described herein or any other agent described herein) that is sufficient to reduce and/or ameliorate the severity and/or duration of a given disease, disorder or condition, and/or a symptom related thereto. A therapeutically effective amount of an agent, including a therapeutic agent, can be an amount necessary for (i) reduction or amelioration of the advancement or progression of a given disease, disorder, or condition, (ii) reduction or amelioration of the recurrence, development or onset of a given disease, disorder or conditions, and/or (iii) to improve or enhance the prophylactic or therapeutic effect of another therapy (e.g., a therapy other than the administration of an antibody described herein). A "therapeutically effective amount" of a substance/molecule/agent of the present disclosure (e.g., a PD-L1 antibody) may vary according to factors such as the disease state, age, sex, and weight of the individual, and the ability of the substance/molecule/agent, to elicit a desired response in the individual. A therapeutically effective amount encompasses an amount in which any toxic or detrimental effects of the substance/molecule/agent are outweighed by the therapeutically beneficial effects. In certain embodiments, the term "therapeutically effective amount" refers to an amount of an antibody or other agent (e.g., or drug) effective to "treat" a disease, disorder, or condition, in a subject or mammal.

A "prophylactically effective amount" is an amount of a pharmaceutical composition that, when administered to a subject, will have the intended prophylactic effect, e.g., preventing or delaying the onset (or reoccurrence) of a disease, disorder or condition, or reducing the likelihood of the onset (or reoccurrence) of a disease, disorder, or condition or associated symptom(s). The full therapeutic or prophylactic effect does not necessarily occur by administration of one dose, and may occur only after administration of a series of doses. Thus, a therapeutically or prophylactically effective amount may be administered in one or more administrations.

The term "pharmaceutically acceptable" as used herein means being approved by a regulatory agency of the Federal or a state government, or listed in the U.S. Pharmacopeia, European Pharmacopeia or other generally recognized Pharmacopeia for use in animals, and more particularly in humans.

"Carriers" as used herein include carriers, excipients, or stabilizers that are nontoxic to the cell or mammal being exposed thereto at the dosages and concentrations employed. Often the carrier is an aqueous pH buffered solution. Examples of carriers include buffers such as phosphate, citrate, and other organic acids; antioxidants including ascorbic acid; low molecular weight ((e.g., less than about 10 amino acid residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, polyethylene glycol (PEG), and PLURONICS™. The term "carrier" can also refer to a diluent, adjuvant (e.g., Freund's adjuvant (complete or incomplete)), excipient, or vehicle with which the therapeutic is administered. Such carriers can be sterile liquids, such as water and oils, including those of petroleum, animal, vegetable or synthetic origin, such as peanut oil, soybean oil, mineral oil, sesame oil and the like. Water is an exemplary carrier when a composition (e.g., a pharmaceutical composition) is administered intravenously. Saline solutions and aqueous dextrose and glycerol solutions can also be employed as liquid carriers, particularly for injectable solutions. Suitable excipients (e.g., pharmaceutical excipients) include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. Compositions can take the form of solutions, suspensions, emulsion, tablets, pills, capsules, powders, sustained-release formulations and the like. Oral compositions, including formulations, can include standard carriers such as pharmaceutical grades of mannitol, lactose, starch, magnesium stearate, sodium saccharine, cellulose, magnesium carbonate, etc. Examples of suitable carriers are described in Remington's Pharmaceutical Sciences (1990) Mack Publishing Co., Easton, PA. Compositions, including pharmaceutical compounds, may contain a prophylactically or therapeutically effective amount of a PD-L1 binding agent (e.g., an antibody), for example, in isolated or purified form, together with a suitable amount of carrier so as to provide the form for proper administration to the subject (e.g., patient). The formulation should suit the mode of administration.

In some embodiments, the present disclosure provides PD-L1 binding agents that can be used herein as therapeutic agents. Such agents include antibodies (e.g., monospecific or multispecific, including bispecific) that bind to PD-L1. Exemplary antibodies include polyclonal, monoclonal, humanized, human, bispecific, and heteroconjugate antibodies, as well as variants thereof having increased or decreased affinity or other properties.

In some embodiments, described herein are PD-L1 binding agents (e.g., antibodies) that bind to PD-L1, including a PD-L1 polypeptide, a PD-L1 polypeptide fragment, a PD-L1 peptide or a PD-L1 epitope. In some embodiments, the PD-L1 binding agents are human or humanized antibodies (e.g., comprising human constant regions) that bind PD-L1, including a PD-L1 polypeptide, a PD-L1 polypeptide fragment, a PD-L1 peptide or a PD-L1 epitope. In some embodiments, a PD-L1 binding agent (e.g., an antibody), such as a human PD-L1 binding agent, can bind to PD-L1 expressed on the surface of a mammalian (e.g., human) cell, including a PD-L1 expressing tumor cell. In some embodiments, a PD-L1 binding agent (e.g., an antibody) binds a PD-L1 extracellular epitope exposed on a cell such as a tumor cell (e.g., a PD-L1 epitope). In some embodiments, described herein is a PD-L1 binding agent (e.g., an antibody) that binds to PD-L1, such as human PD-L1 or portions thereof. In some embodiments, PD-L1 is a human PD-L1. In some embodiments, a PD-L1 binding agent is a human PD-L1 binding agent (e.g., an antibody that binds to human PD-L1). An exemplary amino acid sequence of human PD-L1 is described herein.

In some embodiments, the PD-L1 binding agents (e.g., antibodies) described herein compete for the binding to PD-L1, such as human PD-L1, with a PD-L1 binding agent (e.g., an antibody) that comprises a VH region, VL region, VH CDR1, VH CDR2, VH CDR3, VL CDR1, VL CDR2, and/or VL CDR3 of any one of the antibodies described herein, such as an amino acid sequence of a VH region, VL region, VH CDR1, VH CDR2, VH CDR3, VL CDR1, VL CDR2, and/or VL CDR3 depicted in Tables 1-3. Accordingly, in some embodiments, a PD-L1 binding agent (e.g., an antibody) described herein competes for the binding to PD-L1, such as human PD-L1, with a PD-L1 binding agent (e.g., an antibody) that comprises one, two, and/or three VH CDRs and/or one, two, and/or three VL CDRs from: (a) the antibody designated P22; (b) the antibody designated P24; or (c) the antibody designated P31.2, as shown in Tables 1-3. In some embodiments, a PD-L1 binding agent (e.g., an antibody) described herein competes for the binding to PD-L1, such as human PD-L1, with a PD-L1 binding agent (e.g., an antibody) that comprises one, two, and/or three VH CDRs and one, two, and/or three VL CDRs from: (a) the antibody designated P22; (b) the antibody designated P24; or (c) the antibody designated P31.2, as shown in Tables 1-3. In some embodiments, a PD-L1 binding agent (e.g., an antibody) described herein competes for the binding to PD-L1, such as human PD-L1, with a PD-L1 binding agent (e.g., an antibody) that comprises a VH region and VL region from: (a) the antibody designated P22; (b) the antibody designated P24; or (c) the antibody designated P31.2, as shown in Tables 1-3. In some embodiments, a PD-L1 binding agent (e.g., an antibody) described herein competes for the binding to PD-L1, such as human PD-L1, with a PD-L1 binding agent (e.g., an antibody) that comprises: (a) a VH region comprising the amino acid sequence of SEQ ID NO:25 and a VL region comprising the amino acid sequence of SEQ ID NO:26; (b) a VH region comprising the amino acid sequence of SEQ ID NO:51 and a VL region comprising the amino acid sequence of SEQ ID NO:52; or (c) a VH region comprising the amino acid sequence of SEQ ID NO:77 and a VL region comprising the amino acid sequence of SEQ ID NO:78.

In some embodiments, the PD-L1 binding agents (e.g., antibodies) described herein comprise a VH region, VL region, VH CDR1, VH CDR2, VH CDR3, VL CDR1, VL CDR2, and/or VL CDR3 of any one of the antibodies described herein, such as an amino acid sequence of a VH region, VL region, VH CDR1, VH CDR2, VH CDR3, VL CDR1, VL CDR2, and/or VL CDR3 depicted in Tables 1-3. Accordingly, in some embodiments, a PD-L1 binding agent (e.g., an antibody) described herein comprises one, two, and/or three heavy chain CDRs and/or one, two, and/or three light chain CDRs from: (a) the antibody designated P22; (b) the antibody designated P24; or (c) the antibody designated P31.2, as shown in Tables 1-3. In some embodiments, a PD-L1 binding agent (e.g., an antibody) described herein comprises one, two, and/or three heavy chain CDRs and one, two, and/or three light chain CDRs from: (a) the antibody designated P22; (b) the antibody designated P24; or (c) the antibody designated P31.2, as shown in Tables 1-3.

In some embodiments, a PD-L1 binding agent (e.g., an antibody) comprises a VH region, which comprises VH CDR1, VH CDR2, and/or VH CDR3, and a VL region, which comprises VL CDR1, VL CDR2, and/or VL CDR3, of any one of the binding agents described herein (see, e.g., Table 1, Table 2, Table 3). Accordingly, in some embodiments, a PD-L1 binding agent (e.g., an antibody) described herein comprises one, two, and/or three heavy chain CDRs and/or one, two, and/or three light chain CDRs from Table 1. In some embodiments, a PD-L1 binding agent described herein comprises one, two, and/or three heavy chain CDRs and/or one, two, and/or three light chain CDRs from Table 2. In some embodiments, a PD-L1 binding agent (e.g., an antibody) described herein comprises one, two, and/or three heavy chain CDRs and/or one, two, and/or three light chain CDRs from Table 3. In some embodiments, a PD-L1 binding agent (e.g., an antibody) described herein is bispecific and comprises a first binding domain that comprises one, two, and/or three heavy chain CDRs and/or one, two, and/or three light chain CDRs from Table 1, Table 2, or Table 3 and a second binding domain that comprises one, two, and/or three heavy chain CDRs and/or one, two, and/or three light chain CDRs from a binding agent that binds to a second target antigen that is not PD-L1.

The antibody designated P22 comprises a VH sequence that is SEQ ID NO:25 and a VL sequence that is SEQ ID NO:26.

The antibody designated P24 comprises a VH sequence that is SEQ ID NO:51 and a VL sequence that is SEQ ID NO:52.

The antibody designated P31.2 comprises a VH sequence that is SEQ ID NO:77 and a VL sequence that is SEQ ID NO:78.

TABLE 1

Antibody P22

|  |  | Exemplary | IMGT | Kabat | Chothia | Contact | AbM |
|---|---|---|---|---|---|---|---|
| VH CDR Seq. | VH CDR1 | GFTFSSYYIH (SEQ ID NO: 1) | GFTFSSYY (SEQ ID NO: 7) | SYYIH (SEQ ID NO: 12) | GFTFSSY (SEQ ID NO: 13) | SSYYIH (SEQ ID NO: 18) | GFTFSSYYIH (SEQ ID NO: 1) |
|  | VH CDR2 | WITSHGYSTKYAD SVKG (SEQ ID NO: 2) | ITSHGYST (SEQ ID NO: 8) | WITSHGYST KYADSVKG (SEQ ID NO: 2) | SHGY (SEQ ID NO: 14) | WVAWITSHGYST K (SEQ ID NO: 19) | WITSHGYSTK (SEQ ID NO: 24) |
|  | VH CDR3 | DSVIYGLDY (SEQ ID NO: 3) | ARDSVIYGLDY (SEQ ID NO: 9) | DSVIYGLDY (SEQ ID NO: 3) | SVIYGLD (SEQ ID NO: 15) | ARDSVIYGLD (SEQ ID NO: 20) | DSVIYGLDY (SEQ ID NO: 3) |
| VL CDR Seq. | VL CDR1 | RASQSVSSAVA (SEQ ID NO: 4) | QSVSSA (SEQ ID NO: 10) | RASQSVSSA VA (SEQ ID NO: 4) | SQSVSSA (SEQ ID NO: 16) | SSAVAWY (SEQ ID NO: 21) | RASQSVSSAVA (SEQ ID NO: 4) |
|  | VL CDR2 | SASSLYS (SEQ ID NO: 5) | SAS (SEQ ID NO: 11) | SASSLYS (SEQ ID NO: 5) | SAS (SEQ ID NO: 11) | LLIYSASSLY (SEQ ID NO: 22) | SASSLYS (SEQ ID NO: 5) |
|  | VL CDR3 | QQYYTSPYT (SEQ ID NO: 6) | QQYYTSPYT (SEQ ID NO: 6) | QQYYTSPYT (SEQ ID NO: 6) | YYTSPY (SEQ ID NO: 17) | QQYYTSPY (SEQ ID NO: 23) | QQYYTSPYT (SEQ ID NO: 6) |

VH Sequence:
EVQLVESGGGLVQPGGSLRLSCAASGFTFSSYYIHWVRQAPGKGLEWVAWITSHGYSTKYADSVKGRFTISADTSKNTAYLQMNSLRAE
DTAVYYCARDSVIYGLDYWGQGTLVT (SEQ ID NO: 25)

VL Sequence:
DIQMTQSPSSLSASVGDRVTITCRASQSVSSAVAWYQQKPGKAPKLLIYSASSLYSGVPSRFSGSRSGTDFTLTISSLQPEDFATYYCQ
QYYTSPYTFGQGTKVEIK (SEQ ID NO: 26)

TABLE 2

Antibody P24

|  |  | Exemplary | IMGT | Kabat | Chothia | Contact | AbM |
|---|---|---|---|---|---|---|---|
| VH CDR Seq. | VH CDR1 | GFTFDQYYIH (SEQ ID NO: 27) | GFTFDQYY (SEQ ID NO: 33) | QYYIH (SEQ ID NO: 38) | GFTFDQY (SEQ ID NO: 39) | DQYYIH (SEQ ID NO: 44) | GFTFDQYYIH (SEQ ID NO: 27) |
|  | VH CDR2 | EIYPAGSYTYYAD SVKG (SEQ ID NO: 28) | IYPAGSYT (SEQ ID NO: 34) | EIYPAGSYTYYAD SVKG (SEQ ID NO: 28) | PAGS (SEQ ID NO: 40) | WWVAEIYPAGSYTY (SEQ ID NO: 45) | EIYPAGSYTY (SEQ ID NO: 50) |
|  | VH CDR3 | GPYSVRYALDY (SEQ ID NO: 29) | ARGPYSVR YALDY (SEQ ID NO: 35) | GPYSVRYALDY (SEQ ID NO: 29) | PYSVRYALD (SEQ ID NO: 41) | ARGPYSVRYALD (SEQ ID NO: 46) | GPYSVRYALDY (SEQ ID NO: 29) |
| VL CDR Seq. | VL CDR1 | RASQSVSSAVA (SEQ ID NO: 30) | QSVSSA (SEQ ID NO: 36) | RASQSVSSAVA (SEQ ID NO: 30) | SQSVSSA (SEQ ID NO: 42) | SSAVAWY (SEQ ID NO: 47) | RASQSVSSAVA (SEQ ID NO: 30) |
|  | VL CDR2 | SASSLYS (SEQ ID NO: 31) | SAS (SEQ ID NO: 37) | SASSLYS (SEQ ID NO: 31) | SAS (SEQ ID NO: 37) | LLIYSASSLY (SEQ ID NO: 48) | SASSLYS (SEQ ID NO: 31) |
|  | VL CDR3 | QQVSYSPYT (SEQ ID NO: 32) | QQVSYSPYT (SEQ ID NO: 32) | QQVSYSPYT (SEQ ID NO: 32) | VSYSPY (SEQ ID NO: 43) | QQVSYSPY (SEQ ID NO: 49) | QQVSYSPYT (SEQ ID NO: 32) |

TABLE 2-continued

Antibody P24

| Exemplary | IMGT | Kabat | Chothia | Contact | AbM |
|-----------|------|-------|---------|---------|-----|

VH Sequence:
EVQLVESGGGLVQPGGSLRLSCAASGFTFDQYYIHWVRQAPGKGLEWVAEIYPAGSYTYYADSVKGRFTISADTSKNTAYLQMNSLRAE
DTAVYYCARGPYSVRYALDYWGQGTLVT (SEQ ID NO: 51)

VL Sequence:
DIQMTQSPSSLSASVGDRVTITCRASQSVSSAVAWYQQKPGKAPKLLIYSASSLYSGVPSRFSGSRSGTDFTLTISSLQPEDFATYYCQ
QVSYSPYTFGQGTKVEIK (SEQ ID NO: 52)

TABLE 3

Antibody P31.2

| | | Exemplary | IMGT | Kabat | Chothia | Contact | AbM |
|---|---|-----------|------|-------|---------|---------|-----|
| VH CDR Seq. | VH CDR1 | GFTFSSYYIH (SEQ ID NO: 53) | GFTFSSYY (SEQ ID NO: 59) | SYYIH (SEQ ID NO: 64) | GFTFSSY (SEQ ID NO: 65) | SSYYIH (SEQ ID NO: 70) | GFTFSSYYIH (SEQ ID NO: 53) |
| | VH CDR2 | TISSGGGFTYYAD SVKG (SEQ ID NO: 54) | ISSGGGFT (SEQ ID NO: 60) | TISSGGGFTYYA DSVKG (SEQ ID NO: 54) | SGGG (SEQ ID NO: 66) | WVATISSGGGFTY (SEQ ID NO: 71) | TISSGGGFTY (SEQ ID NO: 76) |
| | VH CDR3 | GYTLTPVLDY (SEQ ID NO: 55) | ARGYTLTPVLDY (SEQ ID NO: 61) | GYTLTPVLDY (SEQ ID NO: 55) | YTLTPVLD (SEQ ID NO: 67) | ARGYTLTPVLD (SEQ ID NO: 72) | GYTLTPVLDY (SEQ ID NO: 55) |
| VL CDR Seq. | VL CDR1 | RASQSVSSAVA (SEQ ID NO: 56) | QSVSSA (SEQ ID NO: 62) | RASQSVSSAVA (SEQ ID NO: 56) | SQSVSSA (SEQ ID NO: 68) | SSAVAWY (SEQ ID NO: 73) | RASQSVSSAVA (SEQ ID NO: 56) |
| | VL CDR2 | SASSLYS (SEQ ID NO: 57) | SAS (SEQ ID NO: 63) | SASSLYS (SEQ ID NO: 57) | SAS (SEQ ID NO: 63) | LLIYSASSLY (SEQ ID NO: 74) | SASSLYS (SEQ ID NO: 57) |
| | VL CDR3 | QQFGAEPIT (SEQ ID NO: 58) | QQFGAEPIT (SEQ ID NO: 58) | QQFGAEPIT (SEQ ID NO: 58) | FGAEPI (SEQ ID NO: 69) | QQFGAEPI (SEQ ID NO: 75) | QQFGAEPIT (SEQ ID NO: 58) |

VH Sequence:
EVQLVESGGGLVQPGGSLRLSCAASGFTFSSYYIHWVRQAPGKGLEWVATISSGGGFTYYADSVKGRFTISADTSKNTAYLQMNSLRAE
DTAVYYCARGYTLTPVLDYWGQGTLVT (SEQ ID NO: 77)

VL Sequence:
DIQMTQSPSSLSASVGDRVTITCRASQSVSSAVAWYQQKPGKAPKLLIYSASSLYSGVPSRFSGSRSGTDFTLTISSLQPEDFATYYCQ
QFGAEPITFGQGTKVEIK (SEQ ID NO: 78)

In some embodiments, PD-L1 binding agents (e.g., antibodies, such as bispecific antibodies), including human PD-L1 binding agents, described herein comprise a VH region or VH domain. In other embodiments, PD-L1 binding agents (e.g., antibodies, such as bispecific antibodies), including human PD-L1 binding agents, described herein comprise a VL region or VL domain. In some embodiments, PD-L1 binding agents (e.g., antibodies, such as bispecific antibodies), including human PD-L1 binding agents, described herein have a combination of (i) a VH domain or VH region; and/or (ii) a VL domain or VL region.

In some embodiments, PD-L1 binding agents (e.g., antibodies, such as bispecific antibodies), including human PD-L1 binding agents, described herein comprise heavy chain having a combination of (i) a VH domain described in any one of Tables 1-3; and (ii) one or more heavy chain constant domains (e.g., CH1, Hinge, CH2, and CH3). An exemplary IgG heavy chain comprises any VH domain as described herein and the following CH1, Hinge, CH2, and CH3 amino acid sequence:

ASTKGPSVFPLAPSSKSTSGGTAALGCLVKDYF-
PEPVTVSWNSGALTSGVH TFPAVLQSSGGLYS-
LSSVVTVPSSSLGTQTYICNVNHKPSNTKVDKKVE-

PKSCDKTHTC PPCPAPELLGGPSVFLFPPKPKDTLM-
ISRTPEVTCVVVDVSHEDPEVKFNWYVDGVEV
HNAKTKPREEQYNSTYRVVSVLTVLHQDWLN-
GKEYKCKVSNKALPAPIEKTISKAKGQ PREPQVY-
TLPPSRDELTKNQVSLTCLVKGFYPSDIAVEWESNGQ-
PENNYKTTPPVLDS DGSFFLYSKLTVDKSRWQQGN-
VFSCSVMHEALHNHYTQKSLSLSPGK (SEQ ID NO:96). Another exemplary IgG heavy chain comprises any VH domain as described herein and the following CH1, Hinge, CH2, and CH3 amino acid sequence:

(SEQ ID NO: 98)
ASTKGPSVFPLAPSSKSTSGGTAALGCLVKDYFPEPVTVSWNSGALTSG

VHTFPAVLQSSGLYSLSSVVTVPSSSLGTQTYICNVNHKPSNTKVDKKV

EPKSCDKTHTCPPCPAPEAAGGPSVFLFPPKPKDTLMISRTPEVTCVVV

DVSHEDPEVKFNWYVDGVEVHNAKTKPREEQYNSTYRVVSVLTVLHQDW

LNGKEYKCKVSNKALKAPIEKTISKAKGQPREPQVYTLPPSRDELTKNQ

-continued

```
VSLTCLVKGFYPSDIAVEWESNGQPENNYKTTPPVLDSDGSFFLYSKLT

VDKSRWQQGNVFSCSVMHEALHNHYTQKSLSLSPGK
```

In some embodiments, PD-L1 binding agents (e.g., antibodies, such as bispecific antibodies), including human PD-L1 binding agents, described herein comprise a light chain having a combination of (i) a VL domain described in any one of Tables 1-3; and (ii) a light chain constant domain (CL). An exemplary light chain (e.g., for pairing with an IgG heavy chain) comprises any VL as domain described herein and the following CL amino acid sequence:

```
                                          (SEQ ID NO: 97)
RTVAAPSVFIFPPSDSQLKSGTASVVCLLNNFYPREAKVQWKVDNALQS

GNSQESVTEQDSKDSTYSLSSTLTLSKADYEKHKVYACEVTHQGLSSPV

TKSFNRGEC.
```

In some embodiments, PD-L1 binding agents (e.g., antibodies, such as bispecific antibodies), including human PD-L1 binding agents, described herein comprise (a) a heavy chain have a combination of (i) a VH domain described in any one of Tables 1-3, and (ii) one or more heavy chain constant domains (e.g., CH1, Hinge, CH2, and CH3); and (b) a light chain having a combination of (i) a VL domain described in any one of Tables 1-3, and (ii) a light chain constant domain in an IgG format (CL1). An exemplary PD-L1 binding agent (e.g., an antibody) comprises an IgG heavy chain comprising any VH domain as described herein and the amino acid sequence of SEQ ID NO:96 or 98, and a light chain comprising any VL domain as described herein and the amino acid sequence of SEQ ID NO:97.

In some embodiments, PD-L1 binding agents (e.g., antibodies, such as bispecific antibodies), including a human PD-L1 binding agent, described herein comprises one or more CDRs, including six CDRs, for example, VH CDR1, VH CDR2, VH CDR3, VL CDR1, VL CDR2, and/or VL CDR3 identified in Table 1. In some embodiments, PD-L1 binding agents (e.g., antibodies, such as bispecific antibodies), including a human PD-L1 binding agent, described herein comprises one or more, including six CDRs, for example, VH CDR1, VH CDR2, VH CDR3, VL CDR1, VL CDR2, and/or VL CDR3 identified in Table 2. In some embodiments, PD-L1 binding agents (e.g., antibodies, such as bispecific antibodies), including a human PD-L1 binding agent, described herein comprises one or more, including six CDRs, for example, VH CDR1, VH CDR2, VH CDR3, VL CDR1, VL CDR2, and/or VL CDR3 identified in Table 3. In some embodiments, PD-L1 binding agents (e.g., antibodies, such as bispecific antibodies), including a human PD-L1 binding agent, described herein comprises one or more, including six CDRs, for example, VH CDR1, VH CDR2, VH CDR3, VL CDR1, VL CDR2, and/or VL CDR3 identified in Tables 1, 2 and/or 3.

In some embodiments, PD-L1 binding agents (e.g., antibodies, such as bispecific antibodies), including human PD-L1 binding agents, described herein comprise one or more CDRs, including three VH CDRs, for example, VH CDR1, VH CDR2, VH CDR3, listed in Table 1. In other embodiments, PD-L1 binding agents (e.g., antibodies, such as bispecific antibodies), including human PD-L1 binding agents, described herein comprise one or more CDRs, including three CDRs, for example, VL CDR1, VL CDR2, and/or VL CDR3, listed in Table 1. In yet other embodiments, PD-L1 binding agents (e.g., antibodies, such as bispecific antibodies), including human PD-L1 binding agents, described herein comprise one or more CDRs, including three VH CDRs, for example, VH CDR1, VH CDR2, VH CDR3, listed in Table 1 and one or more CDRs, including three VL CDRs, for example, VL CDR1, VL CDR2, and/or VL CDR3, listed in Table 1.

In some embodiments, a PD-L1 binding agent (e.g., an antibody, such as a bispecific antibody) described herein comprises one or more complementarity determining regions (CDRs) comprising an amino acid sequence selected from a group consisting of SEQ ID NOS: 1-24, 27-50, and 53-76. In some embodiments, a PD-L1 binding agent (e.g., an antibody, such as a bispecific antibody) described herein comprises two or more complementarity determining regions (CDRs) comprising an amino acid sequence selected from a group consisting of SEQ ID NOS: 1-24, 27-50, and 53-76. In some embodiments, a PD-L1 binding agent (e.g., an antibody, such as a bispecific antibody) described herein comprises three or more complementarity determining regions (CDRs) comprising an amino acid sequence selected from a group consisting of SEQ ID NOS: 1-24, 27-50, and 53-76. In some embodiments, a PD-L1 binding agent (e.g., an antibody, such as a bispecific antibody) described herein comprises four or more complementarity determining regions (CDRs) comprising an amino acid sequence selected from a group consisting of SEQ ID NOS: 1-24, 27-50, and 53-76. In some embodiments, a PD-L1 binding agent (e.g., an antibody, such as a bispecific antibody) described herein comprises five or more complementarity determining regions (CDRs) comprising an amino acid sequence selected from a group consisting of SEQ ID NOS: 1-24, 27-50, 53-76. In some embodiments, a PD-L1 binding agent (e.g., an antibody, such as a bispecific antibody) described herein comprises six or more complementarity determining regions (CDRs) comprising an amino acid sequence selected from a group consisting of SEQ ID NOS: 1-24, 27-50, 53-76.

In some embodiments, a PD-L1 binding agent (e.g., an antibody, such as a bispecific antibody) described herein comprise one or more (e.g., one, two or three) VH CDRs listed in Tables 1-3. In other embodiments, a PD-L1 binding agent (e.g., an antibody, such as a bispecific antibody) described herein comprises one or more (e.g., one, two or three) VL CDRs listed in Tables 1-3. In yet other embodiments, a PD-L1 binding agent (e.g., an antibody, such as a bispecific antibody) described herein comprises one or more (e.g., one, two or three) VH CDRs listed in Tables 1-3 and one or more VL CDRs listed in Tables 1-3. Accordingly, in some embodiments, a PD-L1 binding agent (e.g., an antibody, such as a bispecific antibody) described herein comprises a VH CDR1 having the amino acid sequence of any one of SEQ ID NOS: 1, 7, 12, 13, 18, 27, 33, 38, 39, 44, 53, 59, 64, 65, and 70. In some embodiments, a PD-L1 binding agent (e.g., an antibody, such as a bispecific antibody) described herein comprises a VH CDR2 having the amino acid sequence of any one of SEQ ID NOS: 2, 8, 14, 19, 24, 28, 34, 40, 45, 50, 54, 60, 66, 71, and 76. In some embodiments, a PD-L1 binding agent (e.g., an antibody, such as a bispecific antibody) described herein comprises a VH CDR3 having the amino acid sequence of any one of SEQ ID NOS: 3, 9, 15, 20, 29, 35, 41, 46, 55, 61, 67, and 72. In some embodiments, a PD-L1 binding agent (e.g., an antibody, such as a bispecific antibody) described herein comprises a VH CDR1 and/or a VH CDR2 and/or a VH CDR3 independently selected from a VH CDR1, VH CDR2, VH CDR3 as depicted in any one of the amino acid sequences depicted in Table 1-3. In some embodiments, a PD-L1 binding agent (e.g., an antibody, such as a bispecific antibody) described herein comprises a VL CDR1 having the amino acid sequence of any one of SEQ ID NOS: 4, 10, 16, 21, 30, 36, 42, 47, 56, 62, 68, and 73. In another embodiment, a PD-L1 binding agent (e.g., an antibody, such as a bispecific antibody) described herein comprises a VL CDR2 having the amino acid sequence of any one of SEQ ID NOS: 5, 11, 22, 31, 37, 48, 57, 63, and 74. In some embodiments, a PD-L1 binding agent (e.g., an antibody, such as a bispecific antibody) described herein comprises a VL CDR3 having the amino acid sequence of any one of SEQ ID NOS: 6, 17, 23, 32, 43, 49, 58, 69, and 75. In some embodiments, a PD-L1 binding agent (e.g., an antibody, such as a bispecific antibody) described herein comprises a VL CDR1 and/or a VL CDR2 and/or a VL CDR3 independently selected from a VL CDR1, VL CDR2, VL CDR3 as depicted in any one of the amino acid sequences depicted in Tables 1-3.

In some embodiments, a PD-L1 binding agent (e.g., an antibody, such as a bispecific antibody) described herein comprises a heavy chain variable (VH) region comprising: (1) a VH CDR1 having an amino acid sequence of selected from the group consisting of: (i) SEQ ID NO:1, 27, or 53, (ii) SEQ ID NO:7, 33, or 59, (iii) SEQ ID NO:12, 38, or 64, (iv) SEQ ID NO:13, 39, or 65, and (v) SEQ ID NO:18, 44, or 70; (2) a VH CDR2 having an amino acid sequence of selected from the group consisting of: (i) SEQ ID NO:2, 28, or 54, (ii) SEQ ID NO:8, 34, or 60, (iii) SEQ ID NO:14, 40, or 66, (iv) SEQ ID NO:19, 45, or 71, and (v) SEQ ID NO:24, 50, or 76; and (3) a VH CDR3 having an amino acid sequence of selected from the group consisting of: (i) SEQ ID NO:3, 29, or 55, (ii) SEQ ID NO:9, 35, or 61, (iii) SEQ ID NO:15, 41, or 67, and (iv) SEQ ID NO:20, 46, or 72; and/or a light chain variable (VL) region comprising: (1) a VL CDR1 having an amino acid sequence of selected from the group consisting of: (i) SEQ ID NO:4, 30, or 56, (ii) SEQ ID NO:10, 36, or 62, (iii) SEQ ID NO:16, 42, or 68, and (iv) SEQ ID NO:21, 47, or 73; (2) a VL CDR2 having an amino acid sequence of selected from the group consisting of: (i) SEQ ID NO:5, 31, or 57, (ii) SEQ ID NO:11, 37, or 63, and (iii) SEQ ID NO:22, 48, or 74; and (3) a VL CDR3 having an amino acid sequence of selected from the group consisting of: (i) SEQ ID NO:6, 32, or 58, (ii) SEQ ID NO:17, 43, or 69, and (iii) SEQ ID NO:23, 49, or 75.

In some embodiments, a PD-L1 binding agent (e.g., an antibody, such as a bispecific antibody) described herein comprises a heavy chain variable (VH) region comprising: (1) a VH CDR1 having an amino acid sequence of selected from the group consisting of: (i) SEQ ID NO:1, 27, or 53, (ii) SEQ ID NO:7, 33, or 59, (iii) SEQ ID NO:12, 38, or 64, (iv) SEQ ID NO:13, 39, or 65, and (v) SEQ ID NO:18, 44, or 70; (2) a VH CDR2 having an amino acid sequence of selected from the group consisting of: (i) SEQ ID NO:2, 28, or 54, (ii) SEQ ID NO:8, 34, or 60, (iii) SEQ ID NO:14, 40, or 66, (iv) SEQ ID NO:19, 45, or 71, and (v) SEQ ID NO:24, 50, or 76; and (3) a VH CDR3 having an amino acid sequence of selected from the group consisting of: (i) SEQ ID NO:3, 29, or 55, (ii) SEQ ID NO:9, 35, or 61, (iii) SEQ ID NO:15, 41, or 67, and (iv) SEQ ID NO:20, 46, or 72.

In some embodiments, a PD-L1 binding agent (e.g., an antibody, such as a bispecific antibody) described herein comprises a light chain variable (VL) region comprising: (1) a VL CDR1 having an amino acid sequence of selected from the group consisting of: (i) SEQ ID NO:4, 30, or 56, (ii) SEQ ID NO:10, 36, or 62, (iii) SEQ ID NO:16, 42, or 68, and (iv) SEQ ID NO:21, 47, or 73; (2) a VL CDR2 having an amino acid sequence of selected from the group consisting of: (i)

SEQ ID NO:5, 31, or 57, (ii) SEQ ID NO:11, 37, or 63, and (iii) SEQ ID NO:22, 48, or 74; and (3) a VL CDR3 having an amino acid sequence of selected from the group consisting of: (i) SEQ ID NO:6, 32, or 58, (ii) SEQ ID NO:17, 43, or 69, and (iii) SEQ ID NO:23, 49, or 75.

Also described herein are PD-L1 binding agents (e.g., antibodies, such as bispecific antibodies) comprising one or more (e.g., one, two or three) VH CDRs and one or more (e.g., one, two or three) VL CDRs listed in Tables 1-3. In particular, described herein is PD-L1 binding agent (e.g., antibody, such as a bispecific antibody) comprising: a VH CDR1 (SEQ ID NOS: 1, 7, 12, 13, 18, 27, 33, 38, 39, 44, 53, 59, 64, 65, or 70) and a VL CDR1 (SEQ ID NOS: 4, 10, 16, 21, 30, 36, 42, 47, 56, 62, 68, or 73); a VH CDR1 (SEQ ID NOS: 1, 7, 12, 13, 18, 27, 33, 38, 39, 44, 53, 59, 64, 65, or 70) and a VL CDR2 (SEQ ID NOS: 5, 11, 22, 31, 37, 48, 57, 63, or 74); a VH CDR1 (SEQ ID NOS: 1, 7, 12, 13, 18, 27, 33, 38, 39, 44, 53, 59, 64, 65, or 70) and a VL CDR3 (SEQ ID NOS: 6, 17, 23, 32, 43, 49, 58, 69, or 75); a VH CDR2 (SEQ ID NOS: 2, 8, 14, 19, 24, 28, 34, 40, 45, 50, 54, 60, 66, 71, or 76) and a VL CDR1 (SEQ ID NOS: 4, 10, 16, 21, 30, 36, 42, 47, 56, 62, 68, or 73); a VH CDR2 (SEQ ID NOS: 2, 8, 14, 19, 24, 28, 34, 40, 45, 50, 54, 60, 66, 71, or 76) and a VL CDR2 (SEQ ID NOS: 5, 11, 22, 31, 37, 48, 57, 63, or 74); a VH CDR2 (SEQ ID NOS: 2, 8, 14, 19, 24, 28, 34, 40, 45, 50, 54, 60, 66, 71, or 76) and a VL CDR3 (SEQ ID NOS: 6, 17, 23, 32, 43, 49, 58, 69, or 75); a VH CDR3 (SEQ ID NOS: 3, 9, 15, 20, 29, 35, 41, 46, 55, 61, 67, or 72) and a VL CDR1 (SEQ ID NOS: 4, 10, 16, 21, 30, 36, 42, 47, 56, 62, 68, or 73); a VH CDR3 (SEQ ID NOS: 3, 9, 15, 20, 29, 35, 41, 46, 55, 61, 67, or 72) and a VL CDR2 (SEQ ID NOS: 5, 11, 22, 31, 37, 48, 57, 63, or 74); a VH CDR3 (SEQ ID NOS: 3, 9, 15, 20, 29, 35, 41, 46, 55, 61, 67, or 72) and a VL CDR3 (SEQ ID NOS: 6, 17, 23, 32, 43, 49, 58, 69, or 75); a VH CDR1 (SEQ ID NOS: 1, 7, 12, 13, 18, 27, 33, 38, 39, 44, 53, 59, 64, 65, or 70), a VH CDR2 (SEQ ID NOS: 2, 8, 14, 19, 24, 28, 34, 40, 45, 50, 54, 60, 66, 71, or 76) and a VL CDR1 (SEQ ID NOS: 4, 10, 16, 21, 30, 36, 42, 47, 56, 62, 68, or 73); a VH CDR1 (SEQ ID NOS: 1, 7, 12, 13, 18, 27, 33, 38, 39, 44, 53, 59, 64, 65, or 70), a VH CDR2 (SEQ ID NOS: 2, 8, 14, 19, 24, 28, 34, 40, 45, 50, 54, 60, 66, 71, or 76) and a VL CDR2 (SEQ ID NOS: 5, 11, 22, 31, 37, 48, 57, 63, or 74); a VH CDR1 (SEQ ID NOS: 1, 7, 12, 13, 18, 27, 33, 38, 39, 44, 53, 59, 64, 65, or 70), a VH CDR2 (SEQ ID NOS: 2, 8, 14, 19, 24, 28, 34, 40, 45, 50, 54, 60, 66, 71, or 76) and a VL CDR3 (SEQ ID NOS: 6, 17, 23, 32, 43, 49, 58, 69, or 75); a VH CDR2 (SEQ ID NOS: 2, 8, 14, 19, 24, 28, 34, 40, 45, 50, 54, 60, 66, 71, or 76), a VH CDR3 (SEQ ID NOS: 3, 9, 15, 20, 29, 35, 41, 46, 55, 61, 67, or 72) and a VL CDR1 (SEQ ID NOS: 4, 10, 16, 21, 30, 36, 42, 47, 56, 62, 68, or 73), a VH CDR2 (SEQ ID NOS: 2, 8, 14, 19, 24, 28, 34, 40, 45, 50, 54, 60, 66, 71, or 76), a VH CDR3 (SEQ ID NOS: 3, 9, 15, 20, 29, 35, 41, 46, 55, 61, 67, or 72) and a VL CDR2 (SEQ ID NOS: 5, 11, 22, 31, 37, 48, 57, 63, or 74); a VH CDR2 (SEQ ID NOS: 2, 8, 14, 19, 24, 28, 34, 40, 45, 50, 54, 60, 66, 71, or 76), a VH CDR3 (SEQ ID NOS: 3, 9, 15, 20, 29, 35, 41, 46, 55, 61, 67, or 72) and a VL CDR3 (SEQ ID NOS: 6, 17, 23, 32, 43, 49, 58, 69, or 75); a VH CDR1 (SEQ ID NOS: 1, 7, 12, 13, 18, 27, 33, 38, 39, 44, 53, 59, 64, 65, or 70), a VL CDR1 (SEQ ID NOS: 4, 10, 16, 21, 30, 36, 42, 47, 56, 62, 68, or 73) and a VL CDR2 (SEQ ID NOS: 5, 11, 22, 31, 37, 48, 57, 63, or 74); a VH CDR1 (SEQ ID NOS: 1, 7, 12, 13, 18, 27, 33, 38, 39, 44, 53, 59, 64, 65, or 70), a VL CDR1 (SEQ ID NOS: 4, 10, 16, 21, 30, 36, 42, 47, 56, 62, 68, or 73) and a VL CDR3 (SEQ ID NOS: 6, 17, 23, 32, 43, 49, 58, 69, or 75); a VH CDR1 (SEQ ID NOS: 1, 7, 12, 13, 18, 27, 33, 38, 39, 44, 53, 59, 64, 65, or 70), a VL CDR2 (SEQ ID NOS: 5, 11, 22, 31, 37, 48, 57, 63, or 74) and a VL CDR3 (SEQ ID NOS: 6, 17, 23, 32, 43, 49, 58, 69, or 75); a VH CDR2 (SEQ ID NOS: 2, 8, 14, 19, 24, 28, 34, 40, 45, 50, 54, 60, 66, 71, or 76), a VL CDR1 (SEQ ID NOS: 4, 10, 16, 21, 30, 36, 42, 47, 56, 62, 68, or 73) and a VL CDR2 (SEQ ID NOS: 5, 11, 22, 31, 37, 48, 57, 63, or 74); a VH CDR2 (SEQ ID NOS: 2, 8, 14, 19, 24, 28, 34, 40, 45, 50, 54, 60, 66, 71, or 76), a VL CDR1 (SEQ ID NOS: 4, 10, 16, 21, 30, 36, 42, 47, 56, 62, 68, or 73) and a VL CDR3 (SEQ ID NOS: 6, 17, 23, 32, 43, 49, 58, 69, or 75); a VH CDR2 (SEQ ID NOS: 2, 8, 14, 19, 24, 28, 34, 40, 45, 50, 54, 60, 66, 71, or 76), a VL CDR2 (SEQ ID NOS: 5, 11, 22, 31, 37, 48, 57, 63, or 74) and a VL CDR3 (SEQ ID NOS: 6, 17, 23, 32, 43, 49, 58, 69, or 75); a VH CDR3 (SEQ ID NOS: 3, 9, 15, 20, 29, 35, 41, 46, 55, 61, 67, or 72), a VL CDR1 (SEQ ID NOS: 4, 10, 16, 21, 30, 36, 42, 47, 56, 62, 68, or 73) and a VL CDR2 (SEQ ID NOS: 5, 11, 22, 31, 37, 48, 57, 63, or 74); a VH CDR3 (SEQ ID NOS: 3, 9, 15, 20, 29, 35, 41, 46, 55, 61, 67, or 72), a VL CDR1 (SEQ ID NOS: 4, 10, 16, 21, 30, 36, 42, 47, 56, 62, 68, or 73) and a VL CDR3 (SEQ ID NOS: 6, 17, 23, 32, 43, 49, 58, 69, or 75); a VH CDR3 (SEQ ID NOS: 3, 9, 15, 20, 29, 35, 41, 46, 55, 61, 67, or 72), a VL CDR2 (SEQ ID NOS: 5, 11, 22, 31, 37, 48, 57, 63, or 74) and a VL CDR3 (SEQ ID NOS: 6, 17, 23, 32, 43, 49, 58, 69, or 75); a VH CDR1 (SEQ ID NOS: 1, 7, 12, 13, 18, 27, 33, 38, 39, 44, 53, 59, 64, 65, or 70), a VH CDR2 (SEQ ID NOS: 2, 8, 14, 19, 24, 28, 34, 40, 45, 50, 54, 60, 66, 71, or 76), a VH CDR3 (SEQ ID NOS: 3, 9, 15, 20, 29, 35, 41, 46, 55, 61, 67, or 72) and a VL CDR1 (SEQ ID NOS: 4, 10, 16, 21, 30, 36, 42, 47, 56, 62, 68, or 73); a VH CDR1 (SEQ ID NOS: 1, 7, 12, 13, 18, 27, 33, 38, 39, 44, 53, 59, 64, 65, or 70), a VH CDR2 (SEQ ID NOS: 2, 8, 14, 19, 24, 28, 34, 40, 45, 50, 54, 60, 66, 71, or 76), a VH CDR3 (SEQ ID NOS: 3, 9, 15, 20, 29, 35, 41, 46, 55, 61, 67, or 72) and a VL CDR2 (SEQ ID NOS: 5, 11, 22, 31, 37, 48, 57, 63, or 74); a VH CDR1 (SEQ ID NOS: 1, 7, 12, 13, 18, 27, 33, 38, 39, 44, 53, 59, 64, 65, or 70), a VH CDR2 (SEQ ID NOS: 2, 8, 14, 19, 24, 28, 34, 40, 45, 50, 54, 60, 66, 71, or 76), a VH CDR3 (SEQ ID NOS: 3, 9, 15, 20, 29, 35, 41, 46, 55, 61, 67, or 72) and a VL CDR3 (SEQ ID NOS: 6, 17, 23, 32, 43, 49, 58, 69, or 75); a VH CDR1 (SEQ ID NOS: 1, 7, 12, 13, 18, 27, 33, 38, 39, 44, 53, 59, 64, 65, or 70), a VH CDR2 (SEQ ID NOS: 2, 8, 14, 19, 24, 28, 34, 40, 45, 50, 54, 60, 66, 71, or 76), a VL CDR1 (SEQ ID NOS: 4, 10, 16, 21, 30, 36, 42, 47, 56, 62, 68, or 73) and a VL CDR2 (SEQ ID NOS: 5, 11, 22, 31, 37, 48, 57, 63, or 74); a VH CDR1 (SEQ ID NOS: 1, 7, 12, 13, 18, 27, 33, 38, 39, 44, 53, 59, 64, 65, or 70), a VH CDR2 (SEQ ID NOS: 2, 8, 14, 19, 24, 28, 34, 40, 45, 50, 54, 60, 66, 71, or 76), a VL CDR1 (SEQ ID NOS: 4, 10, 16, 21, 30, 36, 42, 47, 56, 62, 68, or 73) and a VL CDR3 (SEQ ID NOS: 6, 17, 23, 32, 43, 49, 58, 69, or 75); a VH CDR1 (SEQ ID NOS: 1, 7, 12, 13, 18, 27, 33, 38, 39, 44, 53, 59, 64, 65, or 70), a VH CDR2 (SEQ ID NOS: 2, 8, 14, 19, 24, 28, 34, 40, 45, 50, 54, 60, 66, 71, or 76), a VL CDR2 (SEQ ID NOS: 5, 11, 22, 31, 37, 48, 57, 63, or 74) and a VL CDR3 (SEQ ID NOS: 6, 17, 23, 32, 43, 49, 58, 69, or 75); a VH CDR1 (SEQ ID NOS: 1, 7, 12, 13, 18, 27, 33, 38, 39, 44, 53, 59, 64, 65, or 70), a VH CDR3 (SEQ ID NOS: 3, 9, 15, 20, 29, 35, 41, 46, 55, 61, 67, or 72), a VL CDR1 (SEQ ID NOS: 4, 10, 16, 21, 30, 36, 42, 47, 56, 62, 68, or 73) and a VL CDR2 (SEQ ID NOS: 5, 11, 22, 31, 37, 48, 57, 63, or 74); a VH CDR1 (SEQ ID NOS: 1, 7, 12, 13, 18, 27, 33, 38, 39, 44, 53, 59, 64, 65, or 70), a VH CDR3 (SEQ ID NOS: 3, 9, 15, 20, 29, 35, 41, 46, 55, 61, 67, or 72), a VL CDR1 (SEQ ID NOS: 4, 10, 16, 21, 30, 36, 42, 47, 56, 62, 68, or 73) and a VL CDR3 (SEQ ID NOS: 6, 17, 23, 32, 43, 49, 58, 69, or 75); a VH CDR1 (SEQ ID NOS: 1, 7, 12, 13, 18, 27, 33, 38, 39, 44, 53, 59, 64, 65, or 70), a VH CDR3 (SEQ ID NOS: 3, 9, 15, 20, 29, 35, 41, 46, 55, 61, 67, or 72), a VL CDR2 (SEQ ID NOS: 5, 11, 22, 31, 37, 48, 57, 63, or 74) and a VL CDR3 (SEQ ID NOS: 6, 17, 23, 32, 43, 49, 58, 69, or 75); a VH CDR1 (SEQ ID NOS: 1, 7, 12, 13, 18, 27, 33, 38, 39, 44, 53, 59, 64, 65, or 70), a VH CDR3 (SEQ ID NOS: 3, 9, 15, 20, 29, 35, 41, 46, 55, 61, 67, or 72), a VL CDR2 (SEQ ID NOS: 5, 11, 22, 31, 37, 48, 57, 63, or 74) and a VL CDR3 (SEQ ID NOS: 6, 17, 23, 32, 43, 49, 58, 69, or 75); a VH CDR2 (SEQ ID NOS: 2, 8, 14, 19, 24, 28, 34, 40, 45, 50, 54, 60, 66, 71, or 76), a VH CDR3 (SEQ ID NOS: 3, 9, 15, 20, 29, 35, 41, 46, 55, 61, 67, or 72), a VL CDR1 (SEQ ID NOS: 4, 10, 16, 21, 30, 36, 42, 47, 56, 62, 68, or 73) and a VL CDR2 (SEQ ID NOS: 5, 11, 22, 31, 37, 48, 57, 63, or 74); a VH CDR2 (SEQ ID NOS: 2, 8, 14, 19, 24, 28, 34, 40, 45, 50, 54, 60, 66, 71, or 76), a VH CDR3 (SEQ ID NOS: 3, 9, 15, 20, 29, 35, 41, 46, 55, 61, 67, or 72), a VL CDR1 (SEQ ID NOS: 4, 10, 16, 21, 30, 36, 42, 47, 56, 62, 68, or 73) and a VL CDR3 (SEQ ID NOS: 6, 17, 23, 32, 43, 49, 58, 69, or 75); a VH CDR2 (SEQ ID NOS: 2, 8, 14, 19, 24, 28, 34, 40, 45, 50, 54, 60, 66, 71, or 76), a VH CDR3 (SEQ ID NOS: 3, 9, 15, 20, 29, 35, 41, 46, 55, 61, 67, or 72), a VL CDR2 (SEQ ID NOS: 5, 11, 22, 31, 37, 48, 57, 63, or 74) and a VL CDR3 (SEQ ID NOS: 6, 17, 23, 32, 43, 49, 58, 69, or 75); a VH CDR1 (SEQ ID NOS: 1, 7, 12, 13, 18, 27, 33, 38, 39, 44, 53, 59, 64, 65, or 70), a VH CDR2 (SEQ ID NOS: 2, 8, 14, 19, 24, 28, 34, 40, 45, 50, 54, 60, 66, 71, or 76), a VH CDR3 (SEQ ID NOS: 3, 9, 15, 20, 29, 35, 41, 46, 55, 61, 67, or 72), a VL CDR1 (SEQ ID NOS: 4, 10, 16, 21, 30, 36, 42, 47, 56, 62, 68, or 73) and a VL CDR2 (SEQ ID NOS: 5, 11, 22, 31, 37, 48, 57, 63, or 74); a VH CDR1 (SEQ ID NOS: 1, 7, 12, 13, 18, 27, 33, 38, 39, 44, 53, 59, 64, 65, or 70), a VH CDR2 (SEQ ID NOS: 2, 8, 14, 19, 24, 28, 34, 40, 45, 50, 54, 60, 66, 71, or 76), a VH CDR3 (SEQ ID NOS: 3, 9, 15, 20, 29, 35, 41, 46, 55, 61, 67, or 72), a VL CDR1 (SEQ ID NOS: 4, 10, 16, 21, 30, 36, 42, 47, 56, 62, 68, or 73) and a VL CDR3 (SEQ ID NOS: 6, 17, 23, 32, 43, 49, 58, 69, or 75); a VH CDR1 (SEQ ID NOS: 1, 7, 12, 13, 18, 27, 33, 38, 39, 44, 53, 59, 64, 65, or 70), a VH CDR2 (SEQ ID NOS: 2, 8, 14, 19, 24, 28, 34, 40, 45, 50, 54, 60, 66, 71, or 76), a VH CDR3 (SEQ ID NOS: 3, 9, 15, 20, 29, 35, 41, 46, 55, 61, 67, or 72), a VL CDR2 (SEQ ID NOS: 5, 11, 22, 31, 37, 48, 57, 63, or 74) and a VL CDR3 (SEQ ID NOS: 6, 17, 23, 32, 43, 49, 58, 69, or 75); a VH CDR1 (SEQ ID NOS: 1, 7, 12, 13, 18, 27, 33, 38, 39, 44, 53, 59, 64, 65, or 70), a VH CDR2 (SEQ ID NOS: 2, 8, 14, 19, 24, 28, 34, 40, 45, 50, 54, 60, 66, 71, or 76), a VL CDR1 (SEQ ID NOS: 4, 10, 16, 21, 30, 36, 42, 47, 56, 62, 68, or 73), a VL CDR2 (SEQ ID NOS: 5, 11, 22, 31, 37, 48, 57, 63, or 74), and a VL CDR3 (SEQ ID NOS: 6, 17, 23, 32, 43, 49, 58, 69, or 75); a VH CDR1 (SEQ ID NOS: 1, 7, 12, 13, 18, 27, 33, 38, 39, 44, 53, 59, 64, 65, or 70), a VH CDR3 (SEQ ID NOS: 3, 9, 15, 20, 29, 35, 41, 46, 55, 61, 67, or 72), a VL CDR1 (SEQ ID NOS: 4, 10, 16, 21, 30, 36, 42, 47, 56, 62, 68, or 73), a VL CDR2 (SEQ ID NOS: 5, 11, 22, 31, 37, 48, 57, 63, or 74), and a VL CDR3 (SEQ ID NOS: 6, 17, 23, 32, 43, 49, 58, 69, or 75); a VH CDR2 (SEQ ID NOS: 2, 8, 14, 19, 24, 28, 34, 40, 45, 50, 54, 60, 66, 71, or 76), a VH CDR3 (SEQ ID NOS: 3, 9, 15, 20, 29, 35, 41, 46, 55, 61, 67, or 72), a VL CDR1 (SEQ ID NOS: 4, 10, 16, 21, 30, 36, 42, 47, 56, 62, 68, or 73), a VL CDR2 (SEQ ID NOS: 5, 11, 22, 31, 37, 48, 57, 63, or 74), and a VL CDR3 (SEQ ID NOS: 6, 17, 23, 32, 43, 49, 58, 69, or 75); or any combination thereof of the VH CDRs (SEQ ID NOS: 1, 7, 12, 13, 18, 27, 33, 38, 39, 44, 53, 59, 64, 65, 70, 2, 8, 14, 19, 24, 28, 34, 40, 45, 50, 54, 60, 66, 71, 76, 3, 9, 15, 20, 29, 35, 41, 46, 55, 61, 67, or 72) and VL CDRs (SEQ ID NOS: 4, 10, 16, 21, 30, 36, 42, 47, 56, 62, 68, 73, 5, 11, 22, 31, 37, 48, 57, 63, 74, 6, 17, 23, 32, 43, 49, 58, 69, or 75) listed in Tables 1-3.

In some embodiments, described herein is an antibody or fragment thereof that binds to PD-L1, wherein the antibody or fragment thereof comprises: (a) a heavy chain variable (VH) region comprising: (1) a VH CDR1 having an amino acid sequence selected from the group consisting of: (i) SEQ ID NO:1, 27, or 53, (ii) SEQ ID NO:7, 33, or 59, (iii) SEQ ID NO:12, 38, or 64, (iv) SEQ ID NO:13, 39, or 65, and (v) SEQ ID NO:18, 44, or 70; (2) a VH CDR2 having an amino acid sequence selected from the group consisting of: (i) SEQ ID NO:2, 28, or 54, (ii) SEQ ID NO:8, 34, or 60, (iii) SEQ ID NO:14, 40, or 66, (iv) SEQ ID NO:19, 45, or 71, and (v) SEQ ID NO:24, 50, or 76; and (3) a VH CDR3 having an amino acid sequence selected from the group consisting of: (i) SEQ ID NO:3, 29, or 55, (ii) SEQ ID NO:9, 35, or 61, (iii) SEQ ID NO:15, 41, or 67, (iv) SEQ ID NO:20, 46, or 72; and/or (b) a light chain variable (VL) region comprising: (1) a VL CDR1 having an amino acid sequence selected from the group consisting of: (i) SEQ ID NO:4, 30, or 56, (ii) SEQ ID NO:10, 36, or 62, (iii) SEQ ID NO:16, 42, or 68, an (iv) SEQ ID NO:21, 47, or 73; (2) a VL CDR2 having an amino acid sequence selected from the group consisting of: (i) SEQ ID NO:5, 31, or 57, (ii) SEQ ID NO:11, 37, or 63, an (iii) SEQ ID NO:22, 48, or 74; and (3) a VL CDR3 having an amino acid sequence selected from the group consisting of: (i) SEQ ID NO:6, 32, or 58, (ii) SEQ ID NO:17, 43, or 69, an (iii) SEQ ID NO:23, 49, or 75.

In some embodiments, described herein is an antibody or fragment thereof that binds to PD-L1, wherein the antibody or fragment thereof comprises a heavy chain variable (VH) region comprising: (1) a VH CDR1 having an amino acid sequence selected from the group consisting of: (i) SEQ ID NO:1, 27, or 53, (ii) SEQ ID NO:7, 33, or 59, (iii) SEQ ID NO:12, 38, or 64, (iv) SEQ ID NO:13, 39, or 65, and (v) SEQ ID NO:18, 44, or 70; (2) a VH CDR2 having an amino acid sequence selected from the group consisting of: (i) SEQ ID NO:2, 28, or 54, (ii) SEQ ID NO:8, 34, or 60, (iii) SEQ ID NO:14, 40, or 66, (iv) SEQ ID NO:19, 45, or 71, and (v) SEQ ID NO:24, 50, or 76; and (3) a VH CDR3 having an amino acid sequence selected from the group consisting of: (i) SEQ ID NO:3, 29, or 55, (ii) SEQ ID NO:9, 35, or 61, (iii) SEQ ID NO:15, 41, or 67, and (iv) SEQ ID NO:20, 46, or 72.

In some embodiments, described herein is an antibody or fragment thereof that binds to PD-L1, wherein the antibody or fragment thereof comprises a light chain variable (VL) region comprising: (1) a VL CDR1 having an amino acid sequence selected from the group consisting of: (i) SEQ ID NO:4, 30, or 56, (ii) SEQ ID NO:10, 36, or 62, (iii) SEQ ID NO:16, 42, or 68, and (iv) SEQ ID NO:21, 47, or 73; (2) a VL CDR2 having an amino acid sequence selected from the group consisting of: (i) SEQ ID NO:5, 31, or 57, (ii) SEQ ID NO:11, 37, or 63, and (iii) SEQ ID NO:22, 48, or 74; and (3) a VL CDR3 having an amino acid sequence selected from the group consisting of: (i) SEQ ID NO:6, 32, or 58, (ii) SEQ ID NO:17, 43, or 69, and (iii) SEQ ID NO:23, 49, or 75.

In some embodiments, described herein is an antibody or fragment thereof that binds to PD-L1 comprising all three heavy chain complementarity determining regions (CDRs) and/or all three light chain CDRs from: the antibody designated P22 that comprises a VH sequence that is SEQ ID NO:25 and a VL sequence that is SEQ ID NO:26; the antibody designated P24 that comprises a VH sequence that is SEQ ID NO:51 and a VL sequence that is SEQ ID NO:52; or the antibody designated P31.2 that comprises a VH sequence that is SEQ ID NO:77 and a VL sequence that is SEQ ID NO:78. In some embodiments, the antibody or fragment thereof comprises all three heavy chain CDRs and/or all three light chain CDRs from the antibody designated P22. In some embodiments, antibody or fragment thereof comprises all three heavy chain CDRs and/or all three light chain CDRs from the antibody designated P24. In some embodiments, the antibody or fragment thereof comprises all three heavy chain CDRs and/or all three light chain CDRs from the antibody designated P31.2.

In some embodiments, described herein is an antibody or fragment thereof that binds to PD-L1, wherein the antibody comprises: (a) a heavy chain variable (VH) region comprising a VH CDR1, a VH CDR2, and a VH CDR3 amino acid sequence depicted in Tables 1-3; and/or (b) a light chain variable (VL) region comprising a VL CDR1, a VL CDR2, and a VL CDR3 amino acid sequence depicted in Tables 1-3. In some embodiments, the antibody comprises a heavy chain variable (VH) region comprising a VH CDR1, a VH CDR2, and a VH CDR3 amino acid sequence depicted in Tables 1-3. In some embodiments, the antibody comprises a light chain variable (VL) region comprising a VL CDR1, a VL CDR2, and a VL CDR3 amino acid sequence depicted in Tables 1-3.

In some embodiments, described herein is an antibody comprising: (a) a heavy chain variable (VH) region comprising: (1) a VH CDR1 having an amino acid sequence selected from the group consisting of SEQ ID NO:1, 7, 12, 13, and 18; (2) a VH CDR2 having an amino acid sequence selected from the group consisting of SEQ ID NO:2, 8, 14, 19, and 24; and (3) a VH CDR3 having an amino acid sequence selected from the group consisting of SEQ ID NO:3, 9, 15, and 20; and (b) a light chain variable (VL) region comprising: (1) a VL CDR1 having an amino acid sequence selected from the group consisting of SEQ ID NO:4, 10, 16, and 21; (2) a VL CDR2 having an amino acid sequence selected from the group consisting of SEQ ID NO:5, 11, and 22; and (3) a VL CDR3 having an amino acid sequence selected from the group consisting of SEQ ID NO:6, 17, and 23.

In some embodiments, described herein is an antibody comprising: (a) a heavy chain variable (VH) region comprising: (1) a VH CDR1 having the amino acid sequence of SEQ ID NO:1; (2) a VH CDR2 having the amino acid sequence of SEQ ID NO:2; and (3) a VH CDR3 having the amino acid sequence of SEQ ID NO:3; and (b) a light chain variable (VL) region comprising: (1) a VL CDR1 having the amino acid sequence of SEQ ID NO:4; (2) a VL CDR2 having the amino acid sequence of SEQ ID NO:5; and (3) a VL CDR3 having the amino acid sequence of SEQ ID NO:6.

In some embodiments, described herein is an antibody comprising: (a) a heavy chain variable (VH) region comprising: (1) a VH CDR1 having the amino acid sequence of SEQ ID NO:7; (2) a VH CDR2 having the amino acid sequence of SEQ ID NO:8; and (3) a VH CDR3 having the amino acid sequence of SEQ ID NO:9; and (b) a light chain variable (VL) region comprising: (1) a VL CDR1 having the amino acid sequence of SEQ ID NO:10; (2) a VL CDR2 having the amino acid sequence of SEQ ID NO:11; and (3) a VL CDR3 having the amino acid sequence of SEQ ID NO:6.

In some embodiments, described herein is an antibody comprising: (a) a heavy chain variable (VH) region comprising: (1) a VH CDR1 having the amino acid sequence of SEQ ID NO:12; (2) a VH CDR2 having the amino acid sequence of SEQ ID NO:2; and (3) a VH CDR3 having the amino acid sequence of SEQ ID NO:3; and (b) a light chain variable (VL) region comprising: (1) a VL CDR1 having the amino acid sequence of SEQ ID NO:4; (2) a VL CDR2 having the amino acid sequence of SEQ ID NO:5; and (3) a VL CDR3 having the amino acid sequence of SEQ ID NO:6.

In some embodiments, described herein is an antibody comprising: (a) a heavy chain variable (VH) region comprising: (1) a VH CDR1 having the amino acid sequence of SEQ ID NO:13; (2) a VH CDR2 having the amino acid sequence of SEQ ID NO:14; and (3) a VH CDR3 having the amino acid sequence of SEQ ID NO:15; and (b) a light chain variable (VL) region comprising: (1) a VL CDR1 having the amino acid sequence of SEQ ID NO:16; (2) a VL CDR2 having the amino acid sequence of SEQ ID NO:11; and (3) a VL CDR3 having the amino acid sequence of SEQ ID NO:17.

In some embodiments, described herein is an antibody comprising: (a) a heavy chain variable (VH) region comprising: (1) a VH CDR1 having the amino acid sequence of SEQ ID NO:18; (2) a VH CDR2 having the amino acid sequence of SEQ ID NO:19; and (3) a VH CDR3 having the amino acid sequence of SEQ ID NO:20; and (b) a light chain variable (VL) region comprising: (1) a VL CDR1 having the amino acid sequence of SEQ ID NO:21; (2) a VL CDR2 having the amino acid sequence of SEQ ID NO:22; and (3) a VL CDR3 having the amino acid sequence of SEQ ID NO:23.

In some embodiments, described herein is an antibody comprising: (a) a heavy chain variable (VH) region comprising: (1) a VH CDR1 having the amino acid sequence of SEQ ID NO:1; (2) a VH CDR2 having the amino acid sequence of SEQ ID NO:24; and (3) a VH CDR3 having the amino acid sequence of SEQ ID NO:3; and (b) a light chain variable (VL) region comprising: (1) a VL CDR1 having the amino acid sequence of SEQ ID NO:4; (2) a VL CDR2 having the amino acid sequence of SEQ ID NO:5; and (3) a VL CDR3 having the amino acid sequence of SEQ ID NO:6.

In some embodiments, described herein is an antibody comprising: (a) a heavy chain variable (VH) region comprising: (1) a VH CDR1 having an amino acid sequence selected from the group consisting of SEQ ID NO:27, 33, 38, 39, and 44; (2) a VH CDR2 having an amino acid sequence selected from the group consisting of SEQ ID NO:28, 34, 40, 45, and 50; and (3) a VH CDR3 having an amino acid sequence selected from the group consisting of SEQ ID NO:29, 35, 41, and 46; and (b) a light chain variable (VL) region comprising: (1) a VL CDR1 having an amino acid sequence selected from the group consisting of SEQ ID NO:30, 36, 42, and 47; (2) a VL CDR2 having an amino acid sequence selected from the group consisting of SEQ ID NO:31, 37, and 48 and (3) a VL CDR3 having an amino acid sequence selected from the group consisting of SEQ ID NO:32, 43, and 49.

In some embodiments, described herein is an antibody comprising: (a) a heavy chain variable (VH) region comprising: (1) a VH CDR1 having the amino acid sequence of SEQ ID NO:27; (2) a VH CDR2 having the amino acid sequence of SEQ ID NO:28; and (3) a VH CDR3 having the amino acid sequence of SEQ ID NO:29; and (b) a light chain variable (VL) region comprising: (1) a VL CDR1 having the amino acid sequence of SEQ ID NO:30; (2) a VL CDR2 having the amino acid sequence of SEQ ID NO:31; and (3) a VL CDR3 having the amino acid sequence of SEQ ID NO:32.

In some embodiments, described herein is an antibody comprising: (a) a heavy chain variable (VH) region comprising: (1) a VH CDR1 having the amino acid sequence of SEQ ID NO:33; (2) a VH CDR2 having the amino acid sequence of SEQ ID NO:34; and (3) a VH CDR3 having the amino acid sequence of SEQ ID NO:35; and (b) a light chain variable (VL) region comprising: (1) a VL CDR1 having the amino acid sequence of SEQ ID NO:36; (2) a VL CDR2 having the amino acid sequence of SEQ ID NO:37; and (3) a VL CDR3 having the amino acid sequence of SEQ ID NO:32.

In some embodiments, described herein is an antibody comprising: (a) a heavy chain variable (VH) region comprising: (1) a VH CDR1 having the amino acid sequence of SEQ ID NO:38; (2) a VH CDR2 having the amino acid sequence of SEQ ID NO:28; and (3) a VH CDR3 having the amino acid sequence of SEQ ID NO:29; and (b) a light chain variable (VL) region comprising: (1) a VL CDR1 having the amino acid sequence of SEQ ID NO:30; (2) a VL CDR2 having the amino acid sequence of SEQ ID NO:31; and (3) a VL CDR3 having the amino acid sequence of SEQ ID NO:32.

In some embodiments, described herein is an antibody comprising: (a) a heavy chain variable (VH) region comprising: (1) a VH CDR1 having the amino acid sequence of SEQ ID NO:39; (2) a VH CDR2 having the amino acid sequence of SEQ ID NO:40; and (3) a VH CDR3 having the amino acid sequence of SEQ ID NO:41; and (b) a light chain variable (VL) region comprising: (1) a VL CDR1 having the amino acid sequence of SEQ ID NO:42; (2) a VL CDR2 having the amino acid sequence of SEQ ID NO:37; and (3) a VL CDR3 having the amino acid sequence of SEQ ID NO:43.

In some embodiments, described herein is an antibody comprising: (a) a heavy chain variable (VH) region comprising: (1) a VH CDR1 having the amino acid sequence of SEQ ID NO:44; (2) a VH CDR2 having the amino acid sequence of SEQ ID NO:45; and (3) a VH CDR3 having the amino acid sequence of SEQ ID NO:46; and (b) a light chain variable (VL) region comprising: (1) a VL CDR1 having the amino acid sequence of SEQ ID NO:47; (2) a VL CDR2 having the amino acid sequence of SEQ ID NO:48; and (3) a VL CDR3 having the amino acid sequence of SEQ ID NO:49.

In some embodiments, described herein is an antibody comprising: (a) a heavy chain variable (VH) region comprising: (1) a VH CDR1 having the amino acid sequence of SEQ ID NO:27; (2) a VH CDR2 having the amino acid sequence of SEQ ID NO:50; and (3) a VH CDR3 having the amino acid sequence of SEQ ID NO:29; and (b) a light chain variable (VL) region comprising: (1) a VL CDR1 having the amino acid sequence of SEQ ID NO:30; (2) a VL CDR2 having the amino acid sequence of SEQ ID NO:31; and (3) a VL CDR3 having the amino acid sequence of SEQ ID NO:32. In some embodiments, described herein is an antibody comprising: (a) a heavy chain variable (VH) region comprising: (1) a VH CDR1 having an amino acid sequence selected from the group consisting of SEQ ID NO:53, 59, 64, 65, and 70; (2) a VH CDR2 having an amino acid sequence selected from the group consisting of SEQ ID NO:54, 60, 66, 71, and 76; and (3) a VH CDR3 having an amino acid sequence selected from the group consisting of SEQ ID NO:55, 61, 67, and 72; and (b) a light chain variable (VL) region comprising: (1) a VL CDR1 having an amino acid sequence selected from the group consisting of SEQ ID NO:56, 62, 68, and 73; (2) a VL CDR2 having an amino acid sequence selected from the group consisting of SEQ ID NO:57, 63 and 74; and (3) a VL CDR3 having an amino acid sequence selected from the group consisting of SEQ ID NO:58, 69, and 75.

In some embodiments, described herein is an antibody comprising: (a) a heavy chain variable (VH) region comprising: (1) a VH CDR1 having the amino acid sequence of SEQ ID NO:53; (2) a VH CDR2 having the amino acid sequence of SEQ ID NO:54; and (3) a VH CDR3 having the amino acid sequence of SEQ ID NO:55; and (b) a light chain variable (VL) region comprising: (1) a VL CDR1 having the amino acid sequence of SEQ ID NO:56; (2) a VL CDR2 having the amino acid sequence of SEQ ID NO:57; and (3) a VL CDR3 having the amino acid sequence of SEQ ID NO:58.

In some embodiments, described herein is an antibody comprising: (a) a heavy chain variable (VH) region comprising: (1) a VH CDR1 having the amino acid sequence of SEQ ID NO:59; (2) a VH CDR2 having the amino acid sequence of SEQ ID NO:60; and (3) a VH CDR3 having the amino acid sequence of SEQ ID NO:61; and (b) a light chain variable (VL) region comprising: (1) a VL CDR1 having the amino acid sequence of SEQ ID NO:62; (2) a VL CDR2 having the amino acid sequence of SEQ ID NO:63; and (3) a VL CDR3 having the amino acid sequence of SEQ ID NO:58.

In some embodiments, described herein is an antibody comprising: (a) a heavy chain variable (VH) region comprising: (1) a VH CDR1 having the amino acid sequence of SEQ ID NO:64; (2) a VH CDR2 having the amino acid sequence of SEQ ID NO:54; and (3) a VH CDR3 having the amino acid sequence of SEQ ID NO:55; and (b) a light chain variable (VL) region comprising: (1) a VL CDR1 having the amino acid sequence of SEQ ID NO:56; (2) a VL CDR2 having the amino acid sequence of SEQ ID NO:57; and (3) a VL CDR3 having the amino acid sequence of SEQ ID NO:58.

In some embodiments, described herein is an antibody comprising: (a) a heavy chain variable (VH) region comprising: (1) a VH CDR1 having the amino acid sequence of SEQ ID NO:65; (2) a VH CDR2 having the amino acid sequence of SEQ ID NO:66; and (3) a VH CDR3 having the amino acid sequence of SEQ ID NO:67; and (b) a light chain variable (VL) region comprising: (1) a VL CDR1 having the amino acid sequence of SEQ ID NO:68; (2) a VL CDR2 having the amino acid sequence of SEQ ID NO:63; and (3) a VL CDR3 having the amino acid sequence of SEQ ID NO:69.

In some embodiments, described herein is an antibody comprising: (a) a heavy chain variable (VH) region comprising: (1) a VH CDR1 having the amino acid sequence of SEQ ID NO:70; (2) a VH CDR2 having the amino acid sequence of SEQ ID NO:71; and (3) a VH CDR3 having the amino acid sequence of SEQ ID NO:72; and (b) a light chain variable (VL) region comprising: (1) a VL CDR1 having the amino acid sequence of SEQ ID NO:73; (2) a VL CDR2 having the amino acid sequence of SEQ ID NO:74; and (3) a VL CDR3 having the amino acid sequence of SEQ ID NO:75.

In some embodiments, described herein is an antibody comprising: (a) a heavy chain variable (VH) region comprising: (1) a VH CDR1 having the amino acid sequence of SEQ ID NO:53; (2) a VH CDR2 having the amino acid sequence of SEQ ID NO:76; and (3) a VH CDR3 having the amino acid sequence of SEQ ID NO:55; and (b) a light chain variable (VL) region comprising: (1) a VL CDR1 having the amino acid sequence of SEQ ID NO:56; (2) a VL CDR2 having the amino acid sequence of SEQ ID NO:57; and (3) a VL CDR3 having the amino acid sequence of SEQ ID NO:58.

In some embodiments, described herein is an antibody comprising a VH region and/or VL region described herein, which further comprises human framework sequences. In some embodiment, the VH region and/or VL region further comprises a framework 1 (FR1), a framework 2 (FR2), a framework 3 (FR3) and/or a framework 4 (FR4) sequence.

In some embodiments, the antibody described herein is a monoclonal antibody. In some embodiments, the monoclonal antibody is a humanized, human or chimeric antibody. In some embodiments, the antibody described herein is a Fab, Fab', F(ab')2, Fv, scFv, (scFv)2, single chain antibody molecule, dual variable region antibody, single variable region antibody, linear antibody, V region, or a multispecific antibody formed from antibody fragments.

In some embodiments, the CDRs disclosed herein include consensus sequences derived from groups of related antibodies (see, e.g., Tables 1-3). As described herein, a "consensus sequence" refers to amino acid sequences having conserved amino acids common among a number of sequences and variable amino acids that vary within a given amino acid sequences. The CDR consensus sequences provided include CDRs corresponding to CDRH1, CDRH2, CDRH3, CDRL1, CDRL2 and/or CDRL3. Consensus sequences of CDRs of PD-L1 binding agents (e.g., antibodies, such as bispecific antibodies) are shown in FIGS. 7A and 7B. Accordingly, in some embodiments, a PD-L1 binding agent (e.g., an antibody, such as a bispecific antibody) described herein comprises (a) a heavy chain variable (VH) region comprising: (1) a VH CDR1 having the amino acid sequence GFTFX$_1$X$_2$YYIH (SEQ ID NO:83), wherein X$_1$ and X$_2$ are each independently a naturally occurring amino acid; (2) a VH CDR2 having the amino acid sequence of X$_1$IX2X$_3$X$_4$GX$_5$X$_6$TX$_7$YADSVKG (SEQ ID NO:84), wherein X$_1$, X$_2$, X$_3$, X$_4$, X$_5$, X$_6$, and X$_7$ are each independently a naturally occurring amino acid; and (3) a VH CDR3 having the amino acid of X$_1$X$_2$X$_3$X$_4$X$_5$X$_6$X$_7$X$_8$LDY (SEQ ID NO:85), wherein X$_1$, X$_2$, X$_3$, X$_4$, X$_5$, X$_6$, X$_7$ and Xa are each independendy a naturally occurring amino acid, and/or (b) a light chain variable (VL) region comprising: (1) a VL CDR1 having the amino acid sequence RASQSVSSAVA (SEQ ID NO:86); (2) a VL CDR2 having the amino acid sequence SASSLYS (SEQ ID NO:87); and (3) a VL CDR3 having the amino acid sequence QQX$_1$X$_2$X$_3$X$_4$PX$_5$T (SEQ ID NO:88), wherein X$_1$, X$_2$, X$_3$, X$_4$, and X$_5$ are each independenty a naturally occurring amino acid. In some embodiments, the VH CDR1 of a PD-L1 binding agent described herein has the amino acid sequence of GFTFX$_1$X$_2$YYIH (SEQ ID NO:101), wherein X$_1$ is a D or S, X$_2$ is a Q or S. In some embodiments, the VH CDR2 of a PD-L1 binding agent described herein has the amino acid sequence of X$_1$IX2X$_3$X$_4$GX$_5$X$_6$TX$_7$YADSVKG (SEQ ID NO:89), wherein X$_1$ is a E, W, or T, X$_2$ is a Y, T, or S, X$_3$ is a P or S, X$_4$ is a A, H, or G, X$_5$ is a S, Y, or G, X$_6$ is a Y, S, or F, and X$_7$ is Y or K. In some embodiments, the VH CDR3 of a PD-L1 binding agent described herein has the amino acid sequence of X$_1$X$_2$X$_3$X$_4$X$_5$X$_6$X$_7$X$_8$LDY (SEQ ID NO:90), wherein X$_1$ is a G or D, X$_2$ is a P, S, or Y, X$_3$ is a Y, V, or T, X$_4$ is a S, I, or L, X$_5$ is a V, Y, or T, X$_6$ is a R, G or P, X$_7$ is a Y or V (or not present), and X$_8$ is an A (or not present). In some embodiments, the VL CDR1 of a PD-L1 binding agent described herein has the amino acid sequence of RASQSVSSAVA (SEQ ID NO:86). In some embodiments, the VL CDR2 of a PD-L1 binding agent described herein has the amino acid sequence of SASSLYS (SEQ ID NO:87). In some embodiments, the VL CDR3 of a PD-L1 binding agent described herein has the amino acid sequence of QQX$_1$X$_2$X$_3$X$_4$PX$_5$T (SEQ ID NO:91), wherein X$_1$ is a V, Y, or F, X$_2$ is a S, Y, or G, X$_3$ is a Y, T, or A, X$_4$ is a S or E, and X$_5$ is a Y or I.

In some embodiments, described herein is a binding agent that binds to essentially the same epitope as an antibody or fragment thereof of any one of the antibodies described herein. In some embodiments, described hereins is a binding agent that competes for binding to human PD-L1 with an antibody or fragment thereof of any one described herein. In some embodiments, the binding agent is an antibody or fragment thereof.

In certain aspects, the CDRs of a PD-L1 binding agent (e.g., an antibody), including a human PD-L1 binding agent, can be determined according to the Kabat system (Kabat et al. (1971) Ann. NY Acad. Sci. 190:382-391 and, Kabat et al. (1991) *Sequences of Proteins of Immunological Interest*, Fifth Edition, U.S. Department of Health and Human Services, NIH Publication No. 91-3242).

In certain aspects, the CDRs of a PD-L1 binding agent (e.g., an antibody), including a human PD-L1 binding agent, can be determined according to the Chothia system, which will be referred to herein as the "Chothia CDRs" (see, e.g., Chothia and Lesk, 1987, J. Mol. Biol., 196:901-917; Al-Lazikani et al., 1997, J. Mol. Biol., 273:927-948; Chothia et al., 1992, J. Mol. Biol., 227:799-817; Tramontano A et al., 1990, J. Mol. Biol. 215(1):175-82; and U.S. Pat. No. 7,709, 226).

In certain aspects, the CDRs of a PD-L1 binding agent (e.g., an antibody), including a human PD-L1 binding agent, can be determined according to the ImMunoGeneTics (IMGT) system, for example, as described in Lefranc, M.-P., 1999, The Immunologist, 7:132-136 and Lefranc, M.-P. et al., 1999, Nucleic Acids Res., 27:209-212 ("IMGT CDRs").

In certain aspects, the CDRs of a PD-L1 binding agent (e.g., an antibody), including a human PD-L1 binding agent, can be determined according to the AbM system, which will be referred to herein as the "AbM CDRs," for example as described in MacCallum et al., 1996, J. Mol. Biol., 262: 732-745. See also, e.g., Martin, A., "Protein Sequence and Structure Analysis of Antibody Variable Domains," in Antibody Engineering, Kontermann and Dübel, eds., Chapter 31, pp. 422-439, Springer-Verlag, Berlin (2001).

In certain aspects, the CDRs of a PD-L1 binding agent (e.g., an antibody), including a human PD-L1 binding agent, can be determined according to the Contact system, which will be referred to herein as the "Contact CDRs" (see, e.g., MacCallum R M et al., 1996, J Mol Biol 5: 732-745). The Contact CDRs are based on an analysis of the available complex crystal structures.

In some embodiments, the position of one or more CDRs along the VH (e.g., CDR1, CDR2, or CDR3) and/or VL (e.g., CDR1, CDR2, or CDR3) region of a PD-L1 binding agent (e.g., an antibody), including a human PD-L1 binding agent, described herein may vary by one, two, three, four, five, or six amino acid positions so long as binding to PD-L1 (e.g., human PD-L1) is maintained (e.g., substantially maintained, for example, at least 50%, at least 60%, at least 70%, at least 80%, at least 90%, at least 95%). For example, in some embodiments, the position defining a CDR of any of Table 1 or 2 may vary by shifting the N-terminal and/or C-terminal boundary of the CDR by one, two, three, four, five, or six amino acids, relative to the current CDR position, so long as binding to PD-L1 (e.g., human PD-L1) is maintained (e.g., substantially maintained, for example, at least 50%, at least 60%, at least 70%, at least 80%, at least 90%, at least 95%). In other embodiments, the length of one or more CDRs along the VH (e.g., CDR1, CDR2, or CDR3) and/or VL (e.g., CDR1, CDR2, or CDR3) region of a PD-L1 binding agent (e.g., an antibody), including a human PD-L1 binding agent, described herein may vary (e.g., be shorter or longer) by one, two, three, four, five, or more amino acids, so long as binding to PD-L1 (e.g., human PD-L1) is maintained (e.g., substantially maintained, for example, at least 50%, at least 60%, at least 70%, at least 80%, at least 90%, at least 95%). For example, in some embodiments, a VH and/or VL CDR1, CDR2, and/or CDR3 described herein may be one, two, three, four, five or more amino acids shorter than one or more of the CDRs described by SEQ ID NOS: 1-24, 27-50, or 53-76, so long as binding to PD-L1 (e.g., human PD-L1) is maintained (e.g., substantially maintained, for example, at least 50%, at least 60%, at least 70%, at least 80%, at least 90%, at least 95%). In other embodiments, a VH and/or VL CDR1, CDR2, and/or CDR3 described herein may be one, two, three, four, five or more amino acids longer than one or more of the CDRs described by SEQ ID NOS: 1-24, 27-50, or 53-76, so long as binding to PD-L1 (e.g., human PD-L1) is maintained (e.g., substantially maintained, for example, at least 50%, at least 60%, at least 70%, at least 80%, at least 90%, at least 95%). In other embodiments, the amino terminus of a VH and/or VL CDR1, CDR2, and/or CDR3 described herein may be extended by one, two, three, four, five or more amino acids compared to one or more of the CDRs described by SEQ ID NOS: 1-24, 27-50, or 53-76, so long as binding to PD-L1 (e.g., human PD-L1) is maintained (e.g., substantially maintained, for example, at least 50%, at least 60%, at least 70%, at least 80%, at least 90%, at least 95%). In other embodiments, the carboxy terminus of a VH and/or VL CDR1, CDR2, and/or CDR3 described herein may be extended by one, two, three, four, five or more amino acids compared to one or more of the CDRs described by SEQ ID NOS: 1-24, 27-50, or 53-76, so long as binding to PD-L1 (e.g., human PD-L1) is maintained (e.g., substantially maintained, for example, at least 50%, at least 60%, at least 70%, at least 80%, at least 90%, at least 95%). In other embodiments, the amino terminus of a VH and/or VL CDR1, CDR2, and/or CDR3 described herein may be shortened by one, two, three, four, five or more amino acids compared to one or more of the CDRs described by SEQ ID NOS: 1-24, 27-50, or 53-76, so long as binding to PD-L1 (e.g., human PD-L1) is maintained (e.g., substantially maintained, for example, at least 50%, at least 60%, at least 70%, at least 80%, at least 90%, at least 95%). In some embodiments, the carboxy terminus of a VH and/or VL CDR1, CDR2, and/or CDR3 described herein may be shortened by one, two, three, four, five or more amino acids compared to one or more of the CDRs described by SEQ ID NOS: 1-24, 27-50, or 53-76, so long as binding to PD-L1 (e.g., human PD-L1) is maintained (e.g., substantially maintained, for example, at least 50%, at least 60%, at least 70%, at least 80%, at least 90%, at least 95%). Any method known in the art can be used to ascertain whether binding to PD-L1 (e.g., human PD-L1) is maintained, for example, the binding assays and conditions described in the "Examples" section described herein. For example, Example 2 described herein describes an assay for measuring binding to PD-L1 (e.g., human PD-L1).

In other embodiments, the PD-L1 binding agents (e.g., antibodies), including human PD-L1 binding agents, presented herein that bind to PD-L1, comprise conservative sequence modifications. With respect to polypeptides that are PD-L1 binding agents (e.g., antibodies), such as human PD-L1 binding agents, conservative sequence modifications include conservative amino acid substitutions that include ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, in some embodiments, a predicted nonessential amino acid residue in a PD-L1 is replaced with another amino acid residue from the same side chain family. Methods of identifying nucleotide and amino acid conservative substitutions which do not eliminate antigen binding are well-known in the art (see, e.g., Brummell et al., Biochem. 32:1180-1187 (1993); Kobayashi et al. Protein Eng. 12(10):879-884 (1999); and Burks et al. Proc. Natl. Acad. Sci. USA 94:412-417 (1997)). In some embodiments, the conservative sequence modifications described herein modify the amino acid sequences of the PD-L1 binding agents (e.g., antibodies), including human PD-L1 binding agents, by 50%, or 55%, or 60%, or 65%, or 70%, or 75%, or 80%, or 85%, or 90%, or 95%, or 98%, or 99%. In some embodiments, the nucleotide and amino acid sequence modifications refer to at most 1, 2, 3, 4, 5, or 6 amino acid substitutions to the CDRs described in Table 1, Table 2, or Table 3. Thus, for example, each such CDR may contain up to 5 conservative amino acid substitutions, for example up to (not more than) 4 conservative amino acid substitutions, for example up to (not more than) 3 conservative amino acid substitutions, for example up to (not more than) 2 conservative amino acid substitutions, or no more than 1 conservative amino acid substitution.

The present disclosure provides PD-L1 binding agents (e.g., antibodies) with a masking moiety and/or cleavable moiety in which one or more of the PD-L1 binding domains of the PD-L1 binding agent (e.g., antibody) are masked (e.g., via a masking moiety) and/or activatable (e.g., via a cleavable moiety). Technologies for masking of a PD-L1 binding agent (e.g., an antibody) are well known in the art, including SAFE body masking technology (see, e.g., US Patent Application Publication No. 2019/0241886) and Probody masking technology (see, e.g., US Patent Application Publication No. 2015/0079088). Such technologies can be used to generate a PD-L1 binding agent (e.g., an antibody) that is masked and/or activatable. Such masked and/or activatable PD-L1 binding agents (e.g., antibodies) are useful for the preparation of conjugates, including immunoconjugates, antibody-drug conjugates (ADCs), masked ADCs and activatable antibody-drug conjugates (AADCs), comprising any one of the PD-L1 binding agents (e.g., antibodies), such as human PD-L1 binding agents, of the present disclosure, including those directly or indirectly linked another agent such as a drug. For example, PD-L1 binding agents (e.g., antibodies), such as human PD-L1 binding agents, of the present disclosure may be covalently bound by a synthetic linker to one or more agents such as drugs.

If desired, a PD-L1 binding agent (e.g., an antibody), including a human PD-L1 binding agent, is linked or conjugated (directly or indirectly) to a moiety with effector function, such as cytotoxic activity (e.g., a chemotherapeutic moiety or a radioisotope) or immune recruitment activity. Moieties that are linked or conjugated (directly or indirectly) include drugs that are cytotoxic (e.g., toxins such as auristatins) or non-cytotoxic (e.g., signal transduction modulators such as kinases or masking moieties that mask one or more binding domains of a PD-L1 binding agent (e.g., antibody), or cleavable moieties that allow for activating a PD-L1 binding agent by cleaving of a cleavable moiety to unmask one or more binding domains of a PD-L1 binding agent (e.g., antibody) in the tumor microenvironment) in the form of masked conjugates. Moieties that promote immune recruitment can include other antigen-binding agents, such as viral proteins that bind selectively to cells of the innate immune system. Alternatively or in addition, a PD-L1 binding agent (e.g., an antibody), including a human PD-L1 binding agent, is optionally linked or conjugated (directly or indirectly) to a moiety that facilitates isolation from a mixture (e.g., a tag) or a moiety with reporter activity (e.g., a detection label or reporter protein). It will be appreciated that the features of a PD-L1 binding agent (e.g., an antibody), including a human PD-L1 binding agent, described herein extend also to a polypeptide comprising a PD-L1 binding agent fragment.

In some embodiments, PD-L1 binding agents (e.g., antibodies), including PD-L1 binding agents, described herein which bind to human PD-L1, may be linked or conjugated (directly or indirectly) to a polypeptide, which can result in the generation of an activatable antibody. In some embodiments, a PD-L1 binding agent (e.g., an antibody), including a human PD-L1 binding agent, is linked or conjugated (directly or indirectly) to an agent. In some embodiments, the agent is a drug, resulting in an ADC or an AADC when the antibody of the ADC comprises a masking moiety and a cleavable moiety.

In some embodiments, PD-L1 binding agents (e.g., antibodies), including human PD-L1 binding agents, described herein are conjugated or recombinantly linked (directly or indirectly) to a therapeutic agent (e.g., a cytotoxic agent) or to a diagnostic or detectable agent. The conjugated or recombinantly linked antibodies, including masked or activatable conjugates, can be useful, for example, for treating or preventing a disease, disorder or condition such as a PD-L1-mediated disease, disorder or condition. The conjugated or recombinantly linked PD-L1 binding agents (e.g., antibodies), including masked or activatable conjugates, can be useful, for example, for monitoring or prognosing the onset, development, progression, and/or severity of a T cell dysfunctional disease, disorder or condition.

Such diagnosis and detection can be accomplished, for example, by coupling a PD-L1 binding agent (e.g., an antibody) to detectable substances including, for example: enzymes, including, but not limited to, horseradish peroxidase, alkaline phosphatase, beta-galactosidase, or acetylcholinesterase; prosthetic groups, including, but not limited to, streptavidin/biotin or avidin/biotin; fluorescent materials, including, but not limited to, umbelliferone, fluorescein, fluorescein isothiocynate, rhodamine, dichlorotriazinylamine fluorescein, dansyl chloride, or phycoerythrin; luminescent materials, including, but not limited to, luminol; bioluminescent materials, including, but not limited to, luciferase, luciferin, or aequorin; chemiluminescent material, including, but not limited to, an acridinium based compound or a HALOTAG; radioactive materials, including, but not limited to, iodine (131I, 125I, 123I, and 121I), carbon (14C), sulfur (35S), tritium (3H), indium (115In, 113In, 112In, and 111In), technetium (99Tc), thallium (201Ti), gallium (68Ga and 67Ga), palladium (103Pd), molybdenum (99Mo), xenon (133Xe), fluorine (18F), 153Sm, 177Lu, 159Gd, 149Pm, 140La, 175Yb, 166Ho, 90Y, 47Sc, 186Re, 188Re, 142Pr, 105Rh, 97Ru, 68Ge, 57Co, 65Zn, 85Sr, 32P, 153Gd, 169Yb, 51Cr, 54Mn, 75Se, 113Sn, or 117Sn; positron emitting metals using various positron emission tomographies; and non-radioactive paramagnetic metal ions.

Also described herein are PD-L1 binding agents (e.g., antibodies) that are recombinantly linked or conjugated (covalent or non-covalent conjugations, directly or indirectly) to a heterologous protein or polypeptide (or fragment thereof, for example, to a polypeptide (e.g., of about 10, about 20, about 30, about 40, about 50, about 60, about 70, about 80, about 90, or about 100 amino acids) to generate fusion proteins, as well as uses thereof. In particular, described herein are fusion proteins comprising an antigen-binding fragment of a PD-L1 binding agent (e.g., an anti-body), including a human PD-L1 binding agent, described herein (e.g., comprising CDR1, CDR2, and/or CDR3 of VH and/or VL) and a heterologous protein, polypeptide, or peptide. In some embodiments, the heterologous protein, polypeptide, or peptide that a PD-L1 binding agent (e.g., an antibody) is linked to is useful for targeting the PD-L1 binding agent to a particular cell (e.g., a PD-L1-expressing cell, including a tumor cell).

Moreover, PD-L1 binding agents (e.g., antibodies), including human PD-L1 binding agents, described herein can be linked (directly or indirectly) to marker or "tag" sequences, such as a peptide, to facilitate purification. In some embodiments, the marker or tag amino acid sequence is a hexa-histidine peptide, such as the tag provided in a pQE vector (see, e.g., QIAGEN, Inc.), among others, many of which are commercially available. For example, as described in Gentz et al., 1989, Proc. Natl. Acad. Sci. USA 86:821-24, hexa-histidine provides for convenient purifica-tion of a fusion protein. Other peptide tags useful for purification include, but are not limited to, the hemaggluti-nin ("HA") tag, which corresponds to an epitope derived from the influenza hemagglutinin protein (Wilson et al., 1984, Cell 37:767-78), and the "FLAG" tag.

Methods for linking or conjugating (directly or indirectly) moieties (including polypeptides) to antibodies are well known in the art, any one of which can be used to make an antibody-drug conjugate or fusion protein described herein.

In some embodiments, a PD-L1 binding agent (e.g., an antibody) described herein is a fusion protein. The term "fusion protein" as used herein refers to a polypeptide that comprises an amino acid sequence of a binding agent (e.g., an antibody) and an amino acid sequence of a heterologous polypeptide or protein (e.g., a polypeptide or protein not normally a part of the antibody (e.g., a non-PD-L1 binding antibody)). In certain embodiments, the fusion protein retains the biological activity of a PD-L1 binding agent. In certain embodiments, the fusion protein comprises a PD-L1 antibody VH region, VL region, VH CDR (one, two or three VH CDRs), and/or VL CDR (one, two or three VL CDRs), wherein the fusion protein binds to a PD-L1 epitope, a PD-L1 fragment and/or a PD-L1 polypeptide.

Fusion proteins may be generated, for example, through the techniques of gene-shuffling, motif-shuffling, exon-shuf-fling, and/or codon-shuffling (collectively referred to as "DNA shuffling"). DNA shuffling may be employed to alter the activities of PD-L1 binding agents (e.g., antibodies), including human PD-L1 binding agents, as described herein, including, for example, PD-L1 binding agents with higher affinities and lower dissociation rates (see, e.g., U.S. Pat. Nos. 5,605,793; 5,811,238; 5,830,721; 5,834,252; and U.S. Pat. No. 5,837,458; Patten et al., 1997, Curr. Opinion Biotechnol. 8:724-33; Harayama, 1998, Trends Biotechnol. 16(2):76-82; Hansson et al., 1999, J. Mol. Biol. 287:265-76; and Lorenzo and Blasco, 1998, Biotechniques 24(2):308-13). In some embodiments, PD-L1 binding agents, including human PD-L1 binding agents, may be altered by being subjected to random mutagenesis by error-prone PCR, ran-dom nucleotide insertion, or other methods prior to recom-bination. A polynucleotide encoding a PD-L1 binding agent described herein may be recombined with one or more components, motifs, sections, parts, domains, fragments, etc. of one or more heterologous molecules.

PD-L1 binding agents (e.g., antibodies), including human PD-L1 binding agents, described herein may also be attached to solid supports, which are useful for immunoas-says or purification of the target antigen. Such solid supports include, but are not limited to, glass, cellulose, polyacryl-amide, nylon, polystyrene, polyvinyl chloride, or polypro-pylene.

PD-L1 binding agents (e.g., antibodies), including human PD-L1 binding agents, described herein can also be linked or conjugated (directly or indirectly) to a second antibody to form an antibody heteroconjugate.

The linker may be a "cleavable moiety" facilitating release of the linked or conjugated agent in a cell, but non-cleavable linkers are also contemplated herein. Linkers for use in conjugates (e.g., antibody-drug conjugates) of the present disclosure include, without limitation, acid labile linkers (e.g., hydrazone linkers), disulfide-containing link-ers, peptidase-sensitive linkers (e.g., peptide linkers com-prising amino acids, for example, valine and/or citrulline such as citrulline-valine or phenylalanine-lysine), photola-bile linkers, dimethyl linkers, thioether linkers, or hydro-philic linkers designed to evade multidrug transporter-me-diated resistance.

Conjugates of an antibody and agent, including wherein the agent is a drug for the preparation of ADC or an AADC, may be made using a variety of bifunctional protein cou-pling agents such as BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, sulfo-SMPB, and SVSB (succinimidyl-(4-vinylsulfone)benzoate). The present dis-closure further contemplates that conjugates of antibodies and agents, including wherein the agent is a drug for the preparation of ADC or AADC, may be prepared using any suitable methods as disclosed in the art (see, e.g., Biocon-jugate Techniques (Hermanson ed., 2d ed. 2008)).

Conventional conjugation strategies for antibodies and agents, including wherein the agent is a drug for the prepa-ration of ADC or AADC, have been based on random conjugation chemistries involving the ε-amino group of Lys residues or the thiol group of Cys residues, which results in heterogeneous conjugates. Recently developed techniques allow site-specific conjugation to antibodies, resulting in homogeneous loading and avoiding conjugate subpopula-tions with altered antigen-binding or pharmacokinetics. These include engineering of "thiomabs" comprising cyste-ine substitutions at positions on the heavy and light chains that provide reactive thiol groups and do not disrupt immu-noglobulin folding and assembly or alter antigen binding (see, e.g., Junutula et al., 2008, J. Immunol. Meth. 332: 41-52; and Junutula et al., 2008, Nature Biotechnol. 26:925-32). In another method, selenocysteine is cotranslationally inserted into an antibody sequence by recoding the stop codon UGA from termination to selenocysteine insertion, allowing site specific covalent conjugation at the nucleo-philic selenol group of selenocysteine in the presence of the other natural amino acids (see, e.g., Hofer et al., 2008, Proc. Natl. Acad. Sci. USA 105:12451-56; and Hofer et al., 2009, Biochemistry 48(50):12047-57).

In some embodiments, a PD-L1 binding agent (e.g., an antibody), including a human PD-L1 binding agent, described herein is conjugated to a cytotoxic agent. In some embodiments, a PD-L1 binding agent (e.g., an antibody), including a human PD-L1 binding agent, disclosed herein can be optionally conjugated with one or more cytotoxic agent(s) disclosed herein or known in the art in order to generate an ADC or AADC. In some embodiments, the cytotoxic agent is a chemotherapeutic agent including, but not limited to, methotrexate, adriamycin, doxorubicin, melphalan, mitomycin C, chlorambucil, daunorubicin or other intercalating agents. In some embodiments, the cytotoxic agent is an enzymatically active toxin of bacterial, fungal, plant, or animal origin, or fragments thereof, including, but not limited to, diphtheria A chain, nonbinding active fragments of diphtheria toxin, exotoxin A chain, ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes. In some embodiments, the cytotoxic agent is a radioisotope to produce a radioconjugate or a radioconjugated agent. A variety of radionuclides are available for the production of radioconjugated agents including, but not limited to, 90Y, 125I, 131I, 123I, 111In, 131In, 105Rh, 153Sm, 67Cu, 67Ga, 166Ho, 177Lu, 186Re, 188Re, and 212Bi. Conjugates of a polypeptide or molecule and one or more small molecule toxins, such as a calicheamicin, maytansinoids, a trichothene, and CC1065, and the derivatives of these toxins that have toxin activity, can also be used. Conjugates of a polypeptide or molecule and cytotoxic agent are made using a variety of bifunctional protein-coupling agents such as N-succinimidyl-3-(2-pyridyidithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis(p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene).

In some embodiments, a PD-L1 binding agent (e.g., an antibody), including a human PD-L1 binding agent, described herein is conjugated to a drug such as a signal transduction modulator, a pro-apoptotic agent, a mitotic inhibitor, an anti-tumor antibiotic, an immunomodulating agent, a nucleic acid for gene therapy, an alkylating agent, an anti-angiogenic agent, an anti-metabolite, a boron-containing agent, a chemoprotective agent, a hormone agent, an anti-hormone agent, a corticosteroid, a photoactive therapeutic agent, an oligonucleotide, a radionuclide agent, a radiosensitizer, a topoisomerase inhibitor, and a tyrosine kinase inhibitor. In some embodiments, the mitotic inhibitor is a dolastatin, an auristatin, a maytansinoid, and a plant alkaloid. In some embodiments, the drug is a dolastatin, an auristatin, a maytansinoid, and a plant alkaloid. An example of an auristatin is monomethylaurisatin F (MMAF) or monomethyauristatin E (MMAE). Examples of maytansinoids include, but are not limited to, DM1, DM2, DM3, and DM4. In some embodiments, the anti-tumor antibiotic is selected from the group consisting of an actinomycine, an anthracycline, a calicheamicin, and a duocarmycin. In some embodiments, the actinomycine is a pyrrolobenzodiazepine (PBD).

PD-L1 binding agents (e.g., antibodies), including human PD-L1 binding agents, described herein may be monospecific, bispecific, trispecific, or of greater multispecificity. Such agents may include antibodies. Multispecific antibodies, such as bispecific antibodies, are monoclonal antibodies that have binding specificities for at least two different targets (e.g., antigens) or two different epitopes on the same target (e.g., a bispecific antibody directed to PD-L1 with a first binding domain for a first epitope of a PD-L1, and a second binding domain for a second epitope of PD-L1). In some embodiments, the multispecific (e.g., bispecific) antibodies can be constructed based on the sequences of the antibodies described herein, e.g., the CDR sequences listed in Table 1, Table 2, and Table 3. In some embodiments, the multispecific antibodies described herein are bispecific antibodies. In some embodiments, bispecific antibodies are mouse, chimeric, human or humanized antibodies. In some embodiments, one of the binding specificities of the multispecific antibody is for PD-L1 and the other is for any other target (e.g., antigen). In some embodiments, a multispecific (e.g., bispecific) antibody can comprise more than one target (e.g., antigen) binding domain, in which different binding domains are specific for different targets (e.g., a first binding domain that binds to PD-L1 and a second binding domain that binds another target (e.g., antigen), such as an immune checkpoint regulator (e.g., a negative checkpoint regulator). In some embodiments, multispecific (e.g., bispecific) antibody molecules can bind than one (e.g., two or more) epitopes on the same target (e.g., antigen). In some embodiments, one of the binding specificities is PD-L1 and the other is for one or more of Cytotoxic T-lymphocyte antigen-4 (CTLA-4), CD80, CD86, Programmed cell death 1 (PD-1), Programmed cell death ligand 2 (PD-L2), Lymphocyte activation gene-3 (LAG-3; also known as CD223), Galectin-3, B and T lymphocyte attenuator (BTLA), T-cell membrane protein 3 (TIM3), Galectin-9 (GAL9), B7-H1, B7-H3, B7-H4, T-Cell immunoreceptor with Ig and ITIM domains (TIGIT/Vstm3/WUCAM/VSIG9), V-domain Ig suppressor of T-Cell activation (VISTA), Glucocorticoid-induced tumor necrosis factor receptor-related (GITR) protein, Herpes Virus Entry Mediator (HVEM), OX40, CD27, CD28, CD137. CGEN-15001T, CGEN-15022, CGEN-15027, CGEN-15049, CGEN-15052, and CGEN-15092.

Methods for making multispecific antibodies are known in the art, such as, by co-expression of two immunoglobulin heavy chain-light chain pairs, where the two heavy chains have different specificities (see, e.g., Milstein and Cuello, 1983, Nature 305:537-40). For further details of generating multispecific antibodies (e.g., bispecific antibodies), see, for example, Bispecific Antibodies (Kontermann ed., 2011).

Exemplary structures of multispecific antibodies are known in the art and are further described in Weidle et al., 2013, Cancer Genomics & Proteomics 10: 1-18; Brinkman et al., 2017, MABS, 9:2, 182-212; Godar et al., 2018, Expert Opinion on Therapeutic Patents, 28:3, 251-276; and Spiess et al., 2015, Mol. Immunol. 67 95-106.

For example, bispecific antibody molecules can be classified into different structural groups: (i) bispecific immunoglobulin G (BsIgG); (ii) IgG appended with an additional antigen-binding moiety; (iii) bispecific antibody fragments; (iv) bispecific fusion proteins; and (v) bispecific antibody conjugates. As a non-limiting example, BsIgG formats can include crossMab, DAF (two-in-one), DAF (four-in-one), DutaMab, DT-IgG, knobs-in-holes common LC, knobs-in-holes assembly, charge pair, Fab-arm exchange, SEEDbody, triomab, LUZ-Y, Fcab, κλ-body, orthogonal Fab.

In some embodiments, BsIgG comprises heavy chains that are engineered for heterodimerization. For example, heavy chains can be engineered for heterodimerization using a "knobs-into-holes" strategy, a SEED platform, a common heavy chain (e.g., in KA-bodies), and use of heterodimeric Fc regions. Strategies are known in the art to avoid heavy chain pairing of homodimers in BsIgG, including knobsinto-holes, DuoBody®, azymetric, charge pair, HA-TF, SEEDbody, and differential protein A affinity.

Another bispecific antibody format is IgG appended with an additional antigen-binding moiety. For example, mono-specific IgG can be engineered to have bispecificity by appending an additional antigen-binding unit onto the monospecific IgG, e.g., at the N- or C-terminus of either the heavy or light chain. Exemplary additional antigen-binding units include single domain antibodies (e.g., variable heavy chain or variable light chain), engineered protein scaffolds, and paired antibody variable domains (e.g., single chain variable fragments or variable fragments). Non-limiting examples of appended IgG formats include dual variable domain IgG (DVD-Ig), IgG(H)-scFv, scFv-(H)IgG, IgG(L)-scFv, scFv-(L)IgG, IgG(L, H)-Fv, IgG(H)-V, V(H)-IgG, IgG(L)-V, V(L)-IgG, KIH IgG-scFab, 2scFv-IgG, IgG-2scFv, scFv4-Ig, zybody, and DVI-IgG (four-in-one). See Spiess et al. Mol. Immunol. 67(2015):95-106. In some embodiments, an exemplary antibody format is a B-Body format for monospecific or multispecific (e.g., bispecific antibodies) as described in e.g. International Patent Application Publication No. WO 2018/075692 and US Patent Application Publication No. 2018/0118811.

Bispecific antibody fragments (BsAb) are a format of bispecific antibody molecules that lack some or all of the antibody constant domains. For example, some BsAb lack an Fc region. In embodiments, bispecific antibody fragments include heavy and light chain regions that are connected by a peptide linker that permits efficient expression of the BsAb in a single host cell. Non-limiting examples of bispecific antibody fragments include, but are not limited to, NANO-BODY®, NANOBODY®-HAS, BiTE®, Diabody, DART®, TandAb, scDiabody, scDiabody-CH3, Diabody-CH3, triple body, miniantibody, minibody, TriBi minibody, scFv-CH3 KIH, Fab-scFv, scFv-CH-CL-scFv, F(ab')2, F(ab')2-scFv2, scFv-KIH, Fab-scFv-Fc, tetravalent HCAb, scDiabody-Fc, Diabody-Fc, tandem scFv-Fc, and intrabody.

Bispecific fusion proteins include antibody fragments linked to other proteins. For example bispecific fusion proteins can be linked to other proteins to add additional specificity and/or functionality. In some embodiments, the dock-and-lock (DNL) method can be used to generate bispecific antibody molecules with higher valency. For example, bispecific antibody fusions to albumin binding proteins or human serum albumin can be extend the serum half-life of antibody fragments. In embodiments, chemical conjugation, e.g., chemical conjugation of antibodies and/or antibody fragments, can be used to create BsAb molecules. An exemplary bispecific antibody conjugate includes the CovX-body format, in which a low molecular weight drug is conjugated site-specifically to a single reactive lysine in each Fab arm or an antibody or fragment thereof. In embodiments, the conjugation improves the serum half-life.

Methods of production of multispecific antibodies, including bispecific antibodies, are known in the art. For example, multispecific antibodies, including bispecific antibodies, can be produced by separate expression of the component antibodies in different host cells and subsequent purification/assembly or by expression of the component antibodies in a single host cell. Purification of multispecific (e.g., bispecific) antibody molecules can be performed by various methods known in the art, including affinity chromatography.

In some embodiments, PD-L1 binding agents (e.g., antibodies), including human PD-L1 binding agents, disclosed herein can be provided in any antibody format disclosed herein or known in the art. As a non-limiting example, in some embodiments, the PD-L1 binding agents (e.g., antibodies), including human PD-L1 binding agents, can be selected from Fabs-in-tandem-Ig (FIT-Ig); DVD-Ig; hybrid hybridoma (quadroma or tetradoma); anticalin platform (Pieris); diabodies; single chain diabodies; tandem single chain Fv fragments; TandAbs, Trispecific Abs (Affimed); DART® dual affinity retargeting (Macrogenics); Bispecific Xmabs (Xencor); Bispecific T cell engagers (BiTE®; Amgen; 55 kDa); Triplebodies; Tribody=Fab-scFv Fusion Protein multifunctional recombinant antibody derivates (CreativeBiolabs); DuoBody® platform (Genmab); dock and lock platform; knobs-into-holes (KIH) platform; Humanized bispecific IgG antibody (REGN1979) (Regeneron); Mab2 bispecific antibodies (F-Star); DVD-Ig=dual variable domain immunoglobulin (Abbott); kappa-lambda bodies; TBTI=tetravalent bispecific tandem Ig; and CrossMab (Roche).

In some embodiments, a multispecific (e.g., bispecific) antibody disclosed herein comprises a PD-L1 binding domain and one or more additional binding domains that bind to one or more targets that are not PD-L1. In some embodiments, a multispecific (e.g., bispecific) antibody disclosed herein comprises a PD-L1 binding domain that e.g. comprises the VH and/or VL amino acid sequences of Table 1. In some embodiments, a multispecific (e.g., bispecific) antibody disclosed herein comprises a PD-L1 binding domain that comprises the VH and/or VL amino acid sequences of Table 2. In some embodiments, a multispecific (e.g., bispecific) antibody disclosed herein comprises a PD-L1 binding domain that comprises the VH and/or VL amino acid sequences of Table 3.

In some embodiments, described herein is a multispecific (e.g., bispecific) antibody comprising a binding domain which binds to PD-L1 that comprises VH and VL CDRs as set forth in Table 1. In some embodiments, described herein is a multispecific (e.g., bispecific) antibody comprising a binding domain which binds to PD-L1 that comprises VH and VL CDRs as set for in Table 2. In some embodiments, described herein is a multispecific (e.g., bispecific) antibody comprising a binding domain which binds to PD-L1 that comprises VH and VL CDRs as set for in Table 3.

Antibodies that bind PD-L1 may be obtained by any suitable method, such as (but not limited to) immunization with whole tumor cells comprising PD-L1 and collection of antibodies, recombinant techniques, or screening libraries of antibodies or antibody fragments using PD-L1 extracellular domain epitopes. Monoclonal antibodies may be generated using a variety of known techniques (see, for example, Coligan et al. (eds.), Current Protocols in Immunology, 1:2.5.12.6.7 (John Wiley & Sons 1991); Monoclonal Antibodies, Hybridomas: A New Dimension in Biological Analyses, Plenum Press, Kennett, McKearn, and Bechtol (eds.) (1980); Antibodies: A Laboratory Manual, Harlow and Lane (eds.), Cold Spring Harbor Laboratory Press (1988); and Picksley et al., "Production of monoclonal antibodies against proteins expressed in E. coli," in DNA Cloning 2: Expression Systems, 2nd Edition, Glover et al. (eds.), page 93 (Oxford University Press 1995)). One exemplary technique for generating monoclonal antibodies comprises immunizing an animal with a human PD-L1 antigen and generating a hybridoma from spleen cells taken from the animal. A hybridoma may produce a monoclonal antibody or antibody fragment that binds PD-L1.

In a further embodiment, monoclonal antibodies or antibody fragments can be isolated from antibody phage libraries generated using the techniques described in, for example, Antibody Phage Display: Methods and Protocols, P. M.

O'Brien and R. Aitken, eds, Humana Press, Totawa N.J., 2002. In principle, synthetic antibody clones are selected by screening phage libraries containing phage that display various fragments of antibody variable region (Fv) fused to phage coat protein. Such phage libraries are screened for against the desired antigen. Clones expressing Fv fragments capable of binding to the desired antigen are adsorbed to the antigen and thus separated from the non-binding clones in the library. The binding clones are then eluted from the antigen, and can be further enriched by additional cycles of antigen adsorption/elution.

Variable domains can be displayed functionally on phage, either as single-chain Fv (scFv) fragments, in which VH and VL are covalently linked through a short, flexible peptide, or as Fab fragments, in which they are each fused to a constant domain and interact non-covalently, as described, for example, in Winter et al., *Ann. Rev. Immunol.*, 12: 433-455 (1994).

Repertoires of VH and VL genes can be separately cloned by polymerase chain reaction (PCR) and recombined randomly in phage libraries, which can then be searched for antigen-binding clones as described in Winter et al., supra. Libraries from immunized sources provide high-affinity antibodies to the immunogen without the requirement of constructing hybridomas. Alternatively, the naive repertoire can be cloned to provide a single source of human antibodies to a wide range of non-self and also self antigens without any immunization as described by Griffiths et al., *EMBO J*, 12: 725-734 (1993). Finally, naive libraries can also be made synthetically by cloning the unrearranged V-gene segments from stem cells, and using PCR primers containing random sequence to encode the highly variable CDR3 regions and to accomplish rearrangement in vitro as described, for example, by Hoogenboom and Winter, *J. Mol. Biol.*, 227: 381-388 (1992).

Screening of the libraries can be accomplished by various techniques known in the art. For example, PD-L1 (e.g., a PD-L1 polypeptide, fragment or epitope) can be used to coat the wells of adsorption plates, expressed on host cells affixed to adsorption plates or used in cell sorting, or conjugated to biotin for capture with streptavidin-coated beads, or used in any other method for panning display libraries. The selection of antibodies with slow dissociation kinetics (e.g., good binding affinities) can be promoted by use of long washes and monovalent phage display as described in Bass et al., *Proteins*, 8: 309-314 (1990) and in WO 92/09690, and a low coating density of antigen as described in Marks et al., *Biotechnol.*, 10: 779-783 (1992).

PD-L1 binding agents (e.g., antibodies) can be obtained by designing a suitable antigen screening procedure to select for the phage clone of interest followed by construction of a full length PD-L1 binding agent (e.g., an antibody) clone using VH and/or VL sequences (e.g., the Fv sequences), or various CDR sequences from VH and VL sequences, from the phage clone of interest and suitable constant region (e.g., Fc) sequences described in Kabat et al., *Sequences of Proteins of Immunological Interest*, Fifth Edition, NIH Publication 91-3242, Bethesda MD (1991), vols. 1-3.

Likewise, human antibodies that bind PD-L1 may be generated by any of a number of techniques including, but not limited to, Epstein Barr Virus (EBV) transformation of human peripheral blood cells (e.g., containing B lymphocytes), in vitro immunization of human B cells, fusion of spleen cells from immunized transgenic mice carrying inserted human immunoglobulin genes, isolation from human immunoglobulin V region phage libraries, or other procedures as known in the art and based on the disclosure herein. Methods for obtaining human antibodies from transgenic animals are further described, for example, in Bruggemann et al., *Curr. Opin. Biotechnol.*, 8: 455 58, 1997; Jakobovits et al., *Ann. N. Y. Acad. Sci.*, 764: 525 35, 1995; Green et al., *Nature Genet.*, 7: 13-21, 1994; Lonberg et al., *Nature*, 368: 856-859, 1994; Taylor et al., *Int. Immun.* 6: 579-591, 1994; and U.S. Pat. No. 5,877,397.

For example, human antibodies that bind PD-L1 may be obtained from transgenic animals that have been engineered to produce specific human antibodies in response to antigenic challenge. For example, International Patent Publication No. WO 98/24893 discloses transgenic animals having a human Ig locus, wherein the animals do not produce functional endogenous immunoglobulins due to the inactivation of endogenous heavy and light chain loci. Transgenic non-primate mammalian hosts capable of mounting an immune response to an immunogen, wherein the antibodies have primate constant and/or variable regions, and wherein the endogenous immunoglobulin encoding loci are substituted or inactivated, also have been described. International Patent Publication No. WO 96/30498 discloses the use of the Cre/Lox system to modify the immunoglobulin locus in a mammal, such as to replace all or a portion of the constant or variable region to form a modified antibody molecule. International Patent Publication No. WO 94/02602 discloses non-human mammalian hosts having inactivated endogenous Ig loci and functional human Ig loci. U.S. Pat. No. 5,939,598 discloses methods of making transgenic mice in which the mice lack endogenous heavy chains, and express an exogenous immunoglobulin locus comprising one or more xenogeneic constant regions. Using a transgenic animal, such as a transgenic animal described herein, an immune response can be produced to a selected antigenic molecule, and antibody producing cells can be removed from the animal and used to produce hybridomas that secrete human-derived monoclonal antibodies. Immunization protocols, adjuvants, and the like are known in the art, and are used in immunization of, for example, a transgenic mouse as described in International Patent Publication No. WO 96/33735. The monoclonal antibodies can be tested for the ability to inhibit or neutralize the biological activity or physiological effect of the corresponding protein.

The present disclosure provides humanized antibodies that bind PD-L1, including human PD-L1. Humanized antibodies of the present disclosure may comprise one or more CDRs as shown in Tables 1-3. Various methods for humanizing non-human antibodies are known in the art. For example, a humanized antibody can have one or more amino acid residues introduced into it from a source that is non-human. These non-human amino acid residues are often referred to as "import" residues, which are typically taken from an "import" variable domain. Humanized antibodies that bind PD-L1 may be produced using techniques known to those skilled in the art (Zhang et al., *Molecular Immunology*, 42(12): 1445-1451, 2005; Hwang et al., *Methods*, 36(1): 35-42, 2005; Dall'Acqua et al., Methods, 36(1): 43-60, 2005; Clark, *Immunology Today*, 21(8): 397-402, 2000, and U.S. Pat. Nos. 6,180,370; 6,054,927; 5,869,619; 5,861,155; 5,712,120; and 4,816,567, all of which are all hereby expressly incorporated herein by reference).

In some cases, the humanized antibodies are constructed by CDR grafting, in which the amino acid sequences of the six complementarity determining regions (CDRs) of the parent non-human antibody (e.g., rodent) are grafted onto a human antibody framework. For example, Padlan et al. (*FASEB J.* 9:133-139, 1995) determined that only about one third of the residues in the CDRs actually contact the antigen, and termed these the "specificity determining residues," or SDRs. In the technique of SDR grafting, only the SDR residues are grafted onto the human antibody framework (see, e.g., Kashmiri et al., *Methods* 36: 25-34, 2005).

The choice of human variable domains, both light and heavy, to be used in making the humanized antibodies can be important to reduce antigenicity. For example, according to the so-called "best-fit" method, the sequence of the variable domain of a non-human (e.g., rodent) antibody is screened against the entire library of known human variable-domain sequences. The human sequence which is closest to that of the rodent may be selected as the human framework for the humanized antibody (Sims et al. (1993) *J. Immunol.* 151:2296; Chothia et al. (1987) *J. Mol. Biol.* 196:901. Another method uses a particular framework derived from the consensus sequence of all human antibodies of a particular subgroup of light or heavy chains. The same framework may be used for several different humanized antibodies (Carter et al. (1992) *Proc. Natl. Acad. Sci. USA,* 89:4285; Presta et al. (1993) *J. Immunol.,* 151:2623. In some cases, the framework is derived from the consensus sequences of the most abundant human subclasses, $V_L6$ subgroup I ($V_L6I$) and $V_H$ subgroup III ($V_HIII$). In another method, human germline genes are used at the source of the framework regions.

In an alternative paradigm based on comparison of CDRs, called Superhumanization, FR homology is irrelevant. The method consists of comparison of the non-human sequence with the functional human germline gene repertoire. Those genes encoding the same or closely related canonical structures to the murine sequences are then selected. Next, within the genes sharing the canonical structures with the non-human antibody, those with highest homology within the CDRs are chosen as FR donors. Finally, the non-human CDRs are grafted onto these FRs (see, e.g., Tan et al., *J. Immunol.* 169: 1119-1125, 2002).

It is further generally desirable that antibodies be humanized with retention of their affinity for the antigen and other favorable biological properties. To achieve this goal, according to one method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. These include, for example, WAM (Whitelegg and Rees, *Protein Eng.* 13: 819-824, 2000), Modeller (Sali and Blundell, *J. Mol. Biol.* 234: 779-815, 1993), and Swiss PDB Viewer (Guex and Peitsch, Electrophoresis 18: 2714-2713, 1997). Inspection of these displays permits analysis of the likely role of the residues in the functioning of the candidate immunoglobulin sequence, e.g., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and most substantially involved in influencing antigen binding.

Another method for antibody humanization is based on a metric of antibody humanness termed Human String Content (HSC). This method compares the mouse sequence with the repertoire of human germline genes and the differences are scored as HSC. The target sequence is then humanized by maximizing its HSC rather than using a global identity measure to generate multiple diverse humanized variants. (Lazar et al., *Mol. Immunol.* 44: 1986-1998, 2007).

In addition to the methods described above, empirical methods may be used to generate and select humanized antibodies. These methods include those that are based upon the generation of large libraries of humanized variants and selection of the best clones using enrichment technologies or high throughput screening techniques. Antibody variants may be isolated from phage, ribosome and yeast display libraries as well as by bacterial colony screening (see, e.g., Hoogenboom, *Nat. Biotechnol.* 23: 1105-1116, 2005; Dufner et al., *Trends Biotechnol.* 24: 523-529, 2006; Feldhaus et al., *Nat. Biotechnol.* 21: 163-70, 2003; Schlapschy et al., *Protein Eng. Des. Sel.* 17: 847-60, 2004).

In the FR library approach, a collection of residue variants are introduced at specific positions in the FR followed by selection of the library to select the FR that best supports the grafted CDR. The residues to be substituted may include some or all of the "Vernier" residues identified as potentially contributing to CDR structure (see, e.g., Foote and Winter, *J. Mol. Biol.* 224: 487-499, 1992), or from the more limited set of target residues identified by Baca et al. (*J. Biol. Chem.* 272: 10678-10684, 1997).

In FR shuffling, whole FRs are combined with the non-human CDRs instead of creating combinatorial libraries of selected residue variants (see, e.g., Dall'Acqua et al., Methods 36: 43-60, 2005). The libraries may be screened for binding in a two-step selection process, first humanizing VL, followed by VH. Alternatively, a one-step FR shuffling process may be used. Such a process has been shown to be more efficient than the two-step screening, as the resulting antibodies exhibited improved biochemical and physicochemical properties including enhanced expression, increased affinity and thermal stability (see, e.g., Damschroder et al., *Mol. Immunol.* 44: 3049-60, 2007).

The "humaneering" method is based on experimental identification of essential minimum specificity determinants (MSDs) and is based on sequential replacement of non-human fragments into libraries of human FRs and assessment of binding. It begins with regions of the CDR3 of non-human VH and VL chains and progressively replaces other regions of the non-human antibody into the human FRs, including the CDR1 and CDR2 of both VH and VL. This methodology typically results in epitope retention and identification of antibodies from multiple sub-classes with distinct human V-segment CDRs. Humaneering allows for isolation of antibodies that are 91-96% homologous to human germline gene antibodies. (see, e.g., Alfenito, Cambridge Healthtech Institute's Third Annual PEGS, The Protein Engineering Summit, 2007).

The "human engineering" method involves altering an non-human antibody or antibody fragment, such as a mouse or chimeric antibody or antibody fragment, by making specific changes to the amino acid sequence of the antibody so as to produce a modified antibody with reduced immunogenicity in a human that nonetheless retains the desirable binding properties of the original non-human antibodies. Generally, the technique involves classifying amino acid residues of a non-human (e.g., mouse) antibody as "low risk", "moderate risk", or "high risk" residues. The classification is performed using a global risk/reward calculation that evaluates the predicted benefits of making particular substitution (e.g., for immunogenicity in humans) against the risk that the substitution will affect the resulting antibody's folding and/or are substituted with human residues. The particular human amino acid residue to be substituted at a given position (e.g., low or moderate risk) of a non-human (e.g., mouse) antibody sequence can be selected by aligning an amino acid sequence from the non-human antibody's variable regions with the corresponding region of a specific or consensus human antibody sequence. The amino acid residues at low or moderate risk positions in the non-human sequence can be substituted for the corresponding residues in the human antibody sequence according to the alignment. Techniques for making human engineered proteins are described in greater detail in Studnicka et al., Protein Engineering, 7: 805-814 (1994), U.S. Pat. Nos. 5,766,886, 5,770,196, 5,821,123, and 5,869,619, and PCT Application Publication WO 93/11794.

In some embodiments, a PD-L1 binding agent described herein comprises a non-antibody protein scaffold. Non-limiting examples of such a non-antibody protein scaffold include a fibronectin scaffold, an anticalin, an adnectin, an Affibody©, a DARPin®, a fynomer, an affitin, an Affilin®, an avimer, a cysteine-rich knottin peptide, or an engineered Kunitz-type inhibitor. Methods for generating such non-antibody protein scaffolds are well known in the art, any one of which can be used to generate a PD-L1 binding agent comprising a non-antibody protein scaffold (see, e.g., Simeon and Chen, *Protein Cell,* 9(1):3-14 (2018); Yang et al., *Annu Rev Anal Chem* (Palo Alto Calif). 10(1):293-320 (2017)).

Further provided are the materials for generating PD-L1 binding agents, e.g., human PD-L1 binding agents, and fragments thereof. For example, an isolated cell (e.g., a hybridoma) may produce a PD-L1 binding agent (e.g., antibody or antibody fragment). In this regard, a cell (e.g., an isolated cell) may produce an antibody or fragment thereof comprising a VH and a VL as shown in Table 1, 2, or 3 for P22, P24, or P31.2, respectively. In some embodiments, polynucleotides described herein may comprise one or more nucleic acid sequences encoding a PD-L1 binding agent (e.g., antibody or antibody fragment). In some embodiments, the polynucleotide is an isolated and/or recombinant polynucleotide. In various aspects, the isolated polynucleotide comprises a nucleotide sequence that encodes an antibody heavy chain variable region (VH) and/or an antibody light chain variable region (VL), wherein the VH and the VL comprise complementarity determining regions (CDRs) identical to CDRs as shown in Table 1, CDRs as shown in Table 2, or CDRs as shown in Table 3.

In some embodiments, one or more vectors (e.g., expression vectors) may comprise one or more polynucleotides for expression of the one or more polynucleotides in a suitable host cell. Such vectors are useful, e.g., for amplifying the polynucleotides in host cells to create useful quantities thereof, and for expressing binding agents, such as antibodies or antibody fragments, using recombinant techniques.

In some embodiments, one or more vectors are expression vectors wherein one or more polynucleotides are operatively linked to one or more polynucleotides comprising expression control sequences. Autonomously replicating recombinant expression constructs such as plasmid and viral DNA vectors incorporating one or more polynucleotides encoding antibody sequences that bind PD-L1 are specifically contemplated. Expression control DNA sequences include promoters, enhancers, and operators, and are generally selected based on the expression systems in which the expression construct is to be utilized. Promoter and enhancer sequences are generally selected for the ability to increase gene expression, while operator sequences are generally selected for the ability to regulate gene expression. Expression constructs may also include sequences encoding one or more selectable markers that permit identification of host cells bearing the construct. Expression constructs may also include sequences that facilitate, and preferably promote, homologous recombination in a host cell. In some embodiments, expression constructs of the can also include sequences necessary for replication in a host cell.

Exemplary expression control sequences include promoter/enhancer sequences, e.g., cytomegalovirus promoter/enhancer (Lehner et al., *J. Clin. Microbiol.,* 29: 2494-2502, 1991; Boshart et al., *Cell,* 41: 521-530, 1985); Rous sarcoma virus promoter (Davis et al., *Hum. Gene Ther.,* 4: 151, 1993); Tie promoter (Korhonen et al., *Blood,* 86(5): 1828-1835, 1995); simian virus 40 promoter; DRA (downregulated in adenoma; Alrefai et al., *Am. J. Physiol. Gastrointest. Liver Physiol.,* 293: G923-G934, 2007); MCT1 (monocarboxylate transporter 1; Cuff et al., *Am. J. Physiol. Gastrointet. Liver Physiol., G977-G979.* 2005); and Math1 (mouse atonal homolog 1; Shroyer et al., *Gastroenterology,* 132: 2477-2478, 2007), for expression in mammalian cells, the promoter being operatively linked upstream (e.g., 5') of a polypeptide coding sequence. In another variation, the promoter is an epithelial-specific promoter or endothelial-specific promoter. Polynucleotides may also optionally include a suitable polyadenylation sequence (e.g., the SV40 or human growth hormone gene polyadenylation sequence) operably linked downstream (e.g., 3') of the polypeptide coding sequence.

If desired, the one or more polynucleotides also optionally comprise nucleotide sequences encoding secretory signal peptides fused in frame with the polypeptide sequences. The secretory signal peptides direct secretion of the antibody polypeptides by the cells that express the one or more polynucleotides, and are cleaved by the cell from the secreted polypeptides. The one or more polynucleotides may further optionally comprise sequences whose only intended function is to facilitate large scale production of the vector. One can manufacture and administer polynucleotides for gene therapy using procedures that have been described in the literature for a variety of transgenes. See, e.g., Isner et al., *Circulation,* 91: 2687-2692, 1995; and Isner et al., *Human Gene Therapy,* 7: 989-1011, 1996.

In some embodiments, polynucleotides may further comprise additional sequences to facilitate uptake by host cells and expression of the antibody or fragment thereof (and/or any other peptide). In some embodiments, a "naked" transgene encoding an antibody or fragment thereof described herein (e.g., a transgene without a viral, liposomal, or other vector to facilitate transfection) is employed.

Any suitable vectors may be used to introduce one or more polynucleotides that encode an antibody or fragment thereof into the host. Exemplary vectors that have been described include replication deficient retroviral vectors, including but not limited to lentivirus vectors (Kim et al., *J. Virol.,* 72(1): 811-816, 1998; Kingsman & Johnson, *Scrip Magazine,* October, 1998, pp. 43-46); parvoviral vectors, such as adeno-associated viral (AAV) vectors (U.S. Pat. Nos. 5,474,935I; 5,139,941; 5,622,856; 5,658,776; 5,773, 289; 5,789,390; 5,834,441; 5,863,541; 5,851,521; 5,252, 479; Gnatenko et al., *J. Invest. Med.,* 45: 87-98, 1997); adenoviral (AV) vectors (U.S. Pat. Nos. 5,792,453; 5,824, 544; 5,707,618; 5,693,509; 5,670,488; 5,585,362; Quantin et al., Proc. Natl. Acad. Sci. USA, 89: 2581-2584, 1992; Stratford Perricaudet et al., *J. Clin. Invest.,* 90: 626-630, 1992; and Rosenfeld et al., *Cell,* 68: 143-155, 1992); an adenoviral adeno-associated viral chimeric (U.S. Pat. No. 5,856,152) or a vaccinia viral or a herpesviral vector (U.S. Pat. Nos. 5,879,934; 5,849,571; 5,830,727; 5,661,033;

5,328,688); Lipofectin mediated gene transfer (BRL); liposomal vectors (U.S. Pat. No. 5,631,237); and combinations thereof. Any of these expression vectors can be prepared using standard recombinant DNA techniques described in, e.g., Sambrook et al., *Molecular Cloning, a Laboratory Manual*, 2d edition, Cold Spring Harbor Press, Cold Spring Harbor, N.Y. (1989), and Ausubel et al., *Current Protocols in Molecular Biology*, Greene Publishing Associates and John Wiley & Sons, New York, N.Y. (1994). Optionally, viral vectors are rendered replication-deficient by, e.g., deleting or disrupting select genes required for viral replication.

Other non-viral delivery mechanisms contemplated include calcium phosphate precipitation (Graham and Van Der Eb, *Virology*, 52: 456-467, 1973; Chen and Okayama, *Mol. Cell Biol.*, 7: 2745-2752, 1987; Rippe et al., *Mol. Cell Biol.*, 10: 689-695, 1990) DEAE-dextran (Gopal, *Mol. Cell Biol.*, 5: 1188-1190, 1985), electroporation (Tur-Kaspa et al., *Mol. Cell Biol.*, 6: 716-718, 1986; Potter et al., *Proc. Nat. Acad. Sci. USA*, 81: 7161-7165, 1984), direct microinjection (Harland and Weintraub, *J. Cell Biol.*, 101: 1094-1099, 1985, DNA-loaded liposomes (Nicolau and Sene, *Biochim. Biophys. Acta*, 721: 185-190, 1982; Fraley et al., *Proc. Natl. Acad. Sci. USA*, 76: 3348-3352, 1979; Felgner, *Sci Am.*, 276(6): 102-6, 1997; Felgner, *Hum Gene Ther.*, 7(15): 1791-3, 1996), cell sonication (Fechheimer et al., *Proc. Natl. Acad. Sci. USA*, 84: 8463-8467, 1987), gene bombardment using high velocity microprojectiles (Yang et al., *Proc. Natl. Acad. Sci USA*, 87: 9568-9572, 1990), and receptor-mediated transfection (Wu and Wu, *J. Biol. Chem.*, 262: 4429-4432, 1987; Wu and Wu, *Biochemistry*, 27: 887-892, 1988; Wu and Wu, *Adv. Drug Delivery Rev.*, 12: 159-167, 1993).

An expression vector (or the antibody or fragment thereof discussed herein) may be entrapped in a liposome. See, e.g., Ghosh and Bachhawat, In: *Liver diseases, targeted diagnosis and therapy using specific receptors and ligands*, Wu G, Wu C ed., New York: Marcel Dekker, pp. 87-104 (1991); Radler et al., *Science*, 275(5301): 810-814, 1997). Also contemplated are various commercial approaches involving "lipofection" technology. In some embodiments, the liposome may be complexed with a hemagglutinating virus (HVJ). This has been shown to facilitate fusion with the cell membrane and promote cell entry of liposome-encapsulated DNA (Kaneda et al., Science, 243: 375-378, 1989). In some embodiments, the liposome is complexed or employed in conjunction with nuclear nonhistone chromosomal proteins (HMG-1) (Kato et al., *J. Biol. Chem.*, 266: 3361-3364, 1991). In some embodiments, the liposome are complexed or employed in conjunction with both HVJ and HMG-1. Such expression constructs have been successfully employed in transfer and expression of nucleic acid in vitro and in vivo. In some embodiments, a PD-L1 binding agent (e.g., an antibody), including a human PD-L1 binding agent, is included in the liposome to target the liposome to cells (such as tumor cells) expressing PD-L1 on their surface.

A cell may comprise one or more polynucleotides or one or more vectors, e.g., the cell is transformed or transfected with one or more polynucleotides encoding a PD-L1 binding agent (e.g., an antibody), including a human PD-L1 binding agent, or the one or more vectors comprising the one or more polynucleotides. In some embodiments, cells express a PD-L1 binding agent (e.g., an antibody), including a human PD-L1 binding agent, containing one or more, including six CDRs having at least 75% identity to the CDRs of P22 (see, e.g., Table 1). In some embodiments, the cell expresses a PD-L1 binding agent (e.g., an antibody), including a human PD-L1 binding agent, containing the $V_H$ and the $V_L$ comprising CDRs identical to those of P24 (see, e.g., Table 2). In some embodiments, the cell expresses a PD-L1 binding agent (e.g., an antibody), including a human PD-L1 binding agent, containing the VH and the VL comprising CDRs identical to those of P31.2 (see, e.g., Table 3). The cells may be prokaryotic cells, such as *Escherichia coli* (see, e.g., Pluckthun et al., *Methods Enzymol.*, 178: 497-515, 1989), or eukaryotic cells, such as an animal cell (e.g., a myeloma cell, Chinese Hamster Ovary (CHO) cell, or hybridoma cell), yeast (e.g., *Saccharomyces cerevisiae*), or a plant cell (e.g., a tobacco, corn, soybean, or rice cell). Use of mammalian host cells may provide for translational modifications (e.g., glycosylation, truncation, lipidation, and phosphorylation) that may be desirable to confer optimal biological activity on recombinant expression products. Similarly, polypeptides (e.g., PD-L1 binding agents (e.g., antibodies), including human PD-L1 binding agents) may be glycosylated or non-glycosylated and/or have been covalently modified to include one or more water soluble polymer attachments such as polyethylene glycol, polyoxyethylene glycol, or polypropylene glycol.

Methods for introducing DNA or RNA into host cells are well known and include transformation, transfection, electroporation, nuclear injection, or fusion with carriers such as liposomes, micelles, ghost cells, and protoplasts. Such host cells are useful for amplifying polynucleotides and also for expressing polypeptides encoded by the polynucleotides. In this regard, a process for the production of a PD-L1 binding agent (e.g., an antibody) may comprise culturing a host cell and isolating the PD-L1 binding agent. Transferring a naked DNA expression construct into cells can be accomplished using particle bombardment, which depends on the ability to accelerate DNA coated microprojectiles to a high velocity allowing them to pierce cell membranes and enter cells without killing them (Klein et al., *Nature*, 327: 70-73, 1987). Several devices for accelerating small particles have been developed. One such device relies on a high voltage discharge to generate an electrical current, which in turn provides the motive force (Yang et al., *Proc. Natl. Acad. Sci USA*, 87: 9568-9572, 1990). The microprojectiles used have consisted of biologically inert substances such as tungsten or gold beads. A host cell may be isolated and/or purified. A host cell also may be a cell transformed in vivo to cause transient or permanent expression of the polypeptide in vivo. A host cell may also be an isolated cell transformed ex vivo and introduced post-transformation, e.g., to produce the polypeptide in vivo for therapeutic purposes. The definition of host cell explicitly excludes a transgenic human being.

A variety of methods for producing antibodies from polynucleotides are generally well-known. For example, basic molecular biology procedures are described by Maniatis et al., *Molecular Cloning, A Laboratory Manual*, 2nd ed., Cold Spring Harbor Laboratory, New York, 1989 (see also Maniatis et al, 3rd ed., Cold Spring Harbor Laboratory, New York, 2001). Additionally, numerous publications describe techniques suitable for the preparation of antibodies by manipulation of DNA, creation of expression vectors, and transformation and culture of appropriate cells (see, e.g., Mountain and Adair, Chapter 1 in *Biotechnology and Genetic Engineering Reviews*, Tombs ed., Intercept, Andover, UK, 1992); and *Current Protocols in Molecular Biology*, Ausubel ed., Wiley Interscience, New York, 1999).

A PD-L1 binding agent (e.g., an antibody), including a human PD-L1 binding agent, is produced using any suitable method, e.g., isolated from an immunized animal, recombinantly or synthetically generated, or genetically-engineered, including as described above. Antibody fragments derived from an antibody are obtained by, e.g., proteolytic hydrolysis of an antibody. For example, papain or pepsin digestion of whole antibodies yields a 5S fragment termed F(ab')$_2$ or two monovalent Fab fragments and an Fc fragment, respectively. F(ab)$_2$ can be further cleaved using a thiol reducing agent to produce 3.5S Fab monovalent fragments. Methods of generating antibody fragments are further described in, for example, Edelman et al., *Methods in Enzymology*, 1: 422 Academic Press (1967); Nisonoff et al., *Arch. Biochem. Biophys.*, 89: 230-244, 1960; Porter, Biochem. J., 73: 119-127, 1959; U.S. Pat. No. 4,331,647; and by Andrews, S. M. and Titus, J. A. in *Current Protocols in Immunology* (Coligan et al., eds), John Wiley & Sons, New York (2003), pages 2.8.1 2.8.10 and 2.10A.1 2.10A.5.

A PD-L1 binding agent (e.g., an antibody), including a human PD-L1 binding agent, can be genetically engineered. For example, a PD-L1 binding agent (e.g., an antibody), including a human PD-L1 binding agent, comprises, for example, a variable region domain generated by recombinant DNA engineering techniques. In this regard, a variable region is optionally modified by insertions, deletions, or changes in the amino acid sequence of the antibody to produce an antibody of interest, including as described above. Polynucleotides encoding complementarity determining regions (CDRs) of interest are prepared, for example, by using polymerase chain reaction to synthesize variable regions using mRNA of antibody producing cells as a template (see, for example, Courtenay Luck, "Genetic Manipulation of Monoclonal Antibodies," in *Monoclonal Antibodies: Production, Engineering and Clinical Application*, Ritter et al. (eds.), page 166 (Cambridge University Press 1995); Ward et al., "Genetic Manipulation and Expression of Antibodies," in *Monoclonal Antibodies: Principles and Applications*, Birch et al., (eds.), page 137 (Wiley Liss, Inc. 1995); and Larrick et al., *Methods: A Companion to Methods in Enzymology*, 2: 106-110, 1991). Current antibody manipulation techniques allow construction of engineered variable region domains containing at least one CDR and, optionally, one or more framework amino acids from a first antibody and the remainder of the variable region domain from a second antibody. Such techniques are used, e.g., to humanize an antibody or to improve its affinity for a binding target.

"Humanized antibodies" are antibodies in which CDRs of heavy and light variable chains of non-human immunoglobulins are transferred into a human variable domain. Constant regions need not be present, but if they are, they optionally are substantially identical to human immunoglobulin constant regions, e.g., at least about 85-90%, about 95%, 96%, 97%, 98%, 99% or more identical, in some embodiments. Hence, in some instances, all parts of a humanized immunoglobulin, except possibly the CDRs, are substantially identical to corresponding parts of natural human immunoglobulin sequences. For example, humanized antibodies are human immunoglobulins (e.g., host antibody) in which hypervariable region residues of the host antibody are replaced by hypervariable region residues from a non-human species (donor antibody) such as mouse, rat, rabbit, or a non-human primate having the desired specificity, affinity, and capacity.

In some embodiments, PD-L1 binding agents (e.g., antibodies) described herein are useful in compositions and in methods of treating, preventing, or alleviating a T cell dysfunctional disease, disorder, or condition, including one or more symptoms of the disease, disorder, or condition. T cell dysfunctional diseases, disorders, and conditions include tumor immunity and associated cancers, including, but not limited to, any cancer wherein the tumor cells overexpress PD-L1. Such PD-L1 over-expressing tumor cells may help tumor cells escape immune surveillance and removal. In addition, PD-L1 binding agents described herein, such as PD-L1 binding antibodies (e.g., monospecific or multispecific antibodies, including bispecific antibodies), are useful to inhibit PD-1 signaling and/or enhance T cell function (e.g., secrete cytokines, proliferate, execute cytolytic activity) and thus enhance immune surveillance and removal of tumor cells.

In some embodiments, described herein is a method for treating tumor immunity in a subject comprising administering to the subject a PD-L1 binding agent (e.g., an antibody) described herein or fragment thereof or a pharmaceutical composition comprising the binding agent (e.g., antibody) described herein.

In some embodiments, described herein is a method for treating a cancer or a tumor in a subject comprising administering to the subject a PD-L1 binding agent (e.g., an antibody) described herein or fragment thereof or a pharmaceutical composition comprising the binding agent (e.g., antibody) described herein.

In some embodiments, described herein is a method for alleviating one or more symptoms associated with a cancer or a tumor in a subject comprising administering to the subject a PD-L1 binding agent (e.g., an antibody) described herein or fragment thereof or a pharmaceutical composition comprising the binding agent (e.g., antibody) described herein.

In some embodiments, described herein is a method for decreasing tumor size in a subject with a tumor comprising administering to the subject a PD-L1 binding agent (e.g., an antibody) described herein or fragment thereof or a pharmaceutical composition comprising the binding agent (e.g., antibody) described herein.

In some embodiments, described herein is a method for treating a T cell dysfunctional disease, disorder or condition in a subject comprising administering to the subject a PD-L1 binding agent (e.g., an antibody) described herein or fragment thereof or a pharmaceutical composition comprising the binding agent (e.g., antibody) described herein. In some embodiments, the T cell dysfunctional disease, disorder or condition is tumor immunity.

In some embodiments, described herein is a method for enhancing tumor cell removal in a subject with a tumor comprising administering to the subject PD-L1 binding agent (e.g., an antibody) described herein or fragment thereof or a pharmaceutical composition comprising the binding agent (e.g., antibody) described herein.

In some embodiments, described herein is a method for enhancing T cell function in a subject comprising administering to the subject PD-L1 binding agent (e.g., an antibody) described herein or fragment thereof or a pharmaceutical composition comprising the binding agent (e.g., antibody) described herein. In some embodiments, the T cell function is secretion of cytokines. In some embodiments, the T cell function is removal of tumor cells. In some embodiments, the subject is diagnosed with a cancer or a tumor.

The subject of a method described above can be administered one or more therapeutic agents described herein in combination with a PD-L1 binding agent (e.g., an antibody) described herein or fragment thereof or a pharmaceutical composition comprising the binding agent (e.g., antibody) described herein.

In some embodiments, the antibody is a human antibody, including, but not limited to, an antibody having variable regions in which both the framework and CDR regions are derived from human germline immunoglobulin sequences as described, for example, in Kabat et al. (1991) *Sequences of proteins of Immunological Interest*, Fifth Edition, U.S. Department of Health and Human Services, NIH Publication No. 91-3242. If the antibody contains a constant region, the constant region also preferably is derived from human germline immunoglobulin sequences. Human antibodies may comprise amino acid residues not encoded by human germline immunoglobulin sequences, for example, to enhance the activity of the antibody, but do not comprise CDRs derived from other species (e.g., a mouse CDR placed within a human variable framework region).

In some embodiments, a PD-L1 binding agent (e.g., an antibody) increases T cell function and/or enhances cytolytic activity of cells in cell culture. Such cell culture may include tumor cells expressing or overexpressing PD-L1. Tumor cells include, but are not limited to, breast cancer cells, bladder cancer cells, melanoma cells, prostate cancer cells, mesothelioma cells, lung cancer cells, testicular cancer cells, thyroid cancer cells, squamous cell carcinoma cells, glioblastoma cells, neuroblastoma cells, uterine cancer cells, colorectal cancer cells, and pancreatic cancer cells.

In some embodiments, described herein is a method of enhancing the removal of tumor cells in a subject. For example, the method comprises administering an amount of a PD-L1 binding agent (e.g., an antibody), such as a human PD-L1 binding agent described herein, effective to enhance the removal of the tumor cells. In some embodiments, the method includes administering a PD-L1 binding agent (e.g., an antibody), including a PD-L1 binding agent, that competes for binding with antibody P22, antibody P24, and/or antibody P31.2 (see, e.g., CDRs and VH/VL of Tables 1, 2 and/or 3), to human PD-L1 and/or binds the region of a PD-L1 recognized by antibody P22, antibody P24, and/or antibody P31.2 (see, e.g., CDRs and VH/VL of Tables 1, 2 and/or 3), resulting in enhancement of the removal of tumor cells. In some embodiments, one or more binding agents (e.g. antibodies), polynucleotides, vectors, and/or cells as described above can be used in methods of enhancing the removal of tumor cells in vivo (e.g., in a method of treating cancer in a subject).

A method of modulating (e.g., inhibiting, reducing, preventing) tumor growth in a subject also is provided. For example, the method comprises administering to the subject a composition comprising a PD-L1 binding agent (e.g., an antibody) in an amount effective to modulate tumor growth in the subject. "Tumor" refers to any neoplastic cell growth or proliferation, whether malignant or benign, and to all pre-cancerous and cancerous cells and tissues. The terms "cancer" and "cancerous" refer to or describe the physiological condition in mammals that is typically characterized by unregulated cell growth. Examples of cancers include, but are not limited to: breast cancer, colon cancer, renal cancer, lung cancer, squamous cell myeloid leukemia, hemangiomas, melanomas, astrocytomas, and glioblastomas as well as other cellular-proliferative disease states, including but not limited to: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hanlartoma, inesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinorna, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor (nephroblastoma}, lymphoma, leukemia, renal cell carcinoma), bladder and urethra (squamous cell carcinoma, transitional cell carcinoma, adenocarcinoma), prostate (adenocarcinoma, sarcoma, small cell carcinoma of the prostate), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis defornians), meninges (meningioma, meningiosarcoma, gliomatosis), brain (astrocytoma, medulloblastoma, glioma, ependymoma, germinoma (pinealoma), glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma) serous cystadenocarcinoma, mucinous cystadenocarcinoma, unclassified carcinoma, granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma], fallopian tubes (carcinoma); Hematologic: blood (myeloid leukemia (acute and chronic), acute lymphoblastic leukemia, chronic lymphocytic leukemia, myeloproliferative diseases, multiple myeloma, myelodysplastic syndrome), Hodgkin's disease, non-Hodgkin's lymphoma (malignant lymphoma); Skin: malignant melanoma, basal cell carcinoma, squamous cell carcinoma, Karposi's sarcoma, moles dysplastic nevi, lipoma, angioma, dermatofibroma, keloids, psoriasis; and Adrenal glands: neuroblastoma; as well as cancers of the thyroid including medullary thyroid cancer. Also provided is a method of treating cancer by administering a PD-L1 binding agent (e.g., an antibody) such as a human PD-L1 binding agent, to a subject in need thereof, alone or in combination with another agent.

"Enhancing" tumor cell removal does not require a 100% enhancement of removal. Any enhancement in the rate of removal is contemplated. Similarly, "modulating" tumor growth refers to reducing the size of the tumor, slowing tumor growth, or inhibiting an increase in the size of an existing tumor. Complete abolition of a tumor is not required; any decrease in tumor size or slowing of tumor growth constitutes a beneficial biological effect in a subject. In this regard, tumor cell removal may be enhanced by, for example, at least about 5%, at least about 10% or at least about 20% compared to levels of removal observed in the absence of the method (e.g., in a biologically-matched control subject or specimen that is not exposed to the agent of the method). The effect is detected by, for example, a reduction in tumor size, a decrease or maintenance of the levels of tumor markers, or reduction or maintenance of a tumor cell population. In some embodiments, removal of tumor cells is enhanced by, for example, at least about 30%, at least about 40%, at least about 50%, at least about 60%, at least about 70%, at least about 80%, at least about 90%, or more (about 100%) compared to the removal of tumor cells in the absence of a PD-L1 binding agent (e.g., an antibody) of the method.

Additionally, PD-L1 binding agents (e.g., antibodies) may be used to alleviate or reduce side effects associated with cancer such as, for example, bone deterioration, vertebral collapse, and paralysis. In one aspect, the subject suffers from or is at risk of suffering from bone metastases and a PD-L1 binding agent (e.g., an antibody) is administered in an amount to reduce deterioration of surrounding bone. Accordingly, in some aspects, a PD-L1 binding agent prevents bone deterioration due to bone metastases, wherein tumor cell proliferation is or is not reduced. In some aspects, a PD-L1 binding agent (e.g., an antibody) both prevents bone deterioration due to bone metastases and reduces tumor cell proliferation. In general, the effect on tumor cell proliferation (e.g., inhibition of proliferation or no effect on proliferation) depends on the microenvironment of a particular metastasis. For example, proliferation of metastases located in microenvironments with substantial amounts of type 1 collagen may be inhibited. In contrast, proliferation of metastases located in microenvironments lacking substantial amounts of type 1 collagen may not be inhibited, yet bone deterioration in the vicinity of the metastasis is reduced or prevented.

A particular administration regimen of a PD-L1 binding agent (e.g., an antibody) for a particular subject will depend, in part, upon the agent used, the amount of agent administered, the route of administration, and the cause and extent of any side effects. The amount of agent (e.g., an antibody) administered to a subject (e.g., a mammal, such as a human) should be sufficient to effect the desired response over a reasonable time frame. According, in some embodiments, the amount of a PD-L1 binding agent (e.g., an antibody) or pharmaceutical composition described herein administered to a subject is an effective amount. In some embodiments, the amount of a PD-L1 binding agent (e.g., an antibody) or pharmaceutical composition described herein administered to a subject is a therapeutically effective amount. In some aspects, the method comprises administering, e.g., from about 0.1 µg/kg to up to about 100 mg/kg or more. In some embodiments, the dosage ranges from about 1 µg/kg up to about 100 mg/kg; or about 5 µg/kg up to about 100 mg/kg; or about 10 µg/kg up to about 100 mg/kg; or about 1 mg/kg up to about 50 mg/kg; or about 2 mg/kg up to about 30 mg/kg; or about 3 mg/kg up to about 25 mg/kg; or about 3 mg/kg up to about 25 mg/kg; or about 5 mg/kg up to about 10 mg/kg; or about 10 mg/kg up to about 20 mg/kg; or about 10 mg/kg up to about 30 mg/kg. Some conditions or disease states require prolonged treatment, which may or may not entail administering doses of PD-L1 binding agents (e.g., antibodies), including human PD-L1 binding agents (e.g., antibodies), over multiple administrations (e.g., every day, three times a week, once a week, once every two weeks, or once every month for a treatment period of three days, seven days, two weeks, three weeks, one month, three months, six months, nine months, 12 months, 15 months, 18 months, 21 months, two years, or more).

Suitable routes of administering a composition comprising a PD-L1 binding agent (e.g., an antibody), such as a human PD-L1 binding agent (e.g., an antibody), are well known in the art. Although more than one route can be used to administer an agent (e.g., an antibody), a particular route can provide a more immediate and more effective reaction than another route. Depending on the circumstances, a composition comprising a PD-L1 binding agent (e.g., an antibody) such as a human PD-L1 binding agent is applied or instilled into body cavities, absorbed through the skin or mucous membranes, ingested, inhaled, and/or introduced into circulation. For example, it may be desirable to deliver a composition comprising a PD-L1 binding agent (e.g., an antibody), such as a human PD-L1 binding agent, through injection by intravenous, subcutaneous, intraperitoneal, intracerebral (intra-parenchymal), intracerebroventricular, intramuscular, intra-ocular, intraarterial, intraportal, intralesional, intramedullary, intrathecal, intraventricular, transdermal, subcutaneous, intraperitoneal, intranasal, enteral, topical, sublingual, urethral, vaginal, or rectal means, by sustained release systems, or by implantation devices. If desired, a PD-L1 binding agent (e.g., an antibody), such as a human PD-L1 binding agent, is administered regionally via intraarterial or intravenous administration feeding the region of interest, e.g., via the hepatic artery for delivery to the liver. Alternatively, a PD-L1 binding agent (e.g., an antibody), such as a human PD-L1 binding agent, is administered locally via implantation of a membrane, sponge, or another appropriate material on to which the binding agent has been absorbed or encapsulated. Where an implantation device is used, the device is, one aspect, implanted into any suitable tissue or organ, and delivery of a PD-L1 binding agent (e.g., an antibody), such as a human PD-L1 binding agent, is, for example, via diffusion, timed-release bolus, or continuous administration. In other aspects, a PD-L1 binding agent (e.g., an antibody) is administered directly to exposed tissue during tumor resection or other surgical procedures.

The present disclosure provides a composition, such as pharmaceutical composition, comprising a PD-L1 binding agent (e.g., an antibody) such as a human PD-L1 binding agent and a carrier (e.g., a pharmaceutically acceptable carrier). The particular carrier employed may depend on chemico-physical considerations, such as solubility and lack of reactivity with the binding agent or co-therapy, and by the route of administration. Pharmaceutically acceptable carriers are well-known in the art, examples of which are described herein. Illustrative pharmaceutical forms suitable for injectable use include sterile aqueous solutions or dispersions and sterile powders for the extemporaneous preparation of sterile injectable solutions or dispersions. Injectable formulations are further described in, e.g., *Pharmaceutics and Pharmacy Practice*, J. B. Lippincott Co., Philadelphia. Pa., Banker and Chalmers. eds., pages 238-250 (1982), and *ASHP Handbook on Injectable Drugs*, Toissel, 4th ed., pages 622-630 (1986)). A pharmaceutical composition comprising a PD-L1 binding agent (e.g., an antibody) such as a human PD-L1 binding agent is, in one aspect, placed within containers, along with packaging material that provides instructions regarding the use of such pharmaceutical compositions. Generally, such instructions include a tangible expression describing the reagent concentration, as well as, in some embodiments, relative amounts of excipient ingredients or diluents (e.g., water, saline or PBS) that may be necessary to reconstitute the pharmaceutical composition.

In some aspects, a method described herein further comprises administering one or more additional agents, including therapeutic agents, which may be present in a composition or may be administered with a PD-L1 binding agent (e.g., an antibody), such as a human PD-L1 binding agent, or provided in a separate composition using the same or a different route of administration. The one or more additional agents, including therapeutic agents, may be administered (e.g., for combination therapy) together or separately (e.g., simultaneously, alternatively, sequencially) with a PD-L1 binding agent (e.g., antibody). Such additional therapeutic agents include, but are not limited to, therapeutic antibodies, immunotherapies and immunotherapeutic agents, cytotoxic agents, chemotherapeutic agents, and inhibitors.

Therapeutic antibodies that can be used with a PD-L1 binding agent (e.g., an antibody) as described herein (e.g., for combination therapy) include, but are not limited to, trastuzumab; abciximab; daclizumab; BEC2; IMC-C22; vitaxin; Campath 1H/LDP-03; Smart M195; epratuzumab; bectumomab; visilizumab; CM3, a humanized anti-ICAM3 antibody; IDEC-I 14; ibritumomab tiuxetan; IDEC-131; IDEC-151; IDEC-152; SMART anti-CD3; eculizumab; adalimumab; certolizumab; IDEC-I 51; MDX-CD4; CD20-sreptdavidin; CDP571; LDP-02; OrthoClone OKT4A; ruplizumab; natalizumab; and lerdelimumab.

Immunotherapies and immunotherapeutic agents that can be used with a PD-L1 binding agent (e.g., an antibody) as described herein (e.g., for combination therapy) include, but are not limited to, cytokines, such as granulocyte-macrophage colony-stimulating factor (GM-CSF), granulocyte-colony stimulating factor (G-CSF), macrophage inflammatory protein (MIP)-I-alpha, interleukins (including IL-1, IL-2, IL-4, IL-6, IL-7, IL-12, IL-15, IL-18, IL-21, and IL-27), tumor necrosis factors (including TNF-alpha), and interferons (including IFN-alpha, IFN-beta, and IFN-gamma); aluminum hydroxide (alum); Bacille Calmette-Guerin (BCG); Keyhole limpet hemocyanin (KLH); Incomplete Freund's adjuvant (IF A); QS-21; DETOX; Levamisole; and Dinitrophenyl (DNP), and combinations thereof, such as, for example, combinations of, interleukins, for example, IL-2 with other cytokines, such as IFN-alpha. In some embodiments, the immunotherapy includes an immunotherapeutic agent that modulates immune responses, for example, a checkpoint inhibitor or a checkpoint agonist. In some embodiments, the immunotherapeutic agent is an antibody modulator that targets PD-1, PD-L1, PD-L2, CEACAM (e g., CEACAM-1, -3 and/or -5), CTLA-4, TIM-3, LAG-3, VISTA, BTLA, TIGIT, LAIR1, CD160, 2B4, TGF beta, OX40, 41BB, LIGHT, CD40, GITR, TGF-beta, TIM-3, SIRP-alpha, VSIG8, BTLA, SIGLEC7, SIGLEC9, ICOS, B7H3, B7H4, FAS, and/or BTNL2 among others known in the art. In some embodiments, the immunotherapeutic agent is an agent that increases natural killer (NK) cell activity. In some embodiments, the immunotherapeutic agent is an agent that inhibits suppression of an immune response. In some embodiments, the immunotherapeutic agent is an agent that inhibits suppressor cells or suppressor cell activity. In some embodiments, the immunotherapeutic agent is an agent or therapy that inhibits Treg activity. In some embodiments, the immunotherapeutic agent is an agent that inhibits the activity of inhibitory immune checkpoint receptors.

In some embodiments, the immunotherapeutic agent includes a T cell modulator chosen from an agonist or an activator of a costimulatory molecule. In one embodiment, the agonist of the costimulatory molecule is chosen from an agonist (e.g., an agonistic antibody or antigen-binding fragment thereof, or a soluble fusion) of GITR, OX40, ICOS, SLAM (e.g., SLAMF7), HVEM, LIGHT, CD2, CD27, CD28, CDS, ICAM-1, LFA-I (CD1 Ia/CDI8), ICOS (CD278), 4-1BB (CD137), CD30, CD40, BAFFR, CD7, NKG2C, NKp80, CD160, B7-H3, or CD83 ligand. In other embodiments, the effector cell combination includes a bispecific T cell engager (e.g., a bispecific antibody molecule that binds to CD3 and a tumor antigen (e.g., EGFR, PSCA, PSMA, EpCAM, HER2 among others).

Cytotoxic agents that can be used with a PD-L1 binding agent (e.g., an antibody) as described herein (e.g., for combination therapy) include a substance that inhibits or prevents a cellular function and/or causes cell death or destruction. Exemplary cytotoxic agents include, but are not limited to, radioactive isotopes (e.g., At211, 1131, 1125, Y90, Re186, Re188, Sm153, Bi212, P32, Pb212 and radioactive isotopes of Lu); growth inhibitory agents; enzymes and fragments thereof such as nucleolytic enzymes; and toxins such as small molecule toxins or enzymatically active toxins of bacterial, fungal, plant or animal origin, including fragments and/or variants thereof. Other exemplary cytotoxic agents can be selected from anti-microtubule agents, platinum coordination complexes, alkylating agents, antibiotic agents, topoisomerase II inhibitors, antimetabolites, topoisomerase I inhibitors, hormones and hormonal analogues, signal transduction pathway inhibitors, non-receptor tyrosine kinase angiogenesis inhibitors, immunotherapeutic agents, proapoptotic agents, inhibitors of LDH-A; inhibitors of fatty acid biosynthesis; cell cycle signaling inhibitors; HDAC inhibitors, proteasome inhibitors; and inhibitors of cancer metabolism.

Chemotherapeutic agents that can be used with a PD-L1 binding agent (e.g., an antibody) as described herein (e.g., for combination therapy) include chemical compounds useful in the treatment of cancer. Examples of chemotherapeutic agents include, but are not limited to, erlotinib, bortezomib, disulfiram, epigallocatechin gallate, salinosporamide A, carfilzomib, I7-AAG (geldanamycin), radicicol, lactate dehydrogenase A (LDH-A), fulvestrant, sunitib, letrozole, imatinib mesylate, fmasunate, oxaliplatin, 5-FET (5-fluorouracil), leucovorin, Rapamycin, Lapatinib, Lonafamib (SCH 66336), sorafenib, Bayer Labs), gefitinib, AG1478; alkylating agents such as thiotepa and CYTOXAN®; cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including topotecan and irinotecan); bryostatin; cally statin; CC-1065 (including its adozelesin, carzelesin and bizelesin synthetic analogs); cryptophycins (particularly cryptophycin 1 and cryptophycin 8); adrenocorticosteroids (including prednisone and prednisolone); cyproterone acetate; 5 alpha-reductases including finasteride and dutasteride); vorinostat, romidepsin, panobinostat, valproic acid, mocetinostat dolastatin; aldesleukin, talc duocarmycin (including the synthetic analogs, KW-2189 and CB1-TM1); eleutherobin; pancrati statin; a sarcodictyin; spongistatin; nitrogen mustards such as chlorambucil, chlomaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g., calicheamicin, especially calicheamicin gamma II and calicheamicin omega I (Angew Chem. Inti. Ed. Engl. 1994 33: 183-186); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, doxorubicin, morpholinodoxorubicin, cyanomorpholino-doxorubicin, 2-pyrrolinodoxorubicin and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate defofamine; demecolcine; diaziquone; elfornithine; elliptinium acetate; an epothilone; etoglucid; gallium nitrate; hydroxyurea; lentinan; lonidainine; maytansinoids such as maytansine and ansamitocins; mitoguazone; mitoxantrone; mopidamnol; nitraerine; pentostatin; phenamet; pirarubicin; losoxantrone; podophyllinic acid; 2-ethylhydrazide; procarbazine; PSK® polysaccharide complex (JHS Natural Products, Eugene, Ore.); razoxane; rhizoxin; sizofuran; spirogermanium; tenuazonic acid; triaziquone; 2,2',2"-trichlorotriethylamine; trichothecenes especially T-2 toxin, verracurin A, roridin A and anguidine); urethan; vindesine; dacarbazine; mannomustine; mitobronitol; mitolactol; pipobroman; gacytosine; arabinoside "Ara-C"); cyclophosphamide; thiotepa; taxoids, e.g., paclitaxel, ABRAXANE® (Cremophor-free), albumin-engineered nanoparticle formulations of paclitaxel (American Pharmaceutical Partners, Schaumberg, Ill.), and docetaxel/doxetaxel; chloranmbucil; gemcitabine; 6-thioguanine; mercaptopurine; methotrexate; platinum analogs such as cisplatin and carboplatin; vinblastine; etoposide (VP-16); ifosfamide; mitoxantrone; vincristine; vinorelbine; novantrone; teniposide; edatrexate; daunomycin; aminopterin; capecitabine; ibandronate; CPT-I I; topoisomerase inhibitor RFS 2000; difluorom ethyl ornithine (DMFO); retinoids such as retinoic acid; and pharmaceutically acceptable salts, acids and derivatives of any of the above. Chemotherapeutic agent also includes (i) anti-hormonal agents that act to regulate or inhibit hormone action on tumors such as anti-estrogens and selective estrogen receptor modulators (SERMs), including, for example, tamoxifen (including tamoxifen citrate), raloxifene, droloxifene, iodoxyfene, 4-hydroxytamoxifen, trioxifene, keoxifene, LY117018, onapristone, and toremifme citrate; (ii) aromatase inhibitors that inhibit the enzyme aromatase, which regulates estrogen production in the adrenal glands, such as, for example, 4(5)-imidazoles, aminoglutethimide, megestrol acetate, exemestane, formestanie, fadrozole, vorozole, letrozole, and anastrozole; (iii) anti-androgens such as flutamide, nilutamide, bicalutamide, leuprolide and goserelin; buserelin, tripterelin, medroxyprogesterone acetate, diethylstilbestrol, premarin, fluoxymesterone, all transretionic acid, fenretinide, as well as troxacitabine (a 1,3-dioxolane nucleoside cytosine analog); (iv) protein kinase inhibitors; (v) lipid kinase inhibitors; (vi) antisense oligonucleotides, particularly those which inhibit expression of genes in signaling pathways implicated in aberrant cell proliferation, such as, for example, PKC-alpha, Ralf and H-Ras; (vii) ribozymes such as VEGF expression inhibitors (e.g., ANGIOZYME®) and HER2 expression inhibitors; (viii) vaccines such as gene therapy vaccines, for example, ALLOVECTIN®, LEUVECTIN®, and VAXID®; PROLEUKIN®, rIL-2; a topoisomerase 1 inhibitor such as LEIRTOTECAN®; ABARELIX®; and (ix) pharmaceutically acceptable salts, acids and derivatives of any of the above.

Chemotherapeutic agents also include antibodies, as described above, including alemtuzumab, bevacizumab; cetuximab; panitumumab, rituximab, pertuzumab, tositumomab, and the antibody drug conjugate, gemtuzumab ozogamicin. Additional humanized monoclonal antibodies with therapeutic potential as agents in combination with PD-L1 binding agents (e.g., antibodies) as described herein include: apolizumab, aselizumab, atlizumab, bapineuzumab, bivatuzumab mertansine, cantuzumab mertansine, cedelizumab, certolizumab pegol, cidfusituzumab, cidtuzumab, daclizumab, eculizumab, efalizumab, epratuzumab, erlizumab, felvizumab, fontolizumab, gemtuzumab ozogamicin, inotuzumab ozogamicin, ipilimumab, labetuzumab, lintuzumab, matuzumab, mepolizumab, motavizumab, motovizumab, natalizumab, nimotuzumab, nivolumab, nolovizumab, numavizumab, ocrelizumab, omalizumab, palivizumab, pascolizumab, pecfusituzumab, pectuzumab, pexelizumab, ralivizumab, ranibizumab, reslivizumab, reslizumab, resyvizumab, rovelizumab, ruplizumab, sibrotuzumab, siplizumab, sontuzumab, tacatuzumab tetraxetan, tadocizumab, talizumab, tefibazumab, tocilizumab, toralizumab, tucotuzumab celmoleukin, tucusituzumab, umavizumab, urtoxazumab, ustekinumab, visilizumab, and the anti-interleukin-12 (ABT-8744695, Wyeth Research and Abbott Laboratories) which is a recombinant exclusively human-sequence, full-length IgGI λ antibody genetically modified to recognize interleukin-12 p40 protein. Chemotherapeutic agents also include dexamethasone, interferons, colchicine, metoprine, cyclosporine, amphotericin, metronidazole, alemtuzumab, alitretinoin, allopurinol, amifostine, arsenic trioxide, asparaginase, BCG live, bevacuzimab, bexarotene, cladribine, clofarabine, darbepoetin alfa, denileukin, dexrazoxane, epoetin alfa, elotinib, filgrastim, histrelin acetate, ibritumomab, interferon alfa-2a, interferon alfa-2b, lenalidomide, levamisole, mesna, methoxsalen, nandrolone, nelarabine, nofetumomab, oprelvekin, palifermin, pamidronate, pegademase, pegaspargase, pegfilgrastim, pemetrexed disodium, plicamycin, porfimer sodium, quinacrine, rasburicase, sargramostim, temozolomide, VM-26, 6-TG, toremifene, tretinoin, ATRA, valrubicin, zoledronate, and zoledronic acid, and pharmaceutically acceptable salts thereof.

Chemotherapeutic agents also include hydrocortisone, hydrocortisone acetate, cortisone acetate, tixocortol pivalate, triamcinolone acetonide, triamcinolone alcohol, mometasone, amcinonide, budesonide, desonide, fluocinonide, fluocinolone acetonide, betamethasone, betamethasone sodium phosphate, dexamethasone, dexamethasone sodium phosphate, fluocortolone, hydrocortisone-17-butyrate, hydrocortisone-17-valerate, aclometasone dipropionate, betamethasone valerate, betamethasone dipropionate, prednicarbate, clobetasone-I 7-butyrate, clobetasol-I 7-propionate, fluocortolone caproate, fluocortolone pivalate and fluprednidene acetate; immune selective anti-inflammatory peptides (ImSAIDs) such as phenylalanine-glutamine-glycine (FEG) and its D-isomeric form (feG) (IMULAN BioTherapeutics, LLC); anti-rheumatic drugs such as azathioprine, ciclosporin (cyclosporine A), D-penicillamine, gold salts, hydroxychloroquine, leflunomideminocycline, sulfasalazine, tumor necrosis factor alpha (TNF alpha) blockers such as etanercept, infliximab, adalimumab, certolizumab pegol, golimumab (Simponi), Interleukin 1 (IL-1) blockers such as anakinra, T cell costimulation blockers such as abatacept, Interleukin 6 (IL-6) blockers such as tocilizumab; Interleukin 13 (IL-13) blockers such as lebrikizumab; Interferon alpha (IFN) blockers such as Rontalizumab; Beta 7 integrin blockers such as rhuMAb Beta7; IgE pathway blockers such as Anti-MI prime; Secreted homotrimeric LTa3 and membrane bound heterotrimer LTaI/I32 blockers such as Anti-lymphotoxin alpha (LTa); miscellaneous investigational agents such as thioplatin, PS-341, phenylbutyrate, ET-18-OCH3, or famesyl transferase inhibitors (L-739749, L-744832); polyphenols such as quercetin, resveratrol, piceatannol, epigallocatechine gallate, theaflavins, flavanols, procyanidins, betulinic acid and derivatives thereof; autophagy inhibitors such as chloroquine; delta-9-tetrahydrocannabinol (dronabinol); beta-lapachone; lapachol; colchicines; betulinic acid; acetylcamptothecin, scopolectin, and 9-aminocamptothecin); podophyllotoxin; tegafur; bexarotene; bisphosphonates such as clodronate, etidronate, NE-58095, zoledronic acid/zoledronate, alendronate, pamidronate, tiludronate, or risedronate; and epidermal growth factor receptor (EGF-R); vaccines such as THERATOPE® vaccine; perifosine, COX-2 inhibitor (e.g. celecoxib or etoricoxib), proteosome inhibitor (e.g. PS341); CCI-779; tipifamib (R11577); orafenib, ABT510; Bcl-2 inhibitor such as oblimersen sodium pixantrone; farnesyl-transferase inhibitors such as lonafamib (SCH 6636); and pharmaceutically acceptable salts, acids or derivatives of any of the above; as well as combinations of two or more of the above such as CHOP, an abbreviation for a combined therapy of cyclophosphamide, doxorubicin, vincristine, and prednisolone; and FOLFOX, an abbreviation for a treatment regimen with oxaliplatin combined with 5-FU and leucovorin. Chemotherapeutic agents also include Poly ADP ribose polymerase (PARP) inhibitors: olaparib, rucaprib niraparib, talzoparib.

Inhibitors that can be used with a PD-L1 binding agent (e.g., an antibody) as described herein (e.g., for combination therapy) include, but are not limited to, kinase inhibitors such as imatinib, baricitinib gefitinib, erlotinib, sorafenib, dasatinib, sunitinib, lapatinib, nilotinib, pirfenidone, pazopanib, crizotinib, vemurafenib, vandetanib, ruxolitinib, axitinib, bosutinib, regorafenib, tofacitinib, cabozantinib, ponatinib, trametinib, dabrafenib, afatinib, ibrutinib, ceritinib, idelalisib, nintedanib, palbociclib, lenvatinib, cobimetinib, abemaciclib, acalabrutinib, alectinib, binimetinib, brigatinib, encorafenib, erdafitinib, everolimus, fostamatinib, gilter, larotrectinib, lorlatinib, netarsudil, osimertinib pemigatinib, pexidartinib, ribociclib, temsirolimus, XL-092, XL-147, XL-765, XL-499, and XL-880. In some embodiments, a compound as described herein can be used in combination with a HSP90 inhibitor (e.g., XL888), liver X receptor (LXR) modulators, retinoid-related orphan receptor gamma (RORy) modulators, checkpoint inhibitors such as a CK1 inhibitor or aCK1a inhibitor, a Wnt pathway inhibitor (e.g., SST-215), or a mineralocorticoid receptor inhibitor, (e.g., esaxerenone) or XL-888 for the treatment of a disease disclosed herein such as cancer. In some embodiments, a PD-L1 binding agent (e.g., an antibody) as disclosed herein can be combined with one or more inhibitors of the following kinases for the treatment of cancer: Akt1, Akt2, Akt3, TGF-βR, PKA, PKG, PKC, CaM-kinase, phosphorylase kinase, MEKK, ERK, MAPK, mTOR, EGFR, HER2, HER3, HER4, 1NS-R, IGF-1R, IR-R, PDGFαR, PDGFβ/R, CSFIR, KIT, FLK-II, KDR/FLK-1, FLK-4, flt-1, FGFR1, FGFR2, FGFR3, FGFR4, Ron, Sea, TRKA, TRKB, TRKC, FLT3, VEGFR/Flt2, Flt4, EphAI, EphA2, EphA3, EphB2, EphB4, Tie2, Src, Fyn, Lck, Fgr, Btk, Fak, SYR, FRK, JAK (JAK1 and or JAK2), ABL, ALK, CDK7, CDK12, KRAS, and B-Raf.

Additional non-limiting examples of inhibitors that can be used with a PD-L1 binding agent (e.g., an antibody) as described herein e.g. for treatment of cancer (e.g., for combination therapy) include an FGFR inhibitor (FGFR1, FGFR2, FGFR3 or FGFR4, e.g., pemigatinib, an EGFR inhibitor (also known as ErB-1 or HER-1; e.g. erlotinib, gefitinib, vandetanib, orsimertinib, cetuximab, necitumumab, or panitumumab), a VEGFR inhibitor or pathway blocker (e.g., bevacizumab, pazopanib, sunitinib, sorafenib, axitinib, regorafenib, ponatinib, vandetanib, ramucirumab, lenvatinib, ziv-aflibercept), a PARP inhibitor (e.g. olaparib, rucaparib, veliparib or niraparib), a JAK inhibitor (e.g., ruxolitinib, baricitinib, itacitinib), an IDO inhibitor (e.g., epacadostat, NLG919, or BMS-986205, MK7162), an LSD1 inhibitor, a TDO inhibitor, a PI3K-delta inhibitor (e.g., parsaclisib), a PI3K-gamma inhibitor such as PI3K-gamma selective inhibitor, a Pim inhibitor, a CSF1 R inhibitor, a TAM receptor tyrosine kinases (Tyro-3, Axl, and Mer), an adenosine receptor antagonist (e.g., A2a/A2b receptor antagonist), an HPK1 inhibitor, a chemokine receptor inhibitor (e.g. CCR2 or CCR5 inhibitor), a SHP1/2 phosphatase inhibitor, a histone deacetylase inhibitor (HDAC) such as an HDAC8 inhibitor, an angiogenesis inhibitor, an interleukin receptor inhibitor, bromo and extra terminal family members inhibitors (for example, bromodomain inhibitors or BET inhibitors, or combinations thereof.

In some embodiments, a PD-L1 binding agent (e.g., an antibody) as disclosed herein can be used in combination with inhibitors of PD-1 or inhibitors of PD-L1, e.g., an anti-PD-1 monoclonal antibody or an anti-PD-L1 monoclonal antibody, for example, nivolumab (Opdivo®), pembrolizumab (Keytruda®, MK-3475), atezolizumab, avelumab, cemiplimab, spartalizumab, camrelizumab, cetrelimab, toripalimab, sintilimab, AB122, JTX-4014, BGB-108, BCD-100, BAT1306, LZM009, AK105, HLX10, and TSR-042, AMP-224, AMP-514, PDR001, durvalumab, pidilizumab (Imfinzi®, CT-011), CK-301, BMS 936559, MPDL3280A, tislelizumab, BMS-935559, MED14736, FAZ053, KN035, CS1001, CBT-502, A167, STI-A101, BGB-A333, MSB-2311, HLX20, AUNP12, CA-170, BMS-986189, LY3300054, and MSB0010718C.

In some embodiments, a PD-L1 binding agent (e.g., an antibody) as disclosed herein can be used in combination with CTLA-4 inhibitors, e.g., an anti-CTLA-4 antibody, for example, ipilimumab (Yervoy®), tremelimumab and AGEN1884, or with phosphatidylserine inhibitors, for example, bavituximab (PGN401), or with antibodies to cytokines (IL-10, TGF-b, and the like), or with bispecific antibodies that bind to PD-L1 and CTLA-4 (e.g., AK104) or PD-1 and CTLA-4, or with other anti-cancer agents such as cemiplimab.

The additional agent may be a pharmaceutically acceptable salt, ester, amide, hydrate, and/or prodrug of any of these therapeutic agents described above or other agents.

It is understood that modifications which do not substantially affect the activity of the various embodiments described herein are also provided within the definition of the subject matter described herein. Accordingly, the following examples are intended to illustrate but not limit the present disclosure.

EXAMPLES

Example 1. Antibody Generation

To obtain binders for human PD-L1, antibody discovery was conducted by phage display of human Fab libraries was carried out using standard protocols. The extracellular domain of human PD-L1 was purchased from Acro Biosystems (human PD-L1-His tag Acro Cat. No. PD1 H5229, biotinylated human PD-L1-His Avitag Acro Cat. No. PDL-H82E4). The non-biotinylated extracellular domain of PD-L1 was biotinylated using EZ-Link NHS-PEG$_{12}$-Biotin (ThermoScientific Cat. No. 21312) using standard protocol as needed. Phage clones were screened for the ability to bind to biotinylated human PD-L1 by phage ELISA using standard protocols. Briefly, Fab-formatted phage libraries were constructed using expression vectors capable of replication and expression in phage (also referred to as a phagemid). Both the heavy chain and the light chain were encoded in the same expression vector, where the heavy chain was fused to a truncated variant of the phage coat protein pIII. The light chain and heavy chain-pIII fusion were expressed as separate polypeptides and assembled in the bacterial periplasm, where the redox potential enables disulfide bond formation, to form the antigen binding domain (Fab) of the candidate antibody.

The library was created using sequences derived from a specific human heavy chain variable domain (VH3-23) and a specific human light chain variable domain (Vk-1). Light chain variable domains within the screened library were generated with diversity was introduced into the VL CDR3 (L3) and where the light chain VL CDR1 (L1) and CDR2 (L2) remained the human germline sequence. For the screened library, all three CDRs of the VH domain were diversified to match the positional amino acid frequency by CDR length found in the human antibody repertoire. The phage display heavy chain (SEQ ID NO:92) and light chain (SEQ ID NO:93) scaffolds used in the library are listed below, where a lower case "x" represents CDR amino acids that were varied to create the library, and bold italic represents the CDR sequences that were constant.

The sequence for SEQ ID NO: 92 was
EVQLVESGGGLVQPGGSLRLSCAASGFTFSXXXXXWVRQAPGKGLEWVAX

XXXXXXXXXXXXXXXXXRFTISADTSKNTAYLQMNSLRAEDTAVYYCARXX

XXXXXXXXXXXXWGQGTLVTVSSASTKGPSVFPLAPSSKSTSGGTAALGC

LVKDYFPEPVTVSWNSGALTSGVHTFPAVLQSSGLYSLSSVVTVPSSSLG

TQTYICNVNHKPSNTKVDKKVEPKSC.

The sequence for SEQ ID NO: 93 was
DIQMTQSPSSLSASVGDRVTITC*RASQSVSSAVA*WYQQKPGKAPKLLIY*S*

*ASSLYS*GVPSRFSGSRSGTDFTLTISSLQPEDFATYYCXXXXXXXXXFGQ

GTKVEIKRTVAAPSVFIFPPSDSQLKSGTASVVCLLNNFYPREAKVQWKV

DNALQSGNSQESVTEQDSKDSTYSLSSTLTLSKADYEKHKVYACEVTHQG

LSSPVTKSFNRGEC.

Diversity was created through mutagenesis using degenerate DNA oligonucleotide primers to introduce diversity into VL CDR3 and VH CDR1 (H1), CDR2 (H2) and CDR3 (H3) to mimic the diversity found in the natural antibody repertoire, as described in more detail in Kunkel, T A (*PNAS* Jan. 1, 1985. 82 (2) 488-492), herein incorporated by reference in its entirety. Briefly, uracil-incorporated single-stranded circular DNA were prepared from isolated phage using standard procedures and Kunkel mutagenesis carried out to introduce diversity to the four CDRs. Chemically-synthesized DNA was then electroporated into TG1 cells, followed by recovery. Recovered cells were sub-cultured and infected with M13K07 helper phage to produce the phage library.

Phage panning was performed using standard procedures. Briefly, the first round of phage panning was performed with target immobilized on streptavidin magnetic beads which were subjected to approximately 1×10$^2$ phages from the prepared library in a volume of 1 mL in PBST-2% BSA. After a one-hour incubation, the bead-bound phage were separated from the supernatant using a magnetic stand. Beads were washed three times to remove non-specifically bound phage and were then added to ER2738 cells (5 mL) at OD$_{600}$ of approximately 0.6. After 20 minutes incubation at room temperature, infected cells were sub-cultured in 25 mL 2×YT+Ampicillin and M13K07 helper phage (final concentration of approximately 1×10$^{10}$ pfu/ml) and allowed to grow overnight at 37° C. with vigorous shaking. The next day, phage were prepared using standard procedures by PEG precipitation. Pre-clearance of phage specific to SAV-coated beads was performed prior to panning. The second round of panning was performed using the KingFisher magnetic bead handler with 50 or 25 nM bead-immobilized PD-L1 antigen using standard procedures (50 nM PD-L1 for round 3, 25 nM PD-L1 for round 4). In total, 3-4 rounds of phage panning were performed to enrich in phage displaying Fabs specific for the target antigen. Target-specific enrichment was confirmed using polyclonal ELISA and individual clones were isolated and further verified by performing monoclonal phage ELISA. DNA sequencing was used to determine the sequence of the CDRs of isolated Fab clones containing a candidate antibodies.

The genes encoding heavy chain and light chain variable domains of the candidate antibodies were cloned separately into mammalian expression vectors for expression as full length IgGs in mammalian cells.

For the full length IgGs, the heavy chain constant regions (e.g., CH1 = regular text; Hinge = italicized text; CH2 = bold text; and CH3 = underline text) included the following amino acid sequence:
(SEQ ID NO: 94)
ASTKGPSVFPLAPSSKSTSGGTAALGCLVKDYFPEPVTVSWNSGALTSG

VHTFPAVLQSSGLYSLSSVVTVPSSSLGTQTYICNVNHKPSNTKVDKKV

EPKSC*DKTHTCPPCP*APELLGGPSVFLFPPPKPKDTLMISRTPEVTCVVV

DVSHEDPEVKFNWYVDGVEVHNAKTKPREEQYNSTYRVVSVLTVLHQDW

LNGKEYKCKVSNKALPAPIEKTISKAK<u>GQPREPQVYTLPPSRDELTKNQ</u>

<u>VSLTCLVKGFYPSDIAVEWESNGQPENNYKTTPPVLDSDGSFFLYSKLT</u>

<u>VDKSRWQQGNVFSCSVMHEALHNHYTQKSLSLSPGK</u>.

For the full length IgGs, the light chain constant region (e.g., CL) included the following amino acid sequence:
(SEQ ID NO: 95)
RTVAAPSVFIFPPSDSQLKSGTASVVCLLNNFYPREAKVQWKVDNALQS

GNSQESVTEQDSKDSTYSLSSTLTLSKADYEKHKVYACEVTHQGLSSPV

TKSFNRGEC.

The IgG antibodies were purified from culture supernatant using Protein A resin.

Example 2. Screening and Selection

Antibodies to PD-L1 were generated by phage display, for example, such as described in Example 1. For example, to determine qualitative binding, bio-layer interferometry (BLI) was used to confirm the specific interaction of the antigens to the candidate antibodies obtained from Example 1.

The bivalent interaction of binders to the biotinylated human PD-L1 (see Example 1) immobilized on a streptavidin biosensor was monitored using an Octet® (Pall ForteBio) instrument. To monitor monovalent interaction, full-length IgG molecule was immobilized to a Fc capture biosensor and its interaction with soluble antigen was monitored using an Octet® instrument.

Briefly, accurate measurements of affinity (such as $K_D$ values) for the top PD-L1 antibodies was obtained using Octet® in a monovalent binding format. First, the antibodies were immobilized on an Fc capture sensor. In the next association step, the binding interaction of PD-L1 (Acro Cat. No. PD1H5229 (PD-L1-His tag)) to the immobilized IgG was measured. To obtain accurate kinetic constants, a dilution series involving of at least seven concentrations of the analyte (ranging from approximately 10 to $20 \times K_D$ to $0.1 \times K_D$ value, 2-fold dilutions) were measured in the association step. In the next dissociation step, the sensor was dipped into buffer solution that did not contain the analyte, where the bound analyte on the surface of the sensor was allowed to dissociate. Octet® kinetic analysis software was used to calculate the kinetic and equilibrium binding constants from the rate of association and dissociation curves. The analysis was performed using global curve fit where kinetic constants were derived simultaneously from all analyte concentration included in the experiment.

Bivalent qualitative Octet® results are shown in Table 4. For qualitative binding affinity using Octet®, strong binding is indicated by the symbol "+++", moderate binding is indicated by "++", and weak binding is indicated by "+". "ND" indicates that antibody binding was not determined. "NB" indicates that antibody binding was not detected. Results show that 24 antibodies showed strong binding affinity (P1, P2, P3, P4, P5, P9, P10, P18, P19, P21, P22, P24, P26, P31.2, P33, P34, P35, P36, P38, P39, P45, P47, P53 and P54), 12 antibodies showed moderate cell binding affinities (P6, P12, P17, P23, P28, P30, P37, P40, P41, P44, P46 and P49), and 9 antibodies showed weak cell binding affinities (P20, P25, P27, P29, P32, P43, P51, P52, and P55).

TABLE 4

| Bivalent Qualitative Binding Affinity by Octet ® and mPD-L1 Cross-Reactivity | |
| --- | --- |
| Binder | Qualitative Binding Affinity Octet ® |
| P1 | +++ |
| P2 | +++ |
| P3 | +++ |
| P4 | +++ |
| P5 | +++ |
| P6 | ++ |
| P7 | NB |
| P8 | NB |
| P9 | +++ |
| P10 | +++ |

TABLE 4-continued

| Bivalent Qualitative Binding Affinity by Octet ® and mPD-L1 Cross-Reactivity | |
| --- | --- |
| Binder | Qualitative Binding Affinity Octet ® |
| P11 | +++ |
| P12 | ++ |
| P13 | ND |
| P14 | ND |
| P15 | ND |
| P16 | ND |
| P17 | ++ |
| P18 | +++ |
| P19 | +++ |
| P20 | + |
| P21 | +++ |
| P22 | +++ |
| P23 | ++ |
| P24 | +++ |
| P25 | + |
| P26 | +++ |
| P27 | + |
| P28 | ++ |
| P29 | + |
| P30 | ++ |
| P31.2 | +++ |
| P32 | + |
| P33 | +++ |
| P34 | +++ |
| P35 | +++ |
| P36 | +++ |
| P37 | ++ |
| P38 | +++ |
| P39 | +++ |
| P40 | ++ |
| P41 | ++ |
| P42 | ND |
| P43 | + |
| P44 | ++ |
| P45 | +++ |
| P46 | ++ |
| P47 | +++ |
| P48 | ND |
| P49 | ++ |
| P50 | ND |
| P51 | + |
| P52 | + |
| P53 | +++ |
| P54 | +++ |
| P55 | + |

Figure 1B:
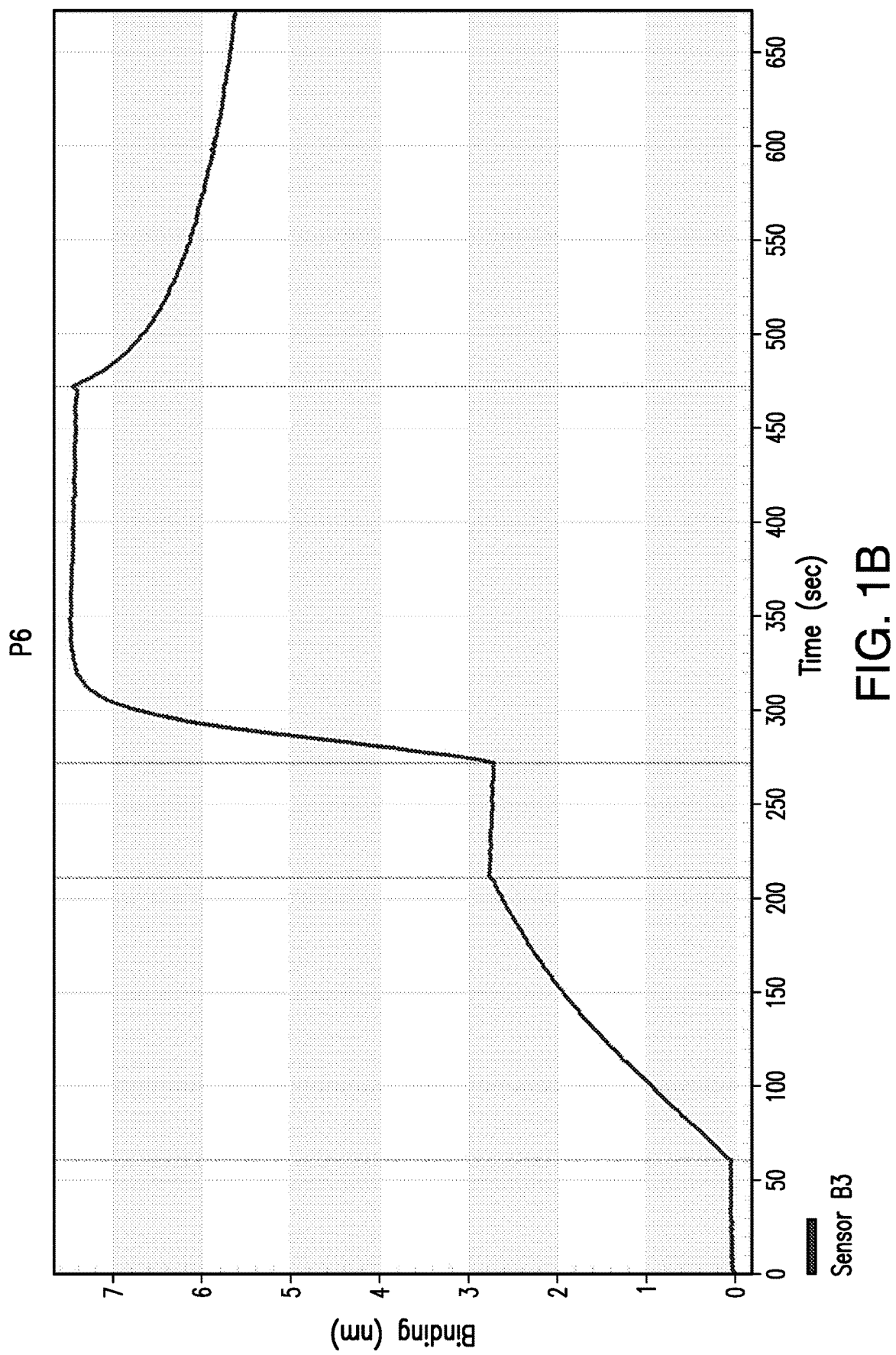
Figure 1C:
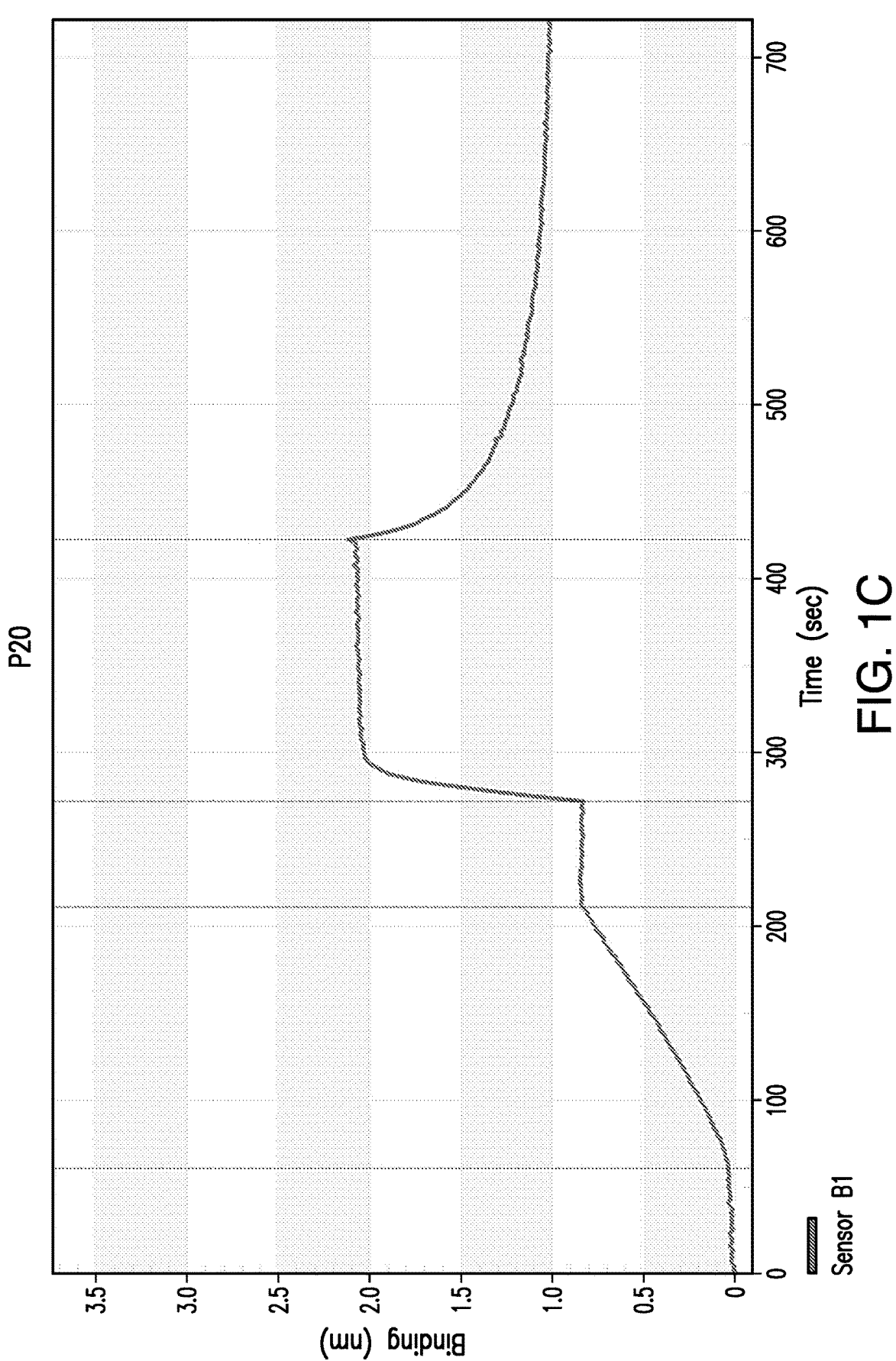

Exemplary sensograms for monovalent antibody binding are shown in FIGS. 1A-1C. Qualitative PD-L1 binding and monovalent $K_D$ results are shown in Table 5. $K_D$ values are listed and strong binding, <2E-08 M (<20 nM), is indicated by the symbol "+++", moderate binding, 2E-08-2E-07 M (20-200 nM), is indicated by "++", and weak binding, >2E-07 M (>200 nM), is indicated by "+". "ND" indicates that antibody binding was not determined. Results indicate that 8 antibodies showed strong binding (P2, P6, P9, P10, P22, P24, P31.2 and P39), 7 antibodies showed moderate binding (P21, P23, P34, P35, P36, P45, and P47), 5 antibodies showed weak binding (P18, P26, P28, P30, and P54), and 2 antibodies showed no binding P7 and P8). No binding was detected for P7 and P8.

TABLE 5

| Monovalent $K_D$ | | |
| --- | --- | --- |
| Binder | PD-L1 Monovalent $K_D$ | $K_D$ |
| P2 | +++ | 7.02E−09 |
| P6 | +++ | 1.44E−08 |

TABLE 5-continued

| | Monovalent $K_D$ | |
| Binder | PD-L1 Monovalent $K_D$ | $K_D$ |
| --- | --- | --- |
| P7 | ND | No binding |
| P8 | ND | No binding |
| P9 | +++ | 1.18E−08 |
| P10 | +++ | 4.81E−09 |
| P18 | + | 1.21E−06 |
| P21 | ++ | 1.08E−07 |
| P22 | +++ | 1.72E−08 |
| P23 | ++ | 1.50E−07 |
| P24 | +++ | 1.75E−08 |
| P26 | + | 2.87E−07 |
| P28 | + | 2.88E−07 |
| P30 | + | 5.63E−07 |
| P31.2 | +++ | 1.30E−08 |
| P34 | ++ | 7.28E−08 |
| P35 | ++ | 1.05E−07 |
| P36 | ++ | 6.21E−08 |
| P37 | ND | ND |
| P39 | +++ | 1.24E−08 |
| P45 | ++ | 8.63E−08 |
| P47 | ++ | 9.20E−08 |
| P54 | + | 3.36E−07 |

Binding to mouse PD-L1 (mPD-L1) was characterized by assessing cell binding to mouse cells. Specifically, binding of the antibodies to mouse cells was determined by flow cytometry. Antibodies were incubated with the indicated cell lines at the indicated concentrations followed by labeling with a fluorescently labeled secondary antibody. Mouse PD-L1 was obtained from Acro Biosystems (Acro Cat. No. PD1-M5220) and biotinylated using standard protocols. The free biotin was removed by extensive dialysis against PBS. Biotinylated antigen (PD-L1) was immobilized on a streptavidin sensor. The cross-reactive antibodies were identified by the association to mouse PD-L1 using Octet®.

Mouse cross-reactivity results are shown in Table 6. Mouse cross-reactivity is indicated with a "Y," and no mouse cross-reactivity is indicated with a "X." Antibody cross-reactivity that was not determined is indicated with a "ND."

TABLE 6

| Mouse PD-L1 Cross-Reactivity | |
| Binder | mPD-L1 Cross-Reactive |
| --- | --- |
| P1 | X |
| P2 | X |
| P3 | X |
| P4 | X |
| P5 | X |
| P6 | X |
| P7 | — |
| P8 | — |
| P9 | X |
| P10 | Y |
| P11 | X |
| P12 | X |
| P13 | Y |
| P14 | X |
| P15 | — |
| P16 | — |
| P17 | X |
| P18 | Y |
| P19 | X |
| P20 | X |
| P21 | X |
| P22 | X |
| P23 | X |
| P24 | X |

TABLE 6-continued

| Mouse PD-L1 Cross-Reactivity | |
| Binder | mPD-L1 Cross-Reactive |
| --- | --- |
| P25 | X |
| P26 | Y |
| P27 | X |
| P28 | Y |
| P29 | X |
| P30 | X |
| P31.2 | X |
| P32 | X |
| P33 | X |
| P34 | X |
| P35 | Y |
| P36 | X |
| P37 | ND |
| P38 | X |
| P39 | Y |
| P40 | X |
| P41 | Y |
| P42 | X |
| P43 | X |
| P44 | X |
| P45 | X |
| P46 | X |
| P47 | Y |
| P48 | X |
| P49 | X |
| P50 | X |
| P51 | X |
| P52 | X |
| P53 | X |
| P54 | Y |
| P55 | X |

Example 3. Additional Screening and Selection

Antibodies that were selected for binding to PD-L1, for example, such as those described in Example 2, were evaluated for binding to cells that express PD-L1. For example, antibodies were tested using flow cytometry for binding to PD-L1 overexpressing CHO-K1 cells (BPS Bioscience PD-L1/TCR Activator—CHO line, catalog No. 30536), which have a surface PD-L1 copy number of approximately 674,000.

Cells were harvested at 70-90% confluence on the day of the assay. Cells were collected by centrifugation at 200×g for 5 minutes and media was removed. Cells were resuspended at $2 \times 10^6$ cells per mL in cold PBS. An 8-point antibody dilution series (2× concentration) was prepared in PBS to cover the expected binding affinities of the antibodies being tested. 50 μL per well of the antibody dilution was plated in a 96 well V-bottom plate (Costar 3897). 50 μL per well of cell suspension was added. Plates were placed at 4° C. for 45-60 minutes.

Cells were collected by centrifugation at 400×g for 7 minutes and primary antibody was removed. 50 μL per well of AF488 goat anti human IgG Fab (Jackson Immuno Research 109-547-003) at 1:100 dilution was added. Plates were placed at 4° C. for 30 minutes.

Cells were collected by centrifugation at 400×g for 7 minutes and secondary antibody was removed. Cells were resuspended in 50 μL per well of PBS and analyzed by flow cytometry. Binding curves were calculated using the mean fluorescence intensity (MFI) of the FITC fluorescence signal on the cells.

Figure 2A:
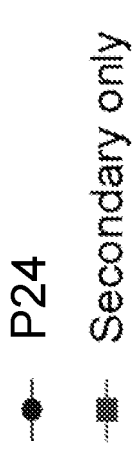
FIGS. 2A-2C illustrate exemplary results from cell binding assays, further described in Example 3.
Figure 2A:
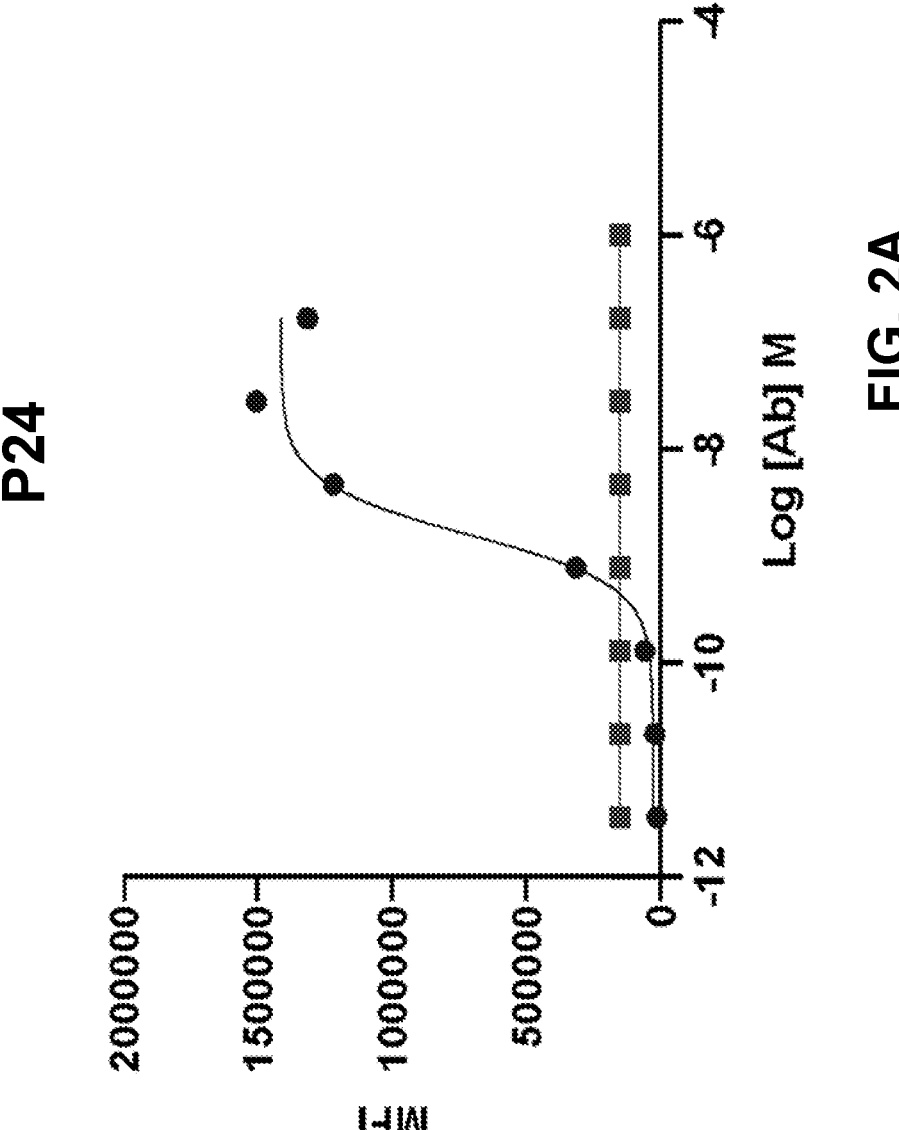
Figure 2B:
Figure 2B:
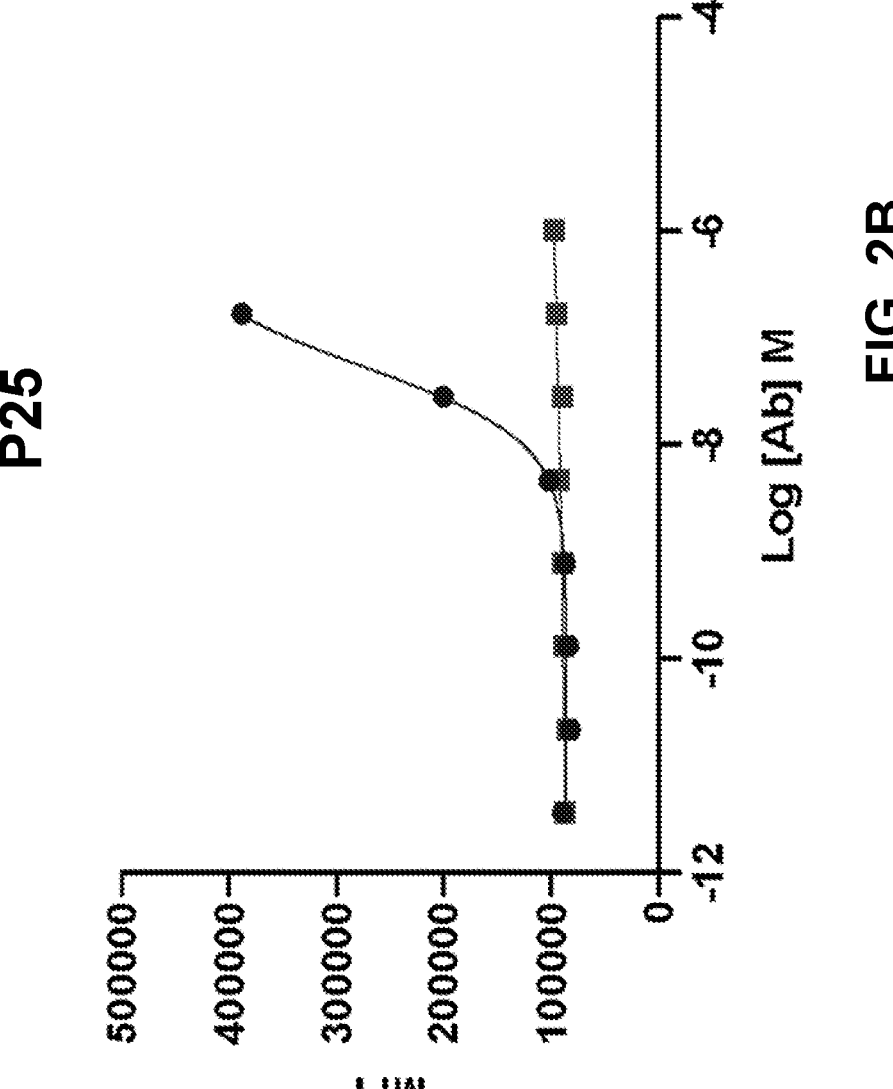
Figure 2C:
Figure 2C:
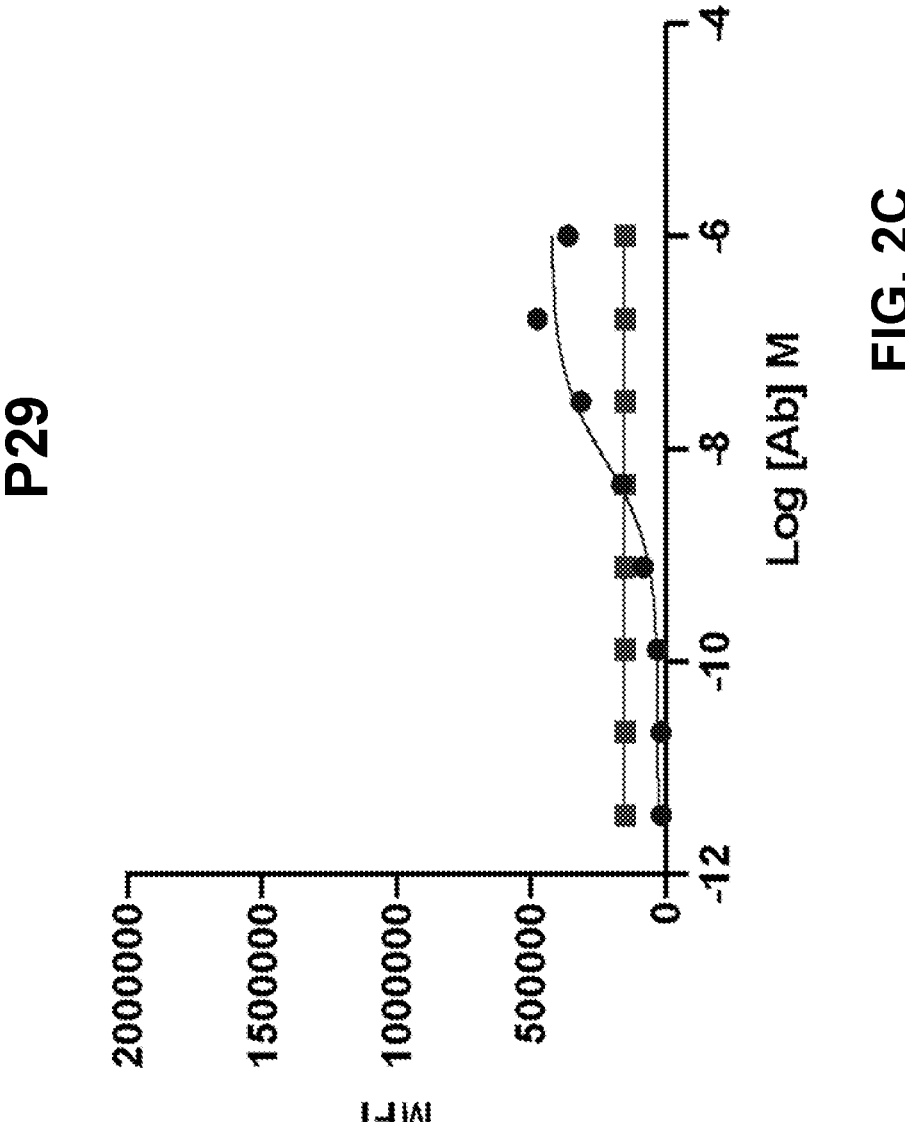

Exemplary binding curves are depicted in FIGS. 2A-2C. Qualitative binding affinity to cells and half maximal effective concentration ($EC_{50}$) of cell binding for the assayed antibodies are summarized in Table 7. For qualitative binding affinity, strong binding, <2E-08 M (<20 nM), is indicated by the symbol "+++", moderate binding, 2E-08-2E-07 M (20-200 nM), is indicated by "++", and weak binding, >2E-07 M (>200 nM), is indicated by "+". "ND" indicates that antibody binding was not determined. Results show that 29 antibodies showed strong cell binding affinity (P2, P3, P6, P7, P8, P9, P10, P11, P12, P13, P14, P18, P19, P21, P22, P23, P24, P26, P28, P31.2, P34, P35, P36, P37, P38, P39, P45, P47, and P54), and 21 antibodies showed weak binding (P1, P4, P5, P15, P17, P27, P29, P30, P32, P33, P40, P41, P42, P43, P46, P49, P50, P51, P52, P53, and P55).

TABLE 7

| Qualitative Binding Affinity and EC$_{50}$ of Antibody Binding to CHO-K1 Cells | | |
| --- | --- | --- |
| Binder | Qualitative Binding Affinity Cells | EC50 |
| P1 | + | ~1.674e-007 |
| P2 | +++ | 1.25E-10 |
| P3 | +++ | 1.57E-10 |
| P4 | + | No binding |
| P5 | + | ~3.898e-011 |
| P6 | +++ | 7.50E-09 |
| P7 | +++ | 3.39E-09 |
| P8 | +++ | 1.02E-08 |
| P9 | +++ | 1.17E-10 |
| P10 | +++ | 2.54E-09 |
| P11 | +++ | ~1.042e-010 |
| P12 | +++ | 5.14E-10 |
| P13 | +++ | ~1.286e-010 |
| P14 | +++ | ~4.863e-009 |
| P15 | + | 4.17E-08 |
| P16 | ND | ND |
| P17 | + | ~5.785e-009 |
| P18 | +++ | 2.79E-10 |
| P19 | +++ | 7.18E-10 |
| P20 | ++ | 6.49E-08 |
| P21 | +++ | 4.40E-10 |
| P22 | +++ | 5.23E-10 |
| P23 | +++ | 2.97E-10 |
| P24 | +++ | 1.62E-09 |
| P25 | ++ | 5.27E-08 |
| P26 | +++ | 1.84E-10 |
| P27 | + | ~2.851e-008 |
| P28 | +++ | 9.22E-09 |
| P29 | + | 8.03E-09 |
| P30 | + | 5.78E-10 |
| P31.2 | +++ | 5.52E-10 |
| P32 | + | ~2.988e-008 |
| P33 | + | 1.77E-09 |
| P34 | +++ | 1.50E-09 |
| P35 | +++ | 3.93E-10 |
| P36 | +++ | 6.52E-10 |
| P37 | +++ | 3.21E-10 |
| P38 | +++ | 9.55E-09 |
| P39 | +++ | 1.81E-10 |
| P40 | + | 3.01E-09 |
| P41 | + | 9.54E-08 |
| P42 | + | 9.22E-07 |
| P43 | + | 1.85E-08 |
| P44 | ND | ND |
| P45 | +++ | 2.04E-10 |
| P46 | + | 7.41E-09 |
| P47 | +++ | 6.04E-10 |
| P48 | ++ | 1.16E-07 |
| P49 | + | 1.98E-08 |
| P50 | + | 1.31E-02 |
| P51 | + | 3.70E-08 |
| P52 | + | ~1.159e-008 |
| P53 | + | 4.89E-09 |
| P54 | +++ | 2.33E-10 |
| P55 | + | ~2.867e-008 |

Example 4. Functional Assays

Antibodies that were selected for binding to PD-L1, for example, such as those described in Examples 2 and 3, were evaluated for inhibition of PD-1/PD-L1 signaling in PD-L1 overexpressing CHO-K1 cells.

To test the ability of antibodies to block PD-1/PD-L1 signaling, antibodies were assayed using a PD-1/PD-L1 Signaling Bioassay Kit (93-1104Y19-00117, Eurofins DiscoverX) using the manufacturer protocol. In this assay, Jurkat cells are engineered to express PD1 tagged with a B-galactosidase ProLink tag and an enzyme acceptor SH1 tag. The engineered Jurkat cells are co-cultured with the CD47/PD-L1 expressing cell line. When PD-L1 is bound to PD1, enzyme complementation occurs and the B-gal signal is high. In the presence of a PD-L1 blocking antibody, SHP-1/2 is not recruited, enzyme complementation does not occur, and B-gal signal is low.

Briefly, 40 µL of target cells (30,000 cells per 40 µL) was added to each well of a white 96-well plate in Cell Plating Reagent 0 (CP0). Plates were incubated at 37° C. overnight. PathHunter® PD-1 Jurkat cells were thawed for overnight recovery from thaw by adding 9.6 mL of pre-warmed Cell Plating Reagent (CP0) to a T25 flask, removing two cryovials of PD-1 Jurkat cells from liquid nitrogen, and thawing the pellet by immediately adding 1 mL of pre-warmed CP0 from the T25 flask to the cryovial. Cells were mixed by gently pipetting up and down several times to break up any clumps. The cell suspension was transferred to the T25 flask containing the remaining CP0 and any media/suspension left in the cryovial was removed to ensure complete recovery of all the cells from the vial. Cells were incubated at 37° C. overnight.

Following the incubation, 20 µL of antibody was added to each well and plates were incubated at 37° C. for 1 hour. 40 µL of PathHunter® PD-1 Jurkat cells in CP0 was added to each well of the 96-well plate and the plate was incubated at room temp in the dark for 1 hour. Then, 10 µL of PathHunter® Bioassay Detection Reagent 1 was added to each well and plates were incubated for 15 minutes at room temperature in the dark. Next, 40 µL of PathHunter® Bioassay Detection Reagent 2 as added to each well of the assay plate and the plate was incubated for 3 hours at room temperature in the dark. Plates were analyzed on a ClarioStar® Plate Reader (BMG Labtech).

Figure 3A:
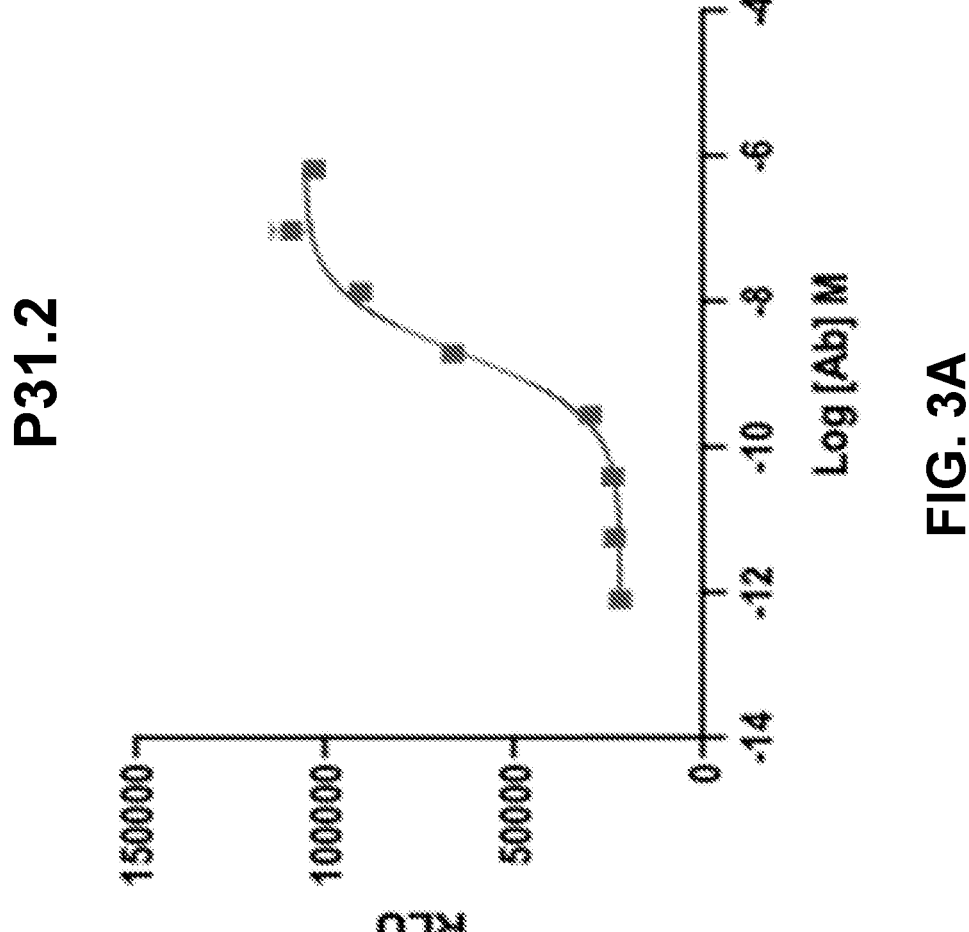
FIGS. 3A-3C illustrate exemplary results from PD-L1/PD-1 inhibiting assays, further described in Example 4.
Figure 3B:
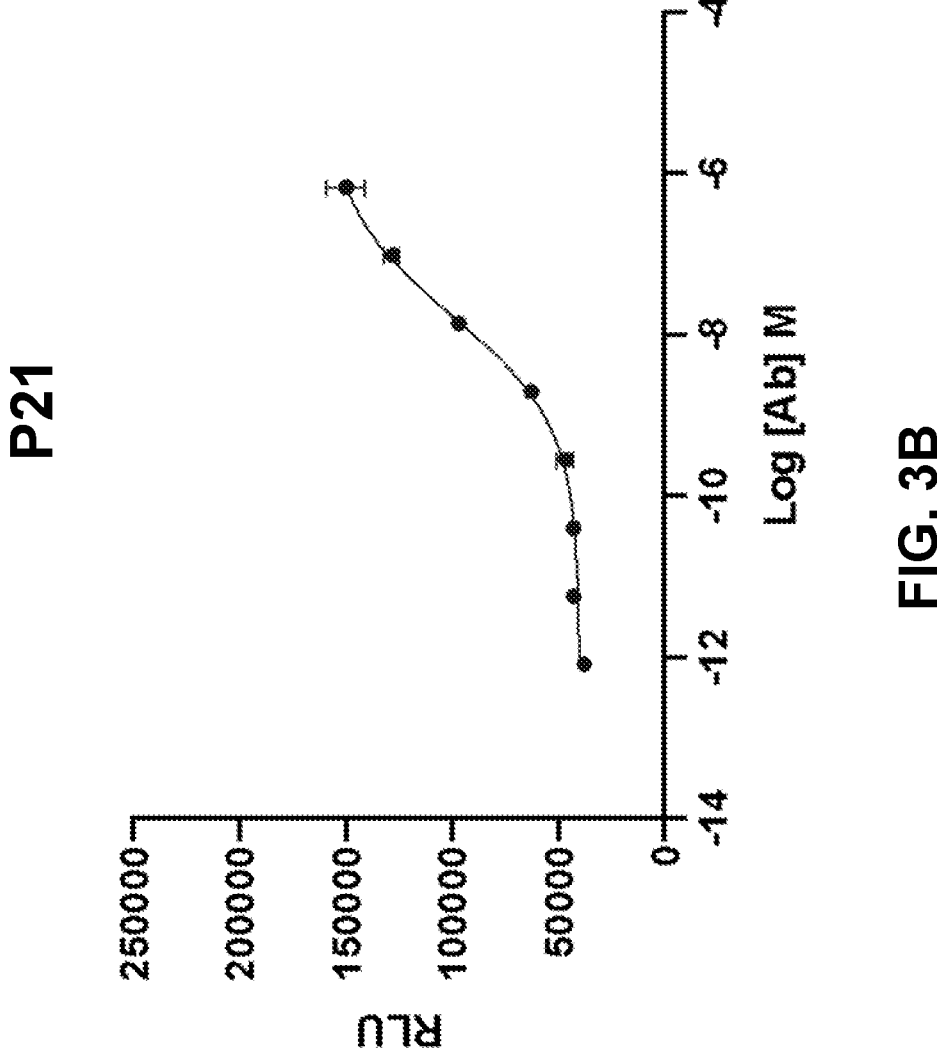
Figure 3C:
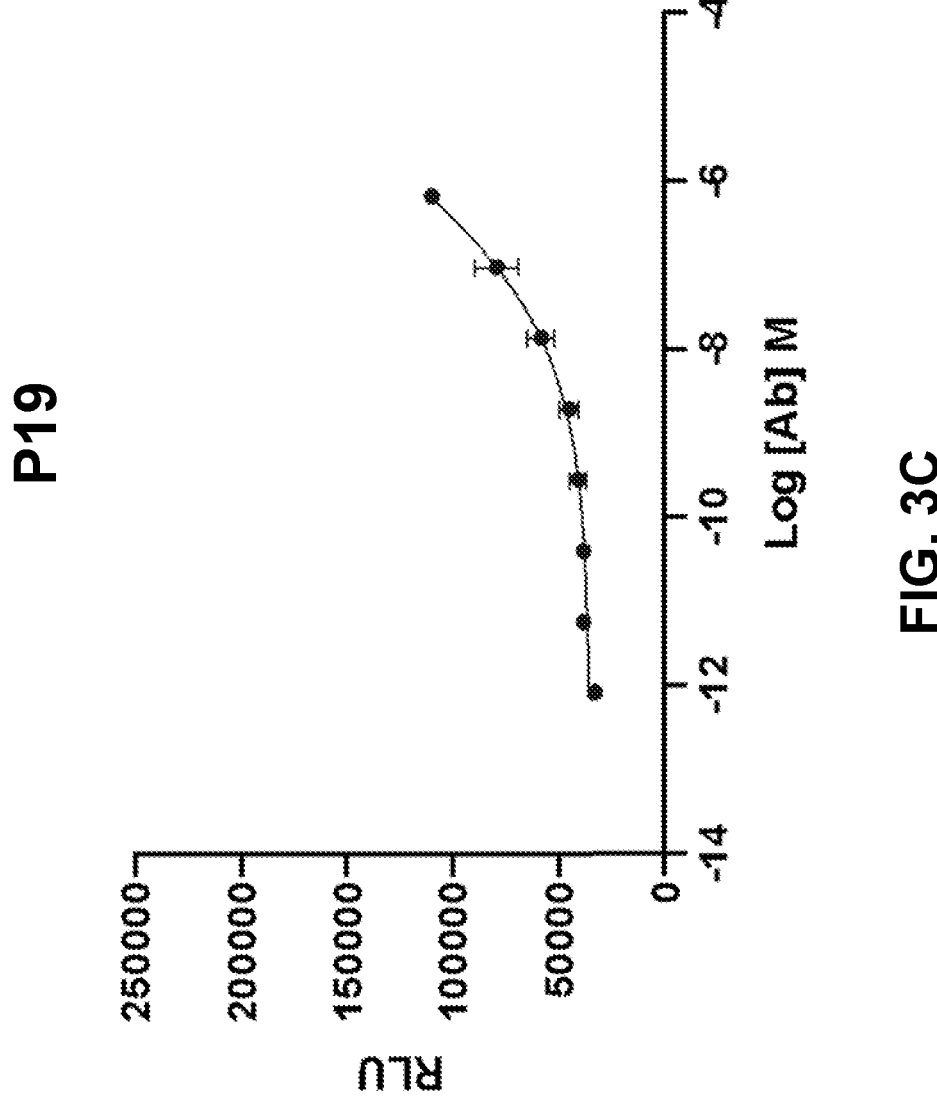

Exemplary results of the PD-1/PD-L1 checkpoint signaling assay in PD-L1 MDA-MB-231 cells are shown in FIGS. 3A-3C. IC$_{50}$ values for the assay in are shown in Table 3. Strong blocking, <2E-08 M (<20 nM), is indicated by the symbol "+++", moderate blocking, 2E-08-2E-07 M (20-200 nM), is indicated by "++", and weak blocking, >2E-07 M (>200 nM), is indicated by "+". "ND" indicates that interaction blocking was not determined.

Results show that 15 antibodies had strong blocking of the PD-1/PD-L1 interaction (P2, P7, P8, P18, P22, P24, P26, P28, P31.2, P34, P35, P36, P39, P45, and P47), 11 antibodies had moderate blocking (P3, P6, P9, P10, P15, P21, P23, P30, P37, P41, and P54). Other tested antibodies had weak blocking. "Low blocking" and "no blocking," indicate that IC50 was not determined due to low or undetectable blocking in the assay.

TABLE 8

| PD-1/PD-L1 Interaction Blocking Reporter Assay | | |
|---|---|---|
| Binder | PD-L1/PD1 interaction blocking | IC50 |
| P1 | --- | No blocking |
| P2 | +++ | 7.55E−09 |
| P3 | ++ | 2.22E−08 |
| P4 | --- | No blocking |
| P5 | --- | No blocking |
| P6 | ++ | 1.09E−07 |
| P7 | +++ | 1.22E−09 |
| P8 | +++ | 1.07E−08 |
| P9 | ++ | ~2.927e−008 |
| P10 | ++ | 1.29E−07 |
| P11 | ND | ND |
| P12 | --- | No blocking |
| P13 | --- | No blocking |
| P14 | + | 8.46E−07 |
| P15 | ++ | ~1.636e−007 |
| P16 | ND | ND |
| P17 | ND | ND |
| P18 | +++ | ~1.138e−009 |
| P19 | + | 1.57E−06 |
| P20 | --- | No blocking |
| P21 | ++ | 1.70E−08 |
| P22 | +++ | 2.43E−09 |
| P23 | ++ | 9.25E−08 |
| P24 | +++ | 4.98E−09 |
| P25 | --- | No blocking |
| P26 | +++ | 1.96E−09 |
| P27 | --- | No blocking |
| P28 | +++ | 1.96E−08 |
| P29 | --- | Low blocking |
| P30 | ++ | 4.79E−08 |
| P31.2 | +++ | 1.23E−09 |
| P32 | --- | Low blocking |
| P33 | + | 2.10E−07 |
| P34 | +++ | 1.31E−08 |
| P35 | +++ | 1.44E−08 |
| P36 | +++ | 1.14E−08 |
| P37 | ++ | 1.51E−07 |
| P38 | --- | No blocking |
| P39 | +++ | 8.40E−10 |
| P40 | ND | ND |
| P41 | ++ | 9.81E−08 |
| P42 | --- | No blocking |
| P43 | --- | No blocking |
| P44 | ND | ND |
| P45 | +++ | 4.02E−09 |
| P46 | --- | Low blocking |
| P47 | +++ | 7.26E−09 |
| P48 | + | ~0.0003176 |
| P49 | --- | Low blocking |
| P50 | --- | No blocking |
| P51 | --- | No blocking |
| P52 | --- | No blocking |
| P53 | --- | No blocking |
| P54 | ++ | 6.96E−08 |
| P55 | + | 2.83E−07 |

Example 5. Developability Assays

Antibodies that were selected for binding to PD-L1, for example, such as those described in Examples 2 and 3, were tested in various developability methods. For example, various chromatographic methods, including size exclusion chromatography (SEC), hydrophobic interaction chromatography (HIC), and standup monolayer adsorption chromatography (SMAC) were employed to assess developability factors, such as monomer percentage, solubility, and antibody aggregation or precipitation.

Size exclusion chromatography (SEC) analysis was performed using a 7.8 mm ID×30 cm TSKgel® G3000SWXL column (Tosoh Bioscience LLC, PN 08541) on an Agilent 1100 HPLC. Antibodies were normalized to 1 mg/mL concentration in Dulbecco's PBS (pH 7.4, without Ca2+/Mg2+) and clarified via centrifugation to pellet particulates while still retaining soluble aggregates. The mobile phase buffer was Dulbecco's PBS (pH 7.4, without Ca2+/Mg2+). For each sample, 10 μL was loaded and isocratically eluted at 1.0 mL/min over 20 minutes. Absorbance was monitored at 280 nm. Chromatographic peaks were integrated to determine % homogeneity and retention time. The column stationary phase along with choice of mobile phase supports hydrophobic interaction in addition to molecular sizing (hydrophobic interaction much milder compared to SMAC). Data analysis was performed using Agilent ChemStation B.04.03.

Figure 4A:
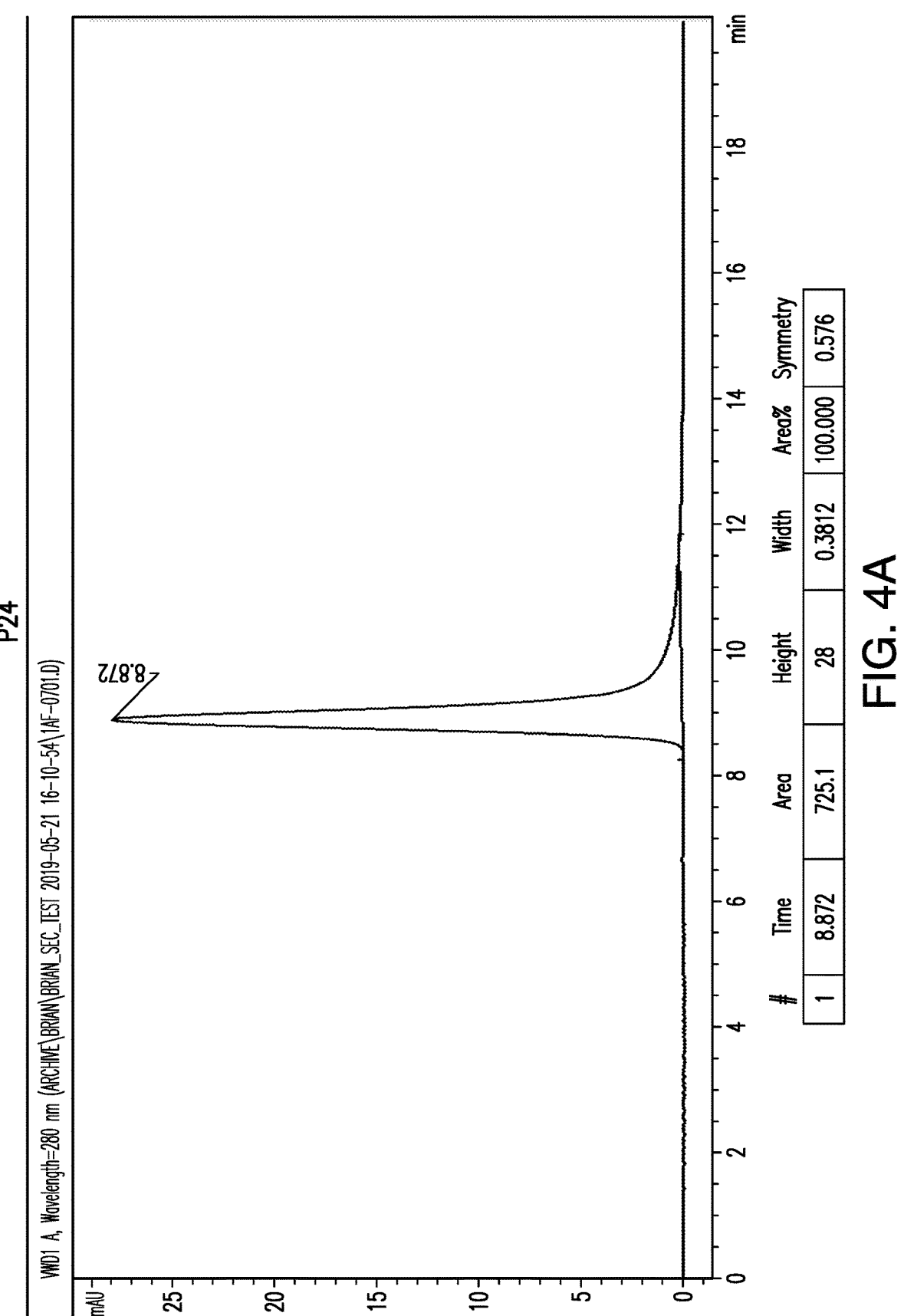
FIGS. 4A-4C illustrate exemplary results from SEC chromatography, further described in Example 5.
Figure 4B:
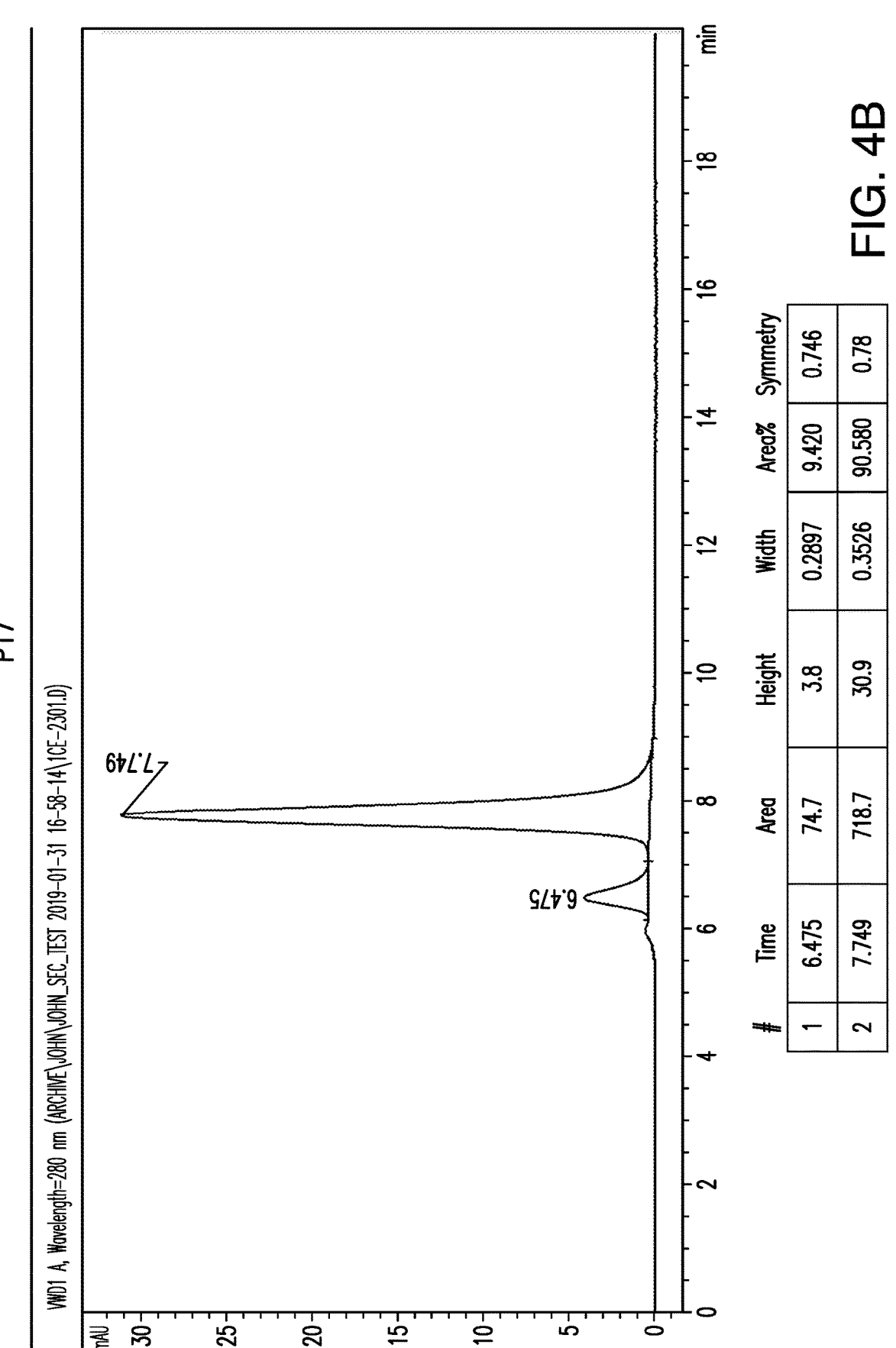
Figure 4C:
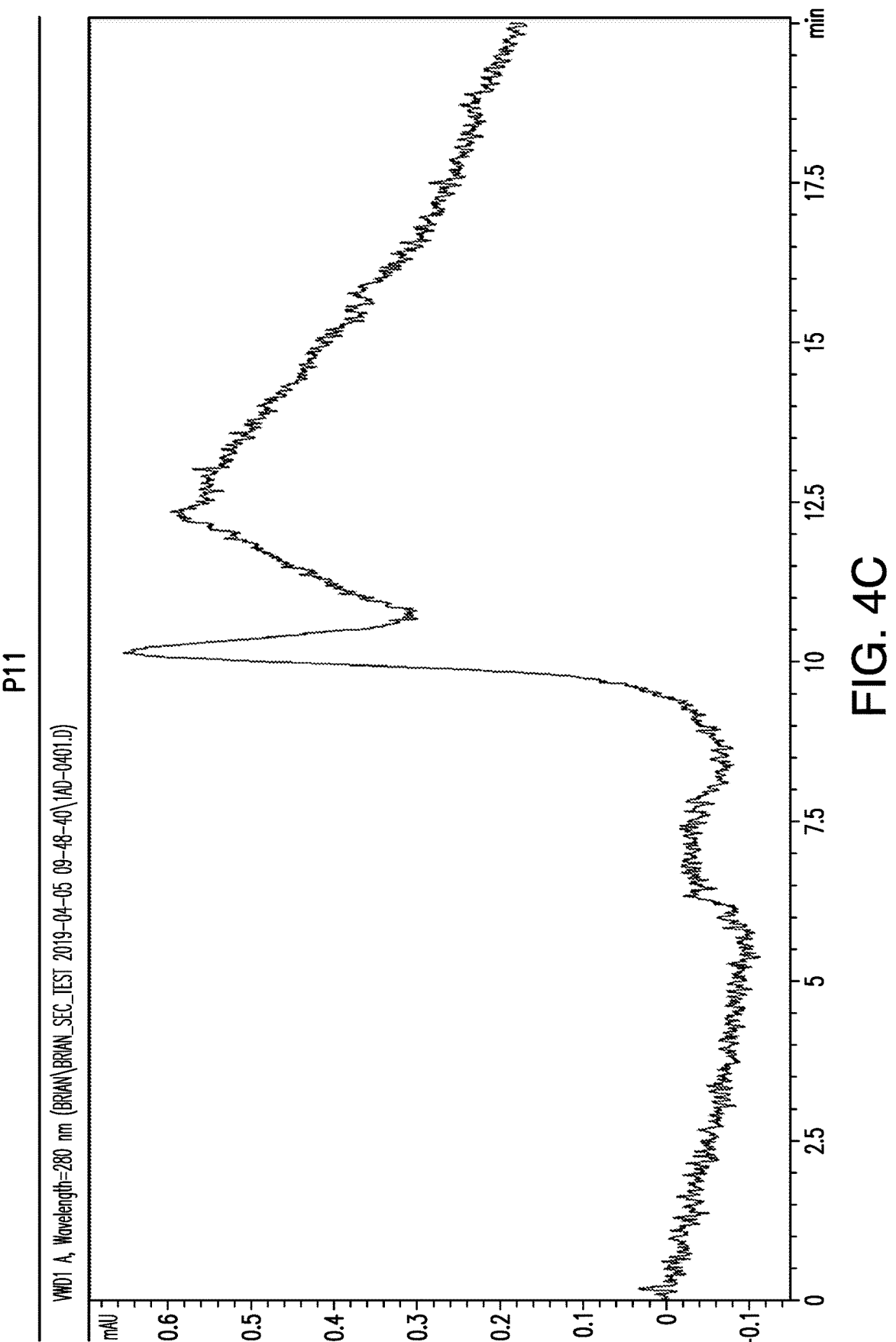

Exemplary SEC results are shown in FIGS. 4A-4C and summarized in Table 9. Strong developability is indicated by the symbol "+++", moderate developability is indicated by the symbol "++", and weak developability is indicated by the symbol "++". "ND" indicates that developability using SEC was not determined. Results show that 2 antibodies, P11 and P26, had weak developability based on the SEC assay, while all other antibodies tested had strong or moderate developability. Results indicate low antibody aggregation and strong developability based on SEC results for most tested antibodies.

TABLE 9

| Developability - Size-Exclusion Chromatography | |
|---|---|
| Binder | SEC |
| P1 | +++ |
| P2 | ++ |
| P3 | +++ |
| P4 | +++ |
| P5 | ++ |
| P6 | +++ |
| P7 | ++ |
| P8 | +++ |
| P9 | +++ |
| P10 | ++ |
| P11 | + |
| P12 | +++ |
| P13 | +++ |
| P14 | +++ |
| P15 | +++ |
| P16 | +++ |
| P17 | ++ |
| P18 | ++ |
| P19 | ND |
| P20 | ND |
| P21 | +++ |
| P22 | +++ |
| P23 | ++ |
| P24 | +++ |
| P25 | ND |
| P26 | + |
| P27 | ND |
| P28 | ++ |
| P29 | ND |
| P30 | +++ |
| P31.2 | +++ |
| P32 | ND |
| P33 | ND |
| P34 | +++ |
| P35 | +++ |
| P36 | +++ |
| P37 | ++ |
| P38 | ND |
| P39 | +++ |
| P40 | ND |
| P41 | ND |
| P42 | ND |
| P43 | ND |
| P44 | ND |
| P45 | +++ |
| P46 | ND |

TABLE 9-continued

| Developability - Size-Exclusion Chromatography | |
| --- | --- |
| Binder | SEC |
| P47 | ++ |
| P48 | ND |
| P49 | ND |
| P50 | ND |
| P51 | ND |
| P52 | ND |
| P53 | ND |
| P54 | +++ |
| P55 | ND |

Hydrophobic interaction chromatography (HIC) analysis was performed using a 4.6 mm ID×3.5 cm TSKgel© Butyl-NPR column (Tosoh Bioscience LLC, PN 14947) on an Agilent 1100 HPLC. Antibodies were normalized to 2 mg/mL concentration in dPBS (pH 7.4) and then diluted with an equal volume of mobile phase buffer B to a final protein concentration of 1 mg/mL. The column was equilibrated with 100% mobile phase Buffer B (2 M ammonium sulfate/20 mM sodium phosphate, pH 7.0) at a flow rate of 1 mL/min. For each sample, 10 μL was loaded and eluted using a gradient from 100% mobile phase buffer B to 100% mobile phase buffer A (20 mM sodium phosphate, pH 7.0) at 1.0 mL/min over 15 min, held at 100% A for 3 min to wash the column, and returned 100% B for 2 min for equilibration. Absorbance was monitored at 280 nm. Sample retention time was calculated and compared to a set of standard controls to identify antibodies with increased retention time (increased hydrophobicity).

Figure 5A:
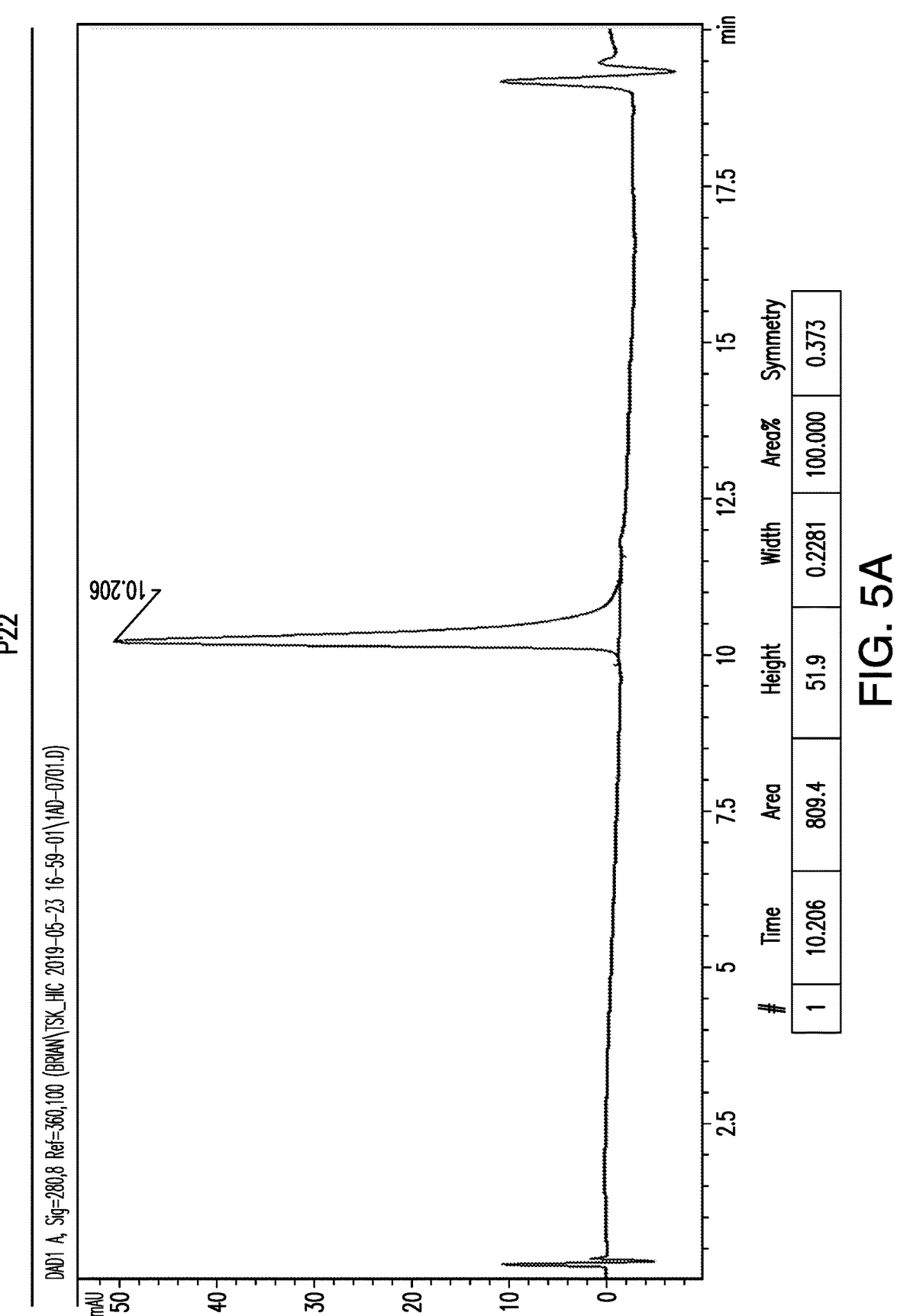
FIGS. 5A-5C illustrate exemplary results from HIC chromatography, further described in Example 5.
Figure 5B:
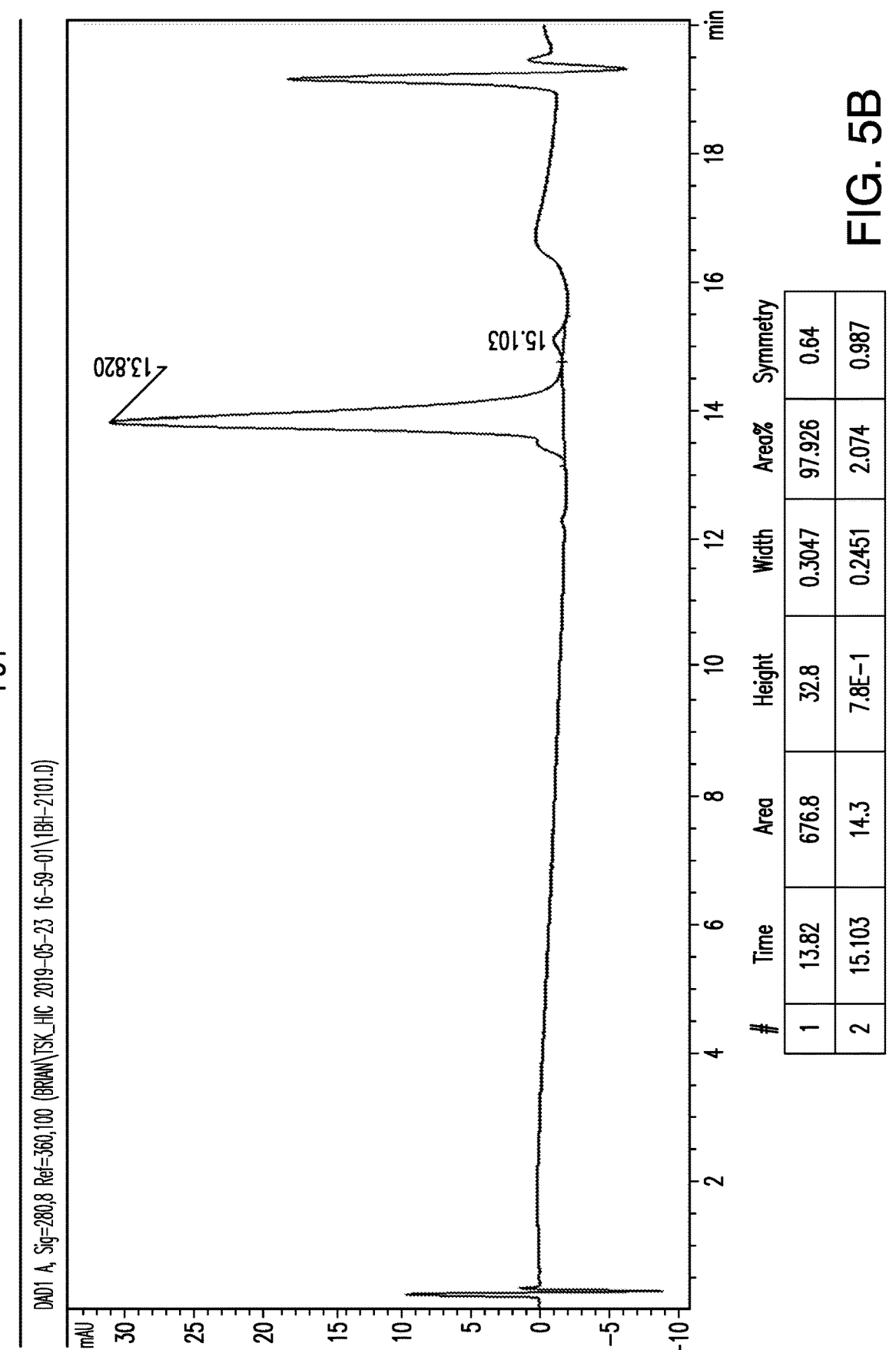
Figure 5C:
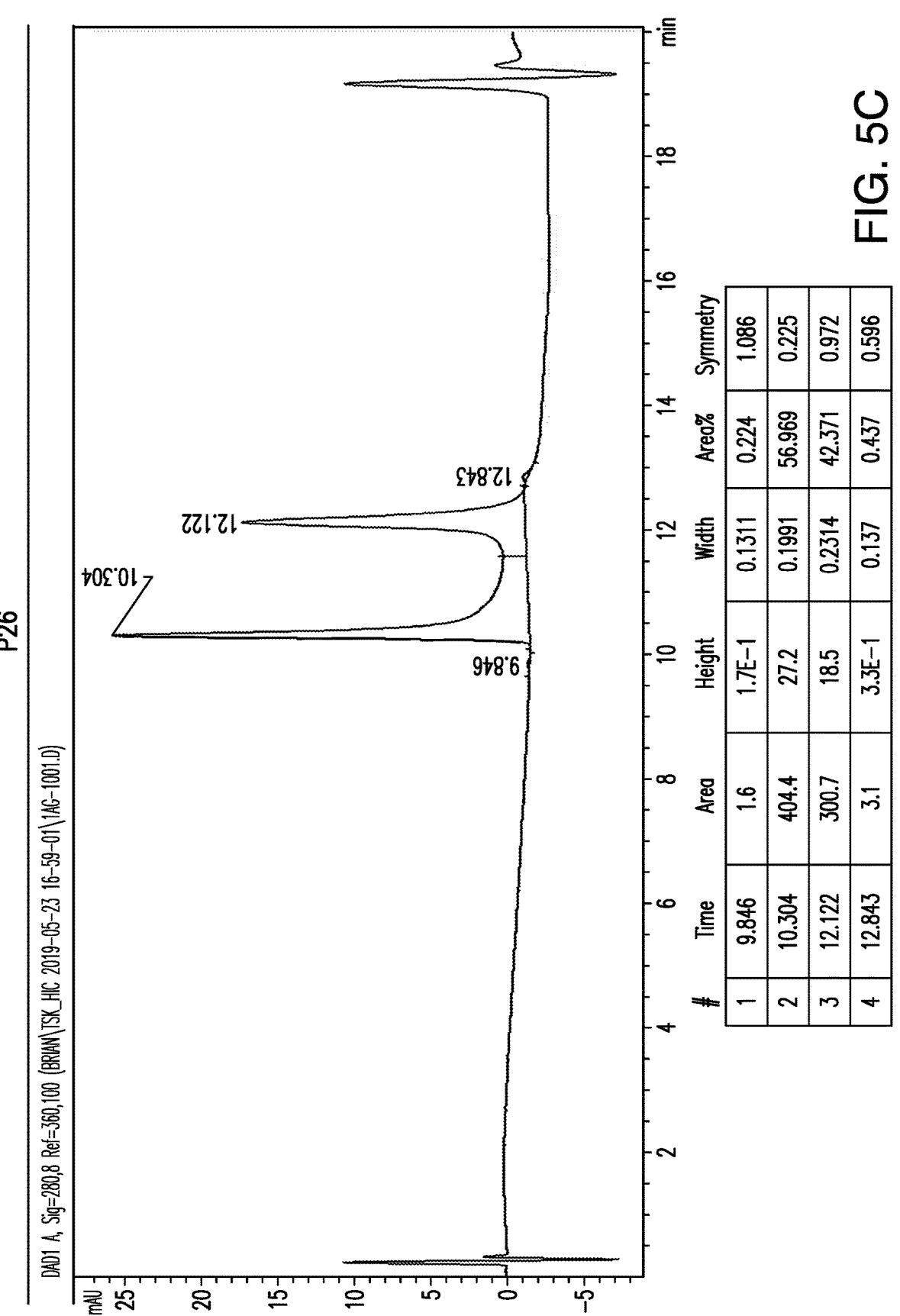

Exemplary HIC results are shown in FIGS. 5A-5C and summarized in Table 10. Strong developability is indicated by the symbol "+++", moderate developability is indicated by the symbol "++", and weak developability is indicated by the symbol "++". "ND" indicates that developability was not determined using HIC. Results show that 23 antibodies had strong developability based on HIC results (P2, P4, P6, P7, P9, P11, P14, P15, P16, P21, P22, P23, P24, P28, P30, P31.2, P34, P35, P36, P37, P39, P45, and P47), 8 antibodies had moderate developability (P3, P8, P10, P12, P13, P17, P18, and P54), and 3 antibodies had weak developability (P1, P5, and P26). Antibody hydrophobicity can impact antibody aggregation, solubility and viscosity. Results indicate a low propensity for aggregation and precipitation of these antibodies.

TABLE 10

| Developability - Hydrophobic Interaction Chromatography | |
| --- | --- |
| Binder | HIC |
| P1 | + |
| P2 | +++ |
| P3 | ++ |
| P4 | +++ |
| P5 | + |
| P6 | +++ |
| P7 | +++ |
| P8 | ++ |
| P9 | +++ |
| P10 | ++ |
| P11 | +++ |
| P12 | ++ |
| P13 | ++ |
| P14 | +++ |
| P15 | +++ |
| P16 | +++ |

TABLE 10-continued

| Developability - Hydrophobic Interaction Chromatography | |
| --- | --- |
| Binder | HIC |
| P17 | ++ |
| P18 | ++ |
| P19 | ND |
| P20 | ND |
| P21 | +++ |
| P22 | +++ |
| P23 | +++ |
| P24 | +++ |
| P25 | ND |
| P26 | + |
| P27 | ND |
| P28 | +++ |
| P29 | ND |
| P30 | +++ |
| P31.2 | +++ |
| P32 | ND |
| P33 | ND |
| P34 | +++ |
| P35 | +++ |
| P36 | +++ |
| P37 | +++ |
| P38 | ND |
| P39 | +++ |
| P40 | ND |
| P41 | ND |
| P42 | ND |
| P43 | ND |
| P44 | ND |
| P45 | +++ |
| P46 | ND |
| P47 | +++ |
| P48 | ND |
| P49 | ND |
| P50 | ND |
| P51 | ND |
| P52 | ND |
| P53 | ND |
| P54 | ++ |
| P55 | ND |

Standup monolayer adsorption chromatography (SMAC) analysis was performed using a 4.6 mm ID×300 mm Zenix® SEC 300 column (Sepax Technologies, PN 213300P-4630) on an Agilent 1100 HPLC. Antibodies were normalized to 1 mg/mL concentration in dPBS (pH 7.4) and clarified via centrifugation to pellet particulates. The mobile phase buffer was dPBS (pH 7.4, without calcium and magnesium). For each sample, 10 μL was loaded and isocratically eluted at 0.25 mL/min over 32 min. Absorbance was monitored at 280 nm. Sample retention time was calculated and compared to a set of standard controls to identify antibodies with increased retention time (increased propensity to form aggregates).

Figure 6A:
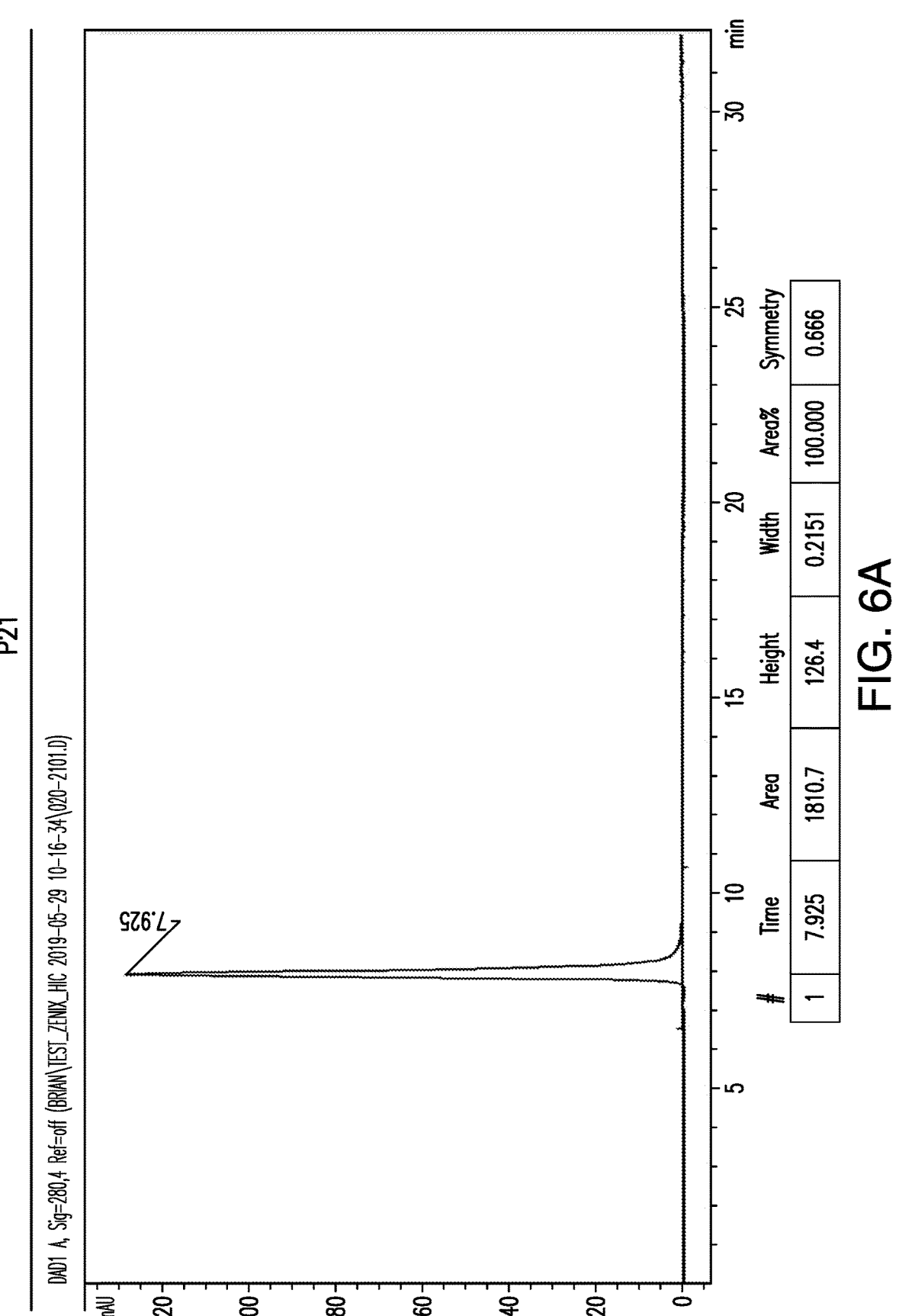
FIGS. 6A-6C illustrate exemplary results from SMAC chromatography, further described in Example 5.
Figure 6B:
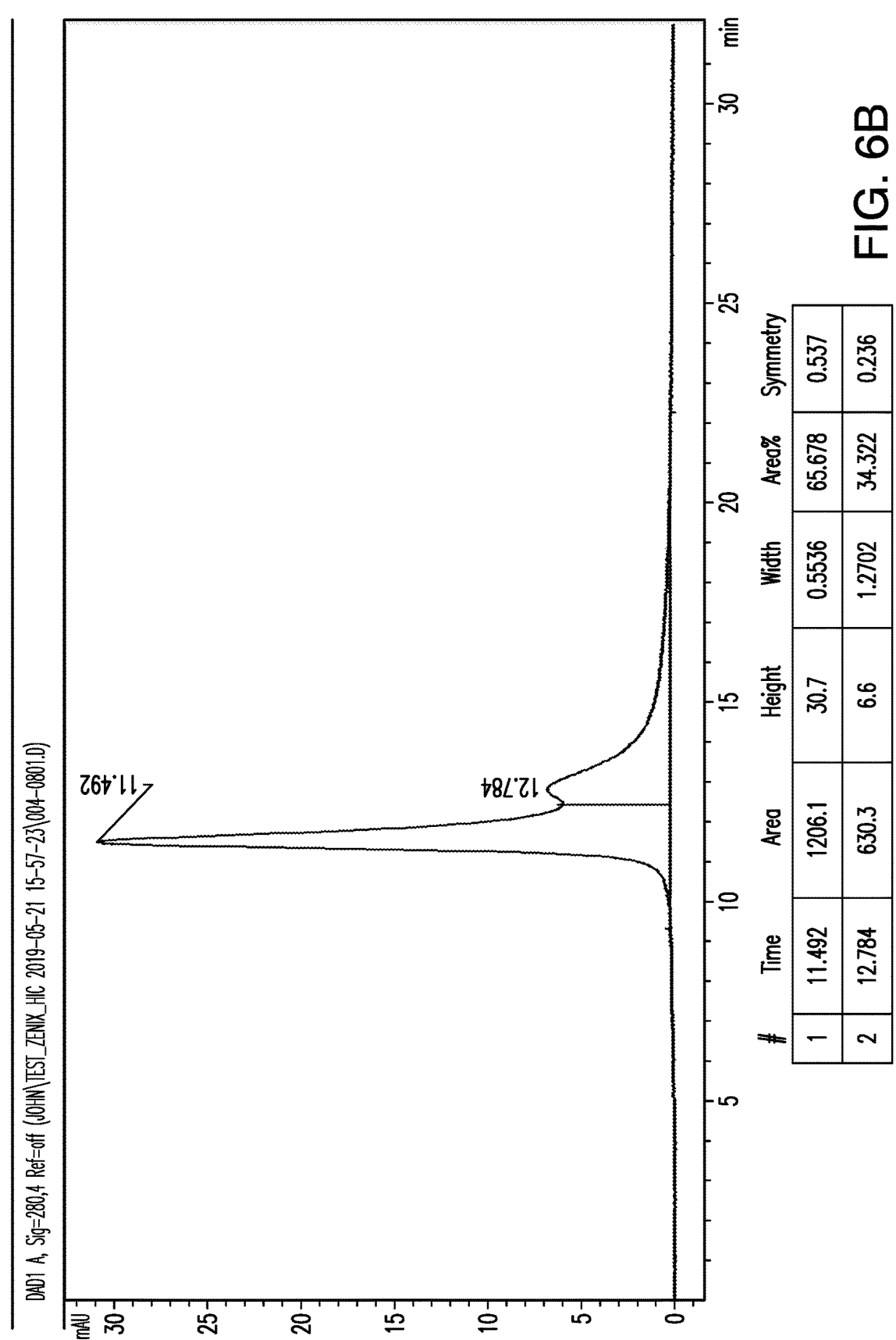
Figure 6C:
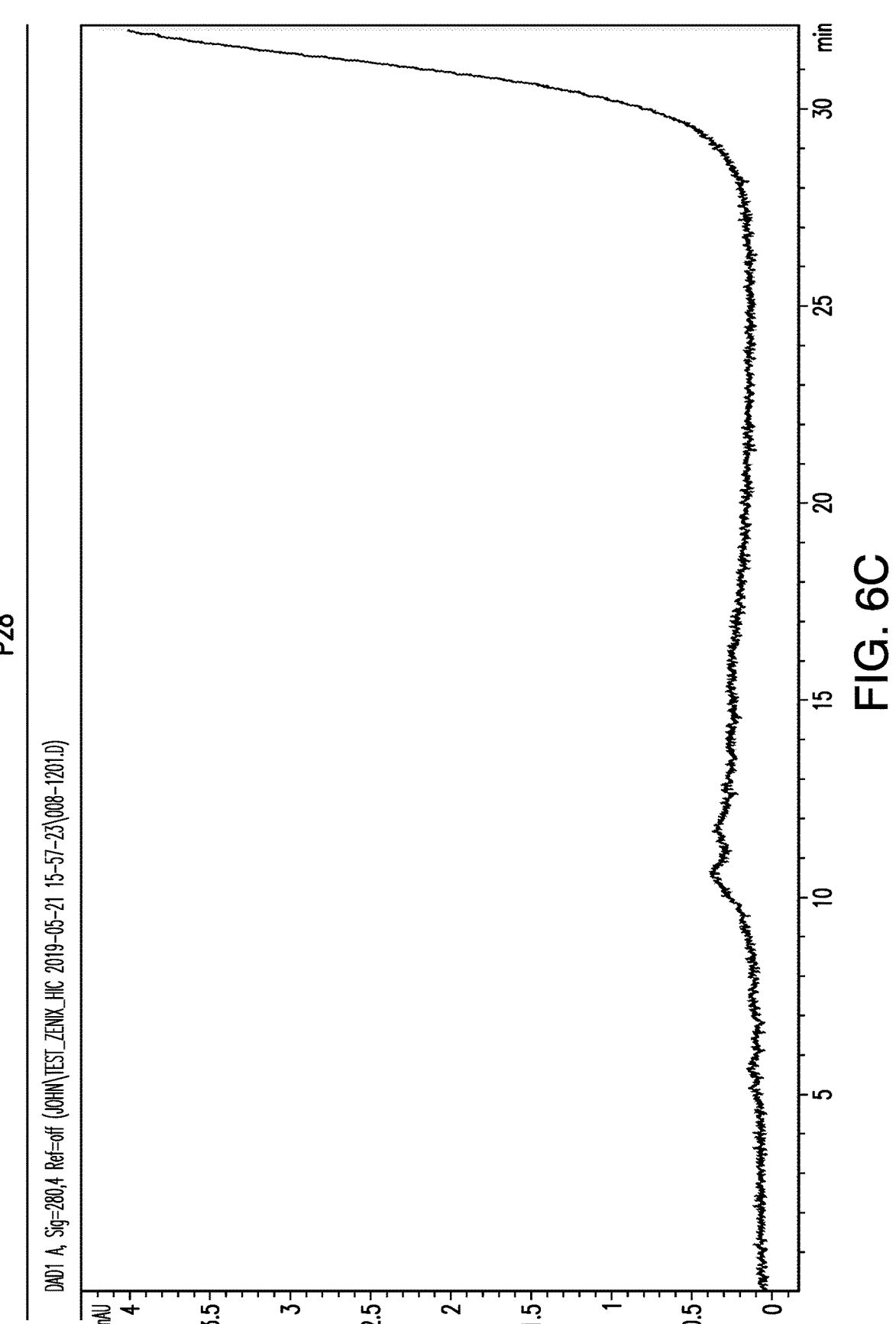

Exemplary SMAC results are shown in FIGS. 6A-6C and summarized in Table 11. Strong developability is indicated by the symbol "+++", moderate developability is indicated by the symbol "++", and weak developability is indicated by the symbol "++". "ND" indicates that developability was not determined using SMAC. Results show that 14 tested antibodies had good retention times, indicating colloidal stability and low propensity to aggregate (P4, P6, P9, P11, P14, P15, P16, P21, P24, P30, P31.2, P34, P35, and P45), 6 antibodies had moderate developability (P8, P12, P17, P22, P36, and P39), and 14 antibodies had weak developability based on SMAC (P1, P2, P3, P5, P7, P10, P13, P18, P23, P26, P28, P37, P47, and P54).

TABLE 11

Developability - Standup Monolayer Adsorption Chromatography

| Binder | SMAC |
|---|---|
| P1 | + |
| P2 | + |
| P3 | + |
| P4 | +++ |
| P5 | + |
| P6 | +++ |
| P7 | + |
| P8 | ++ |
| P9 | +++ |
| P10 | + |
| P11 | +++ |
| P12 | ++ |
| P13 | + |
| P14 | +++ |
| P15 | +++ |
| P16 | +++ |
| P17 | ++ |
| P18 | + |
| P19 | ND |
| P20 | ND |
| P21 | +++ |
| P22 | ++ |
| P23 | + |
| P24 | +++ |
| P25 | ND |
| P26 | + |
| P27 | ND |
| P28 | + |
| P29 | ND |
| P30 | +++ |
| P31.2 | +++ |
| P32 | ND |
| P33 | |
| P34 | +++ |
| P35 | +++ |
| P36 | ++ |
| P37 | + |
| P38 | ND |
| P39 | ++ |
| P40 | ND |
| P41 | ND |
| P42 | ND |
| P43 | ND |
| P44 | ND |
| P45 | +++ |
| P46 | ND |
| P47 | + |
| P48 | ND |
| P49 | ND |
| P50 | ND |
| P51 | ND |
| P52 | ND |
| P53 | ND |
| P54 | + |
| P55 | ND |

The UNcle analytical instrument (Unchained Labs) was employed to assess the biostability of antibodies using multiple assays. Stability analysis of engineered antibody variants was evaluated by measuring the Polydispersity Index (PDI), Hydrodynamic Diameter (Z-ave D), Melting Temperature (Tm), and Aggregation Temperature (Tagg).

Antibodies were assayed at concentrations ranging from to 1-20 mg/mL formulated in Dulbecco's PBS (pH 7.4, without $Ca^{2+}/Mg^{2+}$) and clarified via centrifugation to pellet large particulates while still retaining soluble aggregates. Samples were aliquoted into UNcle's 9 μL quartz capillary cuvette device (Uni) and sealed. PDI and hydrodynamic diameter were measured by DLS at 15° C. The temperature was ramped from 15° C. to 95° C. at 0.5° C./min during which Tm and Tagg were measured by fluorescence and SLS (266 nm, filter 4; 473 nm, filter 3), respectively. Data were analyzed using UNcle Analysis Software v 3.1 or v 3.2.

Exemplary biostability results are shown in Table 12.

TABLE 12

Biostability Assessment

| Binder | PDI | Z-ave D (nm) | Tm | Tagg 266 | Tagg 473 |
|---|---|---|---|---|---|
| P1 | 2.199 | 80 | 71 | 78 | 78 |
| P2 | 0.978 | 129 | 70 | 65 | 68 |
| P3 | 0.732 | 51 | 81 | 78 | 78 |
| P4 | 0.431 | 35 | 71 | 80 | 80 |
| P5 | 2.053 | 85 | 66 | 81 | 82 |
| P6 | 2.124 | 77 | 72 | 80 | 81 |
| P7 | 0.265 | 53 | 70 | 73 | 72 |
| P8 | 2.029 | 72 | 71 | 78 | 78 |
| P9 | 1.95 | 78 | 76 | 75 | 76 |
| P10 | 1.363 | 54 | 76 | 76 | 75 |
| P11 | 1.221 | 42 | 80 | 79 | 80 |
| P12 | 1.416 | 53 | 74 | 73 | 71 |
| P13 | 1.738 | 96 | 76 | 75 | 75 |
| P14 | 1.479 | 17 | 72 | 84 | 85 |
| P15 | 2.437 | 76 | 72 | 82 | 83 |
| P16 | — | — | — | — | — |
| P17 | 0.308 | 21 | 71 | 82 | 83 |
| P18 | 0.237 | 29 | 79 | 77 | 78 |
| P19 | ND | ND | ND | ND | ND |
| P20 | ND | ND | ND | ND | ND |
| P21 | 0.021 | 14 | 73 | 84 | 84 |
| P22 | 1.963 | 99 | 73 | 78 | 80 |
| P23 | 0.845 | 43 | 73 | 77 | 75 |
| P24 | 1.816 | 82 | 74 | 77 | 79 |
| P25 | ND | ND | ND | ND | ND |
| P26 | 0.12 | 18 | 74 | 80 | 75 |
| P27 | ND | ND | ND | ND | ND |
| P28 | 1.524 | 81 | 73 | 69 | 71 |
| P29 | ND | ND | ND | ND | ND |
| P30 | 1.269 | 15 | 74 | 80 | 81 |
| P31.2 | 0.097 | 10 | 74 | 78 | 78 |
| P32 | ND | ND | ND | ND | ND |
| P33 | ND | ND | ND | ND | ND |
| P34 | 0.053 | 12 | 73 | 80 | 81 |
| P35 | 0.754 | 24 | 73 | 80 | 81 |
| P36 | 2.437 | 54 | 74 | 74 | 73 |
| P37 | 2.462 | 83 | 75 | 74 | 74 |
| P38 | ND | ND | ND | ND | ND |
| P39 | 1.625 | 58 | 73 | 80 | 80 |
| P40 | ND | ND | ND | ND | ND |
| P41 | ND | ND | ND | ND | ND |
| P42 | ND | ND | ND | ND | ND |
| P43 | ND | ND | ND | ND | ND |
| P44 | ND | ND | ND | ND | ND |
| P45 | 1.906 | 68 | 72 | 81 | 81 |
| P46 | ND | ND | ND | ND | ND |
| P47 | 0.535 | 26 | 72 | 75 | 74 |
| P48 | ND | ND | ND | ND | ND |
| P49 | ND | ND | ND | ND | ND |
| P50 | ND | ND | ND | ND | ND |
| P51 | ND | ND | ND | ND | ND |
| P52 | ND | ND | ND | ND | ND |
| P53 | ND | ND | ND | ND | ND |
| P54 | 1.181 | 69 | 78 | 74 | 74 |
| P55 | ND | ND | ND | ND | ND |

Example 6: Competitive Binding Assays and Epitope Binning

Competitive binding assays were employed to determine if antibodies compete for the same binding region of human PD-L1. Using a competitive immunoassay, if antigen binding of one antibody prevents the binding of the other, then these two antibodies are considered to bind to the same or similar (e.g., overlapping) epitopes, and are considered to be in the same epitope bin. If binding of an antibody does not interfere with the binding of another antibody, then they are considered to bind to distinct epitopes of PD-L1, and are in different epitope bins.

An Octet®-based "in tandem" assay format was used for the cross-competition assays to establish the competitive binding data and epitope binning. For these assays, 100 nM biotinylated antigen was immobilized on a streptavidin sensor in 10× kinetic buffer (ForteBio). The association of antibodies to PD-L1 were monitored by dipping the sensor in consecutive steps into wells containing saturating concentrations of two competing (or non-competing) antibodies. If the saturation with the first antibody did not block the binding (indicated by further increment in the BLI signal) then the antibodies were considered to be binding to distinct non-overlapping epitopes and belong to different bins.

Results indicate that P22 and P31.2 bin together (data not shown). These bin separately from P24.

Throughout this application various publications, patents, patent applications and other documents have been referenced. The disclosures of these publications, patents, patent applications and other documents in their entireties are hereby incorporated by reference in this application for all purposes, including in order to more fully describe the state of the art to which this the subject matter disclosed herein pertains. Although the disclosed subject matter has been described with reference to the examples provided above, it should be understood that various modifications can be made without departing from the spirit of the disclosed subject matter. Many variations will become apparent to those skilled in the art upon review of this specification.

---

What is claimed is:

1. An antibody or fragment thereof that binds to PD-L1 comprising all three heavy chain complementarity determining regions (CDRs) and/er all three light chain CDRs from:

the antibody designated P22 that comprises a VH sequence that is SEQ ID NO:25 and a VL sequence that is SEQ ID NO:26;

the antibody designated P24 that comprises a VH sequence that is SEQ ID NO:51 and a VL sequence that is SEQ ID NO:52; or the antibody designated P31.2 that comprises a VH sequence that is SEQ ID NO:77 and a VL sequence that is SEQ ID NO:78;

wherein the heavy chain CDRs and the light chain CDRs are determined according to Kabat numbering system, Chothia numbering system, AbM numbering system, Contact numbering system, IMGT numbering system, or Exemplary numbering system.

2. The antibody or fragment thereof of claim 1, wherein the antibody comprises:

(i) (a) a heavy chain variable ($V_H$) region comprising:
(1) a $V_H$ CDR1 having the amino acid sequence of SEQ ID NO:1;
(2) a $V_H$ CDR2 having the amino acid sequence of SEQ ID NO:2; and
(3) a $V_H$ CDR3 having the amino acid sequence of SEQ ID NO:3; and (b) a light chain variable ($V_L$) region comprising:
(1) a $V_L$ CDR1 having the amino acid sequence of SEQ ID NO:4;
(2) a $V_L$ CDR2 having the amino acid sequence of SEQ ID NO:5; and
(3) a $V_L$ CDR3 having the amino acid sequence of SEQ ID NO:6;

(ii) (a) a heavy chain variable ($V_H$) region comprising:
(1) a $V_H$ CDR1 having the amino acid sequence of SEQ ID NO:7;
(2) a $V_H$ CDR2 having the amino acid sequence of SEQ ID NO:8; and
(3) a $V_H$ CDR3 having the amino acid sequence of SEQ ID NO:9; and (b) a light chain variable ($V_L$) region comprising:
(1) a $V_L$ CDR1 having the amino acid sequence of SEQ ID NO:10;
(2) a $V_L$ CDR2 having the amino acid sequence of SAS; and (3) a $V_L$ CDR3 having the amino acid sequence of SEQ ID NO:6;

(iii) (a) a heavy chain variable ($V_H$) region comprising:
    (1) a $V_H$ CDR1 having the amino acid sequence of SEQ ID NO:12;
    (2) a $V_H$ CDR2 having the amino acid sequence of SEQ ID NO:2; and
    (3) a $V_H$ CDR3 having the amino acid sequence of SEQ ID NO:3; and (b) a light chain variable ($V_L$) region comprising:
    (1) a $V_L$ CDR1 having the amino acid sequence of SEQ ID NO:4;
    (2) a $V_L$ CDR2 having the amino acid sequence of SEQ ID NO:5; and
    (3) a $V_L$ CDR3 having the amino acid sequence of SEQ ID NO:6;

(iv) (a) a heavy chain variable ($V_H$) region comprising:
    (1) a $V_H$ CDR1 having the amino acid sequence of SEQ ID NO:13;
    (2) a $V_H$ CDR2 having the amino acid sequence of SEQ ID NO:14; and
    (3) a $V_H$ CDR3 having the amino acid sequence of SEQ ID NO:15; and (b) a light chain variable ($V_L$) region comprising:
    (1) a $V_L$ CDR1 having the amino acid sequence of SEQ ID NO:16;
    (2) a $V_L$ CDR2 having the amino acid sequence of SAS; and
    (3) a $V_L$ CDR3 having the amino acid sequence of SEQ ID NO:17;

(v) (a) a heavy chain variable ($V_H$) region comprising:
    (1) a $V_H$ CDR1 having the amino acid sequence of SEQ ID NO:18;
    (2) a $V_H$ CDR2 having the amino acid sequence of SEQ ID NO: 19; and
    (3) a $V_H$ CDR3 having the amino acid sequence of SEQ ID NO:20; and (b) a light chain variable ($V_L$) region comprising:
    (1) a $V_L$ CDR1 having the amino acid sequence of SEQ ID NO:21;
    (2) a $V_L$ CDR2 having the amino acid sequence of SEQ ID NO:22; and
    (3) a $V_L$ CDR3 having the amino acid sequence of SEQ ID NO:23; or (vi) (a) a heavy chain variable ($V_H$) region comprising:
    (1) a $V_H$ CDR1 having the amino acid sequence of SEQ ID NO:1;
    (2) a $V_H$ CDR2 having the amino acid sequence of SEQ ID NO:24; and
    (3) a $V_H$ CDR3 having the amino acid sequence of SEQ ID NO:3; and (b) a light chain variable ($V_L$) region comprising:
    (1) a $V_L$ CDR1 having the amino acid sequence of SEQ ID NO:4;
    (2) a $V_L$ CDR2 having the amino acid sequence of SEQ ID NO:5; and
    (3) a $V_L$ CDR3 having the amino acid sequence of SEQ ID NO:6.

3. The antibody or fragment thereof of claim 1, wherein the antibody comprises:

(i) (a) a heavy chain variable ($V_H$) region comprising:
    (1) a $V_H$ CDR1 having the amino acid sequence of SEQ ID NO:27;
    (2) a $V_H$ CDR2 having the amino acid sequence of SEQ ID NO:28; and
    (3) a $V_H$ CDR3 having the amino acid sequence of SEQ ID NO:29; and (b) a light chain variable ($V_L$) region comprising:
    (1) a $V_L$ CDR1 having the amino acid sequence of SEQ ID NO:30;
    (2) a $V_L$ CDR2 having the amino acid sequence of SEQ ID NO:31; and
    (3) a $V_L$ CDR3 having the amino acid sequence of SEQ ID NO:32;

(ii) (a) a heavy chain variable ($V_H$) region comprising:
    (1) a $V_H$ CDR1 having the amino acid sequence of SEQ ID NO:33;
    (2) a $V_H$ CDR2 having the amino acid sequence of SEQ ID NO:34; and
    (3) a $V_H$ CDR3 having the amino acid sequence of SEQ ID NO:35; and (b) a light chain variable ($V_L$) region comprising:
    (1) a $V_L$ CDR1 having the amino acid sequence of SEQ ID NO:36;
    (2) a $V_L$ CDR2 having the amino acid sequence of SAS; and
    (3) a $V_L$ CDR3 having the amino acid sequence of SEQ ID NO:32;

(iii) (a) a heavy chain variable ($V_H$) region comprising:
    (1) a $V_H$ CDR1 having the amino acid sequence of SEQ ID NO:38;
    (2) a $V_H$ CDR2 having the amino acid sequence of SEQ ID NO:28; and
    (3) a $V_H$ CDR3 having the amino acid sequence of SEQ ID NO:29; and (b) a light chain variable ($V_L$) region comprising:
    (1) a $V_L$ CDR1 having the amino acid sequence of SEQ ID NO:30;
    (2) a $V_L$ CDR2 having the amino acid sequence of SEQ ID NO:31; and
    (3) a $V_L$ CDR3 having the amino acid sequence of SEQ ID NO:32;

(iv) (a) a heavy chain variable ($V_H$) region comprising:
    (1) a $V_H$ CDR1 having the amino acid sequence of SEQ ID NO:39;
    (2) a $V_H$ CDR2 having the amino acid sequence of SEQ ID NO:40; and
    (3) a $V_H$ CDR3 having the amino acid sequence of SEQ ID NO:41; and (b) a light chain variable ($V_L$) region comprising:
    (1) a $V_L$ CDR1 having the amino acid sequence of SEQ ID NO:42;
    (2) a $V_L$ CDR2 having the amino acid sequence of SAS; and
    (3) a $V_L$ CDR3 having the amino acid sequence of SEQ ID NO:43;

(v) (a) a heavy chain variable ($V_H$) region comprising:
    (1) a $V_H$ CDR1 having the amino acid sequence of SEQ ID NO:44;
    (2) a $V_H$ CDR2 having the amino acid sequence of SEQ ID NO:45; and
    (3) a $V_H$ CDR3 having the amino acid sequence of SEQ ID NO:46; and (b) a light chain variable ($V_L$) region comprising:
    (1) a $V_L$ CDR1 having the amino acid sequence of SEQ ID NO:47;
    (2) a $V_L$ CDR2 having the amino acid sequence of SEQ ID NO:48; and
    (3) a $V_L$ CDR3 having the amino acid sequence of SEQ ID NO:49; or (vi) (a) a heavy chain variable ($V_H$) region comprising:
    (1) a $V_H$ CDR1 having the amino acid sequence of SEQ ID NO:27;

(2) a V$_H$ CDR2 having the amino acid sequence of SEQ ID NO:50; and (3) a V$_H$ CDR3 having the amino acid sequence of SEQ ID NO:29; and (b) a light chain variable (V$_L$) region comprising:

(1) a V$_L$ CDR1 having the amino acid sequence of SEQ ID NO:30;

(2) a V$_L$ CDR2 having the amino acid sequence of SEQ ID NO:31; and (3) a V$_L$ CDR3 having the amino acid sequence of SEQ ID NO:32.

4. The antibody or fragment thereof of claim 1, wherein the antibody comprises:

(i) (a) a heavy chain variable (V$_H$) region comprising:

(1) a V$_H$ CDR1 having the amino acid sequence of SEQ ID NO:53;

(2) a V$_H$ CDR2 having the amino acid sequence of SEQ ID NO:54; and (3) a V$_H$ CDR3 having the amino acid sequence of SEQ ID NO:55; and (b) a light chain variable (V$_L$) region comprising:

(1) a V$_L$ CDR1 having the amino acid sequence of SEQ ID NO:56;

(2) a V$_L$ CDR2 having the amino acid sequence of SEQ ID NO:57; and (3) a V$_L$ CDR3 having the amino acid sequence of SEQ ID NO:58;

(ii) (a) a heavy chain variable (V$_H$) region comprising:

(1) a V$_H$ CDR1 having the amino acid sequence of SEQ ID NO:59;

(2) a V$_H$ CDR2 having the amino acid sequence of SEQ ID NO:60; and (3) a V$_H$ CDR3 having the amino acid sequence of SEQ ID NO:61; and (b) a light chain variable (V$_L$) region comprising:

(1) a V$_L$ CDR1 having the amino acid sequence of SEQ ID NO:62;

(2) a V$_L$ CDR2 having the amino acid sequence of SAS; and (3) a V$_L$ CDR3 having the amino acid sequence of SEQ ID NO:58;

(iii) (a) a heavy chain variable (V$_H$) region comprising:

(1) a V$_H$ CDR1 having the amino acid sequence of SEQ ID NO:64;

(2) a V$_H$ CDR2 having the amino acid sequence of SEQ ID NO:54; and (3) a V$_H$ CDR3 having the amino acid sequence of SEQ ID NO:55; and (b) a light chain variable (V$_L$) region comprising:

(1) a V$_L$ CDR1 having the amino acid sequence of SEQ ID NO:56;

(2) a V$_L$ CDR2 having the amino acid sequence of SEQ ID NO:57; and (3) a V$_L$ CDR3 having the amino acid sequence of SEQ ID NO:58;

(iv) (a) a heavy chain variable (V$_H$) region comprising:

(1) a V$_H$ CDR1 having the amino acid sequence of SEQ ID NO:65;

(2) a V$_H$ CDR2 having the amino acid sequence of SEQ ID NO:66; and (3) a V$_H$ CDR3 having the amino acid sequence of SEQ ID NO:67; and (b) a light chain variable (V$_L$) region comprising:

(1) a V$_L$ CDR1 having the amino acid sequence of SEQ ID NO:68;

(2) a V$_L$ CDR2 having the amino acid sequence of SAS; and (3) a V$_L$ CDR3 having the amino acid sequence of SEQ ID NO:69;

(v) (a) a heavy chain variable (V$_H$) region comprising:

(1) a V$_H$ CDR1 having the amino acid sequence of SEQ ID NO:70;

(2) a V$_H$ CDR2 having the amino acid sequence of SEQ ID NO:71; and (3) a V$_H$ CDR3 having the amino acid sequence of SEQ ID NO:72; and (b) a light chain variable (V$_L$) region comprising:

(1) a V$_L$ CDR1 having the amino acid sequence of SEQ ID NO:73;

(2) a V$_L$ CDR2 having the amino acid sequence of SEQ ID NO:74; and (3) a V$_L$ CDR3 having the amino acid sequence of SEQ ID NO:75; or (vi) (a) a heavy chain variable (V$_H$) region comprising:

(1) a V$_H$ CDR1 having the amino acid sequence of SEQ ID NO:53;

(2) a V$_H$ CDR2 having the amino acid sequence of SEQ ID NO:76; and (3) a V$_H$ CDR3 having the amino acid sequence of SEQ ID NO:55; and (b) a light chain variable (V$_L$) region comprising:

(1) a V$_L$ CDR1 having the amino acid sequence of SEQ ID NO:56;

(2) a V$_L$ CDR2 having the amino acid sequence of SEQ ID NO:57; and (3) a V$_L$ CDR3 having the amino acid sequence of SEQ ID NO:58.

5. The antibody or fragment thereof of claim 1, wherein the V$_H$ region and/or V$_L$ region further comprises (i) human framework sequences; and/or (ii) a framework 1 (FR1), a framework 2 (FR2), a framework 3 (FR3) and/or a framework 4 (FR4) sequence.

6. The antibody or fragment thereof of claim 1, wherein (i) the antibody is a monoclonal antibody;

(ii) the antibody is a humanized, human or chimeric antibody;

(iii) the antibody or fragment thereof is a Fab, Fab', F(ab')$_2$, Fv, scFv, (scFv)$_2$, single chain antibody molecule, dual variable region antibody, single variable region antibody, linear antibody, V region, or a multi-specific antibody formed from antibody fragments; and/or (iv) the antibody or fragment thereof is conjugated or recombinantly fused to a diagnostic agent, detectable agent or therapeutic agent.

7. One or more vectors comprising one or more polynucleotides encoding the antibody or fragment thereof of claim 1.

8. A pharmaceutical composition that comprises the antibody or fragment thereof of claim 1, and a pharmaceutically acceptable carrier.

9. A method for treating a cancer or a tumor in a subject, for alleviating one or more symptoms associated with a cancer or a tumor in a subject, for decreasing tumor size in a subject with a tumor, for enhancing tumor cell removal in a subject with a tumor, for treating a T cell dysfunctional disease, disorder or condition in a subject, or for enhancing T cell function in a subject, comprising administering to the subject the antibody or fragment thereof of claim 1.

10. The antibody or fragment thereof of claim 1, wherein the antibody or fragment thereof comprises a V$_H$ comprising the amino acid sequence of SEQ ID NO.25 and a V$_L$ comprising the amino acid sequence of SEQ ID NO.26.

11. One or more polynucleotides encoding the antibody or fragment thereof of claim 1.

12. A cell comprising the one or more vectors of claim 7.

13. The antibody or fragment thereof of claim 1, wherein the antibody or fragment thereof comprises a VH comprising the amino acid sequence of SEQ ID NO:51 and a VL comprising the amino acid sequence of SEQ ID NO:52.

14. The antibody or fragment thereof of claim 1, wherein the antibody or fragment thereof comprises a VH comprising the amino acid sequence of SEQ ID NO:77 and a VL comprising the amino acid sequence of SEQ ID NO:78.

15. The antibody or fragment thereof of claim 6, wherein the antibody or fragment thereof is conjugated or recombinantly fused to a therapeutic agent, wherein the therapeutic agent is a chemotherapeutic agent or cytotoxin.

16. The method of claim 9, wherein the subject is administered one or more therapeutic agents in combination with the antibody or fragment thereof.

\* \* \* \* \*